United States Patent
Chung et al.

(10) Patent No.: US 10,882,837 B2
(45) Date of Patent: Jan. 5, 2021

(54) AMIDE COMPOUNDS AND USE THEREOF

(71) Applicant: ALPHALA CO., LTD., Taipei (TW)

(72) Inventors: Cheng-Ho Chung, Taipei (TW); Shi-Liang Tseng, Taipei (TW); Yung-Ning Yang, Taipei (TW); Yen-Fu Chen, Taipei (TW)

(73) Assignee: ALPHALA CO., LTD., Taipei (TW)

( * ) Notice: Subject to any disclaimer, the term of this patent is extended or adjusted under 35 U.S.C. 154(b) by 0 days.

(21) Appl. No.: 16/475,900

(22) PCT Filed: Jan. 22, 2018

(86) PCT No.: PCT/US2018/014621
§ 371 (c)(1),
(2) Date: Jul. 3, 2019

(87) PCT Pub. No.: WO2018/140338
PCT Pub. Date: Aug. 2, 2018

(65) Prior Publication Data
US 2019/0345118 A1  Nov. 14, 2019

Related U.S. Application Data

(60) Provisional application No. 62/449,620, filed on Jan. 24, 2017.

(51) Int. Cl.
| | | |
|---|---|---|
| *C07D 271/06* | (2006.01) | |
| *C07D 271/10* | (2006.01) | |
| *C07D 263/57* | (2006.01) | |
| *C07D 277/66* | (2006.01) | |
| *C07D 413/04* | (2006.01) | |
| *C07D 307/79* | (2006.01) | |
| *A61P 3/10* | (2006.01) | |
| *C07C 233/92* | (2006.01) | |
| *C07D 209/08* | (2006.01) | |
| *C07D 213/90* | (2006.01) | |
| *C07D 237/14* | (2006.01) | |
| *C07D 239/34* | (2006.01) | |
| *C07D 271/07* | (2006.01) | |
| *C07D 401/12* | (2006.01) | |

(52) U.S. Cl.
CPC .............. *C07D 307/79* (2013.01); *A61P 3/10* (2018.01); *C07C 233/92* (2013.01); *C07D 209/08* (2013.01); *C07D 213/90* (2013.01); *C07D 237/14* (2013.01); *C07D 239/34* (2013.01); *C07D 263/57* (2013.01); *C07D 271/06* (2013.01); *C07D 271/07* (2013.01); *C07D 271/10* (2013.01); *C07D 277/66* (2013.01); *C07D 401/12* (2013.01); *C07D 413/04* (2013.01)

(58) Field of Classification Search
CPC .. C07D 271/06; C07D 271/10; C07D 413/04; C07D 263/57; C07D 277/66
See application file for complete search history.

(56) References Cited

U.S. PATENT DOCUMENTS

| 7,504,508 B2 | 3/2009 | Ghosh et al. |
| 2004/0197380 A1 | 10/2004 | Wolf et al. |

FOREIGN PATENT DOCUMENTS

| WO | 02089848 A | 11/2002 |
| WO | 2012107850 A | 8/2012 |

OTHER PUBLICATIONS

Matthew F. Sammons and Esther C. Y. Lee, Recent progress in the development of small-molecule glucagon receptor antagonists, Bioorganic & Medicinal Chemistry Letters 25 (2015) 4057-4064.

*Primary Examiner* — Laura L Stockton
(74) *Attorney, Agent, or Firm* — Bacon & Thomas, PLLC

(57) ABSTRACT

Disclosed are compounds of formula (I) below and pharmaceutically acceptable salts thereof, in which each of variables $R_1$, $R_2$, L, and Z is defined herein. Also disclosed are methods for reducing the glycemic level and treating glucagon-associated disorders with a compound of formula (I) or a salt thereof and a pharmaceutical composition containing same.

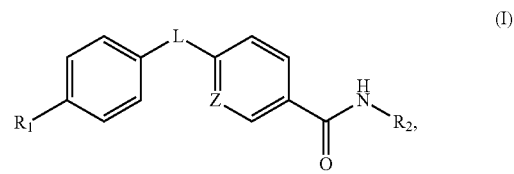

(I)

25 Claims, No Drawings

AMIDE COMPOUNDS AND USE THEREOF

This application claims the benefit of filing date of U.S. Provisional Application Ser. No. 62/449,620, filed Jan. 24, 2017, which is hereby incorporated by reference.

FIELD OF THE INVENTION

The present invention relates to compounds that act as antagonists or inverse agonists of the glucagon receptor, pharmaceutical compositions comprising the compounds, and the uses of the compounds or compositions.

BACKGROUND

Diabetes is a major public health issue and affects millions of people in the world. The two major hormones, insulin and glucagon, which regulate blood sugar homeostasis, play important roles in diabetes. The glucagon is secreted by pancreatic alpha cells and can stimulate glycogenosis and gluconeogenesis. Moreover, the glucagon signaling might also affect lipid metabolism, food intake, cardiovascular system and adipose tissue mass. The antagonism of glucagon signaling has been pursued as a potential therapy for diabetes for a long time. Many of them were done through interfering the receptor-ligand binding. The glucagon receptor is a class B G-protein coupled receptor and is mainly expressed in liver and less in other tissues. Antagonism of glucagon receptor by small molecules reduces the downstream secondary messengers including cAMP and calcium ion which lead to gluconeogenic genes expression and subsequent blood sugar elevation. Glucagon receptor –/– mice exhibit resistance to diet-induced obesity and streptozotocin-induced diabetes. Currently several small molecules glucagon receptor antagonists have entered clinical trials and showed significant blood sugar reduction versus placebo. Glucagon receptor antagonism also may have benefit in cardiovascular disease through cardiomyocytes protection. In glucagon receptor inactivated mouse model, animals showed higher survival rate and lower heart failure after myocardial infarction.

There is a need to develop new glucagon receptor modulators that have fewer and less deterious side effects for therapeutic use.

SUMMARY

The present invention relates to certain amide compounds as glucagon receptor modulators for treating glucagon-associated disorders. Unexpectedly, these compounds, acting as antagonists or inverse agonists of the glucagon receptor, produce higher efficacy in modulating the glucagon receptor for reducing the glycemic level, as compared to known therapeutic agents.

An aspect of this invention is drawn to the compounds of formula (I) below and pharmaceutically acceptable salts thereof:

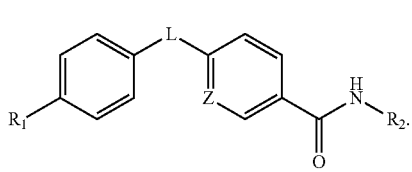

(I)

In this formula, $R_1$ is

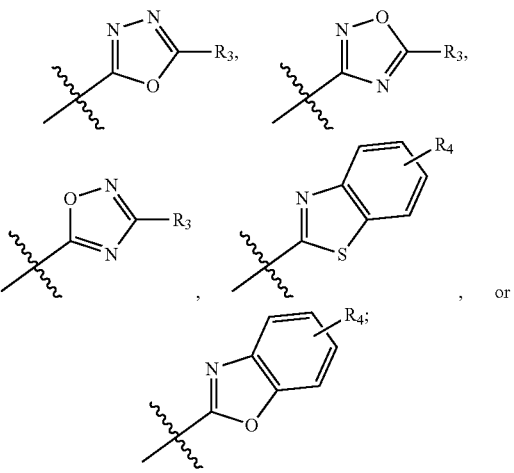

$R_2$ is —$CH_2CH_2CO_2R_5$ or —$CH_2CH_2SO_3H$; L is —X—CH($R_6$)— or —CH($R_6$)—X—, X being NH or O; and Z is C or N, in which $R_3$ is $C_{1-6}$ alkyl, aryl, or heteroaryl, the $C_{1-6}$ alkyl being optionally substituted with one to three halo moieties and each of the aryl and heteroaryl being optionally substituted with one to three moieties selected from the group consisting of $C_{1-6}$ alky, $C_{3-10}$ cycloalkyl, aryl, halogen substituted $C_{1-6}$ alkyl, $C_{1-6}$ alkoxy, and halo; $R_4$ represents one to three moieties selected from H, halo, hydroxyl, cyano, amino, alkyl, $C_{1-6}$ alkoxy, halogen substituted $C_{1-6}$ alkyl; and $C_{3-10}$ cycloalkyl; $R_5$ is H, $C_{1-6}$ alkyl, $C_{3-10}$ cycloalkyl and halogen substituted $C_{1-6}$ alkyl; and is $R_6$ is $C_{1-6}$ alkyl, $C_{3-10}$ cycloalkyl, or $C_{1-10}$ heterocycloalkyl, the $C_{1-6}$ alkyl being optionally substituted with one to three moieties selected from halo, hydroxyl, $C_{1-6}$ alkoxy, and aryl and each of the $C_{3-10}$ cycloalkyl and $C_{1-10}$ heterocycloalkyl being optionally substituted with one to two moieties selected from the group consisting of $C_{1-6}$ alkyl, $C_{1-6}$ alkoxy, and halo.

The term "alkyl" herein refers to a straight or branched hydrocarbon group, containing 1-20 (e.g., 1-10 and 1-6) carbon atoms. Examples include methyl, ethyl, n-propyl, i-propyl, n-butyl, i-butyl, and t-butyl.

The term "cycloalkyl" refers to a saturated and partially unsaturated monocyclic, bicyclic, tricyclic, or tetracyclic hydrocarbon group having 3-12 (e.g., 3-10 and 3-8) carbon atoms. Examples include cyclopropyl, cyclobutyl, cyclopentyl, cyclopentenyl, cyclohexyl, cyclohexenyl, cycloheptyl, and cyclooctyl.

The term "heterocycloalkyl" refers to a nonaromatic 5-8 membered monocyclic, 8-12 membered bicyclic, or 11-14 membered tricyclic ring system having one or more heteroatoms (e.g., O, N, P, and S). Examples include piperazinyl, imidazolidinyl, azepanyl, pyrrolidinyl, dihydrothiadiazolyl, dioxanyl, morpholinyl, tetrahydropuranyl, and tetrahydrofuranyl.

The term "alkoxy" refers to an —O-alkyl group. Examples include methoxy, ethoxy, propoxy, and isopropoxy.

The term "halo" refers to a fluoro, chloro, bromo, or iodo radical. The term "amino" refers to a radical derived from amine, which is unsunstituted or mono-/di-substituted with alkyl, aryl, cycloalkyl, heterocycloalkyl, or heteroaryl.

The term "aryl" refers to a 6-carbon monocyclic, 10-carbon bicyclic, 14-carbon tricyclic aromatic ring system. Examples of aryl groups include phenyl, naphthyl, and anthracenyl.

The term "heteroaryl" refers to an aromatic 5-8 membered monocyclic, 8-12 membered bicyclic, or 11-14 membered tricyclic ring system having one or more heteroatoms (e.g., O, N, P, and S). Examples include triazolyl, oxazolyl, thiadiazolyl, tetrazolyl, pyrazolyl, pyridyl, furyl, imidazolyl, benzimidazolyl, pyrimidinyl, thienyl, quinolinyl, indolyl, thiazolyl, and benzothiazolyl.

Alkyl, cycloalkyl, heterocycloalkyl, alkoxy, aryl, and heteroaryl mentioned herein include both substituted and unsubstituted moieties. Possible substituents on cycloalkyl, heterocycloalkyl, alkoxy, aryl, and heteroaryl include, but are not limited to, $C_1$-$C_{10}$ alkyl $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, $C_1$-$C_{10}$ alkylsulfonamino, arylsulfonamino, $C_1$-$C_{10}$ alkylamino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amido, amidino, guanidine, ureido, thioureido, cyano, nitro, nitroso, azido, acyl, thioacyl, acyloxy, carboxyl, and carboxylic ester. On the other hand, possible substituents on alkyl include all of the above-recited substituents except $C_1$-$C_{10}$ alkyl. Cycloalkyl, heterocycloalkyl, aryl, and heteroaryl can also be fused with each other.

In addition to the compounds of formula (I) described above, their pharmaceutically acceptable salts and solvates, where applicable, are also covered by this invention. A salt can be formed between an anion and a positively charged group (e.g., amino) on a compound. Examples of a suitable anion include chloride, bromide, iodide, sulfate, nitrate, phosphate, citrate, methanesulfonate, trifluoroacetate, acetate, malate, tosylate, tartrate, fumarate, glutamate, glucuronate, lactate, glutarate, and maleate. A salt can also be formed between a cation and a negatively charged group. Examples of a suitable cation include sodium ion, potassium ion, magnesium ion, calcium ion, and an ammonium cation such as tetramethylammonium ion. A salt further includes those containing quaternary nitrogen atoms. A solvate refers to a complex formed between an active compound and a pharmaceutically acceptable solvent. Examples of a pharmaceutically acceptable solvent include water, ethanol, isopropanol, ethyl acetate, acetic acid, and ethanolamine.

Another aspect of this invention is a pharmaceutical composition for treating disorders associated with glucagon, such as a metabolic disorder associated with glucagon (e.g., type I diabetes, type II diabetes).

The pharmaceutical composition contains one of the compounds of formula (I) described above or its pharmaceutically acceptable salt and a pharmaceutically acceptable carrier.

This invention also covers use of such a composition for the manufacture of a medicament for treating disorders (for example, a metabolic disorder) associated with glucagon.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. Oral solid dosage forms can be prepared by spray dried techniques; hot melt extrusion strategy, micronization, and nano milling technologies.

A nasal aerosol or inhalation composition can be prepared according to techniques well knows in the art of pharmaceutical formulation. For example, such a composition can be prepared as a solution in saline, employing benzyl alcohol or other suitable preservatives, absorption promoters, fluorocarbons, and/or other solubilizing or dispersing agents known in the art. A composition having an active compound can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilised as pharmaceutical excipients for delivery of an active compound. Examples of other carriers include colloidal silicon oxide, magnesium stearate, cellulose, sodium lauryl sulfate, and D&C Yellow #10.

Still within the scope of the present invention is a method of treating disorders (for example, a metabolic disorder) associated with glucagon.

The method includes administering to a subject in need thereof an effective amount of a compound of formula (I) or a pharmaceutically acceptable salt thereof.

The above-described compounds or a pharmaceutical composition containing one or more of them, can be administered to a subject orally, parenterally, by inhalation spray, topically, rectally, nasally, buccally, or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

The term "treating" refers to application or administration of the compound to a subject with the purpose to cure, alleviate, relieve, alter, remedy, improve, or affect the disease, the symptom, or the predisposition. "An effective amount" refers to the amount of the compound which is required to confer the desired effect on the subject. Effective amounts vary, as recognized by those skilled in the art, depending on route of administration, excipient usage, and the possibility of co-usage with other therapeutic treatments such as use of oilier active agents.

The details of one or more embodiments of the invention are set forth hi the description below. Other features, objects, and advantages of the invention will be apparent from the description and from the claims.

DETAILED DESCRIPTION

Disclosed in detail below are the compounds of formula (I) and pharmaceutically acceptable salts thereof:

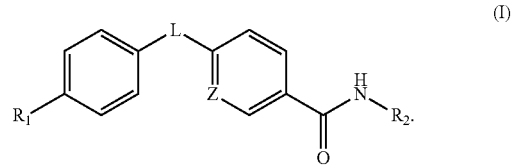

in which each of variables $R_1$, $R_2$, L, and Z is defined as in the SUMMARY section.

In one embodiment, compounds of formula (I) each have $R_1$ being

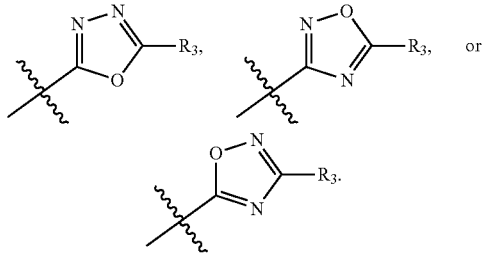

Typically, $R_2$ is —$CH_2CH_2CO_2R_5$; L is —X—$CH(R_6)$— or —$CH(R_6)$—X—, X being NH; and Z is C. For example, $R_1$ is

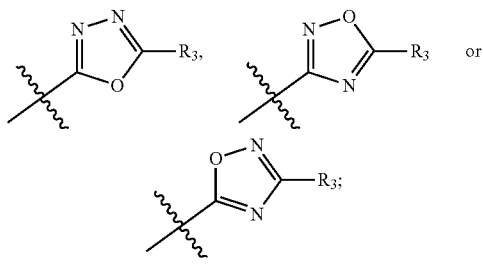

L is —$CH(R_6)$—X—, X being NH or O; and Z is C. L can also be —X—$CH(R_6)$—, X being NH or O. Note that in this embodiment, $R_3$ can be $C_{1-6}$ alkyl, optionally substituted phenyl or pyridinyl; and $R_6$ typically is $C_{1-6}$ alkyl.

An exemplary compound of formula (I) has $R_1$ being

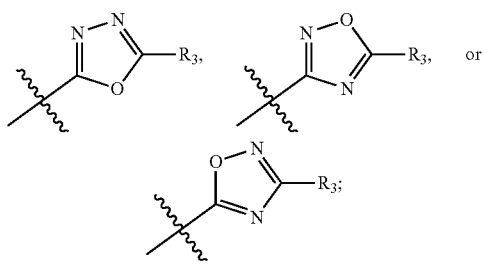

$R_2$ being —$CH_2CH_2CO_2R_5$; L being —X—$CH(R_6)$— or —$CH(R_6)$—; and Z being C, in which $R_3$ is $C_{1-6}$ alkyl, optionally substituted phenyl or pyridinyl, $R_5$ is H or $C_{1-6}$ alkyl, $R_6$ is $C_{1-6}$ alkyl, and X is NH.

In another embodiment, compounds of formula (I) each have $R_1$ being

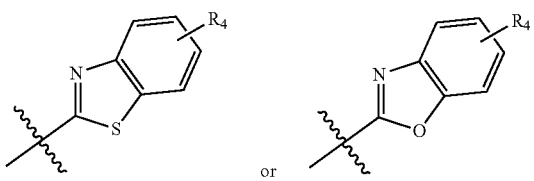

$R_4$ typically is H. Again, $R_2$ can be —$CH_2CH_2CO_2R_5$; L can be —X—$CH(R_6)$— or —$CH(R_6)$—X—, X being NH and $R_6$ being $C_{1-6}$ alkyl; and Z can be C or N. In this embodiment, an exemplary compound of formula (I) has $R_1$ being

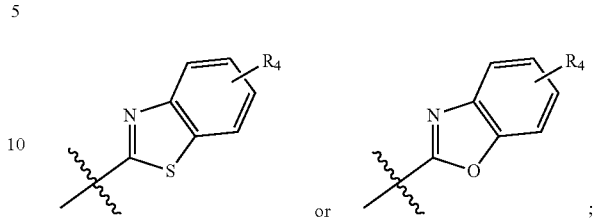

$R_2$ being —$CH_2CH_2CO_2R_5$; L being —X—$CH(R_6)$— or —$CH(R_6)$—X—; and Z being N, in which $R_4$ is H, $R_5$ is H or $C_{1-6}$ alkyl, $R_6$ is $C_{1-6}$ alkyl, and X is NH. In this embodiment, another exemplary compound of formula (I) has $R_1$ being

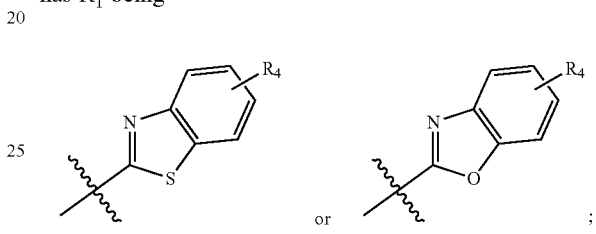

$R_2$ being —$CH_2CH_2CO_2R_5$; L being —X—$CH(R_6)$— or —$CH(R_6)$—X—; and Z being N, hi which $R_4$ is H, $R_5$ is H or $C_{1-6}$ alkyl, $R_6$ is $C_{1-6}$ alkyl, and X is NH.

In the aforesaid embodiments, $R_3$ can be $C_{1-6}$ alkyl, aryl, or 6-membered heteroaryl, the $C_{1-6}$ alkyl being optionally substituted with one to three halo moieties and each of the aryl and 6-membered heteroaryl being optionally substituted with one to three moieties selected from the group consisting of methyl, trifluoromethyl, ethyl propyl, isopropyl, butyl, tert-butyl, F and Cl.

In the aforesaid embodiments, $R_6$ can be $C_{1-6}$ alkyl or $C_{3-10}$ cycloalkyl, the $C_{1-6}$ alkyl being optionally substituted with one to three moieties selected from the group consisting of fluoro, hydroxyl, methoxy, and phenyl.

Referring to variable L in formula (I), the carbon attached to both X and $R_6$ can have a stereoisomeric configuration of R or S, and such compounds can have an enantiomeric excess of 90% or higher (e.g., ≤95% and ≤99%).

Also within this invention is a pharmaceutical composition for treating disorders associated with glucagon, such as a metabolic disorder associated with glucagon (e.g., type I diabetes, and type II diabetes), the composition containing one of the compounds of formula (I) set forth above or a pharmaceutically acceptable salt thereof and a pharmaceutically acceptable carrier.

Further covered by this invention is a method for treating disorders associated with glucagon, the method including administering to a subject in need thereof an effective amount of a compound of formula (I) or a pharmaceutically acceptable salt thereof.

In the present invention, the aforesaid subject can be mammal for example, human.

In the present invention, the diseases, conditions or disorders associated with, glucagon can be, for example, hyperglycemia, Type II diabetes, metabolic syndrome, impaired glucose tolerance, glucosuria, diabetic nephropathy, diabetic neuropathy, diabetic retinopathy, hyperinsulinemia, insulin resistance syndrome, cataracts, obesity, dyslididemia, hypertension and myocardial infarction. However, the present invention is not limited thereto, and the compounds or die pharmaceutically acceptable salt thereof of the present invention can be applied to any other diseases, conditions or disorders associated with the glucagon signaling pathway. In one aspect of the present invention, the diseases, conditions or disorders associated with glucagon is hyperglycemia, Type II diabetes, impaired glucose tolerance, insulin resistance syndrome and obesity. In another aspect of the present invention, the diseases, conditions or disorders associated with glucagon is Type II diabetes.

In one embodiment of the present invention, the compound can be any one selected from the group consisting of compounds 1-1 to 1-62, compounds 2-1 to 2-48, compounds 3-1 to 3-15, compounds 4-1 to 4-30, compounds 5-1 to 5-8, compounds 6-1 to 6-2, and compounds 7-1 to 7-4 listed in the following Tables 1 to 7. In one aspect of the present invention, the compound of the present invention can be any one selected from the group consisting of compound 1-2, compound 1-38, compound 1-39, compound 1-41, compound 1-43, compound 1-45, compound 1-47, compound 1-49, compound 2-18, compound 2-19, compound 2-27, compound 2-28, and compounds 4-27 to 4-30.

Methods for synthesizing the compounds of formula (I) are well known in the art. See, for example, S. Larock, Comprehensive Organic Transformations ($2^{nd}$ Ed., VCH Publishers 1999); P. G. M, Wuts and T. W. Greene, Greene's Protective Groups in Organic Synthesis ($4^{th}$ Ed., John Wiley and Sons 2007); L. Fieser and M, Fieser, Fieser and Fieser's Reagents for Organic Synthesis (John Wiley and Sons 1994); L. Paquette, ed., Encyclopedia of Reagents for Organic Synthesis ($2^{nd}$ ed., John Wiley and Sons 2009); P. Roszkowski, J. K, Maurin, Z. Czarnocki "Enantioselective synthesis of (R)-(-)-praziquantel (PZQ)" Tetrahedron: Asymmetry 17 (2006) 1415-1419; and L. Hu, S. Magesfa, L. Chen, T. Lewis, B. Munoz, L. Wang "Direct inhibitors of keap1-nrf2 interaction as antioxidant inflammation modulators," WO2013/067036.

The compounds of formula (I) thus prepared can be initially screened using in vitro assays, e.g., the glucagon cAMP inhibition assay and $I^{125}$-glucagon binding assay both described in EXAMPLE 6 below, for their potency hi binding to glucagon receptor and inhibiting downstream cAMP. They can be subsequently evaluated using in vivo assays known in the field. The selected compounds can be further tested to verify their efficacy in disease related efficacy and adverse effects models. Based on the results, an appropriate dosage range and administration route can be determined.

Without farther elaboration, it is believed that one skilled in the art can, based on the above description, utilize the present invention to its fullest extent. The following specific examples, i.e., EXAMPLES 1-7, are therefore to be construed as merely illustrative, and not limitative of the remainder of the disclosure in any way whatsoever. All publications cited herein are incorporated by reference in their entirety.

Among the specific examples, EXAMPLES 1-5 set forth the procedures for preparing certain intermediates and 172 exemplary compounds of formula (I), as well as the analytical data for the compounds thus prepared; and EXAMPLES 6 and 7 set forth the protocols for testing these compounds.

Described below are the procedures used to synthesize the above-described 172 exemplary compounds.

Unless otherwise stated, all starting materials used were commercially available and used as supplied. Reactions requiring anhydrous conditions were performed hi flame-dried glassware and cooled under an argon or nitrogen atmosphere. Unless otherwise stated, reactions were carried out under argon or nitrogen and monitored by analytical thin-layer chromatography performed on glass-backed plates (5 cm_10 cm) precoated with silica gel 60 F254 as supplied by Merck. Visualization of the resulting chromatograms was done by looking under an ultraviolet lamp (λ-254 nm), followed by dipping in an nBuOH solution of Ninhydrin (0.3% w/v) containing acetic acid (3% v/v) or ethanol solution of phosphomolybdic acid (2.5% w/v) and charring by heat gun. Solvents for reactions were dried under an argon or nitrogen atmosphere prior to use as follows: THF, Toluene, and DCM were dried by the column of Dried molecular Sieve 5A (LC technology solution Inc). and DMF from calcium hydride or anhydrous with commercial available. Flash chromatography was used routinely for purification and separation of product mixtures using RediSep Rf Silica Gel Disposable Flash Columns, Gold® 20-40/40-60 microns silica gel and Reusable RediSep Rf Gold® C18 Reversed Phase columns, 20-40 microns supplied by RediSep. Eluent systems are given in volume/volume concentrations. 13C and 1H NMR spectra were recorded on Broker AVIII (400 MHz). Chloroform-d or dimethyl sulfoxide-d6 and $CD_3OD$ was used as the solvent and TMS (δ0.00 ppm) as an internal standard. Chemical shift values are reported in ppm relative to the TMS in delta (δ) units. Multiplicities are recorded as s (singlet), br s (broad singlet), d (doublet), t (triplet), q (quartet), dd (doublet of doublet), dt (doublet of triplet), m (multiplet). Coupling constants (J) are expressed in Hz. Electrospray mass spectra (ESMS) were recorded using an Thermo LTQ XL mass spectrometer. Spectral data were recorded as m/z values.

Example 1: Synthesis of the Compounds Shown in the Following Table 1

The following scheme was followed for synthesizing Compounds 1-1 to 1-62.

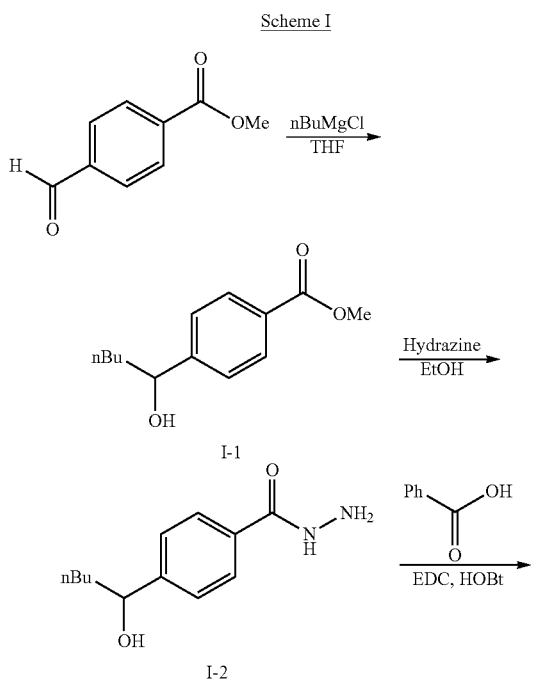

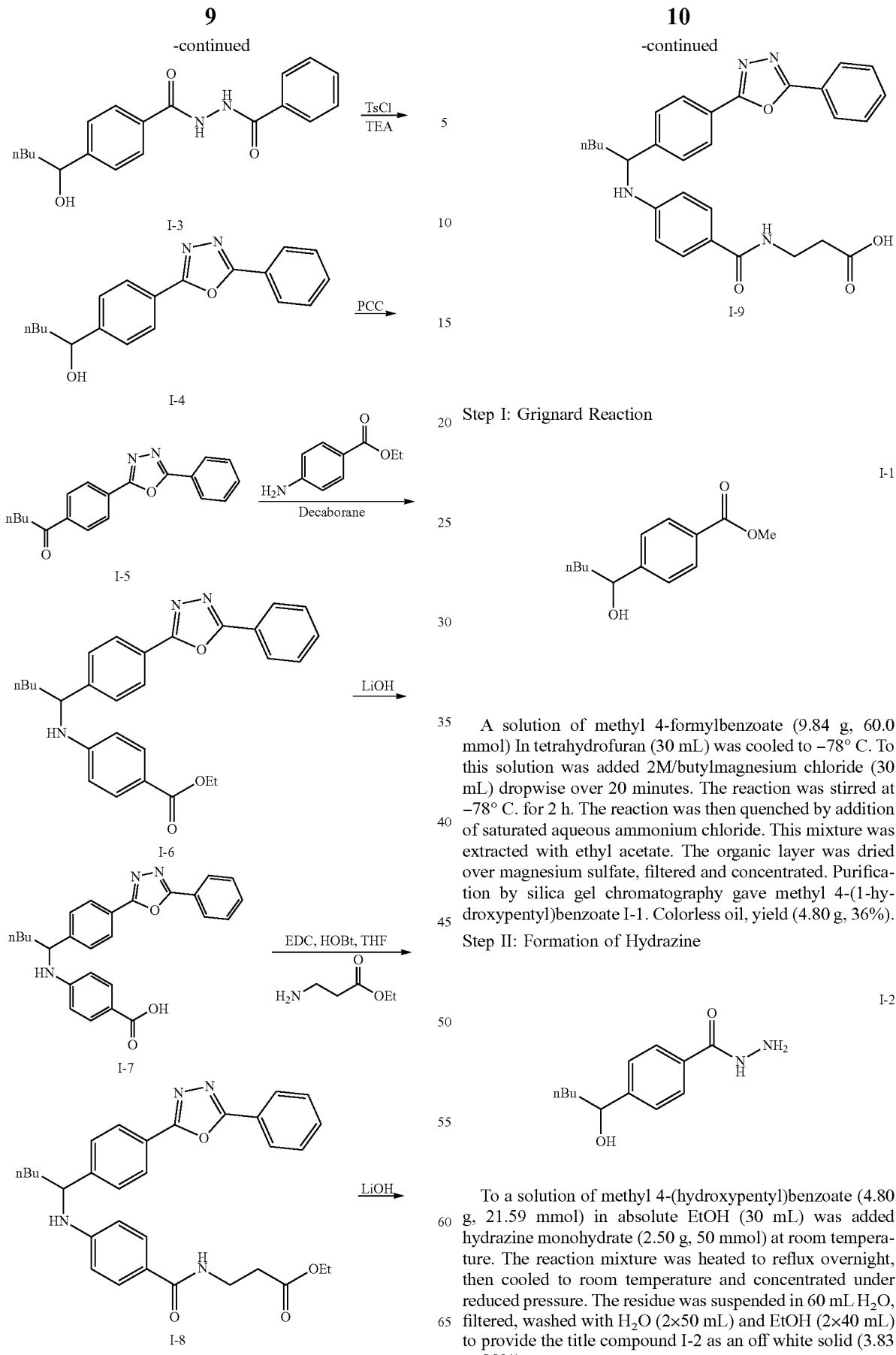

Step I: Grignard Reaction

A solution of methyl 4-formylbenzoate (9.84 g, 60.0 mmol) In tetrahydrofuran (30 mL) was cooled to −78° C. To this solution was added 2M/butylmagnesium chloride (30 mL) dropwise over 20 minutes. The reaction was stirred at −78° C. for 2 h. The reaction was then quenched by addition of saturated aqueous ammonium chloride. This mixture was extracted with ethyl acetate. The organic layer was dried over magnesium sulfate, filtered and concentrated. Purification by silica gel chromatography gave methyl 4-(1-hydroxypentyl)benzoate I-1. Colorless oil, yield (4.80 g, 36%).

Step II: Formation of Hydrazine

To a solution of methyl 4-(hydroxypentyl)benzoate (4.80 g, 21.59 mmol) in absolute EtOH (30 mL) was added hydrazine monohydrate (2.50 g, 50 mmol) at room temperature. The reaction mixture was heated to reflux overnight, then cooled to room temperature and concentrated under reduced pressure. The residue was suspended in 60 mL H₂O, filtered, washed with H₂O (2×50 mL) and EtOH (2×40 mL) to provide the title compound I-2 as an off white solid (3.83 g, 80%).

Step III: Amidation

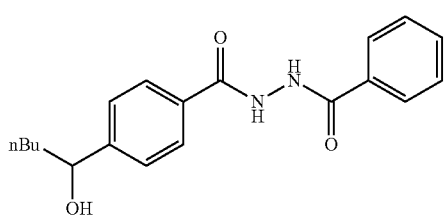

I-3

To a solution of I-2, benzoic acid (0.67 g, 5.5 mmol), EDCI (1.44 g, 7.5 mmol) and HOBt (1.15 g, 7.5 mmole) in 20 ml DMF. The reaction was stirred at room temperature for overnight then concentrated in vacuo. Water was added to the residue and the aqueous layer was extracted with ethyl acetate. It was further concentrated in vacuo to give white solid product I-3 (1.04 g. 64%).

Step IV: Annulations

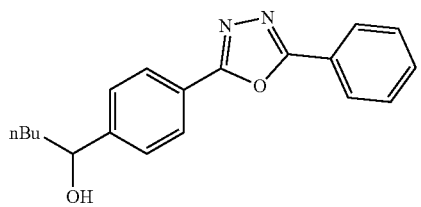

I-4

Compounds I-3 (1.04 g, 3.2 mmol), TsCl (0.91 g, 4.8 mmol), and TEA (1.5 mL, 9.6 mmol) were mixed in ACN (20 mL) was stirred at room temperature for 1 hr. To this reaction solution, concentrated to remove methanol and extracted with EtOAc. The organic layer was washed with water and dried over anhydrous magnesium sulfate. It was filtered, the solvent evaporated under reduced pressure. Purification of the crude oil residue by column chromatography (EA:Hex=30:100) afforded white solid product I-4 (0.80 g, 81%).

Step V: Oxidation

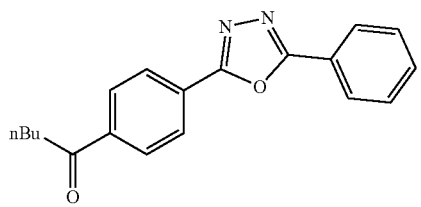

I-5

The crude product was dissolved in DCM (20 mL) and pyridinium chlorochromate (0.30 g, 1.4 mmol) was added. The reaction was stirred at room temperature for 2 h. The solution was filtered by celite and concentrated in vacuo. The residue was purified by flash column chromatography on silica gel (EA:Heaxane=10:100). The product as a white solid compound I-5 (0.30 g, 100%).

Step VI: Reductive Amination

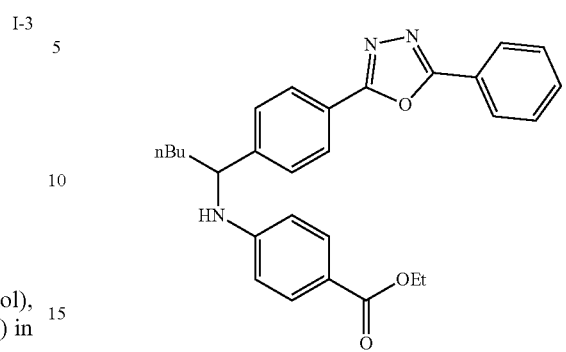

I-6

To a solution of I-5 (0.17 g, 0.58 mmol) in methanol (5 mL) is added ethyl 4-aminobenzoate (0.09 g, 0.53 mmol), and decaborane (0.04 g, 0.32 mmol) stirred for overnight.

The reaction is monitored by TLC. Once the starting material is consumed, then extracted with EtOAc and $H_2O$, dried with $Na_2SO_4$ and concentrated under reduced pressure. The resulting residue is purified by silica gel chromatography, eluting with EA:Heaxane=20:100 to afford 0.36 g of the white solid I-6.

Step VII: Hydrolysis

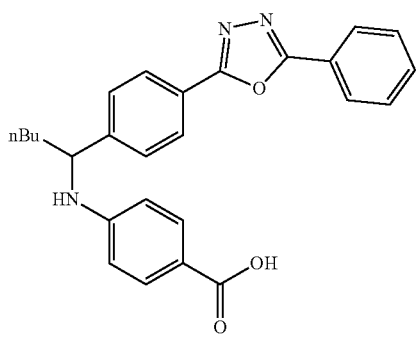

I-7

Compound I-6 (0.45 g, 1.0 mmol) was dissolved indioxane (20 mL) followed by addition of 2M/LiOH(aq) 20 mL. The reaction mixture was heat to 60° C. for 1 hr. The reaction was monitored by TLC. With completion of the reaction, the solvent was removed by rotary evaporation and was added $HCl_{(aq)}$ to pH4~5. The mixture cpd. was extracted with EtOAc. The combined organic layer was dried with anhydrous $MgSO_4$ and concentrated in vacuo to give white solid crude I-7 (0.42 g, 100%).

Step VIII: Amidation

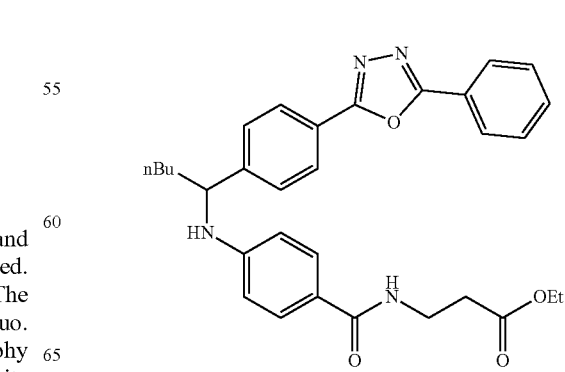

I-8

To a solution of compound I-7 (426 mg, 1 mmole), β-alanine ethyl esterhydrochloride (230 mg, 1.5 mmol), EDCI (288 mg, 1.5 mmol), Et₃N (304 mg, 3 mmol) and HOBt (229 mg, 1.5 mmol) in dry THF (20 ml). The reaction was stirred at room temperature for overnight then concentrated in vacuo. Water was added to the residue and the aqueous layer was extracted with ethyl acetate. It was further concentrated in vacuo to give a residue. Purification, of the crude oil residue by column chromatography (EA:Hex=60:100) afforded colorless oil product I-8.

Step IX: Hydrolysis

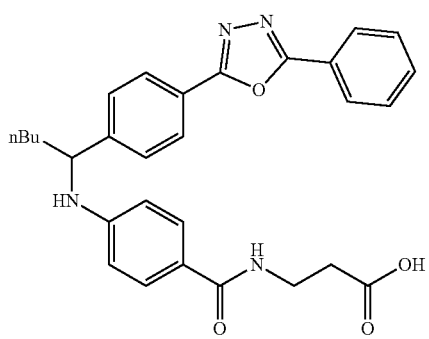

I-9

Compound I-8 (0.52 g, 1 mmol) was dissolved in THF (20 mL) followed by addition of 20 ml of 2M LiOH(aq). The reaction mixture stirred at room temperature for 2 h. The reaction was monitored by TLC. With completion of the reaction, the solvent was removed by rotary evaporation and was added HCl$_{(aq)}$ to pH4~5. The mixture cpd. was extracted with EtOAc. The combined organic layer was dried with anhydrous MgSO₄ and concentrated in vacuo to give brown oil product I-9 (0.21 g, 43%, two steps yield).

Compound 1-1

3-(4-((2-Methyl-1-(4-(5-phenyl-1,3,4-oxadiazol-2-yl)phenyl)propyl)amino)benzamido)propanoic acid

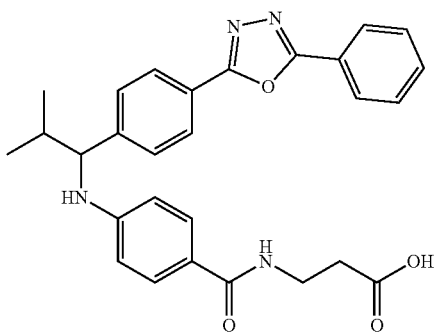 [SMILES: CC(C)C(Nc1ccc(C(=O)NCCC(=O)O)cc1)c1ccc(-c2nnc(-c3ccccc3)o2)cc1]

¹H NMR (400 MHz, DMSO-d₆): δ12.11 (br. s., 1H), 8.04-8.13 (m, 4H), 7.98 (t, J=5.6 Hz, 1H), 7.58-7.67 (m, 5H), 7.50 (d, J=8.4 Hz, 2H), 6.68 (d, J=8.0 Hz, 1H), 6.58 (d, J=8.8 Hz, 2H), 4.28 (t, J=7.6 Hz, 1H), 3.35-3.46 (m, 2H), 2.43 (t, J=7.2 Hz, 2H), 2.05 (m, 1H), 1.04 (d, J=6.0 Hz, 3H), 0.83 (d, J=6.0 Hz, 3H). MS(M+1): 485.

Compound 1-2

Methyl 3-(4-((2-methyl-1-(4-(5-phenyl-1,3,4-oxadiazol-2-yl)phenyl)propyl)amino)benzamido)propanoate

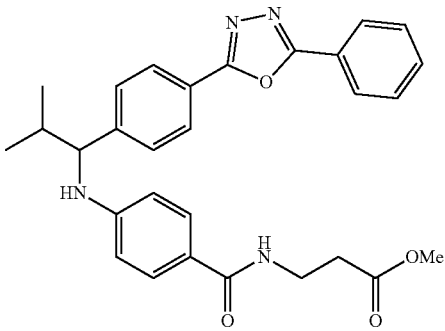 [SMILES: COC(=O)CCNC(=O)c1ccc(NC(c2ccc(-c3nnc(-c4ccccc4)o3)cc2)C(C)C)cc1]

¹H NMR (400 MHz, CDCl₃): δ8.09-8.16 (m, 4H), 7.52-7.57 (m, 5H), 7.47 (d, J=8.4 Hz, 2H), 6.61 (t, J=6.0 Hz, 1H), 6.50 (d, J=8.0 Hz, 2H), 4.48-4.65 (m, 1H), 4.28 (br. s., 1H), 3.64-3.71 (m, 5H), 2.61 (t, J=6.0 Hz, 2H), 2.08-2.21 (m, 1H), 1.05 (d, J=6.8 Hz, 3H), 0.98 (d, J=6.8 Hz, 3H); MS(M+1): 499.

Compound 1-3

Ethyl 3-(4-((2-methyl-1-(4-(5-phenyl-1,3,4-oxadiazol-2-yl)phenyl)propyl)amino)benzamido)propanoate

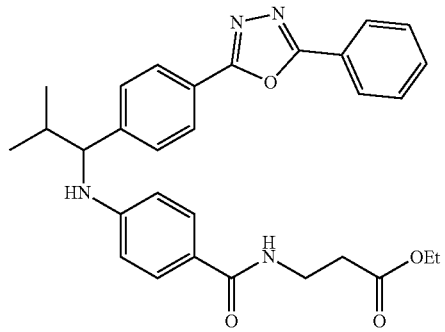 [SMILES: CCOC(=O)CCNC(=O)c1ccc(NC(c2ccc(-c3nnc(-c4ccccc4)o3)cc2)C(C)C)cc1]

¹H NMR (400 MHz, DMSO-d₆): δ8.09-8.15 (m, 2H), 8.06 (d, J=8.3 Hz, 2H), 7.99 (t, J=5.6 Hz, 1H), 7.56-7.68 (m, 5H), 7.49 (d, J=8.8 Hz, 2H), 6.69 (d, J=7.8 Hz, 1H), 6.57 (d, J=8.8 Hz, 2H), 4.29 (t, J=7.6 Hz, 1H), 4.02 (q, J=7.3 Hz, 2H), 3.34-3.42 (m, 2H), 2.45-2.49 (m, 2H), 2.05 (d, J=6.8 Hz, 1H), 1.09-1.19 (m, 3H), 1.04 (d, J=6.4 Hz, 3H), 0.82 (d, J=6.8 Hz, 3H). MS(M+1): 513. HPLC: 99.6%

Compound 1-4

3-(4-((2-Methyl-1-(4-(5-(trifluoromethyl)-1,3,4-oxadiazol-2-yl)phenyl)propyl)amino)benzamido)propanoic acid

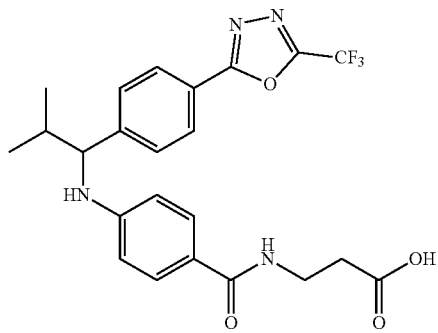 [SMILES: CC(C)C(Nc1ccc(C(=O)NCCC(=O)O)cc1)c1ccc(-c2nnc(C(F)(F)F)o2)cc1]

$^1$H NMR (400 MHZ, DMSO-d$_6$): δ7.95-8.04 (m, 3H), 7.62 (d, J=8.0 Hz, 2H), 7.49 (d, J=8.0 Hz, 2H), 6.63-6.77 (m, 1H), 6.56 (d, J=8.0 Hz, 2H), 4.30 (br. s., 1H), 3.30 (br. s., 2H), 2.42 (t, J=7.2 Hz, 2H), 2.04 (m, 1H), 1.03 (d, J=6.4 Hz, 3H), 0.81 (d, J=6.4 Hz, 3H). MS(M+1): 477.

Compound 1-5

3-(4-((3-Methyl-1-(4-(5-phenyl-1,3,4-oxadiazol-2-yl)phenyl)butyl)amino)benzamido)propanoic acid

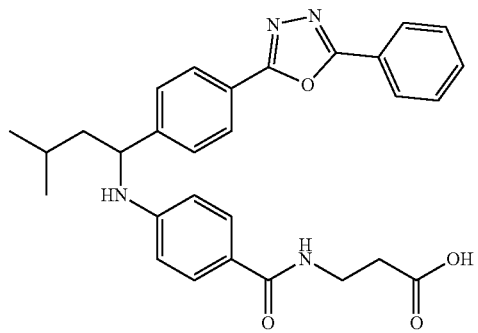 [SMILES: CC(C)CC(Nc1ccc(C(=O)NCCC(=O)O)cc1)c1ccc(-c2nnc(-c3ccccc3)o2)cc1]

$^1$H NMR (400 MHz, DMSO-d$_6$): δ7.95-8.16 (m, 5H), 7.56-7.70 (m, 5H), 7.50 (d, J=8.4 Hz, 2H), 6.75 (d, J=8.0 Hz, 1H), 6.56 (d, J=8.8 Hz, 2H), 4.47-4.64 (m, 1H), 3.50 (t, J=6.6 Hz, 2H), 2.39 (t, J=6.6 Hz, 2H), 1.63-1.88 (m, 2H), 1.36-1.59 (m, 1H), 0.97 (d, J=6.4 Hz, 3H), 0.91 (d, J=6.4 Hz, 3H). MS(M+1): 499.

Compound 1-6

Ethyl 3-(4-((1-(4-(5-phenyl-1,3,4-oxadiazol-2-yl)phenyl)butyl)amino)benzamido)propanoate

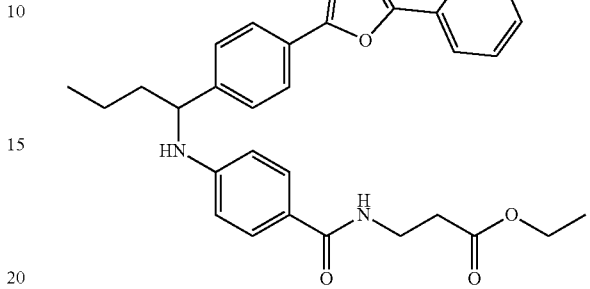

$^1$H NMR (400 MHz, DMSO-d$_6$): δ8.11 (d, J=7.8 Hz, 2H), 8.06 (d, J=8.3 Hz, 2H), 7.95-8.03 (m, 1H), 7.62 (m, 5H), 7.49 (d, J=8.8 Hz, 2H), 6.77 (d, J=8.8 Hz, 1H), 6.54 (d, J=8.8 Hz, 2H), 4.47-4.59 (m, 1H), 4.02 (q, J=7.3 Hz, 2H), 3.35-3.41 (m, 2H), 1.64-1.87 (m, 2H), 1.28-1.50 (m, 2H), 1.14 (t, J=7.1 Hz, 3H), 0.91 (t, J=7.3 Hz, 3H). MS(M+1): 513.

Compound 1-7

3-(4-((5-Phenyl-1,3,4-oxadiazol-2-yl)phenyl)butyl)amino)benzamido)propanoic acid

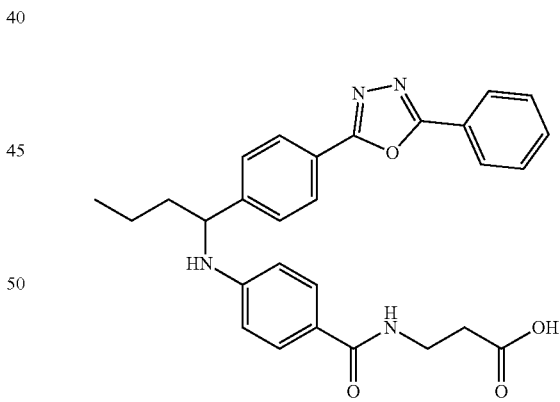

$^1$H NMR (400 MHz, DMSO-d$_6$): δ8.11 (dd, J=7.6, 2.2 Hz, 2H), 8.06 (d, J=8.3 Hz, 2H), 7.99 (t, J=5.4 Hz, 1H), 7.58-7.69 (m, 5H), 7.50 (d, J=8.8 Hz, 2H), 6.77 (d, J=7.3 Hz, 1H), 6.54 (d, J=8.8 Hz, 2H), 4.53 (d, J=6.4 Hz, 1H), 2.41 (t, J=7.1 Hz, 2H), 1.63-1.88 (m, 2H), 1.28-1.50 (m, 2H), 0.91 (t, J=7.3 Hz, 3H).

Compound 1-8

3-(4-((1-(4-(5-(Trifluoromethyl)-1,3,4-oxadiazol-2-yl)phenyl)butyl)amino)benzamido)propanoic acid

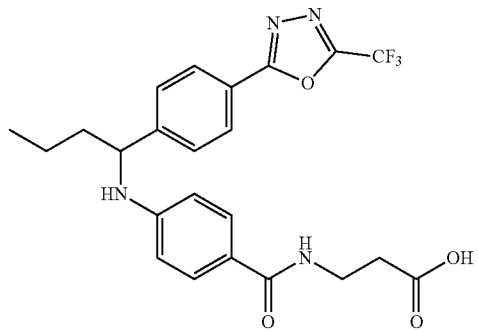 [SMILES: CCCC(Nc1ccc(C(=O)NCCC(=O)O)cc1)c1ccc(-c2nnc(C(F)(F)F)o2)cc1]

¹H NMR (400 MHz, DMSO-d₆): δ7.96-8.04 (m, 3H), 7.63 (d, J=8.4 Hz, 2H), 7.50 (d, J=8.8 Hz, 2H), 6.77 (d, J=8.0 Hz, 1H), 6.52 (d, J=8.4 Hz, 2H), 4.50-4.58 (m, 1H), 3.21-3.46 (m, 2H) 2.43 (t, J=6.0 Hz, 2H), 1.75-1.88 (m, 1H), 1.61-1.74 (m, 1H), 1.22-1.54 (m, 2H), 0.83-1.01 (m, 3H). MS(M+1): 477.

Compound 1-9

3-(4-((3-Methyl-1-(4-(5-(trifluoromethyl)-1,3,4-oxadiazol-2-yl)phenyl)butyl)amino)benzamido)propanoic acid

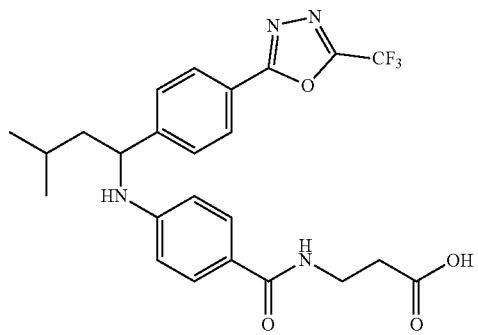 [SMILES: CC(C)CC(Nc1ccc(C(=O)NCCC(=O)O)cc1)c1ccc(-c2nnc(C(F)(F)F)o2)cc1]

¹H NMR (400 MHZ, DMSO-d₆): δ7.96-8.05 (m, 3H), 7.65 (d, J=8.8 Hz, 2H), 7.51 (d, J=8.8 Hz, 2H), 6.76 (d, J=7.2 Hz, 1H), 6.55 (d, J=8.8 Hz, 2H), 4.54-4.63 (m, 1H), 3.22-3.47 (m, 2H), 2.43 (t, J=6.0 Hz, 2H), 1.65-1.82 (m, 2H), 1.34-1.56 (m, 1H), 0.96 (d, J=6.8 Hz, 3H), 0.91 (d, J=6.4 Hz, 3H). MS(M+1): 491.

Compound 1-10

Ethyl 3-(4-((2-methyl-1-(4-(5-phenyl-1,3,4-oxadiazol-2-yl)phenyl)butyl)amino)benzamido)propanoate

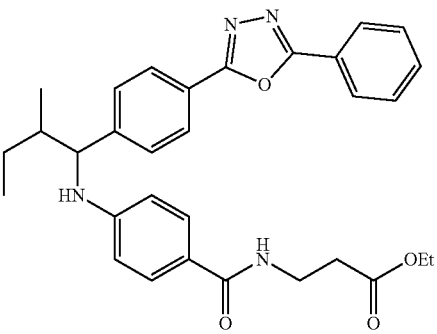 [SMILES: CCOC(=O)CCNC(=O)c1ccc(NC(c2ccc(-c3nnc(-c4ccccc4)o3)cc2)C(C)CC)cc1]

¹H NMR (400 MHz, CDCl₃): δ8.08-8.13 (m, 2H), 8.06 (d, J=8.0 Hz, 2H), 7.47-7.56 (m, 5H), 7.43 (dd, J=8.4, 1.6 Hz, 2H), 6.52-6.60 (m, 1H), 6.46 (dd, J=8.4, 1.2 Hz, 2H), 4.39-4.46 (m, 1H), 4.10 (d, J=7.2 Hz, 2H), 3.58-3.67 (m, 2H), 2.52-2.58 (m, 2H), 1.75-1.92 (m, 1H), 1.45-1.71 (m, 2H), 1.18-1.32 (m, 3H), 0.83-0.97 (m, 6H); MS(M+1): 527.

Compound 1-11

3-(4-((2-Methyl-1-(4-(5-phenyl-1,3,4-oxadiazol-2-yl)phenyl)butyl)amino)benzamido)propanoic acid ¹H NMR (400 MHz, DMSO-d₆): δ8.08-8.15 (m, 2H), 8.06 (d, J=8.4 Hz, 2H), 7.97 (s, 1H), 7.58-7.67 (dd, J=7.48-7.51 (m, 2H), 6.51-6.74 (m, 3H), 4.33-4.45 (m, 1H), 3.33 (t, J=6.8 Hz, 2H), 2.42 (t, J=6.8 Hz, 2H), 1.79-1.91 (m, 1H), 1.22-1.44 (m, 1H) 1.07-1.19 (m, 1H), 0.71-1.00 (m, 6H). MS(M+1): 499.

Compound 1-12

3-(4-((5-(4-(5-(tert-butyl)-1,3,4-oxadiazol-2-yl)phenyl)-3-methylbutyl)amino)benzamido)propanoic acid

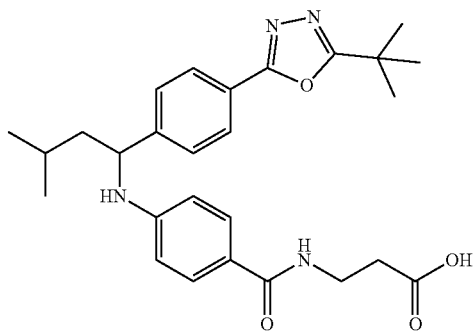 [SMILES: CC(C)CC(Nc1ccc(C(=O)NCCC(=O)O)cc1)c1ccc(-c2nnc(C(C)(C)C)o2)cc1]

$^1$H NMR (400 MHz, DMSO-d$_6$): δ7.98 (s, 1H), 7.92 (d, J=8.4 Hz, 2H), 7.58 (d, J=8.4 Hz, 2H), 7.49 (d, J=8.8 Hz, 2H), 6.73 (d, J=7.6 Hz, 1H), 6.54 (d, J=8.8 Hz, 2H), 4.51-4.57 (m, 1H), 3.32 (t, J=7.2 Hz, 2H), 2.42 (t, J=7.2 Hz, 2H), 1.62-1.81 (m, 2H), 1.44-1.57 (m, 1H), 1.40 (s, 9H), 0.88-1.00 (m, 6H). MS(M+1): 479.

Compound 1-13

2-(4-((1-(4-(5-phenyl-1,3,4-oxadiazol-2-yl)phenyl)pentyl)amino)benzamido)ethane-1-sulfonic acid

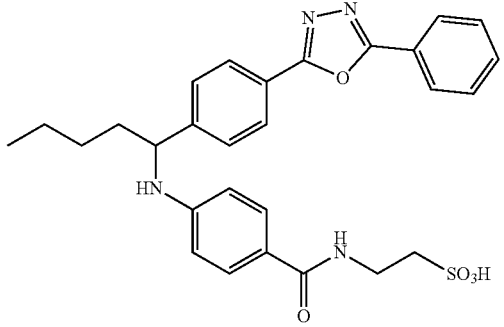 [SMILES: CCCCC(Nc1ccc(C(=O)NCCS(=O)(=O)O)cc1)c1ccc(-c2nnc(-c3ccccc3)o2)cc1]

$^1$H NMR (400 MHz, DMSO-d$_6$) δ8.02-8.13 (m, 5H), 7.59-7.66 (m, 5H), 7.44 (d, J=8.8 Hz, 2H), 6.77 (d, J=7.6 Hz, 1H), 6.55 (d, J=8.8 Hz, 2H), 4.43-4.59 (m, 1H), 3.43 (m, 2H). 2.60 (t, J=7.2 Hz, 2H), 1.78-1.92 (m, 1H), 1.59-1.76 (m, 1H), 1.22-1.46 (m, 4H), 0.86 (t, J=7.2 Hz, 3H). MS(M+1): 535.

Compound 1-14

3-(4-((1-(4-(5-(trifluoromethyl)-1,3,4-oxadiazol-2-yl)phenyl)pentyl)amino)benzamido)propanoic acid

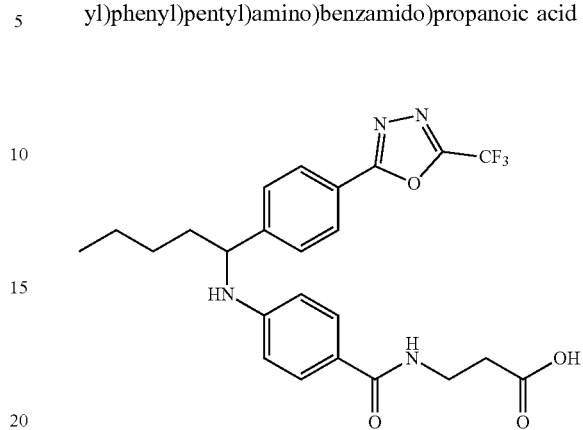

$^1$H NMR (400 MHz, DMSO-d$_6$): δ12.13 (br. s., 1H), 7.87-8.11 (m, 3H), 7.63 (d, J=8.8 Hz, 2H), 7.49 (d, J=8.8 Hz, 2H), 6.40-6.87 (m, 3H), 4.42-4.63 (m, 1H), 3.35-3.49 (m, 2H), 2.42 (t, J=7.2 Hz, 2H), 1.61-1.94 (m, 2H), 1.16-1.54 (m, 4H), 0.74-0.98 (m, 3H). MS(M+1): 491.

Compound 1-15

Ethyl 3-(4-((1-(4-(5-(pyridin-2-yl)-1,3,4-oxadiazol-2-yl)phenyl-pentyl-amino)benzamido)propanoate

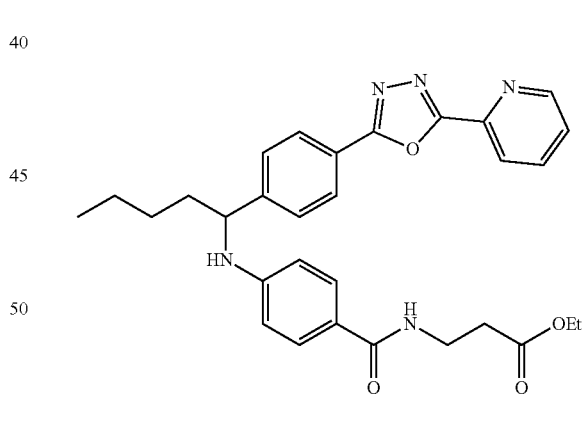

$^1$H NMR (400 MHz, Acetone-d$_6$): δ8.77-8.83 (m, 1H), 8.27-8.31 (m, 1H), 8.03-8.13 (m, 3H), 7.69 (d, J=8.4 Hz, 2H), 7.55-7.63 (m, 3H), 7.34 (t, J=5.6 Hz, 1H), 6.63 (d, J=8.4 Hz, 2H), 6.08 (d, J=7.2 Hz, 1H), 4.61 (m, 1H), 4.06 (d, 6.0 Hz, 2H), 3.51-3.63 (m, 2H), 2.55 (t, J=6.8 Hz, 2H), 1.80-1.99 (m, 2H), 1.30-1.62 (m, 4H), 1.14-1.24 (m, 3H), 0.89 (t J=7.2 Hz, 3H). MS(M+1): 528. Purity: 98.3%

Compound 1-16

3-(4-((1-(4-(5-(Pyridin-2-yl)-1,3,4-oxadiazol-2-yl)phenyl)pentyl)amino)benzamido)propanoic acid

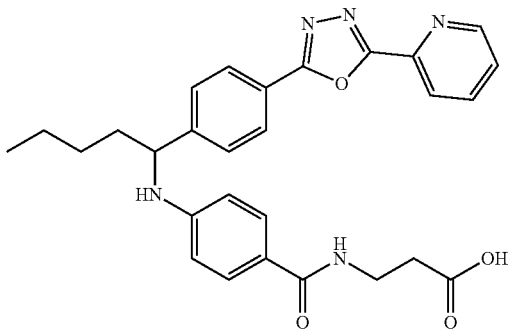 [SMILES: CCCCC(Nc1ccc(C(=O)NCCC(=O)O)cc1)c1ccc(-c2nnc(-c3ccccn3)o2)cc1]

$^1$H NMR (400 MHz, DMSO-d$_6$): δ8.79-8.82 (m, 1H), 8.25 (d, 8.0 Hz, 1H), 7.96-8.09 (m, 4H), 7.60-7.68 (m, 3H), 7.50 (d, J=8.8 Hz, 2H), 6.77 (d, J=7.2 Hz, 1H), 6.54 (d, J=8.8 Hz, 2H), 4.51 (m, 1H), 3.23-3.43 (m, 2H), 2.42 (t, J=7.2 Hz, 2H), 1.79-1.91 (m, 1H), 1.61-1.78 (m, 1H), 1.22-1.47 (m, 4H), 0.82-0.91 (m, 3H). MS(M+1): 500.

Compound 1-17

Ethyl 3-(4-((1-(4-(1-(4-(5-(4-fluorophenyl)-1,3,4-oxadiazol-2-yl)phenyl)-2-methylpropyl)amino)benzamido)propanoate

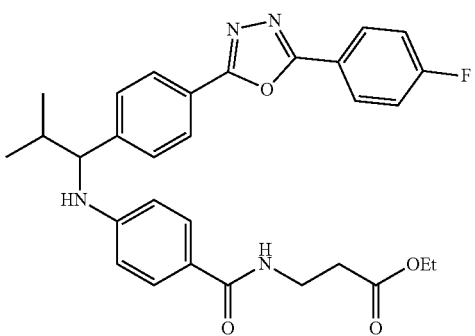 [SMILES: CC(C)C(Nc1ccc(C(=O)NCCC(=O)O)cc1)c1ccc(-c2nnc(-c3ccc(F)cc3)o2)cc1]

$^1$H NMR. (400 MHz, DMSO-d$_6$): δ8.13-8.23 (m, 2H), 8.05 (m, 2H), 7.96-8.02 (m, 1H), 7.56-7.64 (m, 2H), 7.48 (d, J=4.4 Hz, 4H), 6.64-6.73 (m, 1H), 6.51-6.62 (m, 2H), 4.23-4.35 (m, 1H), 4.02 (d, J=6.8 Hz, 2H), 3.35-3.42 (m, 2H), 2.48 (m, 2H), 1.99-2.11 (m, 1H), 1.14 (t, J=7.1 Hz, 3H), 1.04 (d, J=6.8 Hz 3H), 0.82 (d, J=6.8 Hz, 3H). MS(M+1): 531.

Compound 1-18

3-(4-((1-(4-(5-(4-Fluorophenyl)-1,3,4-oxadiazol-2-yl)phenyl)-2-methylpropyl)amino)benzamido)propanoic acid

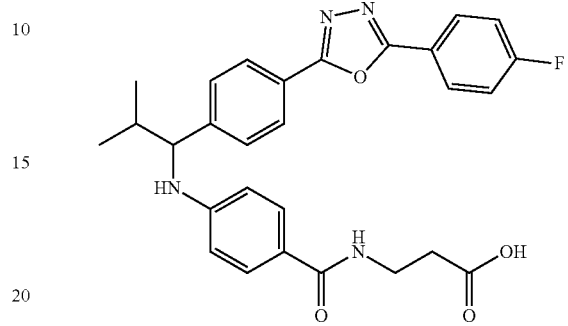

$^1$H NMR (400 MHz, DMSO-d$_6$): δ8.13-8.23 (m, 2H), 8.06 (m, 3H), 7.60 (d, J=8.3 Hz, 2H), 7.48 (t, J=4.4 Hz, 4H), 6.62-6.73 (m, 1H), 6.57 (d, J=8.8 Hz, 2H), 4.22-4.34 (m, 1H), 2.34-2.43 (m, 2H), 1.99-2.11 (m, 1H), 1.04 (d, J=6.4 Hz, 3H), 0.82 (d, J=6.8 Hz, 3H). MS(M+1): 503. HPLC: 100.0%

Compound 1-19

Ethyl 3-(4-((1-(4-(5-(tert-butyl)-1,3,4-oxadiazol-2-yl)phenyl)pentyl)amino)benzamido)propanoate

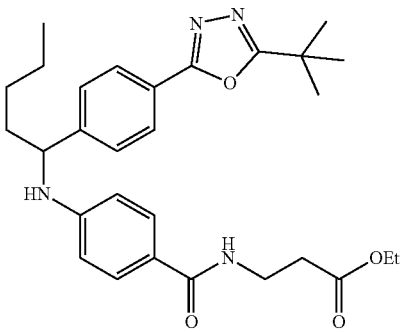 [SMILES: CCCCC(Nc1ccc(C(=O)NCCC(=O)OCC)cc1)c1ccc(-c2nnc(C(C)(C)C)o2)cc1]

$^1$H NMR (400 MHz, DMSO-d$_6$): δ8.00 (s, 1H), 7.92 (d, J=8.4 Hz, 2H), 7.56 (d, J=8.4 Hz, 2H), 7.48 (d, J=8.8 Hz, 2H), 6.75 (d, J=7.2 Hz, 1H), 6.51 (d, J=8.8 Hz, 2H), 4.39-4.56 (m, 1H), 4.03 (q, J=6.8 Hz, 2H), 3.39 (m, 2H), 2.44-2.49 (m, 2H), 1.62-1.89 (m, 2H), 1.22-1.45 (s, 10H), 1.14 (t, J=7.2 Hz, 3H), 0.85 (t, J=7.2 Hz, 3H). MS(M+1): 507.

Compound 1-20

3-(4-((1-(4-(5-(tert-butyl)-1,3,4-oxadiazol-2-yl)phenyl)pentyl)amino)benzamido)propanoic acid

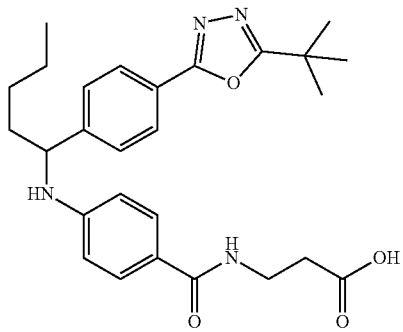 [SMILES: CCCCC(Nc1ccc(C(=O)NCCC(=O)O)cc1)c1ccc(-c2nnc(C(C)(C)C)o2)cc1]

¹H NMR (400 MHz, DMSO-d₆): δ7.98 (s, 1H), 7.92 (d, J=8.4 Hz, 2H), 7.57 (d, J=8.4 Hz, 2H), 7.49 (d, J=8.8 Hz, 2H), 6.74 (d, J=7.8 Hz, 1H), 6.51 (d, J=8.4 Hz, 2H), 4.40-4.55 (m, 1H), 3.36-3.24 (m, 2H), 2.42 (t, J=7.2 Hz, 2H), 1.75-1.89 (m, 1H), 1.60-1.75 (m, 1H), 1.40 (m, 10H), 1.21-1.35 (m, 4H), 0.85 (t, J=7.2 Hz, 3H). MS(M+1): 479.

Compound 1-21

Ethyl 3-(4-((1-(4-(5-(tert-butyl)-1,3,4-oxadiazol-2-yl)phenyl)-2-methylbutyl)amino)benzamido)propanoate

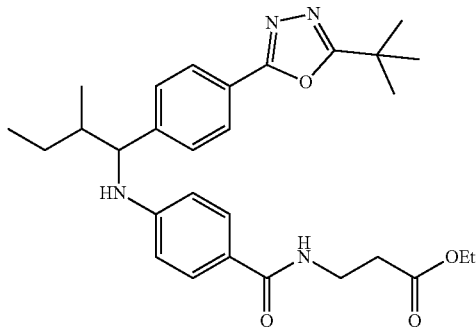 [SMILES: CCOC(=O)CCNC(=O)c1ccc(NC(c2ccc(-c3nnc(C(C)(C)C)o3)cc2)C(C)CC)cc1]

¹H NMR (400 MHz, DMSO-d₆): δ7.95-8.03 (m, 1H), 7.92 (dd, J=8.4, 1.6 Hz, 2H), 7.55 (dd, J=8.4, 6.0 Hz, 2H), 7.47 (dd, J=8.8, 3.2 Hz, 2H), 6.45-6.69 (m, 3H), 4.26-4.46 (m, 1H), 4.03 (q, J=7.2 Hz, 2H), 3.38 (m, 2H), 2.45-2.52 (m, 2H), 1.73-1.91 (m, 1H), 1.40 (s, 9H), 1.14 (t, J=7.1 Hz, 5H), 0.67-1.02 (m, 6H). MS(M+1): 507.

Compound 1-22

3-(4-((1-(4-(5-(tert-butyl)-1,3,4-oxadiazol-2-yl)phenyl)-2-methylbutyl)amino)benzamido)propanoic acid

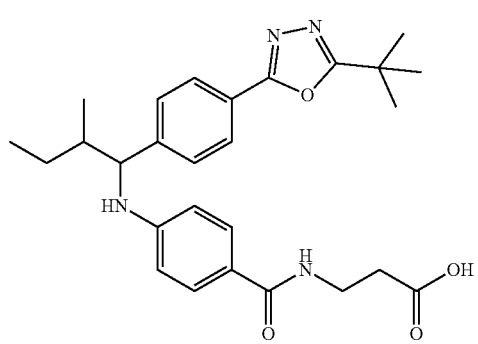 [SMILES: CCC(C)C(Nc1ccc(C(=O)NCCC(=O)O)cc1)c1ccc(-c2nnc(C(C)(C)C)o2)cc1]

¹H NMR (400 MHz, DMSO-d₆): δ7.97 (br. s., 1H), 7.88-7.94 (m, 2H), 7.55 (dd, J=8.0, 5.6 Hz, 2H), 7.48 (dd, J=8.8, 3.2 Hz, 2H), 6.50-6.70 (m, 3H), 4.25-4.45 (m, 1H), 3.22-3.42 (m, 2H), 2.42 (t, J=7.2 Hz, 2H), 1.71-1.92 (m, 1H), 1.40 (s, 9H), 1.17 (m, 2H), 0.65-1.01 (m, 6H). MS(M+1): 479.

Compound 1-23 ethyl 3-(4-((1-(4-(5-(tert-butyl)-1,3,4-oxadiazol-2-yl)phenyl)-2-methylpropyl))amino)benzamido)propanoate

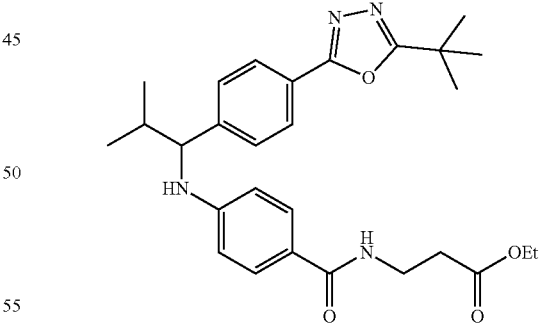

¹H NMR (400 MHz, DMSO-d₆): δ7.99 (t, 1H), 7.92 (d, J=8.3 Hz, 2H), 7.55 (d, J=8.3 Hz, 2H), 7.47 (d, J=8.8 Hz, 2H), 6.66 (d, 1H), 6.55 (d, J=8.8 Hz, 2H), 4.25 (t, 1H), 4.03 (d, J=6.8 Hz, 2H), 3.38 (d, J=5.9 Hz, 2H), 1.96-2.09 (m, 1H), 1.40 (s, 9H), 1.14 (t, J=7.1 Hz, 3H), 1.03 (d, J=6.4 Hz, 3H), 0.80 (d, J=6.8 Hz, 3H). MS(M+1): 493.

Compound 1-24

3-(4-((1-(4-(5-(tert-butyl)-1,3,4-oxadiazol-2-yl)phenyl)-2-methylpropyl)amino)benzamido)propanoic acid

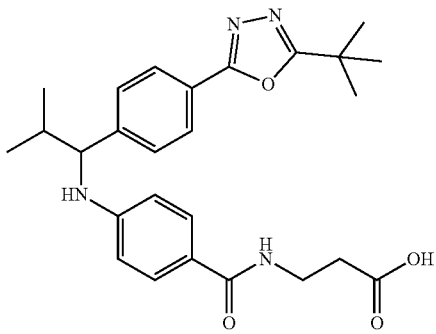 [SMILES: CC(C)C(Nc1ccc(C(=O)NCCC(=O)O)cc1)c1ccc(-c2nnc(C(C)(C)C)o2)cc1]

¹H NMR (400 MHz, DMSO-d₆): δ7.96 (s, 1H), 7.92 (d, J=8.3 Hz, 2H), 7.55 (d, J=8.3 Hz, 2H), 7.48 (d, J=8.8 Hz, 2H), 6.66 (d, J=7.8 Hz, 1H), 6.55 (d, J=8.8 Hz, 2H), 4.25 (s, 1H), 2.42 (t, J=7.1 Hz, 2H), 1.40 (s, 8H), 1.03 (d, J=6.4 Hz, 3H), 0.80 (d, J=6.4 Hz, 3H). MS(M+1): 465.

Compound 1-25 ethyl 3-(4-((1-(4-(5-(4-methoxyphenyl)-1,3,4-oxadiazol-2-yl)phenyl)-2-methylpropyl)amino)benzamido)propanoate

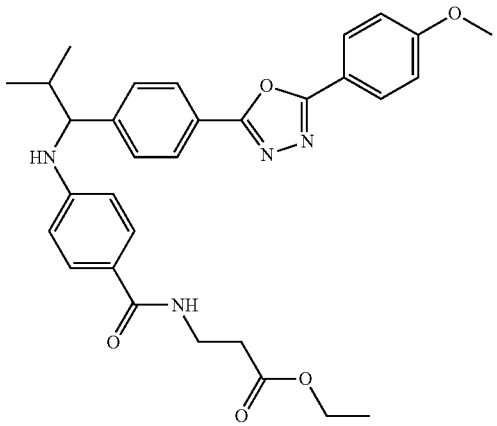 [SMILES: CCOC(=O)CCNC(=O)c1ccc(NC(c2ccc(-c3nnc(-c4ccc(OC)cc4)o3)cc2)C(C)C)cc1]

¹H NMR (400 MHz, DMSO-d₆): δ8.04 (dd, J=8.6, 4.2 Hz, 7H), 7.59 (d, J=8.3 Hz, 3H), 7.48 (d, J=8.8 Hz, 3H), 7.17 (d, J=8.8 Hz, 3H), 6.64-6.74 (m, 1H), 6.57 (d, J=8.8 Hz, 3H), 4.21-4.35 (m, 1H), 4.02 (d, J=7.3 Hz, 3H), 3.86 (s, 4H), 3.34-3.42 (m, 3H), 2.48 (s, 3H), 1.98-2.12 (m, 1H), 1.14 (t, J=7.3 Hz, 4H), 1.04 (d, J=6.8 Hz, 5H), 0.82 (d, J=6.4 Hz, 4H). MS(M+1): 543.

Compound 1-26

3-(4-((1-(4-(5-(4-methoxyphenyl)-1,3,4-oxadiazol-2-yl)phenyl)-2-methylpropyl)amino)benzamido)propanoic acid

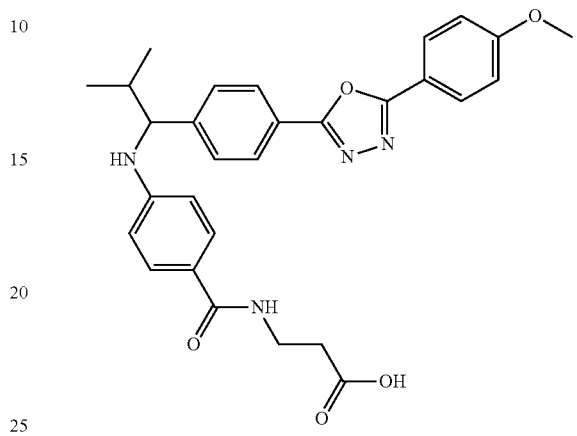

¹H NMR (400 MHz, DMSO-d₆): δ8.01-8.08 (m, 7H), 7.97 (t, J=5.6 Hz, 2H), 7.59 (d, J=8.3 Hz, 3H), 7.49 (d, J=8.8 Hz, 3H), 7.12-7.22 (m, 3H), 6.68 (4 J=7.8 Hz, 1H), 6.57 (d, J=8.8 Hz, 3H), 4.28 (t J=7.6 Hz 1H), 3.86 (s, 3H), 2.42 (t, J=7.1 Hz, 2H), 2.05 (d, J=6.8 Hz, 1H), 1.04 (d, J=6.8 Hz, 3H), 0.82 (d, J=6.8 Hz, 3H). MS(M+1): 515.

Compound 1-27 ethyl 3-(4-((1-(4-(5-(4-fluorophenyl)-1,3,4-oxadiazol-2-yl)phenyl)-3-methylbutyl)amino)benzamido)propanoate

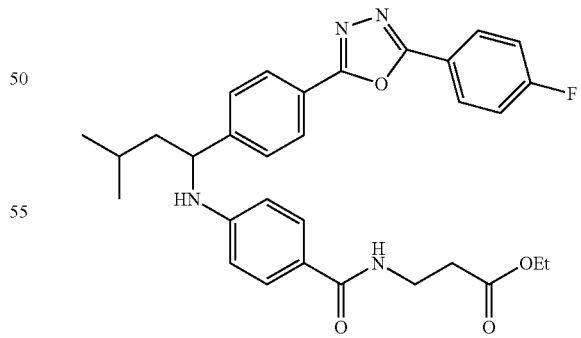

¹H NMR (400 MHz, DMSO-d₆): δ8.11-8.24 (m, 2H), 7.95-8.06 (m, 3H), 7.58-7.68 (m, 2H), 7.49 (d, J=9.2 Hz, 4H), 6.70-6.83 (m, 1H), 6.48-6.61 (m, 2H), 4.48-4.66 (m, 1H), 4.02 (q, J=7.2 Hz, 2H), 3.35-3.38 (m, 2H), 2.46-2.51 (m, 2H), 1.59-1.86 (m, 2H), 1.39-1.59 (m, 1H), 1.11-1.29 (m, 3H), 0.83-0.99 (m, 6H). MS(M+1): 545.

Compound 1-28

3-(4-((1-(4-(5-(4-fluorophenyl)-1,3,4-oxadiazol-2-yl)phenyl)-3-methylbutyl)amino)benzamido)propanoic acid

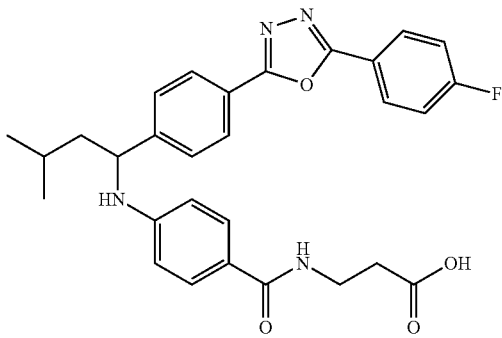 [SMILES: CC(C)CC(Nc1ccc(C(=O)NCCC(=O)O)cc1)c1ccc(-c2nnc(-c3ccc(F)cc3)o2)cc1]

$^1$H NMR (400 MHz, DMSO-d$_6$): δ12.14 (br, s., 1H), 8.17 (br, s., 2H), 8.05 (d, J=7.2 Hz, 2H), 7.99 (br. s., 1H), 7.63 (d, J=7.2 Hz, 2H), 7.39-7.56 (m, 4H), 6.76 (d, J=6.8 Hz, 1H), 6.56 (d, J=7.8 Hz, 2H), 4.48-4.68 (m, 1H), 3.33 (br. s., 2H), 2.42 (br. s., 2H), 1.62-4.84 (m, 2H), 1.42-1.61 (m, 1H), 0.84-1.06 (m, 6H). MS(M+1): 517.

Compound 1-29 ethyl 3-(4-((1-(4-(5-(4-fluorophenyl)-1,3,4-oxadiazol-2-yl)phenyl)-2-methylbutyl)amino)benzamido)propanoate

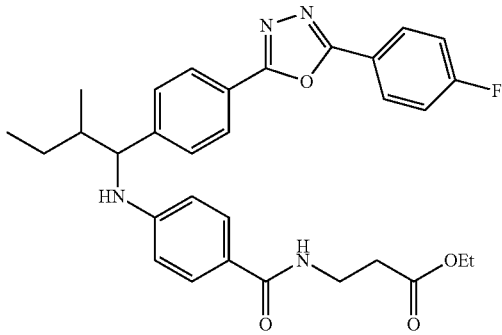 [SMILES: CCOC(=O)CCNC(=O)c1ccc(NC(c2ccc(-c3nnc(-c4ccc(F)cc4)o3)cc2)C(C)CC)cc1]

$^1$H NMR (400 MHz, DMSO-d$_6$): δ8.14-8.20 (m, 2H), 7.97-8.07 (m, 3H), 7.60 (dd, J=8.4, 6.0 Hz, 2H), 7.44-7.51 (m, 4H), 6.55-6.71 (m, 3H), 4.29-4.49 (m, 1H), 3.99-4.05 (m, 2H), 3.38 (m, 2H), 2.46-2.51 (m, 2H), 1.59-1.95 (m, 2H), 1.20-1.32 (m, 1H), 1.08-1.19 (m, 3H), 0.75-1.00 (m, 6H). MS(M+1): 545.

Compound 1-30

3-(4-((1-(4-(5-(4-fluorophenyl)-1,3,4-oxadiazol-2-yl)phenyl)-2-methylbutyl)amino)benzamido)propanoic acid

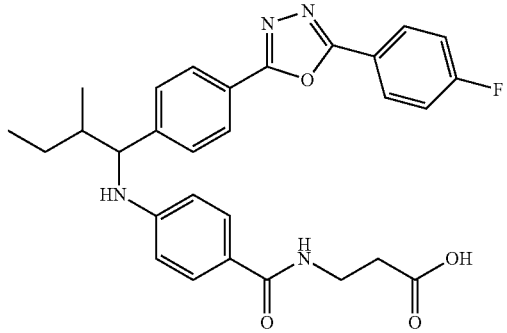 [SMILES: CCC(C)C(Nc1ccc(C(=O)NCCC(=O)O)cc1)c1ccc(-c2nnc(-c3ccc(F)cc3)o2)cc1]

$^1$H NMR (400 MHz, DMSO-d$_6$): δ12.13 (br. s., 1H), 8.14-8.20 (m, 2H), 7.95-8.07 (m, 3H), 7.60 (dd, J=8.4, 6.0 Hz, 2H), 7.44-7.52 (m, 4H), 6.47-6.81 (m, 3H), 4.24-4.50 (m, 1H), 3.24-3.43 (m, 2H), 2.37-2.47 (m, 2H), 1.79-1.89 (m, 1H), 1.24-1.43 (m, 1H), 1.03-1.20 (m, 1H), 0.72-1.01 (m, 6H). MS(M+1): 517.

Compound 1-31 ethyl 3-(4-((2-methyl-1-(4-(5-(trifluoromethyl)-1,3,4-oxadiazol-2-yl)phenyl)butyl)amino)benzamido)propanoate

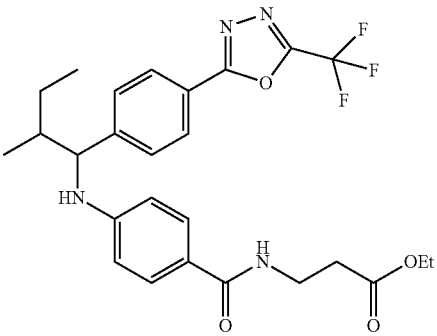 [SMILES: CCOC(=O)CCNC(=O)c1ccc(NC(c2ccc(-c3nnc(C(F)(F)F)o3)cc2)C(C)CC)cc1]

$^1$H NMR (400 MHz, CDCl$_3$): δ8.03 (d, J=8.3 Hz, 2H), 7.56-7.42 (m, 4H), 6.60 (br. s., 1H), 6.49-6.37 (m, 2H), 4.62-4.45 (m, 1H), 4.45-4.28 (m, 1H), 4.10 (q, J=7.3 Hz, 2H), 3.62 (q, J=5.5 Hz, 2H), 2.54 (t, J=5.4 Hz, 2H), 1.92-1.77 (m, 1H), 1.49 (td, J=7.0, 13.8 Hz, 1H), 1.32-1.16 (m, 4H), 0.98-0.83 (m, 6H). MS(M+1): 519.

Compound 1-32

3-(4-((2-methyl-1-(4-(5-(trifluoromethyl)-1,3,4-oxadiazol-2-yl)phenyl)butyl)amino benzamido)propanoic acid

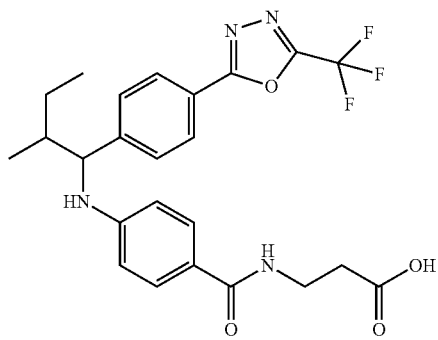 [SMILES: CCC(C)C(Nc1ccc(C(=O)NCCC(=O)O)cc1)c1ccc(-c2nnc(C(F)(F)F)o2)cc1]

$^1$H NMR (400 MHz, CDCl$_3$); δ8.04-7.97 (m, 2H), 7.51-7.40 (m, 4H), 6.82-6.75 (m, 1H), 6.45-6.36 (m, 2H), 4.42-4.24 (m, 1H), 3.65-3.50 (m, 2H), 2.62-2.50 (m, 2H), 1.90-4.77 (m, 1H), 1.62-1.40 (m, 1H), 1.29-1.12 (m, 1H), 0.96-0.80 (m, 6H). MS(M+1): 591.

Compound 1-33 ethyl 3-(4-((1-(4-(5-(trifluoromethyl)-1,3,4-oxadiazol-2-yl)phenyl)pentyl)amino)benzamido)propanoate

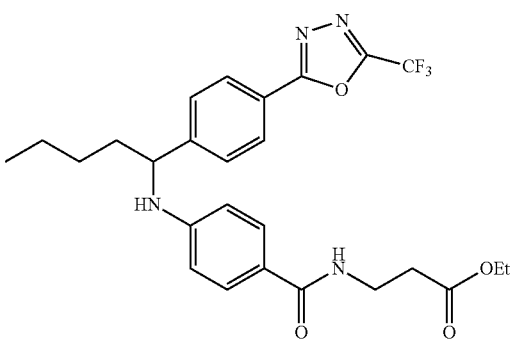 [SMILES: CCCCC(Nc1ccc(C(=O)NCCC(=O)OCC)cc1)c1ccc(-c2nnc(C(F)(F)F)o2)cc1]

$^1$H NMR (400 MHz, DMSO-d$_6$): δ7.96-8.07 (m, 3H), 7.63 (d, J=8.3 Hz, 2H), 7.49 (d, J=9.3 Hz, 2H), 6.78 (d, J=7.8 Hz, 1H), 6.52 (d, J=8.8 Hz, 2H), 4.52 (q, 1H), 4.03 (q, J=6.8 Hz, 2H), 3.39 (d, J=5.9 Hz, 2H), 1.64-1.91 (m, 2H), 1.21-1.50 (m, 4H), 1.14 (t, J=7.1 Hz, 3H), 0.86 (t, 3H). MS(M+1): 519.

Compound 1-34 ethyl 3-(4-(((1S)-2-methyl-1-(4-(5-(trifluoromethyl)-1,3,4-oxadiazol-2-yl)phenyl)butyl)amino)benzamido)propanoate

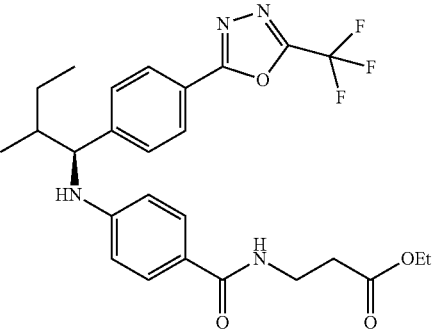 [SMILES: CCOC(=O)CCNC(=O)c1ccc(N[C@H](c2ccc(-c3nnc(C(F)(F)F)o3)cc2)C(C)CC)cc1]

$^1$H NMR (400 MHz, DMSO-d$_6$): δ7.97-8.04 (m, 3H), 7.62 (dd, J=8.4, 6.0 Hz, 2H), 7.48 (dd, J=8.8, 3.6 Hz, 2H), 6.53-6.72 (m, 3H), 4.29-4.52 (m, 1H), 4.00-4.06 (m, 1H), 4.00-4.05 (m, 2H), 3.38 (m, 2H), 2.45-2.49 (m, 2H), 1.21-1.92 (m, 3H), 1.08-1.19 (m, 3H), 0.64-1.01 (m, 6H). MS(M+1): 518.

Compound 1-35 ethyl 3-(4-(((1R)-2-methyl-1-(4-(5-(trifluoromethyl)-1,3,4-oxadiazol-2-yl)phenyl)butyl)amino)benzamido)propanoate

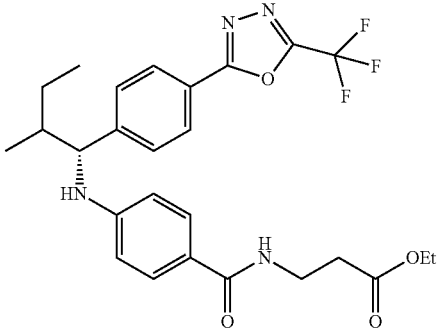 [SMILES: CCOC(=O)CCNC(=O)c1ccc(N[C@@H](c2ccc(-c3nnc(C(F)(F)F)o3)cc2)C(C)CC)cc1]

$^1$H NMR (400 MHz, DMSO-d$_6$): δ7.93-8.08 (m, 3H), 7.62 (dd, J=8.4, 6.0 Hz, 2H), 7.48 (dd, J=8.8, 3.2 Hz, 2H), 6.47-6.76 (m, 3H), 4.31-4.49 (m, 1H), 4.03 (q, J=7.2 Hz, 2H), 3.38-3.50 (m, 2H), 2.46-2.48 (m, 2H), 1.21-1.90 (m, 3H), 1.14 (t, J=6.0 Hz, 3H), 0.79-1.02 (m, 6H). MS(M+1): 518.

Compound 1-36

3-(4-(((1S)-2-methyl-1-(4-(5-(trifluoromethyl)-1,3,4-oxadiazol-2-yl)phenyl)butyl)amino)benzamido)propanoic acid

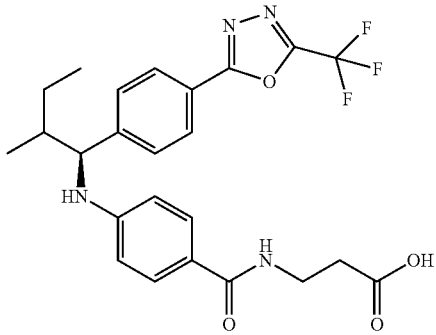 [SMILES: CCC(C)[C@H](Nc1ccc(C(=O)NCCC(=O)O)cc1)c1ccc(-c2nnc(C(F)(F)F)o2)cc1]

¹H NMR (400 MHz, DMSO-d₆): δ7.90-8.08 (m, 3H), 7.62 (dd, J=8.4, 6.4 Hz, 2H), 7.49 (dd, J=8.8, 3.2 Hz, 2H), 6.64-6.71 (m, 3H), 4.45 (t, J=7.2 Hz, 1H), 3.34-3.43 (m, 2H), 2.37-2.47 (m, 2H), 1.04-1.91 (m, 3H), 0.80-0.99 (m, 6H). MS(M+1): 491.

Compound 1-37

3-(4-(((1R)-2-methyl-1-(4-(S-(trifluoromethyl)-1,3,4-oxadiazol-2-yl)phenyl)butyl)amino)benzamido)propanoic acid

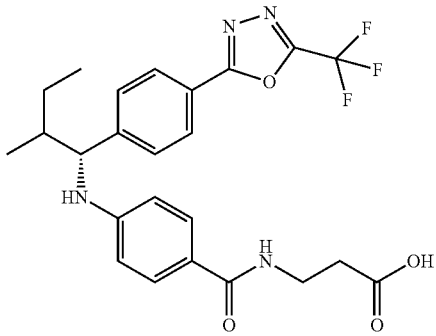 [SMILES: CCC(C)[C@@H](Nc1ccc(C(=O)NCCC(=O)O)cc1)c1ccc(-c2nnc(C(F)(F)F)o2)cc1]

¹H NMR (400 MHz, DMSO-d₆): δ7.90-8.08 (m, 3H), 7.62 (dd, J=8.0, 6.0 Hz, 2H), 7.49 (dd, J=8.8, 3.2 Hz, 2H), 6.48-6.64 (m, 3H), 4.45 (t, J=7.2 Hz, 1H), 3.36-3.41 (m, 2H), 2.36-2.47 (m, 2H), 1.11-1.93 (m, 3H), 0.62-1.04 (m, 6H). MS(M+1): 491.

Compound 1-38 methyl 3-(4-((1-(4-(5-(pyridin-2-yl)-1,3,4-oxadiazol-2-yl)phenyl)pentyl)amino)benzamido)propanoate

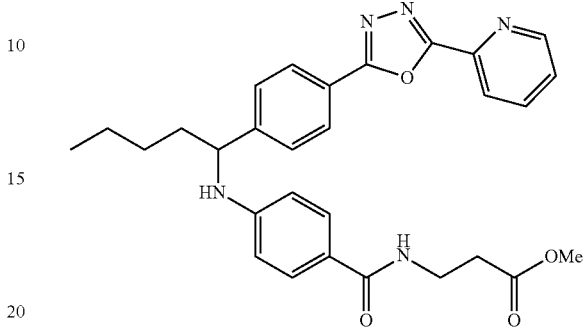

¹H NMR (400 MHz, DMSO-d₆) δ8.78-8.86 (dt, 1H), 8.23-8.28 (d, 1H), 8.06 (m, J=8.3 Hz, 4H), 7.64 (m, 3H), 7.49 (d, J=8.8 Hz, 2H), 6.77 (d, 1H), 6.54 (d, 2H), 4.53 (q, 1H), 3.38 (q, 2H), 1.66-1.90 (m, 2H), 1.37-1.50 (m, 1H), 1.32 (s, 3H), 0.87 (t, 3H). MS(M+1): 514.

Compound 1-39

(S)-ethyl 3-(4-(2-methyl-1-(4-(5-phenyl-1,3,4-oxadiazol-2-yl)phenyl)propylamino)benzamido)propanoate

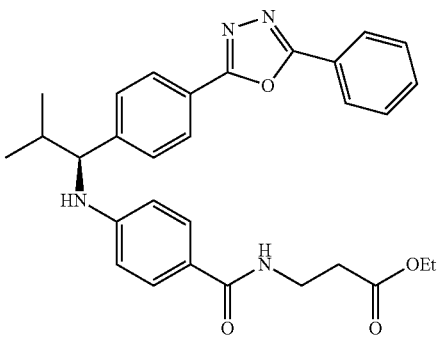 [SMILES: CCOC(=O)CCNC(=O)c1ccc(N[C@H](c2ccc(-c3nnc(-c4ccccc4)o3)cc2)C(C)C)cc1]

¹H NMR (DMSO-d₆): δ8.08-8.15 (m, 2H), 8.06 (d, J=8.8 Hz, 2H), 7.99 (t, J=5.6 Hz, 1H), 7.56-7.67 (m, 5H), 7.49 (d, J=8.8 Hz, 2H), 6.53-6.73 (m, 3H), 4.28 (t J=7.6 Hz, 1H), 4.02 (q, J=7.2 Hz, 2H), 3.38 (q, J=6.8 Hz, 2H), 2.43-2.50 (m, 2H), 2.00-2.13 (m, 1H), 1.10-1.17 (m, 3H), 1.04 (d, J=6.4 Hz, 3H), 0.82 (d, J=6.8 Hz, 3H). MS(M+1): 513.

Compound 1-40

(R)-ethyl 3-(4-(2-methyl-1-(4-(5-phenyl-1,3,4-oxadiazol-2-yl)phenyl)propylamino)benzamido)propanoate

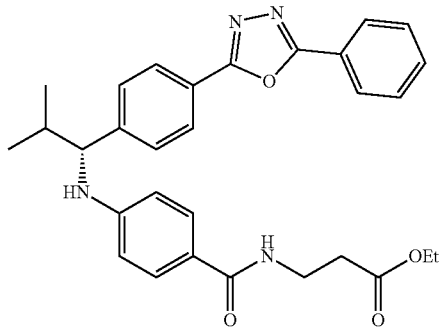 [SMILES: CCOC(=O)CCNC(=O)c1ccc(N[C@@H](c2ccc(-c3nnc(-c4ccccc4)o3)cc2)C(C)C)cc1]

¹H NMR (400 MHz, DMSO-d₆): δ8.09-8.14 (m, 2H), 8.06 (d, J=8.4 Hz, 2H), 7.96-8.03 (m, 1H), 7.56-7.66 (m, 5H), 7.49 (d, J=8.8 Hz, 2H), 6.57 (m, 3H), 4.20-4.35 (m, 1H), 4.02 (d, J=7.2 Hz, 2H), 3.34-3.47 (m, 2H), 2.40-2.53 (m, 2H), 1.97-2.12 (m, 1H), 1.14 (t, J=7.2 Hz, 3H), 1.04 (d, J=6.8 Hz, 3H), 0.82 (d, J=6.8 Hz, 3H). MS(M+1): 513.

Compound 1-41

(S)-3-(4-(2-methyl-1-(4-(5-phenyl-1,3,4-oxadiazol-2-yl)phenyl)propylamino)benzamido)propanoic acid

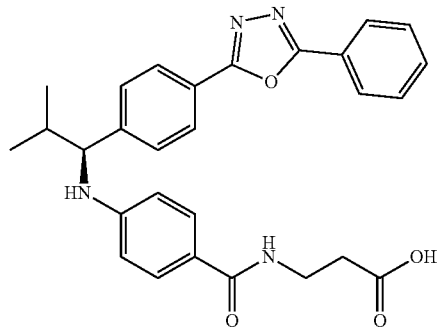

¹H NMR (400 MHz, DMSO-d₆): δ8.09-8.14 (m, 2H), 8.06 (d, J=8.4 Hz, 2H), 7.97 (t, J=5.6 Hz, 1H), 7.57-7.67 (m, 5H), 7.50 (d, J=8.8 Hz, 2H), 6.48-6.75 (m, 3H), 4.29 (t, J=7.6 Hz, 1H), 3.27-3.42 (m, 2H), 2.42 (t, J=7.2 Hz, 2H), 2.00-2.14 (m, 1H), 1.04 (d, J=6.4 Hz, 3H), 0.75-0.90 (d, J=6.4 Hz, 3H). MS(M+1): 485.

Compound 1-42

(R)-3-(4-(2-methyl-1-(4-(5-phenyl-1,3,4-oxadiazol-2-yl)phenyl)propylamino)benzamido)propanoic acid

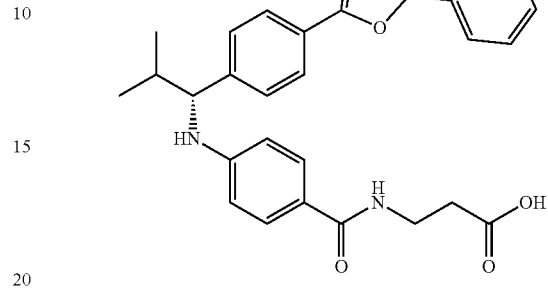

¹H NMR (400 MHz, DMSO-d₆): δ8.08-8.14 (m, 2H), 8.06 (d, J=8.4 Hz, 2H), 7.97 (t, J=5.6 Hz, 1H), 7.57-7.67 (m, 5H), 7.49 (d, J=8.8 Hz, 2H), 6.46-6.76 (m, 3H), 4.28 (t, J=7.6 Hz, 1H), 3.33-3.42 (m, 2H), 2.42 (t, J=7.2 Hz, 2H), 2.00-2.13 (m, 1H), 1.04 (d, J=6.4 Hz, 3H), 0.82 (d, J=6.8 Hz, 3H). MS(M+1): 485.

Compound 1-43 ethyl (S)-3-(4-((1-(4-(5-(pyridin-2-yl)-1,3,4-oxadiazol-2-yl)phenyl)pentyl)amino)benzamido)propanoate

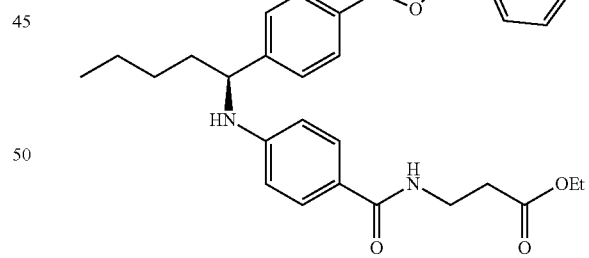

¹H NMR (400 MHz, DMSO-d₆): δ8.79-8.82 (m, 1H), 8.24-8.27 (m, 1H), 7.99-8.09 (m, 4H), 7.60-7.67 (m, 3H), 7.49 d, J=8.8 Hz, 2H), 6.78 (d, J=7.2 Hz, 1H), 6.54 (d, J=8.8 Hz, 2H), 4.44-4.59 (m, 1H), 4.02 (q, J=6.8 Hz, 2H), 3.38 (d, J=6.4 Hz, 2H), 2.45-2.49 (m, 2H), 1.62-1.92 (m, 2H), 1.23-1.46 (m, 4H), 1.14 (t, J=7.1 Hz, 3H), 0.81-0.89 (m, 3H). MS(M+1): 528.

Compound 1-44 ethyl (R)-3-(4-((1-(4-(5-(pyridin-2-yl)-1,1,3,4-oxadiazol-2-yl)phenyl)pentyl)amino)benzamido propanoate

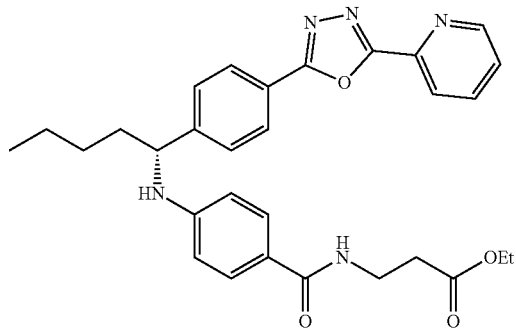

$^1$H NMR (400 MHz, DMSO-d$_6$): δ8.70-8.91 (m, 1H), 8.17-8.34 (m, 1H), 7.92-8.13 (m, 4H), 7.58-7.75 (m, 3H), 7.49 (d, J=8.8 Hz, 2H), 6.42-6.84 (m, 3H), 4.42-4.64 (m, 1H), 4.02 (q, J=6.8 Hz, 2H), 3.38 (d, J=6.4 Hz, 2H), 2.37-2.60 (m, 2H), 1.24-1.93 (m, 6H), 1.14 (t, J=7.2 Hz, 3H), 0.79-0.94 (m, 3H). MS(M+1): 528.

Compound 1-45

(S)-3-(4-((1-(4-(5-(pyridin-2-yl)-1,3,4-oxadiazol-2yl)phenyl)pentyl)amino)benzamido)propanoic acid

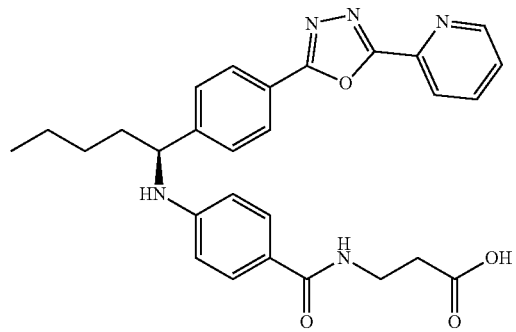 [SMILES: CCCC[C@H](Nc1ccc(C(=O)NCCC(=O)O)cc1)c1ccc(-c2nnc(-c3ccccn3)o2)cc1]

$^1$H NMR (400 MHz, DMSO-d$_6$): δ8.81 (dt, J=4.9, 1.2 Hz, 1H), 8.18-8.32 (m, 1H), 8.02-8.14 (m, 3H), 7.98 (t, J=5.6 Hz, 1H), 7.56-7.71 (m, 3H), 7.42-7.56 (m, J=8.8 Hz, 2H), 6.77 (d, J=7.3 Hz, 1H), 6.43-6.62 (m, J=8.8 Hz, 2H), 4.43-4.61 (m, 1H), 3.34-3.44 (m, 3H), 2.42 (t, J=7.3 Hz, 2H), 1.83 (td, J=8.4, 4.2 Hz, 1H), 1.62-1.77 (m, 1H), 1.39-1.51 (m, 1H), 1.19-1.39 (m, 3H), 0.78-0.96 (m, 3H).

Compound 1-46

(R)-3-(4-((1-(4-(5-(pyridin-2-yl-1,3,4-oxadiazol-2-yl)phenyl)pentyl)amino)benzamido)propanoic acid

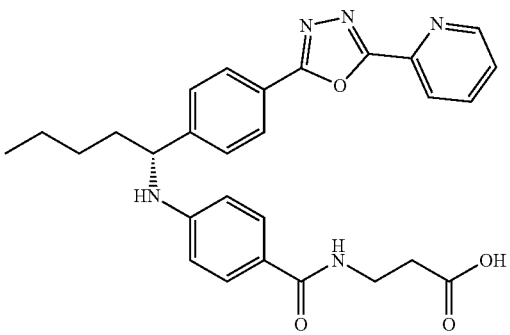 [SMILES: CCCC[C@@H](Nc1ccc(C(=O)NCCC(=O)O)cc1)c1ccc(-c2nnc(-c3ccccn3)o2)cc1]

$^1$H NMR (400 MHz, DMSO-d$_6$): δ8.70-8.82 (m, 1H), 8.19-8.32 (m, 1H), 8.02-8.13 (m, 3H), 7.98 (t, J=5.6 Hz, 1H), 7.58-7.70 (m, 3H), 7.50 (d, J=8.8 Hz, 2H), 6.44-6.87 (m, 3H), 4.42-4.60 (m, 1H), 3.32-3.46 (m, 2H), 2.42 (t, J=7.2 Hz, 2H), 1.19-1.92 (m, 6H), 0.78-0.94 (m, 3H). MS(M+1): 500.

Compound 1-47 ethyl 3-(4-(((1S)-2-methyl-1-(4-(5-phenyl-1,3,4-oxadiazol-2-yl)phenyl)butyl)amino)benzamido)propanoate

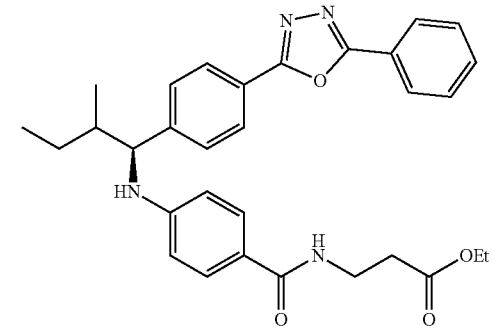 [SMILES: CCOC(=O)CCNC(=O)c1ccc(N[C@H](c2ccc(-c3nnc(-c4ccccc4)o3)cc2)C(C)CC)cc1]

$^1$H NMR (400 MHz, CDCl$_3$): δ8.14-8.08 (m, 2H), 8.06 (d, J=7.8 Hz, 2H), 7.57-7.48 (m, 5H). 7.43 (dd, J=2.0, 8.3 Hz, 2H), 6.62-6.53 (m, 1H), 6.51-6.42 (m, 2H), 4.54-4.27 (m, 2H), 4.14-4.05 (m, 2H), 3.67-3.58 (m, 2H), 2.60-2.50 (m, 2H), 1.86 (dt, J=4.2, 6.2 Hz, 1H), 1.64-1.44 (m, 3H), 1.30-1.17 (m, 4H), 0.98-0.86 (m, 6H). MS(M+1): 527.

Compound 1-48 ethyl 3-(4-(((1R)-2-methyl-1-(4-(5-phenyl-1,3,4-oxadiazol-2-yl)phenyl)butyl)amino)benzamido)propanoate

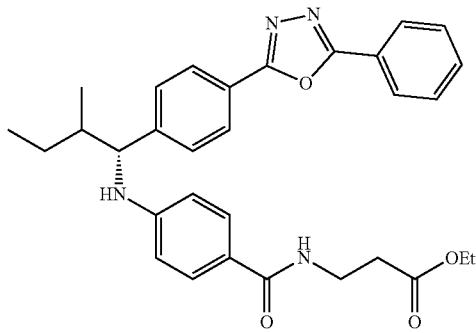 [SMILES: CCOC(=O)CCNC(=O)c1ccc(N[C@@H](c2ccc(-c3nnc(-c4ccccc4)o3)cc2)C(C)CC)cc1]

¹H NMR (400 MHz, CDCl₃): δ8.12-8.09 (m, 2H), 8.06 (d, J=8.3 Hz, 2H), 7.53-7.47 (m, 5H), 7.43 (dd, J=1.5, 8.3 Hz, 2H), 6.56 (br. s., 1H), 6.49-6.41 (m, 2H), 4.50-4.29 (m, 2H), 4.10 (q, J=7.3 Hz, 2H), 3.66-3.59 (m, 2H), 2.58-2.52 (m, 2H), 1.85 (dd, J=2.9, 6.4 Hz, 1H), 1.60-1.44 (m, 1H), 1.35-1.18 (m, 4H), 0.98-0.88 (m, 6H). MS(M+1): 527.

Compound 1-49

3-(4-(((1S)-2-methyl-1-(4-(5-phenyl-1,3,4-oxadiazol-2-yl)phenyl)butyl)amino)benzamido)propanoic acid

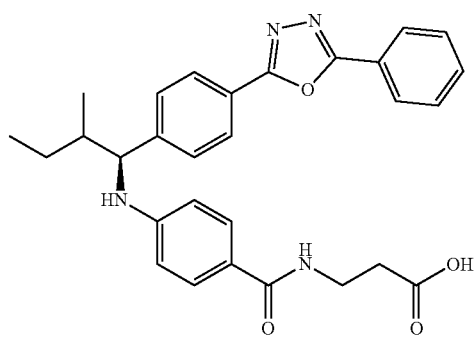 [SMILES: CCC(C)[C@H](Nc1ccc(C(=O)NCCC(=O)O)cc1)c1ccc(-c2nnc(-c3ccccc3)o2)cc1]

¹H NMR (400 MHz, CDCl₃): δ8.09 (dd, J=2.2, 7.6 Hz, 2H), 8.04 (dd, J=1.2, 8.6 Hz, 2H), 7.53-7.45 (m, 5H), 7.41 (dd, J=2.0, 8.3 Hz, 2H), 6.73-6.63 (m, 1H), 6.43 (dd, J=2.0, 8.8 Hz, 2H), 4.42-4.28 (m, 1H), 3.64-3.56 (m, 2H), 2.61-2.56 (m, 2H), 1.90-1.79 (m, 1H), 1.65-1.43 (m, 1H), 1.29-1.17 (m, 1H), 0.95-0.85 (m, 6H). MS(M+1): 499.

Compound 1-50

3-(4-(((1R)-2-methyl-1-(4-(5-phenyl-2,3,4-oxadiazol-2-yl)phenyl)butyl)amino)benzamido)propanoic acid

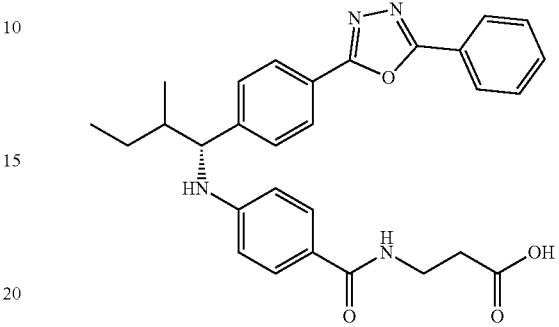

¹H NMR (400 MHz, CDCl₃): δ8.11-8.06 (m, 2H), 8.05-8.00 (m, 2H), 7.53-7.44 (m, 5H), 7.41 (dd, J=1.5, 8.3 Hz, 2H), 6.72 (br. s., 1H), 6.42 (dd, J=2.0, 8.8 Hz, 2H), 4.41-4.25 (m, 1H), 3.63-3.54 (m, 2H), 2.57 (t, J=4.6 Hz, 2H), 1.89-1.78 (m, 1H), 1.63-1.42 (m, 1H), 1.28-1.15 (m, 1H), 0.96-0.83 (m, 6H). MS(M+1): 499.

Compound 1-51 ethyl (S)-3-(4-((1-(4-(5-(trifluoromethyl)-1,3,4-oxadiazol-2-yl)phenyl)pentyl)amino)benzamido)propanoate

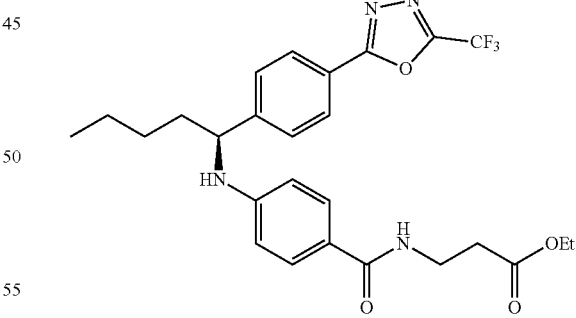

¹H NMR (400 MHz, CDCl₃): δ8.07-8.00 (m, 2H), 7.54-7.44 (m, 4H), 6.59 (t, J=6.1 Hz, 1H), 6.48-6.37 (m, 2H), 4.52-4.36 (m, 2H), 4.11 (q, J=7.0 Hz, 2H), 3.66-3.56 (m, 2H), 2.59-2.51 (m, 2H), 1.81 (dt, J=2.7, 6.0 Hz, 2H), 1.46-1.27 (m, 4H), 1.22 (t, J=7.1 Hz, 3H), 0.92-0.84 (m, 3H). MS(M+1): 519.

Compound 1-52 ethyl (R)-3-(4-((1-(4-(5-(trifluoromethyl)-1,3,4-oxadiazol-2-yl)phenyl)pentyl)amino)benzamido)propanoate

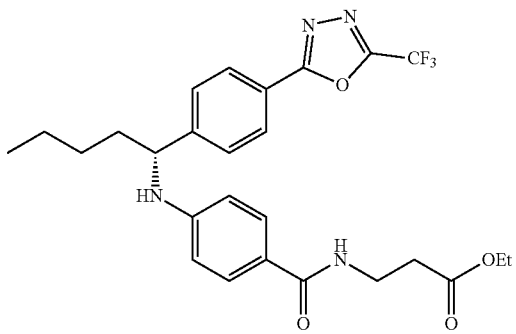 [SMILES: CCCC[C@@H](Nc1ccc(C(=O)NCCC(=O)OCC)cc1)c1ccc(-c2nnc(C(F)(F)F)o2)cc1]

¹H NMR (400 MHz, CDCl₃): δ8.09-7.97 (m, 2H), 7.54-7.44 (m, 4H), 6.59 (t, J=5.9 Hz, 1H), 6.47-6.38 (m, 2H), 4.50-4.36 (m, 2H), 4.11 (q, J=7.0 Hz, 2H), 3.67-3.55 (m, 2H), 2.60-2.49 (m, 2H), 1.87-1.72 (m, 2H), 1.44-1.27 (m, 4H), 1.26-1.17 (m, 3H), 0.91-0.81 (m, 3H). MS(M+1): 519.

Compound 1-53

(S)-3-(4-((1-(4-(5-(trifluoromethyl)-1,3,4-oxadiazol-2-yl)phenyl)pentyl)amino)benzamido)propanoic acid

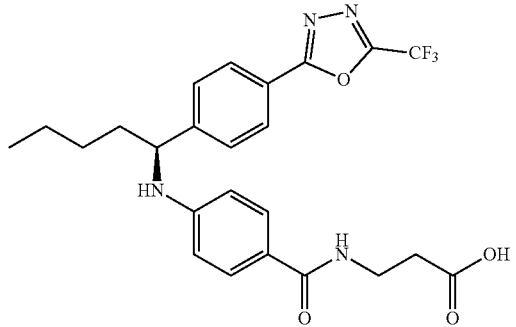 [SMILES: CCCC[C@H](Nc1ccc(C(=O)NCCC(=O)O)cc1)c1ccc(-c2nnc(C(F)(F)F)o2)cc1]

¹H NMR (400 MHz, CDCl₃): δ8.08-7.97 (m, 2H), 7.47 (dd, J=1.7, 8.6 Hz, 4H), 6.66 (t, J=6.1 Hz, 1H), 6.47-6.37 (m, 2H), 4.40 (t J=6.8 Hz, 1H), 3.66-3.50 (m, 2H), 2.59 (t, J=5.9 Hz, 2H), 1.92-1.75 (m, 2H), 1.46-1.27 (m, 4H), 0.91-0.80 (m, 3H), MS(M+1): 491.

Compound 1-54

(R)-3-(4-((1-(4-(5-(trifluoromethyl)-1,3,4-oxadiazol-2-yl)phenyl)pentyl)amino)benzamido)propanoic acid

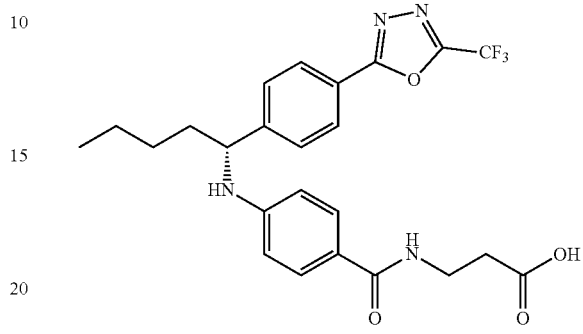

¹H NMR (400 MHz, CDCl₃): δ8.08-7.93 (m, 2H), 7.51-7.43 (m, 4H), 6.82-6.64 (m, 1H), 6.44-6.37 (m, 2H), 4.39 (t, 6.6 Hz, 1H), 3.64-3.51 (m, 2H), 2.57 (q, J=5.5 Hz, 2H), 1.92-1.68 (m, 2H), 1.42-1.24 (m, 4H), 0.86 (dt, J=1.7, 7.0 Hz, 3H). MS(M+1): 491.

Compound 1-55 ethyl (S)-3-(4-((2-methyl-1-(4-(5-(trifluoromethyl)-1,3,4-oxadiazol-2-yl)phenyl) propyl)amino)benzamido)propanoate

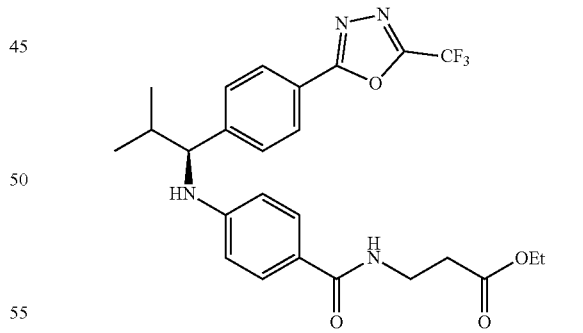

¹H NMR (400 MHz, DMSO-d₆): δ8.05-7.99 (m, 3H), 7.62 (d, J=6 Hz, 2H), 7.47 (d, J=6 Hz, 2H), 6.69 (d, J=6 Hz, 1H), 6.56 (d, J=6 Hz, 2H), 4.30 (t, J=6 Hz, 1H), 4.03 (d, J=7.3 Hz, 2H), 3.35-3.43 (m, 2H), 1.96-2.10 (m, 1H), 1.14 (t, J=7.1 Hz, 3H), 1.03 (d, J=6.4 Hz, 3H), 0.81 (d, J=6.4 Hz, 3H). MS(M+1): 505.

Compound 1-56 ethyl (R)-3-(4-((2-methyl-1-(4-(5-(trifluoromethyl)-1,3,4-oxadiazol-2-yl)phenyl)propyl)amino)benzamido)propanoate

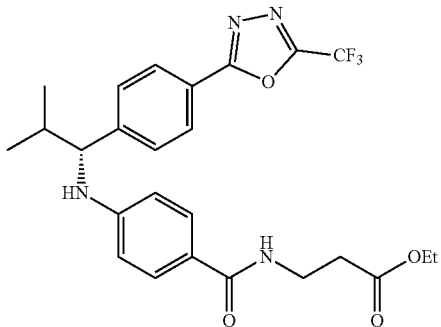 [SMILES: CCOC(=O)CCNC(=O)c1ccc(N[C@@H](c2ccc(-c3nnc(C(F)(F)F)o3)cc2)C(C)C)cc1]

$^1$H NMR (400 MHz, DMSO-d$_6$): δ7.94-8.07 (m, 3H), 7.60-7.64 (m, 2H), 7.45-7.53 (m, 2H), 6.65-6.73 (m, 1H), 6.52-6.60 (m, 2H), 3.99-4.07 (m, 2H), 1.97-2.11 (m, 3H), 1.14 (s, 4H), 1.00-1.06 (m, 3H), 0.77-0.86 (m, 3H). MS(M+1): 505.

Compound 1-57

(RS)-3-(4-((2-methyl-1-(4-(5-(trifluoromethyl)-1,3,4-oxadiazol-2-yl)phenyl)propyl)amino)benzamido)propanoic acid

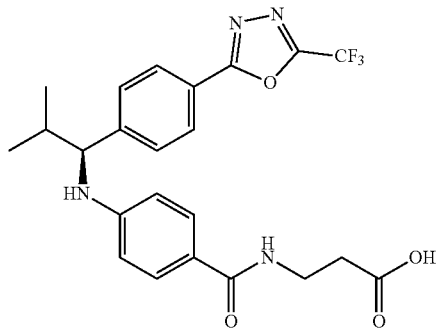 [SMILES: CC(C)[C@H](Nc1ccc(C(=O)NCCC(=O)O)cc1)c1ccc(-c2nnc(C(F)(F)F)o2)cc1]

$^1$H NMR (400 MHz, DMSO-d$_6$): δ8.02 (d, J=8.3 Hz, 2H), 7.98 (t, J=5.4 Hz, 1H), 7.62 (d, J=8.3 Hz, 2H), 7.48 (d, J=8.8 Hz, 2H), 6.68 (d, J=7.8 Hz, 1H), 6.55 (d, J=8.8 Hz, 2H), 4.30 (t, J=7.6 Hz, 1H), 2.41 (t, J=7.1 Hz, 2H), 1.98-2.11 (m, 1H), 1.03 (d, J=6.4 Hz, 3H), 0.81 (d, J=6.8 Hz, 3H). MS(M+1): 477.

Compound 1-58

(R)-3-(4-((2-methyl-1-(4-(5-(trifluoromethyl)-1,3,4-oxadiazol-2-yl)phenyl)propyl)amino)benzamido)propanoic acid

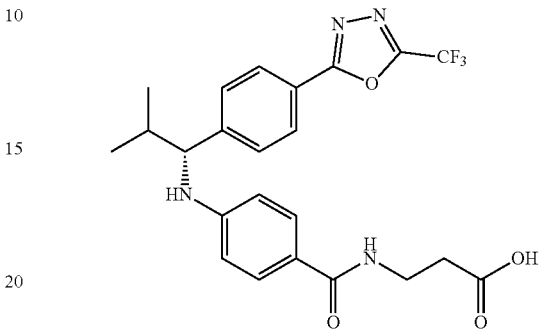

$^1$H NMR (400 MHz, DMSO-d$_6$): δ8.00-8.07 (m, 2H), 7.95-7.99 (m, 1H), 7.59-7.66 (m, 2H), 7.44-7.53 (m, 2H), 6.64-6.72 (m, 1H), 6.51-6.58 (m, 2H), 4.26-4.36 (m, 1H), 2.39-2.46 (m, 2H), 1.98-2.11 (m, 1H), 1.00-1.08 (m, 3H), 0.76-0.84 (m, 2H). MS(M+1): 477.

Compound 1-59 ethyl (S)-3-(4-((3-methyl-1-(4-(5-phenyl-1,3,4-oxadiazol-2-yl)phenyl)butyl)amino)benzamido)propanoate

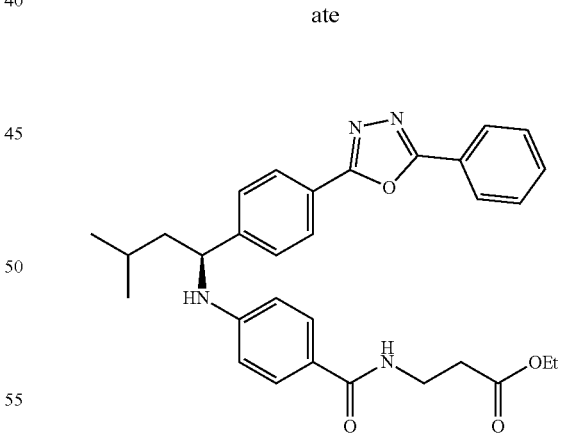

$^1$H NMR (400 MHz, CDCl$_3$): δ8.14-8.03 (m, 4H), 7.56-7.40 (m, 7H), 6.60 (s, 1H), 6.49-6.42 (m, 2H), 4.46 (d, J=5.4 Hz, 2H), 4.10 (q, J=7.0 Hz, 2H), 3.67-3.57 (m, 2H), 2.60-2.51 (m, 2H), 1.79-1.56 (m, 3H), 1.27-1.16 (m, 3H), 0.97 (dd, J=6.1, 18.3 Hz, 6H). MS(M+1): 527.

Compound 1-60 ethyl (R)-3-(4-((3-methyl-1-(4-(5-phenyl-1,3,4-oxadiazol-2-yl)phenyl)butyl)amino)benzamido)propanoate

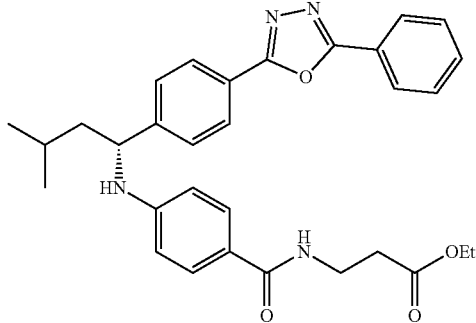 [SMILES: CCOC(=O)CCNC(=O)c1ccc(N[C@H](CC(C)C)c2ccc(-c3nnc(-c4ccccc4)o3)cc2)cc1]

$^1$H NMR (400 MHz, CDCl$_3$): δ8.15-8.00 (m, 4H), 7.55-7.42 (m, 7H), 6.60 (d, J=5.4 Hz, 1H), 6.51-6.42 (m, 2H), 4.54-4.39 (m, 2H), 4.10 (q, J=7.3 Hz, 2H), 3.62 (q, J=6.2 Hz, 2H), 2.59-2.49 (m, 2H), 1.80-1.57 (m, 3H), 1.25-1.17 (m, 3H), 0.96 (dd, J=5.9, 18.1 Hz, 6H). MS(M+1): 527.

Compound 1-61

(S)-3-(4-((3-methyl-1-(4-(5-phenyl-1,3,4-oxadiazol-2-yl)phenyl)butyl)amino)benzamido)propanoic acid

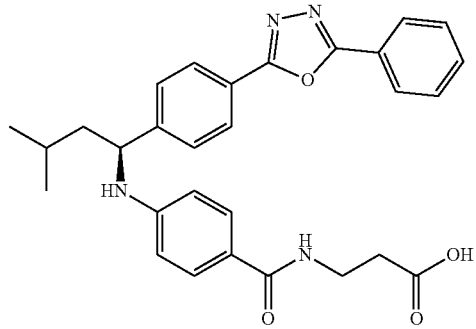 [SMILES: CC(C)C[C@H](Nc1ccc(C(=O)NCCC(=O)O)cc1)c1ccc(-c2nnc(-c3ccccc3)o2)cc1]

$^1$H NMR (400 MHz, CDCl$_3$): δ8.13-7.97 (m, 4H), 7.55-7.38 (m, 7H), 6.83 (dd, J=5.4, 14.2 Hz, 1H), 6.43 (d, J=8.8 Hz, 2H), 4.47-4.42 (m, 2H), 3.62-3.55 (m, 2H), 2.59-2.54 (m, 2H), 1.76-1.51 (m, 3H), 0.98-0.88 (m, 6H). MS(M+1): 499.

Compound 1-62

(R)-3-(4-((3-methyl-1-(4-(5-phenyl-1,3,4-oxadiazol-2-yl)phenyl)butyl)amino)benzamido)propanoic acid

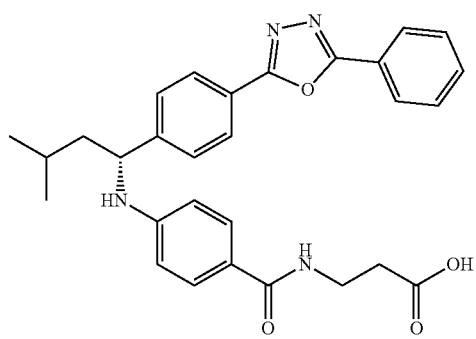 [SMILES: CC(C)C[C@@H](Nc1ccc(C(=O)NCCC(=O)O)cc1)c1ccc(-c2nnc(-c3ccccc3)o2)cc1]

$^1$H NMR (400 MHz, CDCl$_3$): δ8.05 (dddd, J=1.7, 3.9, 6.0, 19.7 Hz, 4H), 7.55-7.40 (m, 7H), 6.77 (dt, J=5.6, 11.4 Hz, 1H), 6.50-6.38 (m, 2H), 4.48-4.42 (m, 2H), 3.63-3.55 (m, 2H), 2.61-2.54 (m, 2H), 1.80-1.53 (m, 3H), 0.99-0.89 (m, 6H). MS(M+1): 499.

Compound 1-63 methyl (S)-3-(4-((2-methyl-1-(4-(5-phenyl-1,3,4-oxadiazol-2-yl)phenyl)propyl)amino)benzamido)propanoate

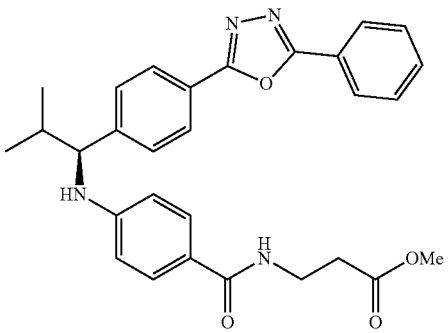 [SMILES: COC(=O)CCNC(=O)c1ccc(N[C@H](c2ccc(-c3nnc(-c4ccccc4)o3)cc2)C(C)C)cc1]

$^1$H NMR (400 MHz, DMSO-d$_6$): δ8.09-8.14 (m, 2H), 8.06 (d, J=8.8 Hz, 2H), 8.00 (t, J=5.6 Hz, 1H), 7.57-7.67 (m, 5H), 7.49 (d, J=8.8 Hz, 2H), 6.69 (d, J=7.8 Hz, 1H), 6.57 (d, J=8.8 Hz, 2H), 4.28 (t, J=7.3 Hz, 1H), 3.56 (s, 3H), 3.29-3.45 (m, 2H), 1.99-2.12 (m, 1H), 1.04 (d, J=6.8 Hz, 3H), 0.82 (d, J=6.8 Hz, 3H). MS(M+1): 499.

Compound 1-64

(S)-2-(4-((2-methyl-1-(4-(5-phenyl-1,3,4-oxadiazol-2-yl)phenyl)propyl)amino)benzamido)ethane-1-sulfonic acid

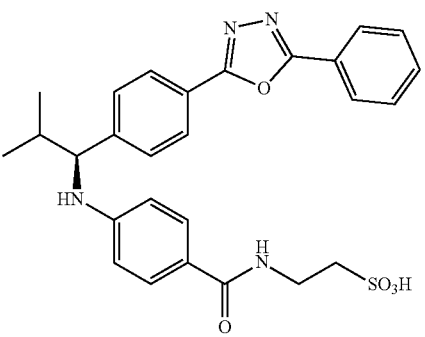 [SMILES: CC(C)[C@H](Nc1ccc(C(=O)NCCS(=O)(=O)O)cc1)c1ccc(-c2nnc(-c3ccccc3)o2)cc1]

$^1$H NMR (400 MHz, DMSO-d$_6$): δ8.09-8.14 (m, 2H), 8.00-8.08 (m, 3H), 7.58-7.66 (m, 5H), 7.44 (d, J=8.8 Hz, 2H), 6.74 (d, J=7.8 Hz, 1H), 6.58 (d, J=8.8 Hz, 2H), 4.28 (t, J=7.6 Hz, 1H), 3.39-3.47 (m, 2H), 2.60 (t, J=6.8 Hz, 2H), 2.00-2.11 (m, 1H), 1.04 (d, J=6.4 Hz, 3H), 0.82 (d, J=6.8 Hz, 3H). MS(M+1): 521.

Example 2: Synthesis of the Compounds Shown in the Following Table 2

The following scheme was followed for synthesizing Compounds 2-1 to 2-48,

Scheme II
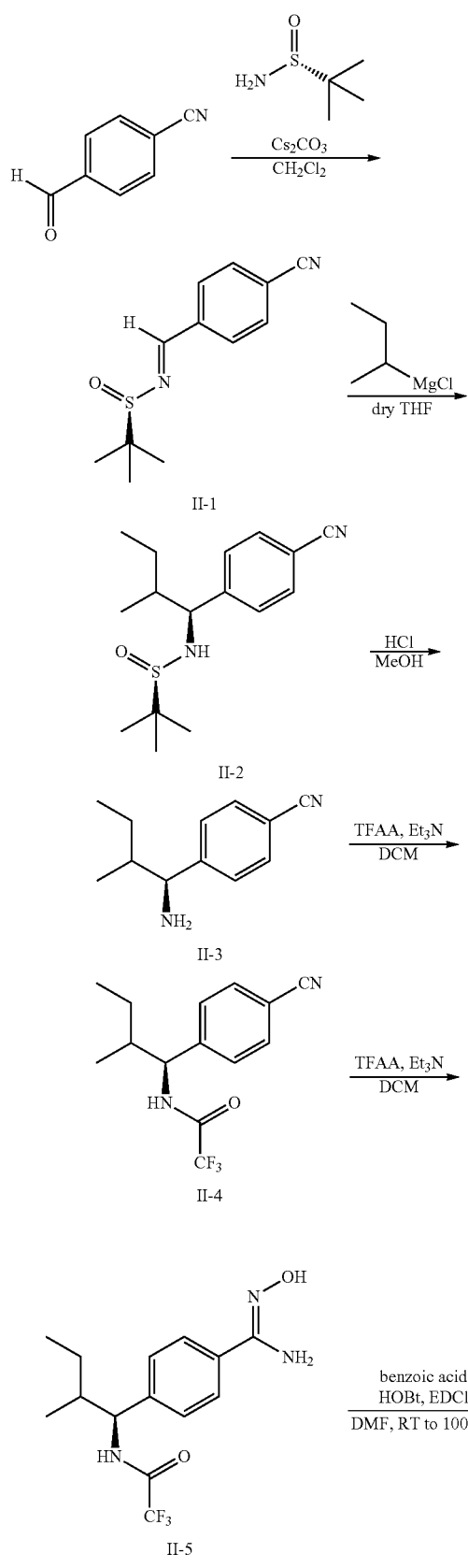

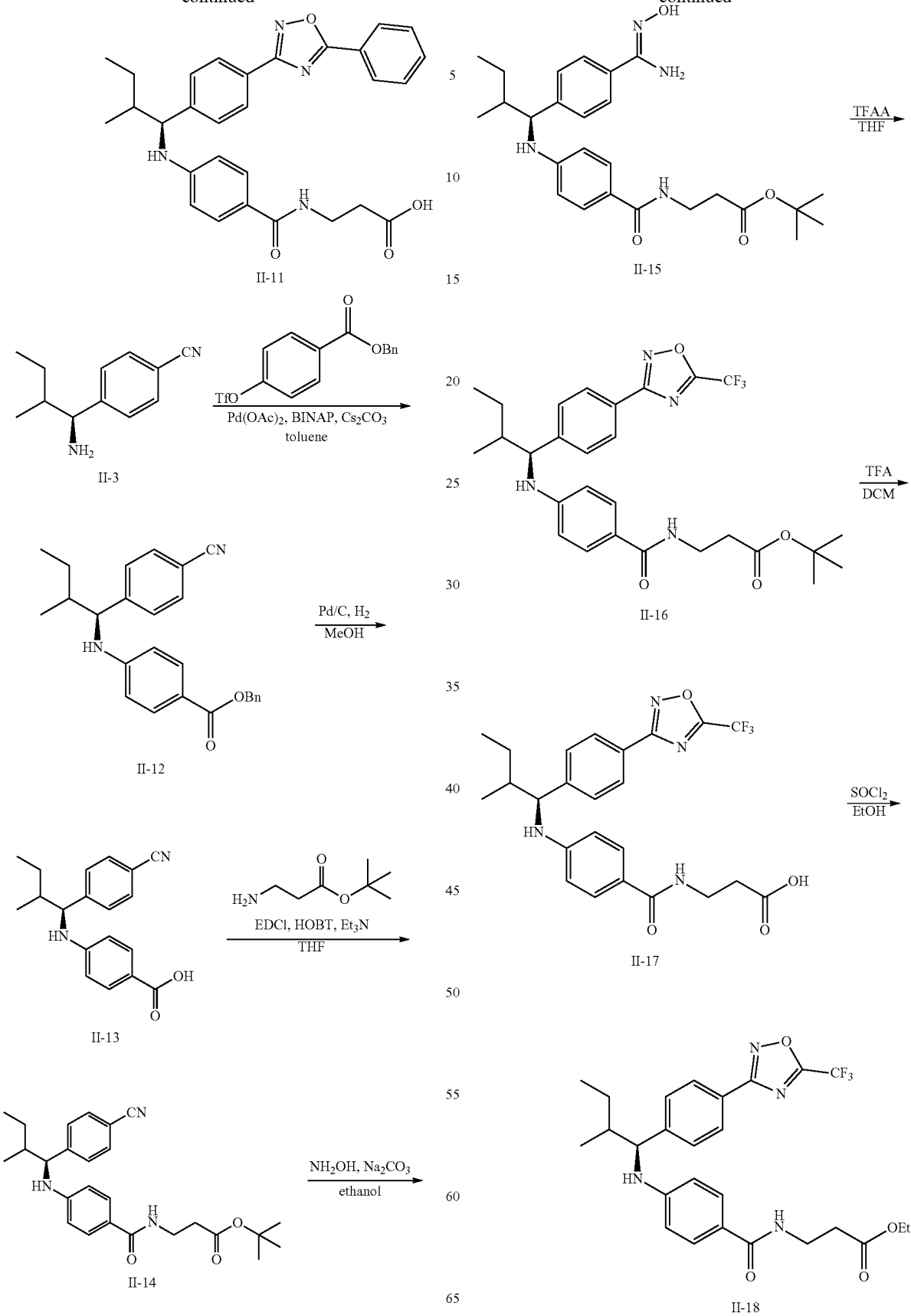

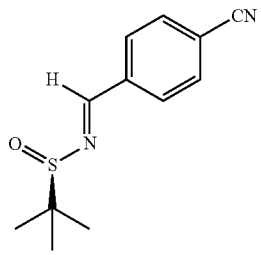

II-1

To a solution of 4-formylbenzonitrile (7.27 g, 55.5 mmol), (S)-(+)-tert-butanesulfinamide (8.06 g, 66.5 mmol), and Cs$_2$CO$_3$ (21.68 g, 66.5 mmol) were mixed in DCM (200 mL) was heat to reflux for 1 hr. To this reaction solution, concentrated to remove methanol and extracted with EtOAc. The organic layer was washed, with water and dried over anhydrous magnesium sulfate. It was filtered, the solvent evaporated under reduced pressure to give white solid product II-1 (13.6 g, 100%).

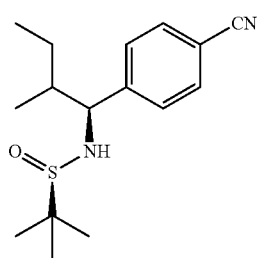

II-2

To a solution of compound II-1 (6.80 g, 29.0 mmol) in tetrahydrofuran (100 mL) was cooled to −78° C. To this solution was added 1.2M/sec-butylmagnesium chloride (25 mL) dropwise over 20 minutes. The reaction was stirred at −78° C. for 2 h. The reaction was then quenched by addition of saturated aqueous ammonium chloride. This mixture was extracted with ethyl acetate. The organic layer was dried over magnesium sulfate, filtered and concentrated. Purification by silica gel chromatography gave compound II-2. Colorless solid, yield (7.2 g, 85%).

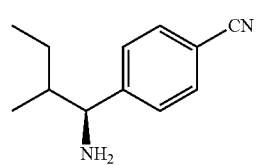

II-3

The compound II-2 (2.00 g, 6.84 mmol) was suspended in 2M/HCl in MeOH (30 mL) at room temperature for 1 h. After evaporation, excess HCl was neutralized by dropwised addition of NaHCO$_{3(aq)}$ until pH=10. Then it was extracted with EA and water. The combined organic layer was dried with anhydrous MgSO$_4$ and concentrated. Purification by silica gel chromatography to give crude product II-3.

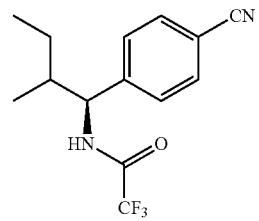

II-4

Trifluoroacetic anhydride (1.0 mL, 6.84 mmol) was added dropwise to a solution of the aniline (1.30 g, 6.84 mmol), triethylamine (1.0 mL, 6.84 mmol) in CH$_2$Cl$_2$. The reaction was allowed to warm to room temperature over a period of 30 minutes. After evaporating the solvents under a reduced pressure, the resulting mixture was washed with water and EA, dried the organic layer over MgSO$_4$. Give the crude product II-4.

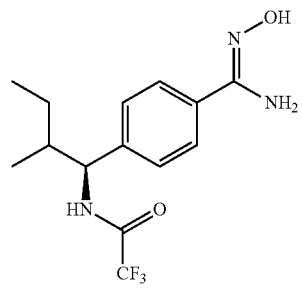

II-5

Hydroxylamine hydrochloride (1.66 g, 23.94 mmol) and sodium carbonate (1.50 g, 13.68 mmol) were added to a solution of II-4 (1.94 g, 6.84 mmol) in ethanol (20 ml) were refluxed for 1 hour. The reaction was cooled to room temperature and concentrated in vacuo. This mixture was extracted with ethyl acetate and water. The organic layer was dried over magnesium sulfate to give crude product II-5 (colorless oil) which was taken to the next step without further purification.

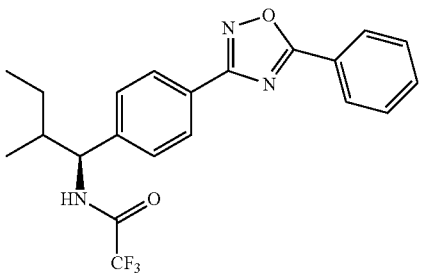

II-6

To a solution of benzoic acid (0.84 g, 6.84 mmol), HOBt (1.26 g, 8.21 mmol) and EDCI (1.44 g, 7.53 mmol) in DMF at room temperature for 30 min. Add a solution of benz-amidine (300 mg, 2.20 mmol, 1.00 equiv) in DMF (abs, 2 mL) to the reaction mixture for 10 min at room temperature, then reflux 3 hr. When, the starting material has been run out, added water to the residue and the aqueous layer was extracted with ethyl acetate. It was further concentrated in vacuo to give a residue. Purification of the crude oil residue by column chromatography (EA:Hex=10:90) afforded white solid product II-6 (1.8 g, 65%). Yield=1.80/2.7593=65%

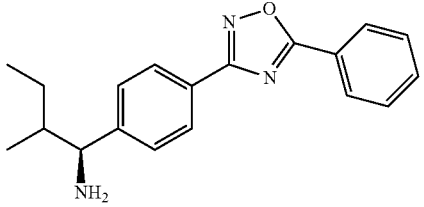

II-7

II-6 (1.80 g, 4.46 mmol) was dissolved in dioxane (30 mL) followed by addition of 6M HCl(aq) 30 mL. The reaction mixture stirred at 100° C. overnight. The reaction was monitored by TLC. With completion of the reaction, the solvent was removed by rotavapor. The mixture cpd. was extracted with EtOAc and water. The combined organic layer was dried with anhydrous MgSO$_4$ and concentrated in vacuo to give crude product (yellow oil) II-7 (1.4 g, 100%).

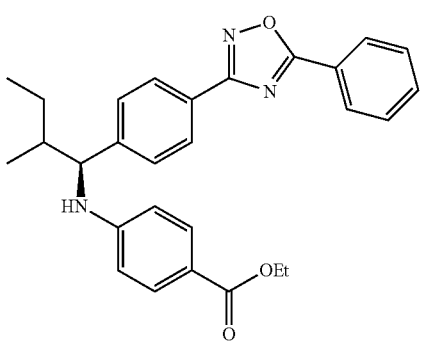

II-8

Pd(OAc)$_2$ (0.11 g, 0.5 mmol), BINAP (0.62 g, 1 mmol), Cesium carbonate (2.91 g, 8.92 mmole), ethyl 4-(trifluoromethylsulfonyloxy)benzoate (1.60 g, 5.35 mmol), and R-ANU-NH$_2$ (1.40 g, 4.46 mmol) in 30 mL toulene were purged with nitrogen for 30 min. The mixture was stirred in an oil bath at 80° C. overnight. Cool the mixture to ambient temperature, dilute with EtOAc, filter through Celite washing with EtOAc. The mixture was washed with water and brine, dried the organic layer over MgSO$_4$, and concentrate to obtain the crude mixture. Purification of the crude oil residue by column chromatography (EA:Hex=8:92) afforded white solid product II-8 (1.1 g, 54%).

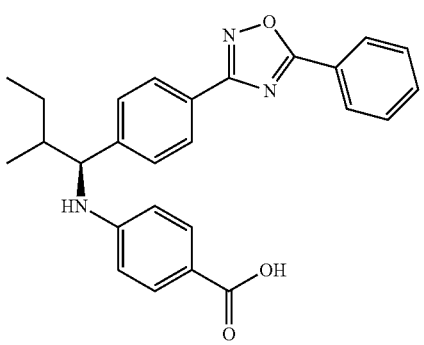

II-9

II-8 (0.5 g, 1.09 mmol) was dissolved in dioxane (20 mL) followed by addition of 2M LiOH(aq) 20 mL. The reaction mixture stirred at 60° C. for 3 h. The reaction was monitored by TLC. With completion of the reaction, the solvent was removed by rotary evaporation and was added HCl$_{(aq)}$ to pH4~5. The mixture cpd. was extracted with EtOAc. The combined organic layer was dried with anhydrous MgSO$_4$ and concentrated in vacuo to give crude product II-9 (0.43 g, 89%).

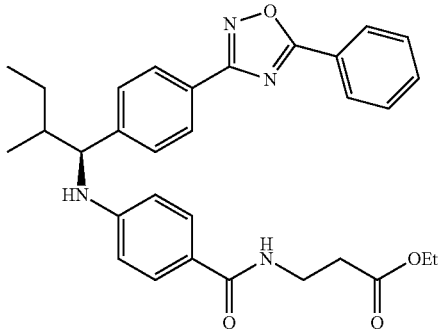

II-10

To a solution of II-9 (1.0 g, 2.34 mmole), beta-alanine ethyl ester.HCl (0.54 g, 3.51 mmole), EDCI (0.67 g, 3.51 mmol), Et$_3$N (0.71 g, 7.02 mmol) and HOBt (0.54 g, 3.51 mmol) in dry 30 ml THF. The reaction was stirred at room temperature for overnight then concentrated in vacuo. Water was added to die residue and the aqueous layer was extracted with ethyl acetate. It was further concentrated in vacuo to give a residue. Purification of the crude oil residue by column chromatography (EA:Hex=30:70) afforded white solid product II-10 (0.9 g, 73%).

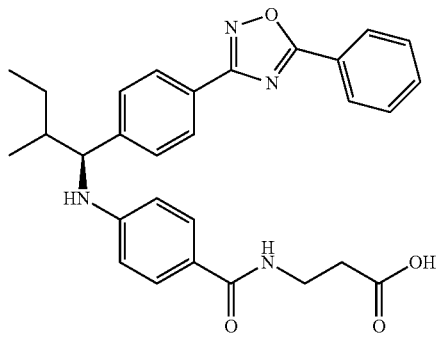

II-11

Compound II-10 (0.6 g, 1.14 mmol) was dissolved in THF (20 mL) followed by addition of 2M/LiOH(aq) 20 mL, The reaction mixture stirred at RT for 3 h. The reaction was monitored by TLC. With completion of the reaction, the solvent w as removed by rotary evaporation and was added HCl(aq) to pH4~5. The mixture cpd, was extracted with EtOAc. The combined organic layer was dried with anhydrous MgSO$_4$ and concentrated in vacuo. Purification of the crude oil residue by column chromatography (EA:Hex=45: 50) afforded white solid product II-11 (0.3 g, 53%).

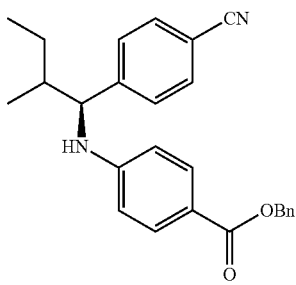

A solution of II-11 (1.9 g, 10 mmol), BINAP (3.1 g, 5 mmol), benzyl 4-(((trifluoromethyl)sulfonyl)oxy)benzoate (4.36 g, 12 mmol) and $Cs_2CO_3$ (6.57 g, 20 mmol) in 70 ml Tol were purged with nitrogen for 30 min. $Pd(OAc)_2$ (0.57 g, 2.5 mmol) was added to the mixture. The mixture was stirred in an oil bath at 80° C. overnight. Cool the mixture to ambient temperature, dilute with EtOAc, filter through Celite washing with EtOAc. The organic mixture was washed with water and brine, dried the organic layer over $MgSO_4$, and concentrate to obtain the crude mixture. Purification of the crude oil residue by 40 g column chromatography with 10% EA in hexane to afford the II-12 (2.6 g, 65%).

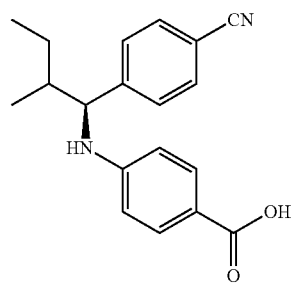

II-12 (2.6 g, 6.5 mmol) was dissolved in 50 mL MeOH, followed by addition of Pd/C. The reaction mixture stirred at room temperature for 1 h. The reaction was monitored by TLC. Removed the catalyst by celite and concentrated in vacuo to give crude product II-13 (2 g, 99%).

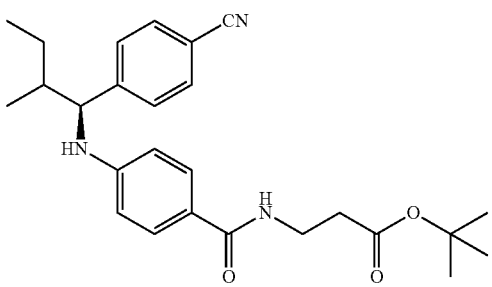

To a solution of II-13 (2.0 g, 6.5 mmole), tert-butyl 3-aminopropanoate hydrochloride (1.76 g, 10 mmol), EDCI (2.5 g, 13 mmole), DIPEA (2.5 g, 13 mmol) and HOBT (2.0 g, 13 mmol) in dry THF (30 ml). The reaction was stirred at room temperature for overnight then concentrated in vacuo. Water was added to the residue and the aqueous layer was extracted with ethyl acetate. It was further concentrated in vacuo to give a crude product II-14 (1.97 g, 70%).

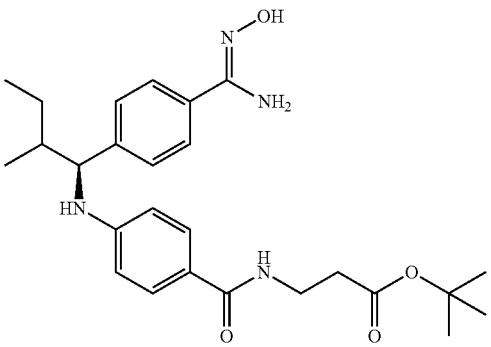

Hydroxylamine hydrochloride (1.1 g, 15.8 mmol) and sodium carbonate (0.96 g, 9 mmol) were added to a solution of II-14 (1.97 g, 4.5 mmol) in ethanol (20 ml) were refluxed for 1 hour. The reaction was cooled to room temperature and concentrated in vacuo. This mixture was extracted with ethyl acetate and water. The organic layer was dried over magnesium sulfate to give crude product II-15 (colorless oil) which was taken to the next step without further purification.

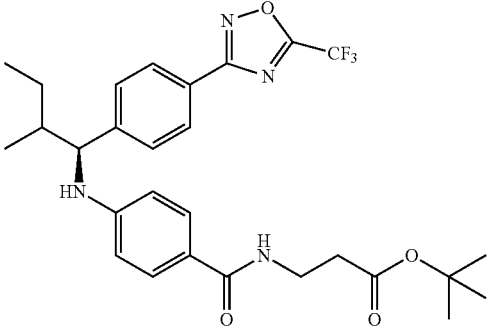

To a solution of II-15 (1.94 g, 4.5 mmol) in dry THF 20 ml was added dropwise TFAA (1.03 g, 4.9 mmol). The light yellow solution was stirred at RT under inert atmosphere for 2 h. The reaction mixture was condensed in vacuo. The crude was washed with EtOAc (100 ml) to afford II-16 (1.68 g, 2 steps 68%).

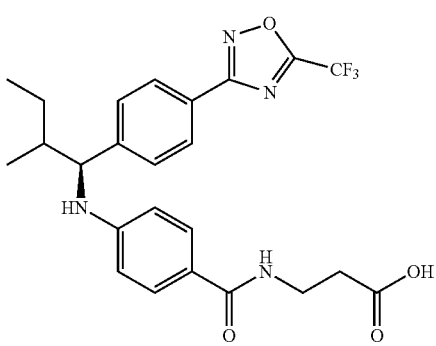

To a solution of II-16 (1.1 g, 2 mmol) in DCM (10 mL), and TFA (1.5 mL) was added. The reaction mixture was stirred at room temperature for 2 h. The mixture was partitioned between DCM and $H_2O$. Drying ($MgSO_4$) and concentration to give product II-17 (0.6 g, 61%).

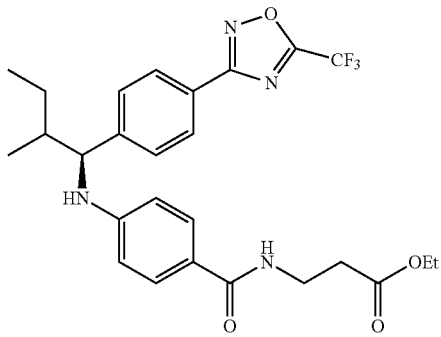

II-17 (0.5 g, 1 mmol) was dissolved in 10 ml EtOH and SOCl₂ (1 mL) was added. The reaction mixture was stirred at room temperature for 15 min. The mixture was partitioned between EA and H₂O. Drying (MgSO₄) and concentration to give product II-18 (0.45 g, 87%).

Compound 2-1 ethyl 3-(4-((1-(4-(5-(tert-butyl)-1,2,4-oxadiazol-3-yl)phenyl)-2-methylpropyl)amino)benzamido)propanoate

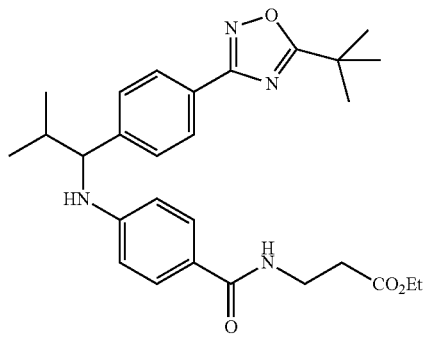 [SMILES: CCOC(=O)CCNC(=O)c1ccc(NC(c2ccc(-c3noc(C(C)(C)C)n3)cc2)C(C)C)cc1]

White solid. $^1$H NMR (400 MHz, CDCl₃): δ7.99 (d, J=7.8 Hz, 2H), 7.48 (d, J=7.8 Hz, 2H), 7.35 (d, J=7.8 Hz, 2H), 6.54 (t, J=7.8 Hz, 1H), 6.45 (d, J=7.8 Hz, 2H), 4.2 (d, J=5.9 Hz, 1H), 4.11 (q, J=6.8 Hz, 1H), 3.61 (q, J=6.3 Hz, 2H), 2.55 (t, J=6.3 Hz, 2H), 2.09-2.02 (m, 1H), 1.45 (s, 9H), 1.22 (t, J=6.8 Hz, 3H), 0.99 (d, J=6.3 Hz, 3H), 0.92 (d, J=6.3 Hz, 3H). MS(M+1): 493.

Compound 2-2

3-(4-((1-(4-(5-(tert-butyl)-1,2,4-oxadiazol-3-yl)phenyl)-2-methylpropyl)amino)benzamido)propanoic acid

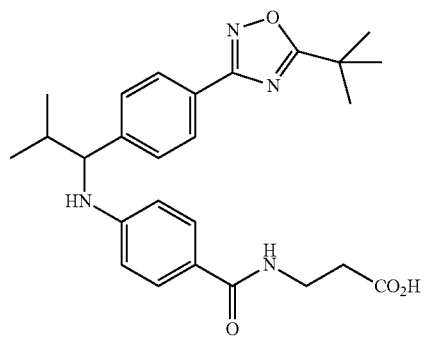 [SMILES: CC(C)C(Nc1ccc(C(=O)NCCC(=O)O)cc1)c1ccc(-c2noc(C(C)(C)C)n2)cc1]

White solid. $^1$H NMR (400 MHz, DMSO-d₆): δ7.97 (t, J=5.6 Hz, 1H), 7.91 (d, J=8.8 Hz, 2H), 7.53-7.47 (m, 4H), 6.65 (d, J=8.3 Hz, 1H), 6.55 (d, J=8.8 Hz, 2H), 4.23 (t, J=5.6 Hz, 1H), 3.38 (q, J=6.8 Hz, 2H), 2.42 (t, J=6.8 Hz, 2H), 2.03-2.01 (m, 1H), 1.45 (s, 9H), 1.02 (d, J=6.3 Hz, 3H), 0.80 (d, J=6.3 Hz, 3H). MS(M+1): 465.

Compound 2-3 ethyl 3-(4-(5-((tert-butyl)-1,2,4-oxadiazol-3-yl)phenyl)amino)benzamido propanoate

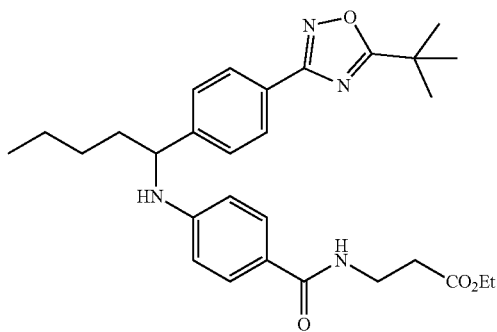 [SMILES: CCCCC(Nc1ccc(C(=O)NCCC(=O)OCC)cc1)c1ccc(-c2noc(C(C)(C)C)n2)cc1]

White solid. $^1$H NMR (400 MHz, DMSO-d₆): δ8.02 (d, J=8.3 Hz, 2H), 7.51 (d, J=8.3 Hz, 2H), 7.41 (d, J=8.3 Hz, 2H), 6.58 (t, J=5.8 Hz, 1H), 6.47 (d, J=8.3 Hz, 2H), 4.46-4.38 (m, 2H), 4.13 (q, J=6.8 Hz, 2H), 3.65 (q, J=6.3 Hz, 2H), 2.58 (d, J=6.3 Hz, 2H), 1.84-1.81 (m, 2H), 1.38-1.31 (m, 4H), 1.48 (s, 9H), 1.24 (t, J=6.8 Hz, 3H), 0.88 (t, J=6.5 Hz, 3H). MS(M+1): 507.

Compound 2-4

3-(4-((1-(4-(5-(tert-butyl)-1,2,4-oxadiazol-3-yl)phenyl)pentyl)amino)benzamido)propanoic acid

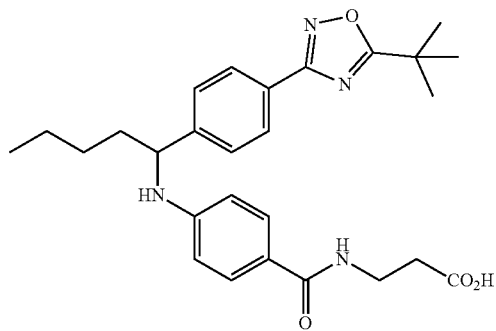 [SMILES: CCCCC(Nc1ccc(C(=O)NCCC(=O)O)cc1)c1ccc(-c2noc(C(C)(C)C)n2)cc1]

White solid. $^1$H NMR (400 MHz, DMSO-d₆): δ7.98 (t, J=5.6 Hz, 1H), 7.92 (d, J=8.8 Hz, 2H), 7.54-7.48 (m, 4H), 6.73 (d, J=8.8 Hz, 1H), 6.51 (d, J=8.8 Hz, 2H), 4.47-4.44 (m, 1H), 3.35 (q, J=6.8 Hz, 2H), 2.40 (t, J=6.8 Hz, 2H), 1.85-1.75 (m, 1H), 1.75-1.68 (m, 1H), 1.42 (s, 9H), 1.33-1.28 (m, 4H), 0.85 (t, J=6.5 Hz, 3H). MS(M+1): 479.

Compound 2-5 ethyl 3-(4-((1-(4-(5-(tert-butyl)-1,2,4-oxadiazol-3-yl)phenyl)-3-methylbutyl)amino)benzamido)propanoate

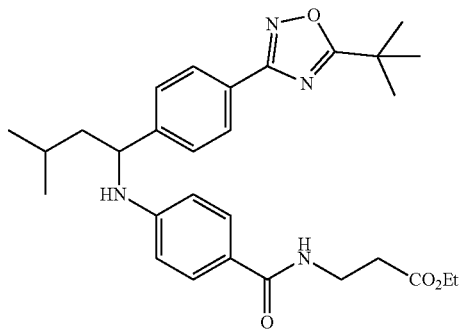 [SMILES: CCOC(=O)CCNC(=O)c1ccc(NC(CC(C)C)c2ccc(-c3noc(C(C)(C)C)n3)cc2)cc1]

White solid. $^1$H NMR (400 MHz, CDCl$_3$): δ7.80 (d, J=7.8 Hz, 2H), 7.49 (d, J=7.8 Hz, 2H), 7.39 (d, J=7.8 Hz, 2H), 6.55 (t, J=7.8 Hz, 1H), 6.46 (d, J=7.8 Hz, 2H), 4.45-4.37 (m, 2H), 4.11 (q, J=6.3 Hz, 2H), 3.63 (q, J=6.3 Hz, 2H), 2.56 (t, J=6.3 Hz, 2H), 1.74-1.59 (m, 3H), 1.46 (s, 9H), 1.22 (t, J=6.8 Hz, 3H), 0.98 (d, J=6.3 Hz, 3H), 0.93 (d, J=6.3 Hz, 3H). MS(M+1): 507.

Compound 2-6

3-(4-((1-(4-(5-(tert-butyl)-1,2,4-oxadiazol-3-yl)phenyl)-3-methylbutyl)amino)benzamido)propanoic acid

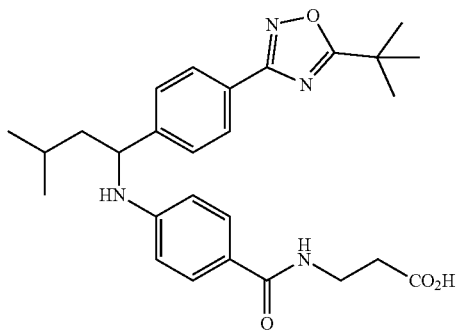 [SMILES: CC(C)CC(Nc1ccc(C(=O)NCCC(=O)O)cc1)c1ccc(-c2noc(C(C)(C)C)n2)cc1]

White solid. $^1$H NMR (400 MHz, DMSO-d$_6$): δ7.98 (t, J=5.6 Hz, 1H), 7.91 (d, J=8.8 Hz, 2H), 7.55 (d, J=8.8 Hz, 2H), 7.49 (d, J=8.8 Hz, 2H), 6.73 (d, J=8.8 Hz, 1H), 6.53 (d, J=8.8 Hz, 2H), 4.54-4.49 (m, 1H), 3.35 (q, J=6.8 Hz, 2H), 2.42 (t, J=6.8 Hz, 2H), 1.75-1.67 (m, 2H), 1.50-1.47 (m, 1H), 1.42 (s, 9H), 0.95 (d, J=6.3 Hz, 3H), 0.90 (d, J=6.3 Hz, 3H). MS(M+1): 479.

Compound 2-7 ethyl 3-(4-((1-(4-(5-phenyl-1,2,4-oxadiazol-3-yl)phenyl)pentyl)amino)benzamido)propanoate

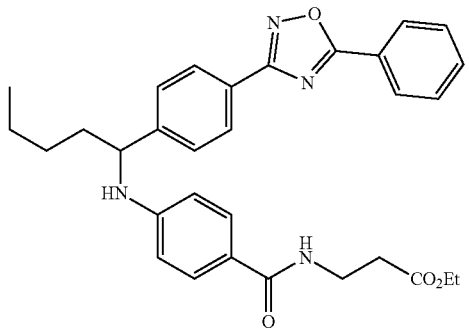 [SMILES: CCCCC(Nc1ccc(C(=O)NCCC(=O)O)cc1)c1ccc(-c2noc(-c3ccccc3)n2)cc1]

White solid. $^1$H NMR (400 MHz, CDCl$_3$): δ8.19 (d, J=8.3 Hz, 2H), 8.10 (d, J=8.3 Hz, 2H), 7.61-7.48 (m, 5H), 7.41 (d, J=8.3 Hz, 2H), 6.59 (t, J=5.8 Hz, 1H), 6.46 (d, J=8.3 Hz, 2H) 4.40 (t, J=6.8 Hz, 1H), 4.11 (q, J=6.8 Hz, 2H), 3.63 (q, J=6.3 Hz, 2H), 2.55 (t, J=6.3 Hz, 2H), 1.84-1.81 (m, 2H), 1.38-1.33 (m, 4H), 1.22 (t J=6.8 Hz, 3H), 0.88 (t, J=6.5 Hz, 3H). MS(M+1): 527

Compound 2-8

3-(4-((1-(4-(5-phenyl-1,2,4-oxadiazol-3-yl)phenyl)pentyl)amino)benzamido)propanoic acid White solid. $^1$H NMR (400 MHz, DMSO-d$_6$): δ8.17 (d, J=8.8 Hz, 2H), 8.03-7.98 (m, 3H), 7.75-7.72 (m, 1H), 7.68-7.64 (m, 2H), 7.58 (d, J=8.8 Hz, 2H), 7.50 (d, J=8.8 Hz, 2H), 6.76 (d, J=8.8 Hz, 1H), 6.53 (d, J=8.8 Hz, 2H), 4.48 (q, J=6.8 Hz, 1H), 3.35 (q, J=6.8 Hz, 2H), 2.42 (t, J=6.8 Hz, 2H), 1.84-1.82 (m, 1H), 1.74-1.70 (m, 1H), 1.42-1.27 (m, 4H), 0.86 (t, J=6.5 Hz, 3H). MS(M+1): 499.

Compound 2-9 ethyl 3-(4-((3-methyl-1-(4-(5-phenyl-1,2,4-oxadiazol-3-yl)phenyl)butyl)amino)benzamido)propanoate

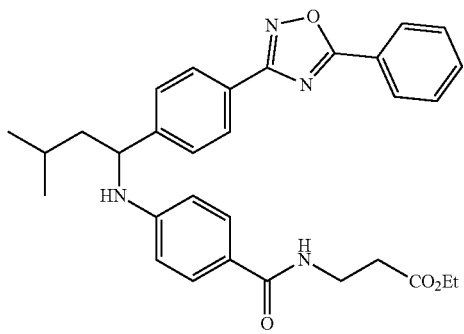 [SMILES: CCOC(=O)CCNC(=O)c1ccc(NC(CC(C)C)c2ccc(-c3noc(-c4ccccc4)n3)cc2)cc1]

White solid. $^1$H NMR (400 MHz, CDCl$_3$): δ 8.19 (d, J=8.3 Hz, 2H), 8.10 (d, J=8.3 Hz, 2H), 7.61-7.49 (m, 5H), 7.44 (d, J=8.3 Hz, 2H), 6.56 (t, J=5.8 Hz, 1H), 6.48 (d, J=8.3 Hz, 2H), 4.47-4.40 (m, 2H), 4.11 (q, J=6.8 Hz, 2H), 3.63 (q, J=6.3 Hz, 2H), 2.55 (t, J=6.3 Hz, 2H), 1.76-1.62 (m, 3H), 1.22 (t, J=6.8 Hz, 3H), 1.00 (t, J=6.5 Hz, 3H), 0.94 (t, J=6.5 Hz, 3H). MS(M+1): 527.

Compound 2-10

3-(4-((3-methyl-1-(4-(5-phenyl-1,2,4-oxadiazol-3-yl)phenyl)butyl)amino)benzamido)propanoic acid

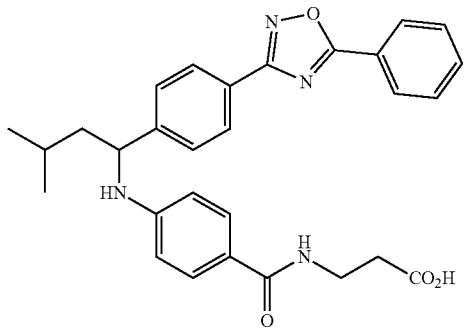 [SMILES: CC(C)CC(Nc1ccc(C(=O)NCCC(=O)O)cc1)c1ccc(-c2noc(-c3ccccc3)n2)cc1]

White solid. $^1$H NMR (400 MHz, DMSO-d$_6$): δ 8.17 (d, J=8.8 Hz, 2H), 8.03-8.01 (m, 3H), 7.75-7.58 (m, 5H), 7.50 (d, J=8.8 Hz, 2H), 6.76 (d, J=8.8 Hz, 1H), 6.55 (d, J=8.8 Hz, 2H), 4.54 (q, J=6.8 Hz, 1H), 3.35 (q, J=6.8 Hz, 2H), 2.39 (t, J=6.8 Hz, 2H), 1.78-1.68 (m, 2H), 1.53-1.48 (m, 1H), 0.96 (t, J=6.5 Hz, 3H), 0.90 (t, J=6.5 Hz, 3H). MS(M+1): 499.

Compound 2-11 ethyl 3-(4-((2-methyl-1-(4-(5-(thiophen-2-yl)-1,2,4-oxadiazol-3-yl)phenyl)propyl)amino)benzamido)propanoate

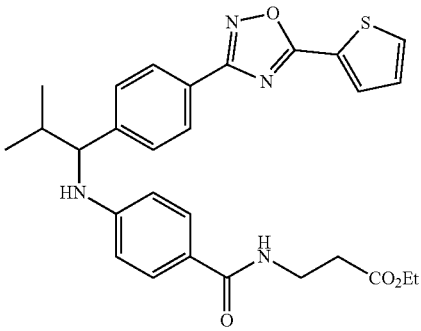 [SMILES: CCOC(=O)CCNC(=O)c1ccc(NC(c2ccc(-c3noc(-c4cccs4)n3)cc2)C(C)C)cc1]

White solid. $^1$H NMR (400 MHz, CDCl$_3$): δ 8.06 (d, J=8.3 Hz, 2H), 7.93-7.92 (m, 1H), 7.64-7.62 (m, 1H), 7.49 (d, J=8.3 Hz, 2H), 7.39 (d, J=8.3 Hz, 2H), 7.21-7.18 (m, 1H), 6.54 (t, J=5.8 Hz, 1H), 6.46 (d, J=6.4 Hz, 1H), 4.22 (t, J=6.8 Hz, 1H), 4.11 (q, J=6.8 Hz, 2H), 3.63 (q, J=6.3 Hz, 2H), 2.55 (t, J=6.3 Hz, 2H), 2.15-2.05 (m, 1H), 1.22 (t, J=6.8 Hz, 3H), 1.00 (d, J=6.5 Hz, 3H), 0.93 (d, J=6.5 Hz, 3H). MS(M+1): 519.

Compound 2-12

3-(4-((2-methyl-1-(4-(5-(thiophen-2-yl)-1,2,4-oxadiazol-3-yl)phenyl)propyl)amino)benzamido)propanoic acid

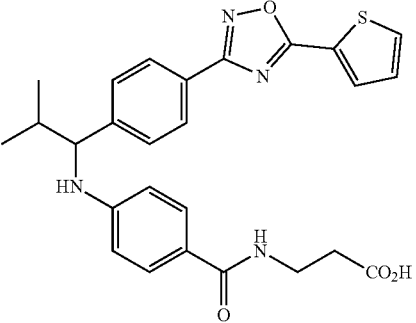 [SMILES: CC(C)C(Nc1ccc(C(=O)NCCC(=O)O)cc1)c1ccc(-c2noc(-c3cccs3)n2)cc1]

White solid. $^1$H NMR (400 MHz, DMSO-d$_6$): δ 8.11-8.06 (m, 2H), 7.99-7.96 (m, 3H), 7.55 (d, J=8.6 Hz, 2H), 7.49 (d, J=8.6 Hz, 2H), 7.37-7.35 (m, 1H), 6.67 (d, J=8.8 Hz, 1H), 6.56 (d, J=8.6 Hz, 2H), 4.26 (t, J=7.6 Hz, 1H), 3.41-3.37 (m, 2H), 2.42 (t, J=6.8 Hz, 2H), 2.06-2.01 (m, 1H), 1.03 (d, J=6.3 Hz, 3H), 0.82 (d, J=6.3 Hz, 3H). MS(M+1): 491.

Compound 2-13

3-(4-((1-(4-(5-(thiophen-2-yl)-1,2,4-oxadiazol-3-yl)phenyl)pentyl)amino)benzamido)propanoic acid

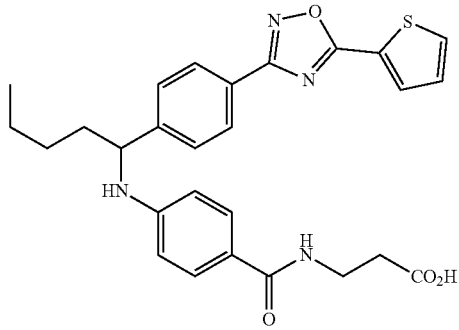 [SMILES: CCCCC(Nc1ccc(C(=O)NCCC(=O)O)cc1)c1ccc(-c2noc(-c3cccs3)n2)cc1]

White solid. $^1$H NMR (400 MHz, DMSO-d$_6$): δ8.11-8.06 (m, 2H), 7.99-7.97 (m, 3H), 7.57 (d, J=8.6 Hz, 2H), 7.50 (d, J=8.6 Hz, 2H), 7.6 (t, J=4.4 Hz, 1H), 6.75 (d, J=8.8 Hz, 1H), 6.53 (d, J=8.6 Hz, 2H), 4.48 (q, J=6.8 Hz, 1H), 3.38-3.33 (m, 2H), 2.41 (t, J=6.8 Hz, 2H), 1.85-1.79 (m, 1H), 1.73-1.70 (m, 1H), 1.43-1.39 (m, 1H), 1.36-1.23 (m, 3H), 0.86 (t, J=6.5 Hz, 3H). MS(M+1): 505.

Compound 2-14

3-(4-((3-methyl-1-(4-(5-(thiophen-2-yl)-1,2,4-oxadiazol-3-yl)phenyl)butyl)amino)benzamido)propanoic acid

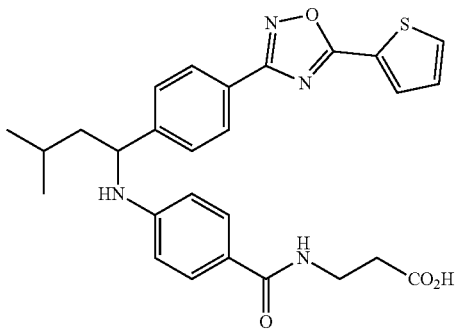 [SMILES: CC(C)CC(Nc1ccc(C(=O)NCCC(=O)O)cc1)c1ccc(-c2noc(-c3cccs3)n2)cc1]

White solid. $^1$H NMR (400 MHz, DMSO-d$_6$): δ8.10-8.08 (m, 1H), 8.07-7.97 (m, 3H), 7.58 (d, J=8.6 Hz, 2H), 7.50 (d, J=8.6 Hz, 2H), 7.35 (dd, J=4.9, 3.4 Hz, 1H), 6.75 (d, J=8.8 Hz, 1H), 6.55 (d, J=8.6 Hz, 2H), 4.54 (q, J=6.8 Hz, 1H), 3.38-3.33 (m, 2H), 2.41 (t, J=6.8 Hz, 2H), 1.78-1.68 (m, 2H), 1.53-1.48 (m, 1H), 0.95 (d, J=6.3 Hz, 3H), 0.90 (d, J=6.3 Hz, 3H). MS(M+1): 505

Compound 2-15

3-(4-((cyclopentyl(4-(5-phenyl-1,2,4-oxadiazol-3-yl)phenyl)methyl)amino)benzamido)propanoic acid

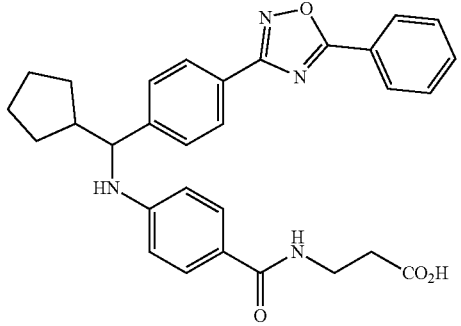 [SMILES: O=C(O)CCNC(=O)c1ccc(NC(c2ccc(-c3noc(-c4ccccc4)n3)cc2)C2CCCC2)cc1]

White solid. $^1$H NMR (400 MHz, CDCl$_3$): δ8.16 (d, J=8.7 Hz, 2H), 8.01-7.98 (m, 3H), 7.73-7.59 (m, 5H), 7.50 (d, J=8.2 Hz, 2H), 6.78 (d, J=8.2 Hz, 1H), 6.56 (d, J=8.7 Hz, 2H), 4.26 (t, J=6.8 Hz, 1H), 3.36 (q, J=6.3 Hz, 2H), 2.42 (t J=6.3 Hz, 2H), 2.25-2.19 (m, 1H), 1.97-1.93 (m, 1H), 1.64-1.41 (m, 5H), 1.26-1.21 (m, 2H). MS(M+1): 511.

Compound 2-16 ethyl 3-(4-((cyclohexyl(4-(5-phenyl-1,2,4-oxadiazol-3-yl)phenyl)methyl)amino)benzamido)propanoate

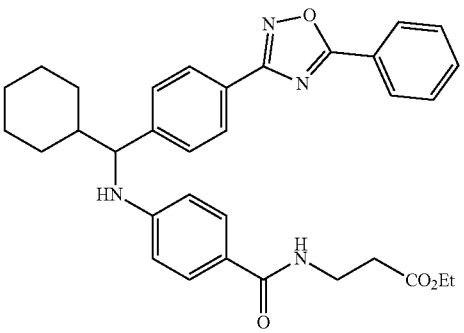 [SMILES: CCOC(=O)CCNC(=O)c1ccc(NC(c2ccc(-c3noc(-c4ccccc4)n3)cc2)C2CCCCC2)cc1]

White solid. $^1$H NMR (400 MHz, DMSO-d$_6$): δ8.21 (d, J=8.6 Hz, 2H), 8.11 (d, J=8.6 Hz, 2H), 7.63-7.49 (m, 5H), 7.41 (4 J=8.6 Hz, 2H), 6.56 (t, J=6.8 Hz, 1H), 6.48 (d, J=8.6 Hz, 2H), 4.53 (d, J=5.4 Hz, 1H), 4.24 (t, J=5.4 Hz, 1H), 4.13 (q, J=5.4 Hz, 2H), 3.64 (q, J=6.3 Hz, 2H), 1.92-1.88 (m, 1H), 1.80-1.69 (m, 4H), 1.27-1.06 (m, 8H). MS(M+1): 553

Compound 2-17

3-(4-((cyclohexyl(4-(5-phenyl-1,2,4-oxadiazol-3-yl)phenyl)methyl)amino)benzamido)propanoic acid

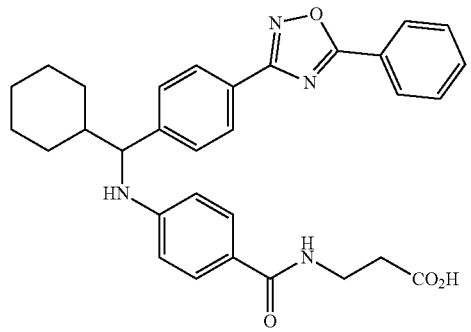 [SMILES: O=C(O)CCNC(=O)c1ccc(NC(c2ccc(-c3noc(-c4ccccc4)n3)cc2)C2CCCCC2)cc1]

White solid. $^1$H NMR (400 MHz, DMSO-d$_6$): δ8.17 (d, J=8.6 Hz, 2H), 8.02-7.95 (m, 3H), 7.75-7.71 (m, 1H), 7.66 (t, J=8.6 Hz, 2H), 7.55 (d, J=8.6 Hz, 2H), 7.48 (d, J=8.6 Hz, 2H), 6.71 (d, J=8.8 Hz, 1H), 6.56 (d, J=8.6 Hz, 2H), 4.28 (t, J=6.8 Hz, 1H), 3.38-3.33 (m, 2H), 2.42 (t, J=6.8 Hz, 2H), 2.01-2.00 (brs, 1H), 1.74-1.61 (m, 4H), 1.37-1.34 (m, 1H), 1.22-0.97 (m, 5H), MS(M+1): 525.

Compound 2-18 ethyl 3-(4-(((1S)-2-methyl-1-(4-(5-phenyl-1,2,4-oxadiazol-3-yl)phenyl)butyl)amino)benzamido)propanoate

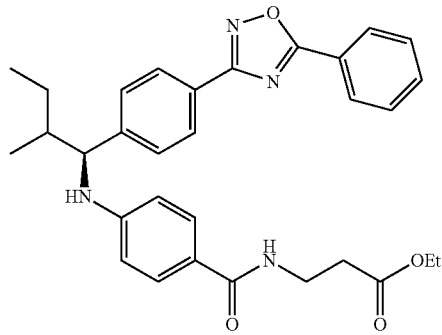 [SMILES: CCOC(=O)CCNC(=O)c1ccc(N[C@H](c2ccc(-c3noc(-c4ccccc4)n3)cc2)C(C)CC)cc1]

$^1$H NMR (400 MHz, DMSO-d$_6$) δ: 8.13-8.23 (m, 2H), 7.94-8.09 (m, 3H), 7.62-7.79 (m, 3H), 7.57 (dd, J=8.0, 5.6 Hz, 2H), 7.49 (dd, J=8.8, 3.2 Hz, 2H), 6.58-6.72 (m, 3H), 4.27-4.45 (m, 1H), 3.95-4.10 (m, 2H), 3.39 (d, J=6.8 Hz, 2H), 2.40-2.55 (m, 2H), 1.76-1.93 (m, 1H), 1.04-1.73 (m, 5H), 0.76-0.97 (m, 6H). MS(M+1): 527.

Compound 2-19

3-(4-(((1S)-2-methyl-1-(4-(5-phenyl-1,2,4-oxadiazol-3-yl)phenyl)butyl)amino)benzamido)propanoic acid

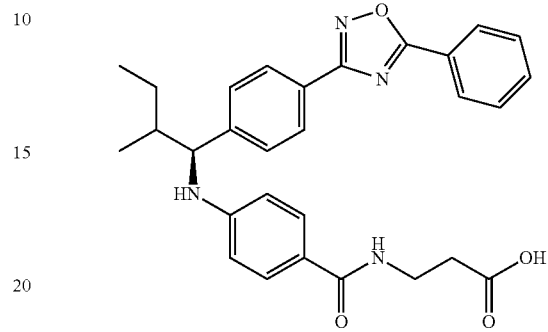

$^1$H NMR (400 MHz, DMSO-d$_6$) δ: 8.18 (d, J=6.8 Hz, 2H), 7.89-8.10 (m, 3H), 7.61-7.80 (m, 3H), 7.40-7.61 (m, 4H) 6.58-6.68 (m, 3H), 4.41 (m, 1H), 3.33-3.43 (m, 2H), 2.42 (t, J=7.2 Hz, 2H), 1.76-1.95 (m, 1H), 1.12-1.66 (m, 2H), 0.75-1.03 (m, 6H). MS(M+1): 499.

Compound 2-20 ethyl 3-(4-(((1R)-2-methyl-1-(4-(5-phenyl-1,2,4-oxadiazol-3-yl)phenyl)butyl)amino)benzamido)propanoate

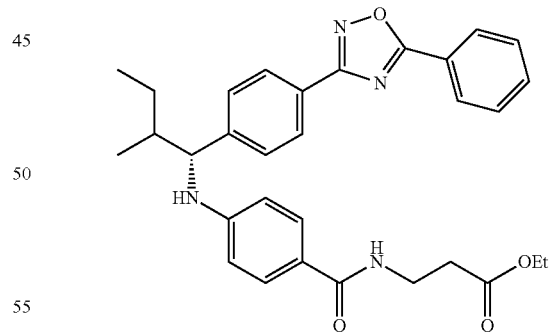

$^1$H NMR. (400 MHz, DMSO-d$_6$) δ: 8.12-8.22 (m, 2H), 7.92-8.08 (m, 3H), 7.69-7.79 (m, 1H), 7.62-7.69 (m, 2H), 7.56 (dd, J=8.0, 5.6 Hz, 2H), 7.49 (dd, J=8.8, 3.2 Hz, 2H), 6.56-6.70 (m, 3H), 4.26-4.49 (m, 1H), 3.94-4.13 (m, 2H), 3.39 (d, J=6.8 Hz, 2H), 2.42-2.53 (m, 2H), 1.57 1.89 (m, 1H), 1.06-1.49 (m, 2H), 0.75-0.97 (m, 6H). MS(M+1): 527.

Compound 1-21

3-(4-(((1R)-2-methyl-1-(4-(5-phenyl-1,2,4-oxadiazol-3-yl)phenyl)butyl)amino)benzamido)propanoic acid

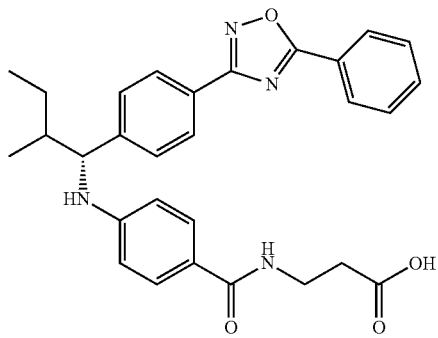 [SMILES: CCC(C)[C@@H](Nc1ccc(C(=O)NCCC(=O)O)cc1)c1ccc(-c2noc(-c3ccccc3)n2)cc1]

$^1$H NMR (400 MHz, DMSO-d$_6$) δ: 8.09-8.24 (m, 2H), 7.92-8.07 (m, 3H), 7.70-7.80 (m, 1H), 7.62-7.70 (m, 2H), 7.57 (dd, J=8.4, 5.6 Hz, 2H), 7.49 (dd, J=8.8, 3.2 Hz, 2H), 6.51-6.68 (m, 3H), 4.32 (m, 1H), 3.31-3.42 (m, 2H), 2.35-2.47 (m, 2H), 1.75-1.92 (m, 1H), 1.05-1.47 (m, 2H), 0.76-1.01 (m, 6H). MS(M+1): 499.

Compound 2-22 ethyl (R)-3-(4-((2-methyl-1-(4-(5-phenyl-1,2,4-oxadiazol-3-yl)phenyl)propyl)amino)benzamido)propanoate

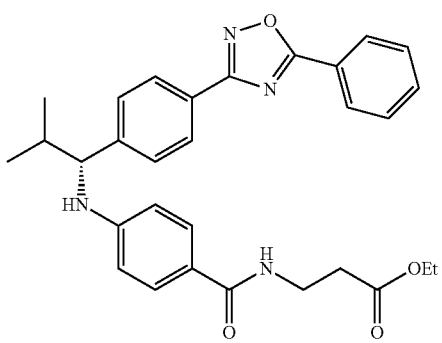 [SMILES: CCOC(=O)CCNC(=O)c1ccc(N[C@@H](c2ccc(-c3noc(-c4ccccc4)n3)cc2)C(C)C)cc1]

$^1$H NMR (400 MHz, DMSO-d$_6$) δ: 8.12-8.24 (m, 2H), 7.93-8.07 (m, 3H), 7.60-7.79 (m, 3H), 7.57 (d, J=8.4 Hz, 2H), 7.43-7.53 (m, 2H), 6.51-6.68 (m, 3H), 4.26 (t, J=7.6 Hz, 1H), 4.02 (q, J=7.2 Hz, 2H), 3.34-3.45 (m, 2H), 2.39-2.55 (m, 2H), 2.05 (m, 1H), 1.14 (t, J=7.2 Hz, 3H), 1.04 (d, J=6.4 Hz, 3H), 0.82 (d, J=6.4 Hz, 3H). MS(M+1): 513.

Compound 2-23

(R)-3-(4-((2-methyl-1-(4-(5-phenyl-1,2,4-oxadiazol-3-yl)phenyl)propyl)amino)benzamido)propanoic acid

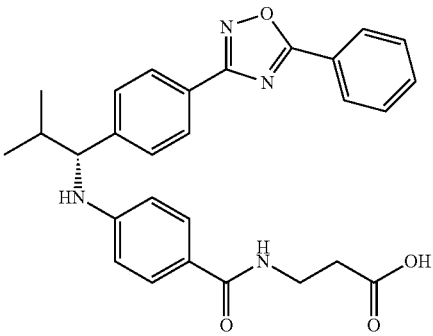 [SMILES: CC(C)[C@@H](Nc1ccc(C(=O)NCCC(=O)O)cc1)c1ccc(-c2noc(-c3ccccc3)n2)cc1]

$^1$H NMR (400 MHz, DMSO-d$_6$): δ8.11-8.26 (m, 2H), 7.90-8.07 (m, 3H), 7.70-7.80 (m, 1H), 7.62-7.70 (m, 2H), 7.57 (d, J=8.4 Hz, 2H), 7.45-7.53 (m, J=8.8 Hz, 2H), 6.47-6.67 (m, 3H), 4.26 (t, J=7.6 Hz, 1H), 3.35 (t, J=7.2 Hz, 2H), 2.42 (t, J=7.2 Hz, 2H), 1.96-2.12 (m, 1H), 1.04 (d, J=6.4 Hz, 3H), 0.82 (d, J=6.8 Hz, 3H), MS(M+1); 485.

Compound 2-24 ethyl 3-(4-((1-(4-(5-(4-fluorophenyl)-1,2,4-oxadiazol-3-yl)phenyl)-2-methylpropyl)amino)benzamido)propanoate

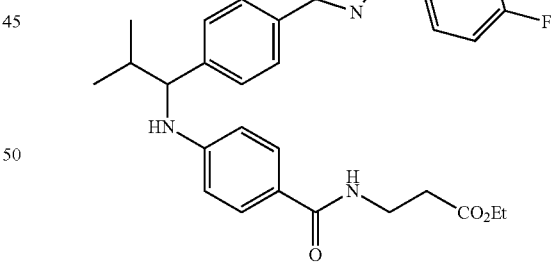

White solid. $^1$H NMR (400 MHz, DMSO-d$_6$): δ8.22-8.19 (m, 2H), 8.08 (d, J=8.8 Hz, 2H), 7.5 (d, J=8.8 Hz, 2H), 7.40 (d, J=8.8 Hz, 2H), 7.23-7.20 (m, 3H), 6.69 (d, J=8.8 Hz, 1H), 6.55 (t, J=8.6 Hz, 1H), 6.47 (d, J=8.6 Hz, 2H), 4.47 (d, J=5.4 Hz, 1H), 4.23 (t, J=5.4 Hz, 1H), 4.11 (q, J=6.8 Hz, 2H), 3.65-3.61 (m, 2H), 2.55 (t, J=6.8 Hz, 2H), 2.12-2.07 (m, 1H), 1.01 (t, J=6.8 Hz, 3H), 0.94 (d, J=6.8 Hz, 3H), 0.82 (d, J=6.8 Hz, 3H). MS(M+1): 531

Compound 2-25

3-(4-((1-(4-(5-(4-fluorophenyl)-1,2,4-oxadiazol-3-yl)phenyl)-2-methylpropyl)amino)benzamido)propanoic acid

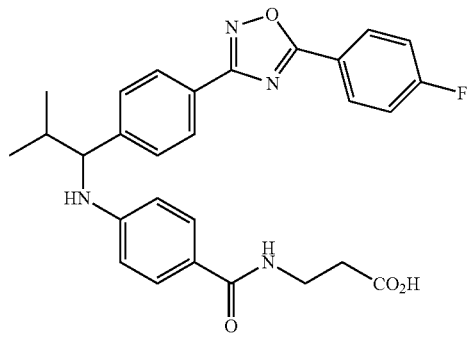 [SMILES: CCOC(=O)CCNC(=O)c1ccc(NC(c2ccc(-c3noc(-c4ccc(F)cc4)n3)cc2)C(C)C)cc1]

White solid. $^1$H NMR (400 MHz, DMSO-$d_6$) δ: 7.46-7.43 (m, 2H), 7.25 (d, J=8.8 Hz, 2H), 6.70 (d, J=8.8 Hz, 4H), 6.54 (t, J=8.8 Hz, 2H), 5.77 (d, J=8.8 Hz, 2H), 3.241 (d, J=5.4 Hz, 1H), 2.75-2.71 (m, 2H), 1.75 (t, J=6.8 Hz, 2H), 1.31-1.26 (m, 1H), 1.23 (t, J=6.8 Hz, 3H), 0.29 (t, J=6.8 Hz, 3H), 0.10 (t, J=6.8 Hz, 3H). MS(M+1): 503

Compound 2-26

3-(4-((2-methyl-1-(4-(5-phenyl-1,2,4-oxadiazol-3-yl)phenyl)propyl)amino)benzamido)propanoic acid

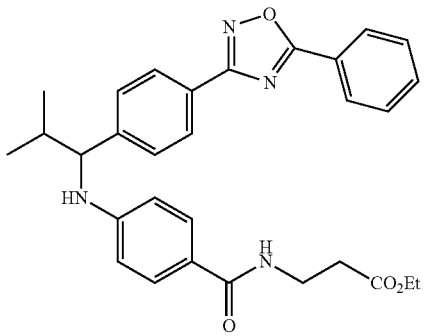 [SMILES: CCOC(=O)CCNC(=O)c1ccc(NC(c2ccc(-c3noc(-c4ccccc4)n3)cc2)C(C)C)cc1]

White solid. $^1$H NMR (400 MHz, DMSO-$d_6$) δ: 8.17 (d, J=8.6 Hz, 2H), 8.02-7.96 (m, 3H), 7.75-7.71 (m, 1H), 7.68-7.64 (m, 2H), 7.57 (d, J=8.6 Hz, 2H), 7.49 (d, J=8.6 Hz, 2H), 6.66 (d, J=8.8 Hz, 2H), 6.57 (d, J=8.6 Hz, 2H), 4.25 (t, J=7.6 Hz, 1H), 2.42 (t, J=6.8 Hz, 2H), 2.05-2.02 (m, 1H), 1.03 (d, J=6.3 Hz, 3H), 0.82 (d, J=6.3 Hz, 3H). MS(M+1): 485.

Compound 2-27 ethyl (S)-3-(4-((2-methyl-1-(4-(5-phenyl-1,2,4-oxadiazol-3-yl)phenyl)propyl)amino)benzamido)propanoate

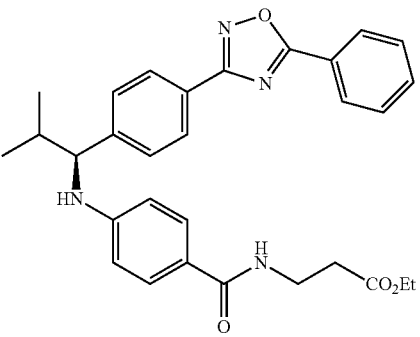

$^1$H NMR (400 MHz, DMSO-$d_6$) δ: 8.13-8.22 (m, 2H), 7.93-8.07 (m, 3H), 7.62-7.78 (m, 3H), 7.57 (d, J=8.4 Hz, 2H), 7.49 (d, J=8.8 Hz, 2H), 6.56-6.69 (m, 3H), 4.26 (s, 1H), 4.02 (q, J=6.8 Hz, 2H), 3.38 (d, J=6.0 Hz, 2H), 2.45-2.49 (m, 2H), 2.00-2.10 (m, 1H), 1.10-1.19 (m, 3H), 1.04 (d, J=6.4 Hz, 3H), 0.82 (d, J=6.4 Hz, 3H). MS(M+1): 513.

Compound 2-28

(S)-3-(4-((2-methyl-1-(4-(5-phenyl-1,2,4-oxadiazol-3-yl)phenyl)propyl)amino)benzamido)propanoic acid

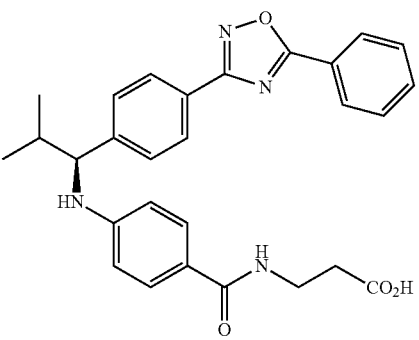 [SMILES: CCOC(=O)CCNC(=O)c1ccc(N[C@H](c2ccc(-c3noc(-c4ccccc4)n3)cc2)C(C)C)cc1]

$^1$H NMR (400 MHz, DMSO-$d_6$) δ: 8.15-8.21 (m, 2H), 7.93-8.05 (m, 3H), 7.61-7.76 (m, 3H), 7.57 (d, J=8.4 Hz, 2H), 7.49 (d, J=8.8 Hz, 2H), 6.56-6.68 (m, 3H), 4.26 (t, J=7.6 Hz, 1H), 3.24-3.42 (m, 2H), 2.42 (t, J=7.2 Hz, 2H), 1.98-2.09 (m, 1H), 1.04 (d, J=6.8 Hz, 3H), 0.82 (d, J=6.8 Hz, 3H). MS(M+1): 485.

Compound 2-29 ethyl 3-(4-(((1S)-2-methyl-1-(4-(5-(trifluoromethyl)-1,2,4-oxadiazol-3-yl)phenyl)butyl)amino)benzamido)propanoate

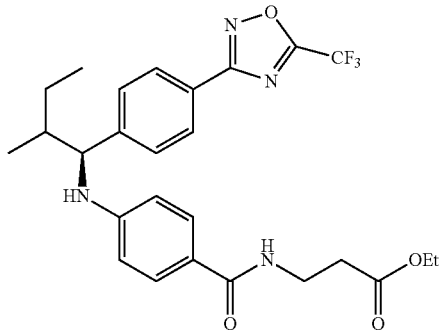 [SMILES: CCOC(=O)CCNC(=O)c1ccc(N[C@H](c2ccc(-c3noc(C(F)(F)F)n3)cc2)C(C)CC)cc1]

$^1$H NMR (400 MHz, DMSO-d$_6$): δ8.05 (dd, J=8.4, 1.6 Hz, 2H), 7.43-7.60 (m, 4H), 6.49-6.64 (m, 2H), 4.24-4.47 (m, 1H), 4.03-4.16 (m, 2H), 3.55 (td, J=6.8, 2.0 Hz, 2H), 2.58 (td, J=6.8, 1.6 Hz, 2H), 1.14-1.99 (m, 6H), 0.75-1.09 (m, 6H). MS(M+1): 519.

Compound 2-30

3-(4-(((1S)-2-methyl-1-(4-(5-(trifluoromethyl)-1,2,4-oxadiazol-3-yl)phenyl)butyl)amino)benzamido)propanoic acid

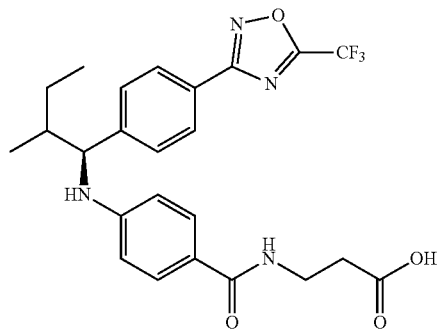 [SMILES: CCC(C)[C@H](Nc1ccc(C(=O)NCCC(=O)O)cc1)c1ccc(-c2noc(C(F)(F)F)n2)cc1]

$^1$H NMR (400 MHz, DMSO-d$_6$) δ: 7.94-8.11 (m, 2H), 7.36-7.60 (m, 4H), 6.46-6.66 (m, 2H), 4.23-4.49 (m, 1H), 3.54 (td, J=6.8, 1.2 Hz, 2H), 2.57 (td, J=6.8, 1.2 Hz, 2H), 1.10-2.01 (m, 3H), 0.71-1.06 (m, 6H). MS(M+1): 491.

Compound 2-31 methyl 3-(4-((2-methyl-1-(4-(5-phenyl-1,2,4-oxadiazol-3-yl)phenyl)propyl)amino)benzamido)propanoate

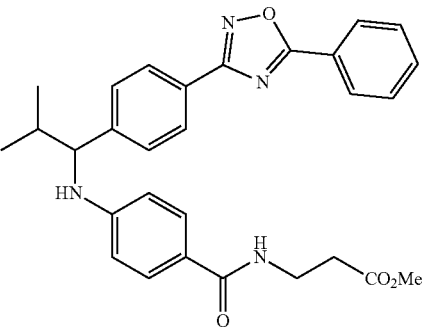 [SMILES: COC(=O)CCNC(=O)c1ccc(NC(c2ccc(-c3noc(-c4ccccc4)n3)cc2)C(C)C)cc1]

White solid. $^1$H NMR (400 MHz, DMSO-d$_6$): δ8.19 (d, J=8.8 Hz, 2H), 8.09 (d, J=8.8 Hz, 2H), 7.61-7.48 (m, 5H), 7.40 (d, J=8.8 Hz, 2H), 6.53 (t, J=8.6 Hz, 1H), 6.47 (d, J=8.8 Hz, 2H), 4.23 (d, J=5.8 Hz, 1H), 3.62-3.60 (m, 2H), 2.57 (t, J=6.8 Hz, 2H), 2.15-2.06 (m, 1H), 1.01 (t, J=6.8 Hz, 3H), 0.94 (t, J=6.8 Hz, 3H). MS(M+1): 499.

Compound 2-32 methyl 3-(4-((1-(4-(5-phenyl-1,2,4-oxadiazol-3-yl)phenyl)pentyl)amino)benzamido)propanoate

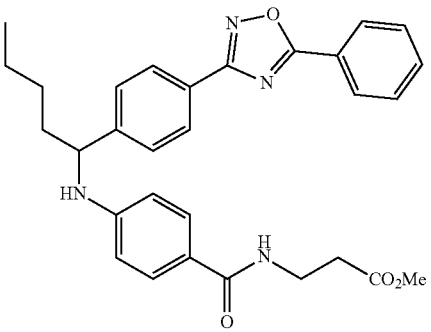 [SMILES: CCCCC(Nc1ccc(C(=O)NCCC(=O)OC)cc1)c1ccc(-c2noc(-c3ccccc3)n2)cc1]

White solid. $^1$H NMR (400 MHz, DMSO-d$_6$): δ8.21 (d, J=8.8 Hz, 2H), 8.12 (d, J=8.8 Hz, 2H), 7.63-7.50 (m, 5H), 7.45 (d, J=8.8 Hz, 2H), 6.55 (t, J=8.6 Hz, 1H), 6.49 (d, K=8.8 Hz, 2H), 4.46-4.40 (m, 2H), 3.66-3.63 (m, 2H), 2.59 (t, J=6.8 Hz, 2H), 1.87-1.81 (m, 2H), 1.43-1.31 (m, 4H), 0.90 (t, J=6.8 Hz, 3H). MS(M+1): 513.

Compound 2-33 ethyl (S)-3-(4-((1-(4-(5-phenyl-1,2,4-oxadiazol-3-yl)phenyl)pentyl)amino)benzamido)propanoate

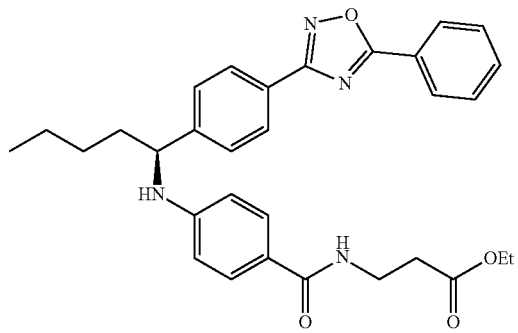

¹H NMR (400 MHz, DMSO-d₆): δ8.17 (d, J=7.3 Hz, 2H), 8.04-7.98 (m, 3H), 7.76-7.70 (m, 1H), 7.69-7.62 (m, 2H), 7.58 (d, J=8.3 Hz, 2H), 7.50 (d, J=8.8 Hz, 2H), 6.75 (d, J=7.3 Hz, 1H), 6.54 (d, J=7.3 Hz, 2H), 4.52-4.45 (m, 1H), 4.03 (q, J=6.8 Hz, 2H), 3.45-3.35 (m, 2H), 2.49-2.46 (m, 2H), 1.89-1.78 (m, 1H), 1.76-1.66 (m, 1H), 1.49-1.22 (m, 4H), 1.14 (t, J=7.1 Hz, 3H), 0.86 (t, J=6.6 Hz, 3H). MS(M+1): 527.

Compound 2-35 ethyl (R)-3-(4-((1-(4-(5-phenyl-1,2,4-oxadiazol-3-yl)phenyl)pentyl)amino)benzamido)propanoate

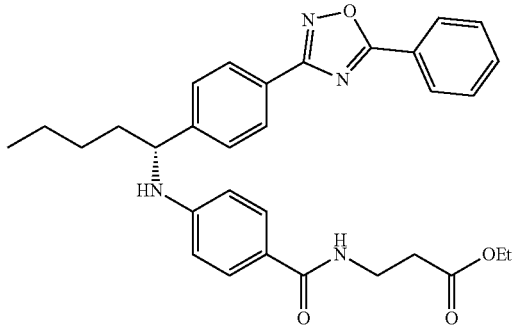

¹H NMR (400 MHz, DMSO-d₆): δ8.18 (d, J=7.3 Hz, 2H), 8.04-7.97 (m, 3H), 7.76-7.71 (m, 1H), 7.69-7.63 (m, 2H), 7.58 (d, J=8.3 Hz, 2H), 7.49 (d, J=8.8 Hz, 2H), 6.75 (d, J=7.3 Hz, 1H), 6.54 (d, J=8.3 Hz, 2H), 4.53-4.44 (m, 1H), 4.03 (q, J=6.8 Hz, 2H), 3.43-3.35 (m, 2H), 2.49-2.44 (m, 2H), 1.89-1.78 (m, 1H), 1.76-1.66 (m, 1H), 1.47-1.23 (m, 4H), 1.14 (t, J=7.1 Hz, 3H), 0.86 (t, J=7.1 Hz, 3H), MS(M+1): 527.

Compound 2-34

(S)-3-(4-((1-(4-(5-phenyl-1,2,4-oxadiazol-3-yl)phenyl)pentyl)amino)benzamido)propanoic acid

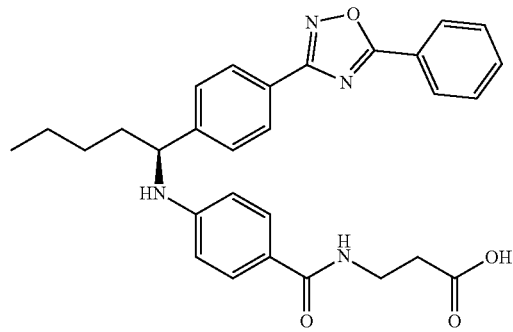 [SMILES: CCCC[C@H](Nc1ccc(C(=O)NCCC(=O)O)cc1)c1ccc(-c2noc(-c3ccccc3)n2)cc1]

¹H NMR (400 MHz, DMSO-d₆): δ8.17 (d, J=7.8 Hz, 2H), 8.02 (d, J=8.3 Hz, 2H), 7.98 (t, J=5.4 Hz, 1H), 7.76-7.70 (m, 1H), 7.69-7.63 (m, 2H), 7.58 (d, J=8.3 Hz, 2H), 7.50 (d, J=8.8 Hz, 2H), 6.75 (d, J=7.3 Hz, 1H), 6.54 (d, J=8.8 Hz, 2H), 4.49 (d, J=6.4 Hz, 1H), 3.39-3.33 (m, 2H), 2.42 (t, J=7.1 Hz, 2H), 1.88-1.78 (m, 1H), 1.76-1.66 (m, 1H), 1.46-1.27 (m, 4H), 0.86 (t, J=6.8 Hz, 3H). MS(M+1): 499.

Compound 2-36

(R)-3-(4-((1-(4-(5-phenyl-1,2,4-oxadiazol-3-yl)phenyl)pentyl)amino)benzamido)propanoic acid

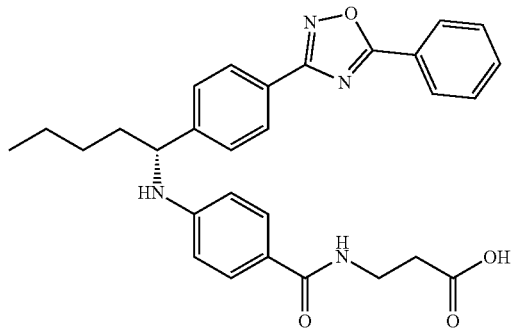 [SMILES: CCCC[C@@H](Nc1ccc(C(=O)NCCC(=O)O)cc1)c1ccc(-c2noc(-c3ccccc3)n2)cc1]

¹H NMR (400 MHz, DMSO-d₆): δ8.17 (d, J=7.8 Hz, 2H), 8.02 (d, J=8.3 Hz, 2H), 7.98 (t, J=5.4 Hz, 1H), 7.76-7.70 (m, 1H), 7.69-7.62 (m, 2H), 7.58 (d, J=8.3 Hz, 2H), 7.50 (d, J=8.3 Hz, 2H), 6.75 (d, J=7.3 Hz, 1H), 6.54 (d, J=8.8 Hz, 2H), 4.49 (d, J=6.8 Hz, 1H), 3.40-3.34 (m, 2H), 2.43 (t, J=7.1 Hz, 2H), 1.88-1.78 (m, 1H), 1.76-1.65 (m, 1H), 1.47-1.26 (m, 4H), 0.86 (t, J=6.8 Hz, 3H). MS(M+1): 499.

Compound 2-37 ethyl (S)-3-(4-((1-(4-(5-(pyridin-2-yl)-1,2,4-oxadiazol-3-yl)phenyl)pentyl)amino)benzamido)propanoate

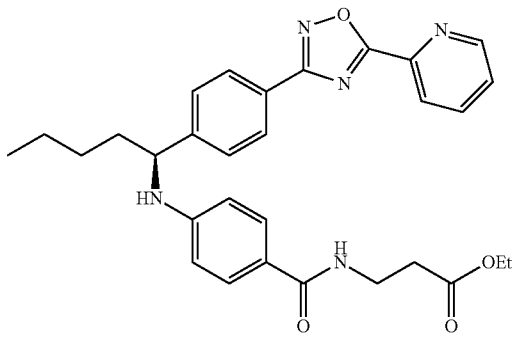 [SMILES: CCCC[C@H](Nc1ccc(C(=O)NCCC(=O)OCC)cc1)c1ccc(-c2noc(-c3ccccn3)n2)cc1]

¹H NMR (400 MHz, DMSO-d₆): δ8.82 (d, J=4.4 Hz, 1H), 8.29 (d, J=7.8 Hz, 1H), 8.08 (dt, J=1.5, 7.8 Hz, 1H), 8.05-7.99 (m, 3H), 7.69 (ddd, J=1.0, 4.9, 7.8 Hz, 1H), 7.58 (d, J=8.3 Hz, 2H), 7.52 (d, J=8.8 Hz, 2H), 6.75 (d, J=7.3 Hz, 1H), 6.55 (d, J=8.8 Hz, 2H), 4.48 (d, J=6.4 Hz, 1H), 4.06-3.97 (m, 2H), 3.44-3.37 (m, 2H), 2.52-2.46 (m, 2H), 1.88-1.78 (m, 1H), 1.75-1.65 (m, 1H), 1.46-1.24 (m, 4H), 1.13 (t, J=7.1 Hz, 3H), 0.84 (t, J=7.1 Hz, 3H). MS(M+1): 528.

Compound 2-38

(S)-3-(4-((1-(4-(5-(pyridin-2-yl)-1,2,4-oxadiazol-3-yl)phenyl)pentyl)amino)benzamido)propanoic acid

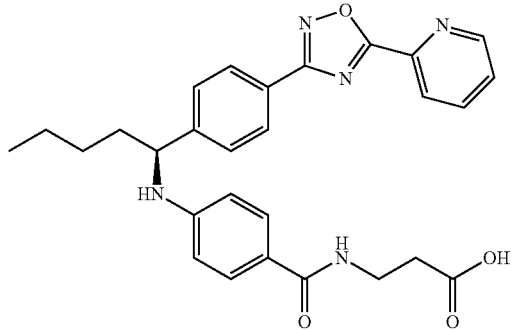 [SMILES: CCCC[C@H](Nc1ccc(C(=O)NCCC(=O)O)cc1)c1ccc(-c2noc(-c3ccccn3)n2)cc1]

¹H NMR (400 MHz, DMSO-d₆): δ8.84 (d, J=4.9 Hz, 1H), 8.31 (d, J=7.8 Hz, 1H), 8.11 (t, J=7.8 Hz, 1H), 8.04 (d, J=8.3 Hz, 2H), 7.98 (t, J=5.6 Hz, 1H), 7.72 (dd, J=4.6, 7.6 Hz, 1H), 7.59 (d, J=8.3 Hz, 2H), 7.51 (d, J=8.3 Hz, 2H), 6.75 (d, J=7.3 Hz, 1H), 6.54 (d, J=8.8 Hz, 2H), 4.49 (q, J=7.3 Hz, 1H), 3.40-3.33 (m, 2H), 2.43 (t, J=7.1 Hz, 2H), 1.90-1.77 (m, 1H), 1.77-1.65 (m, 1H), 1.46-1.25 (m, 4H), 0.86 (t, J=7.1 Hz, 3H). MS(M+1): 500.

Compound 2-39 ethyl (R)-3-(4-((1-(4-(5-(pyridin-2-yl)-1,2,4-oxadiazol-3-yl)phenyl)pentyl)amino)benzamido)propanoate

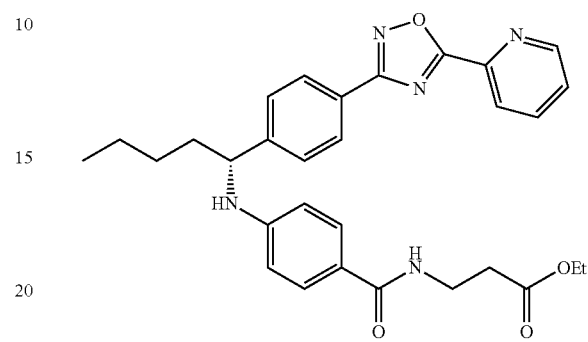

¹H NMR (400 MHz, DMSO-d₆): δ8.82 (dd, J=1.5, 4.4 Hz, 1H), 8.30 (d, J=7.8 Hz, 1H), 8.09 (dt, J=1.7, 7.7 Hz, 1H), 8.05-7.99 (m, 3H), 7.70 (ddd, J=1.0, 4.9, 7.8 Hz, 1H), 7.58 (d, J=8.3 Hz, 2H), 7.52 (d, J=8.8 Hz, 2H), 6.75 (d, J=7.3 Hz, 1H), 6.55 (d, J=8.8 Hz, 2H), 4.48 (d, J=6.8 Hz, 1H), 4.06-3.99 (m, 2H), 3.44-3.37 (m, 2H), 2.52-2.46 (m, 2H), 1.88-1.78 (m, 1H), 1.75-1.66 (m, 1H), 1.46-1.25 (m, 4H), 1.13 (t, J=7.1 Hz, 3H), 0.85 (t, 7.1 Hz, 3H). MS(M+1): 528.

Compound 2-40

(R)-3-(4-((1-(4-(5-(pyridin-2-yl)-1,2,4-oxadiazol-3-yl)phenyl)pentyl)amino)benzamido)propanoic acid

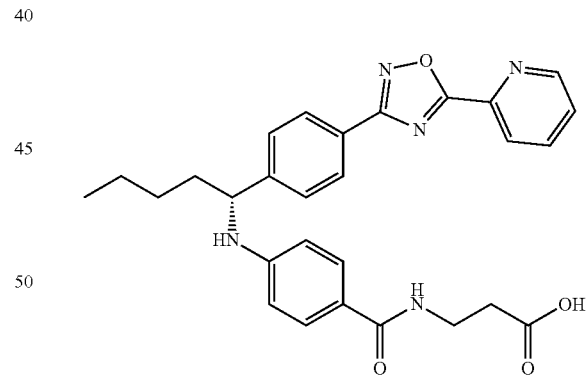

¹H NMR (400 MHz, DMSO-d₆): δ8.84 (d, J=4.9 Hz, 1H), 8.31 (d, J=7.8 Hz, 1H), 8.11 (t, J=7.8 Hz, 1H), 8.04 (d, J=8.3 Hz, 2H), 7.98 (t, J=5.4 Hz, 1H), 7.72 (dd, J=4.6, 7.6 Hz, 1H), 7.59 (d, J=8.3 Hz, 2H), 7.51 (d, 8.3 Hz, 2H), 6.75 (d, J=7.3 Hz, 1H), 6.54 (d, J=8.8 Hz, 2H), 4.49 (q, J=7.3 Hz, 1H), 3.40-3.34 (m, 2H), 2.43 (t, J=7.1 Hz, 2H), 1.90-1.77 (m, 1H), 1.77-1.65 (m, 1H), 1.48-1.24 (m, 4H), 0.86 (t J=7.1 Hz, 3H). MS(M+1): 500.

Compound 2-41 ethyl (S)-3-(4-((3-methyl-1-(4-(5-phenyl-1,2,4-oxadiazol-3-yl)phenyl)butyl)amino)benzamido)propanoate

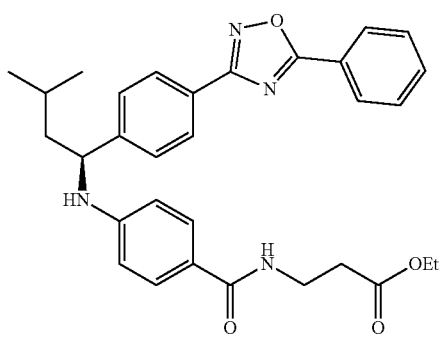 [SMILES: CCOC(=O)CCNC(=O)c1ccc(N[C@@H](CC(C)C)c2ccc(-c3noc(-c4ccccc4)n3)cc2)cc1]

$^1$H NMR (400 MHz, DMSO-d$_6$): δ8.12-8.23 (m, 2H), 7.96-8.07 (m, 3H), 7.72 (d, J=6.8 Hz, 1H), 7.62-7.68 (m, 2H), 7.59 (d, J=8.3 Hz, 2H), 7.51 (d, J=8.3 Hz, 2H), 6.75 (d, J=7.8 Hz, 1H), 6.56 (d, J=8.3 Hz, 2H), 4.50-4.60 (m, 1H), 4.02 (q, J=7.2 Hz, 2H), 3.36-3.45 (m, 2H), 2.44-2.49 (m, 2H), 1.66-1.82 (m, 2H), 1.46-1.56 (m, 1H), 1.14 (t, J=7.1 Hz, 3H), 0.96 (d, J=6.4 Hz, 3H), 0.90 (d, J=6.4 Hz, 3H). MS(M+1): 527.

Compound 2-42 ethyl (R)-3-(4-((3-methyl-1-(4-(5-phenyl-1,2,4-oxadiazol-3-yl)phenyl)butyl)amino)benzamido)propanoate

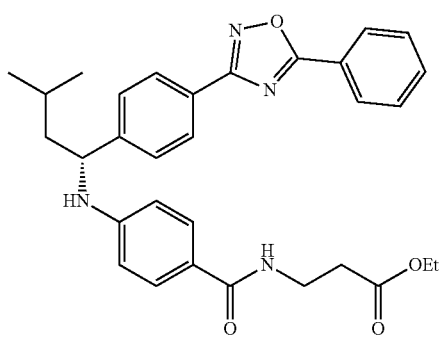 [SMILES: CCOC(=O)CCNC(=O)c1ccc(N[C@H](CC(C)C)c2ccc(-c3noc(-c4ccccc4)n3)cc2)cc1]

$^1$H NMR (400 MHz, DMSO-d$_6$): δ8.12-8.21 (m, 2H), 7.96-8.07 (m, 3H), 7.72 (d, J=6.8 Hz, 1H), 7.62-7.69 (m, 2H), 7.59 (d, J=8.3 Hz, 2H), 7.50 (d, J=8.3 Hz, 2H), 6.74 (d, J=7.8 Hz, 1H), 6.56 (d, J=8.3 Hz, 2H), 4.50-4.60 (m, 1H), 4.02 (q, J=7.3 Hz, 2H), 3.36-3.44 (m, 2H), 2.44-2.49 (m, 2H), 1.62-1.83 (m, 2H), 1.43-1.57 (m, 1H), 1.14 (t, J=7.1 Hz, 3H), 0.96 (d, J=6.4 Hz, 3H), 0.91 (d, J=6.4 Hz, 3H). MS(M+1): 527.

Compound 2-43

(S)-3-(4-((3-methyl-1-(4-(5-phenyl-1,2,4-oxadiazol-3-yl)phenyl)butyl)amino)benzamido)propanoic acid

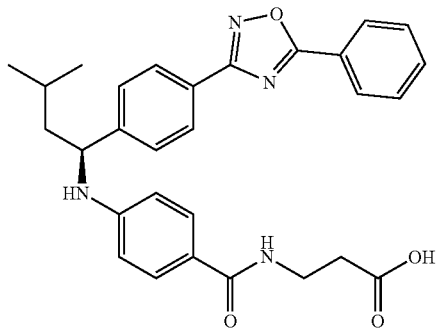 [SMILES: CC(C)C[C@H](Nc1ccc(C(=O)NCCC(=O)O)cc1)c1ccc(-c2noc(-c3ccccc3)n2)cc1]

$^1$H NMR (400 MHz, DMSO-d$_6$): δ8.11-8.22 (m, 2H), 7.95-8.08 (m, 3H), 7.68-7.74 (m, 1H), 7.61-7.67 (m, 2H), 7.59 (d, J=8.3 Hz, 2H), 7.52 (d, J=8.8 Hz, 2H), 6.74 (d, J=7.8 Hz, 1H), 6.57 (d, J=8.8 Hz, 2H), 4.50-4.58 (m, 1H), 3.34-3.41 (m, 2H), 2.43 (t, J=7.1 Hz, 2H), 1.67-1.81 (m, 2H), 1.47-1.55 (m, 1H), 0.96 (d, J=6.4 Hz, 3H), 0.90 (d, J=6.4 Hz, 3H). MS(M+1): 499.

Compound 2-44

(R)-3-(4-((3-methyl-1-(4-(5-phenyl-1,254-oxadiazol-3-yl)phenyl)butyl)amino)benzamido)propanoic acid

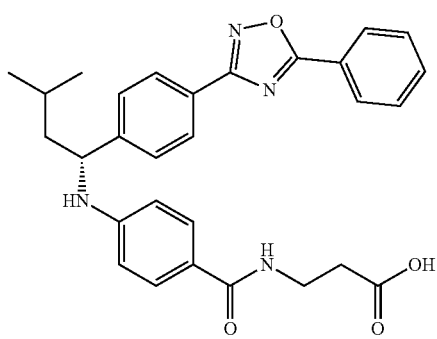 [SMILES: CC(C)C[C@@H](Nc1ccc(C(=O)NCCC(=O)O)cc1)c1ccc(-c2noc(-c3ccccc3)n2)cc1]

$^1$H NMR (400 MHz, DMSO-d$_6$): δ8.12-8.21 (m, 2H), 7.94-8.07 (m, 3H), 7.69-7.75 (m, 1H), 7.62-7.68 (m, 2H), 7.60 (d, J=8.3 Hz, 2H), 7.51 (d, J=8.8 Hz, 2H), 6.74 (d, J=7.3 Hz, 1H), 6.56 (d, J=8.8 Hz, 2H), 4.51-4.60 (m, 1H), 3.34-3.41 (m, 2H), 2.43 (t, J=7.1 Hz, 2H), 1.65-1.82 (m, 2H), 1.45-1.55 (m, 1H), 0.94-0.99 (m, 3H), 0.91 (d, J=6.4 Hz, 3H), MS(M+1): 499.

Compound 2-45 ethyl (S)-3-(4-((1-(4-(5-(trifluoromethyl)-1,2,4-oxadiazol-3-yl)phenyl)pentyl)amino)benzamido)propanoate

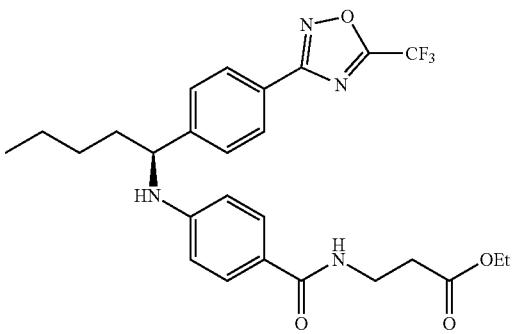 [SMILES: CCCC[C@H](Nc1ccc(C(=O)NCCC(=O)OCC)cc1)c1ccc(-c2noc(C(F)(F)F)n2)cc1]

$^1$H NMR (400 MHz, DMSO-d$_6$): δ7.93-8.05 (m, 3H), 7.60 (d, J=8.3 Hz, 2H), 7.49 (d, J=8.3 Hz, 2H), 6.77 (d, J=7.8 Hz, 1H), 6.53 (d, J=8.8 Hz, 2H), 4.44-4.55 (m, 1H), 4.03 (q, J=7.3 Hz, 2H), 3.39 (q, J=6.5 Hz, 2H), 2.42-2.50 (m, 2H), 1.76-1.88 (m, 1H), 1.63-1.75 (m, 1H), 1.22-1.46 (m, 4H), 1.14 (t, J=7.1 Hz, 3H), 0.85 (t, J=7.1 Hz, 3H). MS(M+1): 519.

Compound 2-46 ethyl (R)-3-(4-((1-(4-(5-(trifluoromethyl)-1,2,4-oxadiazol-3-yl)phenyl)pentyl)amino)benzamido)propanoate

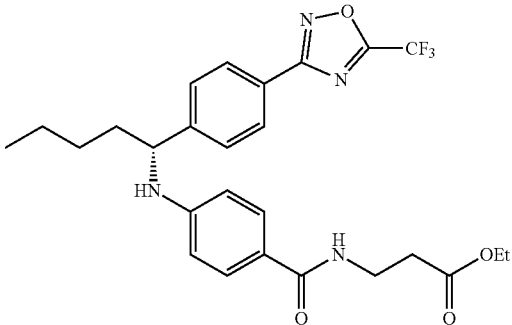 [SMILES: CCCC[C@@H](Nc1ccc(C(=O)NCCC(=O)OCC)cc1)c1ccc(-c2noc(C(F)(F)F)n2)cc1]

$^1$H NMR (400 MHz, DMSO-d$_6$): δ7.93-8.05 (m, 3H), 7.60 (d, J=8.3 Hz, 2H), 7.49 (d, J=8.8 Hz, 2H), 6.77 (d, J=7.8 Hz, 1H), 6.53 (d, J=8.8 Hz, 2H), 4.44-4.55 (m, 1H), 4.03 (q, J=7.3 Hz, 2H), 3.39 (q, J=6.5 Hz, 2H), 2.46-2.50 (m, 2H), 1.77-1.88 (m, 1H), 1.64-1.75 (m, 1H), 1.22-1.45 (m, 4H), 1.14 (t, J=7.1 Hz, 3H), 0.85 (t, J=7.1 Hz, 3H). MS(M+1): 519.

Compound 2-47

(S)-3-(4-((1-(4-(5-(trifluoromethyl)-1,2,4-oxadiazol-3-yl)phenyl)pentyl)amino)benzamido)propanoic acid

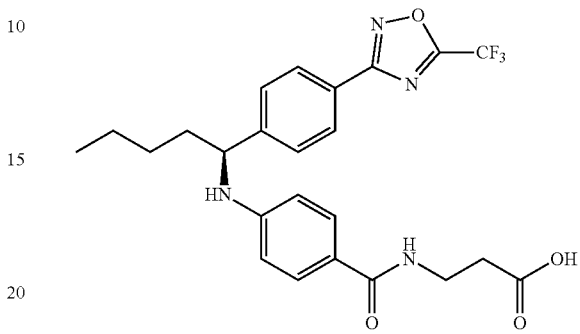

$^1$H NMR (400 MHz, DMSO-d$_6$): δ7.99 (d, J=7.8 Hz, 3H), 7.60 (d, J=8.3 Hz, 2H), 7.49 (d, J=8.8 Hz, 2H), 6.76 (d, J=7.3 Hz, 1H), 6.52 (d, J=8.8 Hz, 2H), 4.43-4.56 (m, 1H), 3.35-3.40 (m, 2H), 2.40-2.47 (m, 2H), 1.76-1.89 (m, 1H, 1.64-1.75 (m, 1H), 1.23-1.46 (m, 4H), 0.85 (t, J=7.1 Hz, 3H). MS(M+1): 491.

Compound 2-48

(R)-3-(4-((1-(4-(5-(trifluoromethyl)-1,2,4-oxadiazol-3-yl)phenyl)pentyl)amino)benzamido)propanoic acid

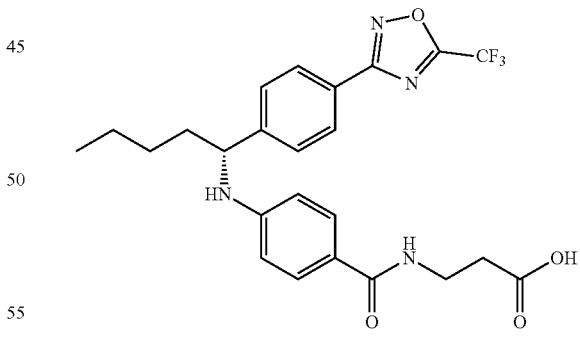

$^1$H NMR (400 MHz, DMSO-d$_6$): δ7.99 (d, J=8.3 Hz, 3H), 7.60 (d, J=8.3 Hz, 2H), 7.50 (d, J=8.8 Hz, 2H), 6.76 (d, J=7.3 Hz, 1H), 6.53 (d, J=8.6 Hz, 2H), 4.43-4.56 (m, 1H), 3.35-3.40 (m, 2H), 2.40-2.47 (m, 2H), 1.77-1.90 (m, 1H), 1.60-1.74 (m, 1H), 1.22-1.45 (m, 4H), 0.85 (t, J=7.1 Hz, 3H). MS(M+1): 491.

Compound 2-49
methyl (S)-3-(4-((2-methyl-1-(4-(5-phenyl-1,2,4-oxadiazol-3-yl)phenyl)propyl)amino)benzamido)propanoate
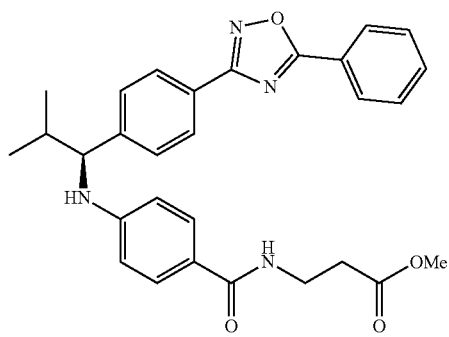 [SMILES: COC(=O)CCNC(=O)c1ccc(N[C@H](c2ccc(-c3noc(-c4ccccc4)n3)cc2)C(C)C)cc1]
$^1$H NMR (400 MHz, DMSO-d$_6$): δ8.14-8.19 (m, 2H), 7.97-8.03 (m, 3H), 7.70-7.76 (m, 1H), 7.62-7.69 (m, 2H), 7.53-7.59 (m, 2H), 7.45-7.50 (m, 2H), 6.64-6.68 (m, 1H), 6.54-6.59 (m, 2H), 4.22-4.28 (m, 1H), 3.55-3.56 (m, 3H), 2.68 (s, 8H), 1.99-2.09 (m, 1H), 1.01-1.06 (m, 3H), 0.79-0.84 (m, 3H) MS(M+1): 499.
Example 3: Synthesis of the Compounds Shown in the Following Table 3
The following scheme was followed for synthesizing Compounds 3-1 to 3-15.
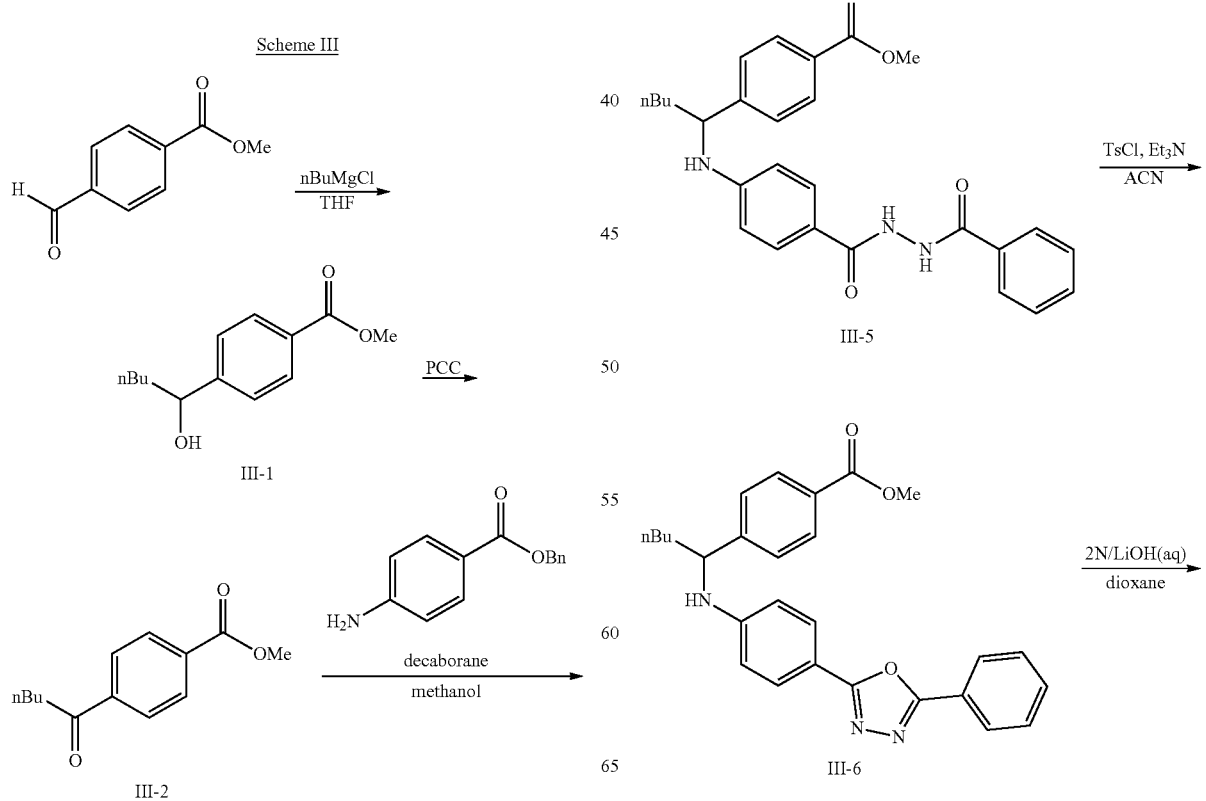
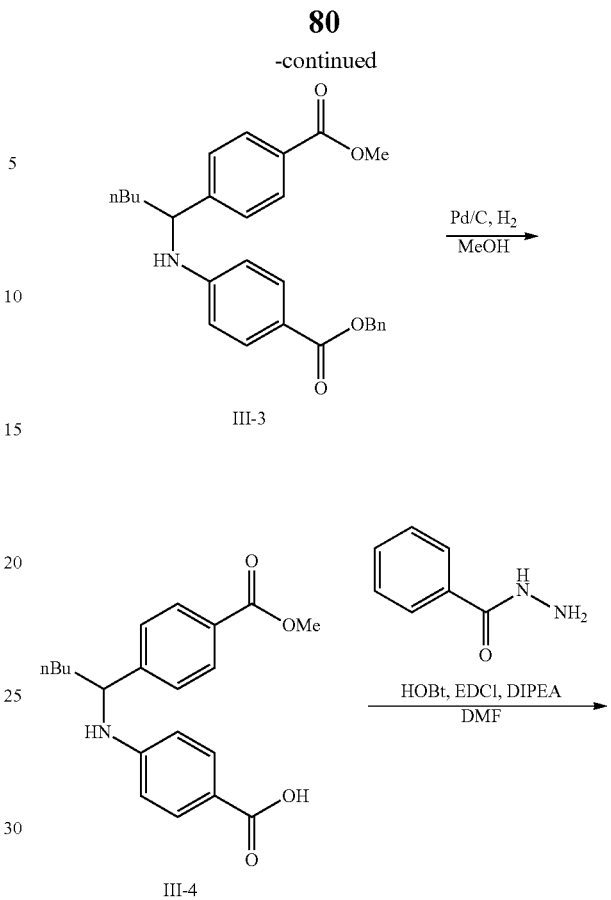

Step II: Oxidation Reaction

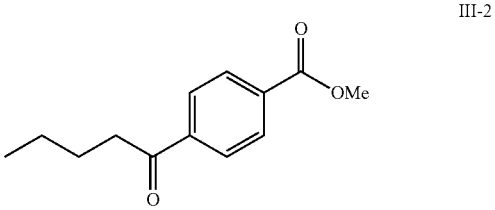 [SMILES: CCCCC(=O)c1ccc(C(=O)OC)cc1]

To a solution of methyl 4-(1-hydroxypentyl)benzoate III-1 (4.45 g, 20.0 mmol) in absolute DCM (100 mL) was added PCC (6.04 g, 28.0 mmol) at room temperature overnight. The mixture was filtered by celite to remove residual PCC. Then extracted with ethyl acetate. The organic layer was dried over magnesium sulfate. Purification by silica gel chromatography (EA:Hex=10:90) gave compound III-2, white solid, yield (4.10 g, 93%).

Step III: Reductive Animation Reaction

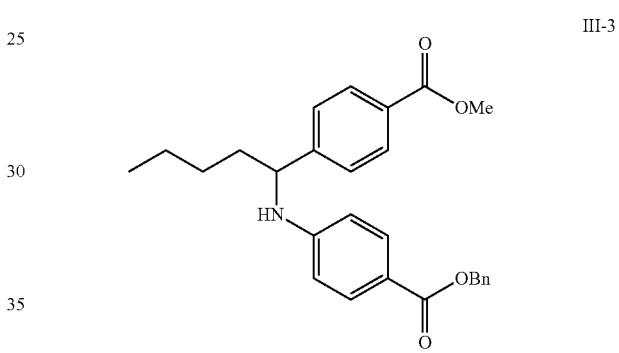

To a solution of compound III-2 (1.10 g, 5 mmol), benzyl 4-aminobenzoate (1.05 g, 4.6 mmol) and decaborane (0.34 g, 2.75 mmol) in 20 mL methanol. The reaction was stirred at room temperature for overnight then concentrated in vacuo. Water was added to the residue and the aqueous layer was extracted with ethyl acetate. Purification of the crude oil residue by column chromatography (EA:Hex=35:65) afforded colorless oil product III-3 (1.90 g, 88%).

Step IV: Deprotection Reaction

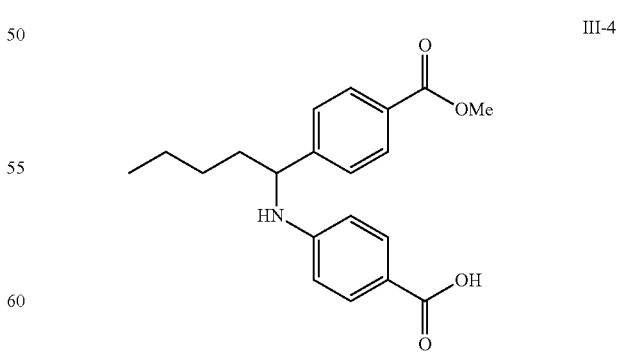

Compound III-3 (1.90 g, 4.40 mmol) was dissolved in methanol (100 mL) followed by addition Pd/C and H₂ balloon. The reaction was still for overnight. The reaction was monitored by TLC. With completion of the reaction, the

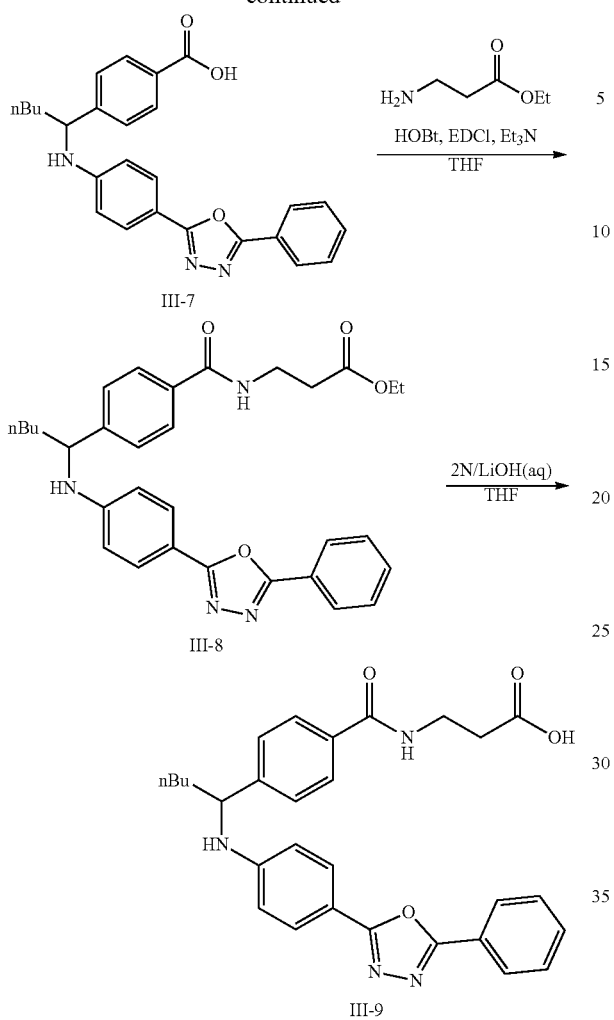

Step I: Grignard Reaction

A solution of methyl 4-formylbenzoate (9.84 g, 60.0 mmol) in tetrahydrofuran (30 mL) was cooled to −78° C. To this solution was added 2M/butylmagnesium chloride (30 mL) dropwise over 20 minutes. The reaction was stirred at −78° C. for 2 h. The reaction was then quenched by addition of saturated aqueous ammonium chloride. This mixture was extracted with ethyl acetate. The organic layer was dried over magnesium sulfate, filtered and concentrated. Purification by silica gel chromatography gave methyl 4-(1-hydroxypentyl)benzoate III-1. Colorless oil, yield (4.80 g, 36%).

solvent was removed by rotary evaporation. It was extracted with EtOAc. The combined organic layer was dried with anhydrous Mg₂SO₄ and concentrated in vacuo to give white solid product III-4 (0.8 g, 53%).

Step V: Amidation Reaction

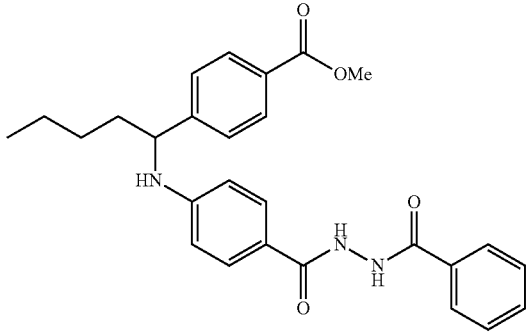

A solution of III-4 (2.34 g, 6.85 mmol), benzohydrazide (7.7 g, 7.53 mmol), EDCI (2.0 g, 10.28 mmol) and HOBt (1.58 g, 10.28 mmol) was prepared in 30 mL DMF. The reaction was stirred at room temperature for overnight then concentrated in vacuo. Water was added to the residue and the aqueous layer was extracted with ethyl acetate. It was further concentrated in vacuo to give white solid product III-5 (1.0 g, 93%).

Step VI: Annulation Reaction

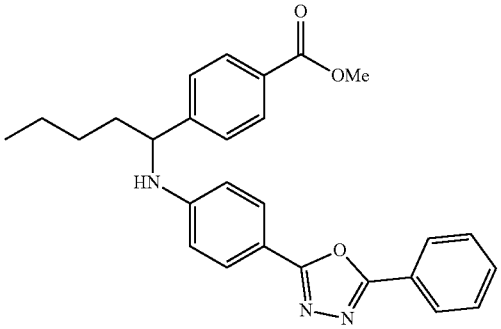

Compounds III-5 (1.0 g, 2.2 mmol), TsCl (0.62 g, 3.3 mmol), and TEA (1.0 mL, 6.51 mmol) were mixed in ACN (30 mL) was stirred at room temperature for 1 hr. To this reaction solution, concentrated to remove methanol and extracted with EtOAc. The organic layer was washed with water and dried over anhydrous magnesium sulfate. It was filtered, the solvent evaporated under reduced pressure. Purification of the crude oil residue by column chromatography (EA:Hex=40:60) afforded colorless oil product III-6 (0.70 g, 73%).

Step VII: Hydrolysis Reaction

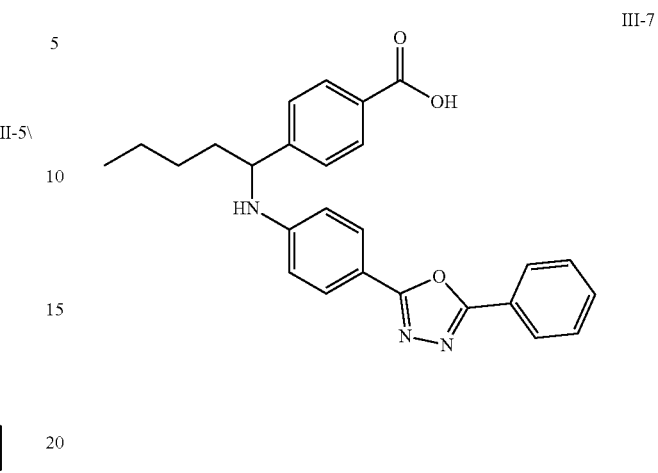

Compound III-6 (0.70 g, 1.58 mmol) was dissolved in dioxane (20 mL) followed by addition of 2M LiOH(aq) 20 mL. The reaction mixture was heat to 60° C. for overnight. The reaction was monitored by TLC. With completion of the reaction, the solvent was removed by rotary evaporation and was added HCl$_{(aq)}$ to pH4~5. The mixture cpd. was extracted with EtOAc. The combined organic layer was dried with anhydrous MgSO₄ and concentrated in vacuo to give (white solid) crude III-7 (0.74 g, 108%).

Step VIII: Amidation Reaction

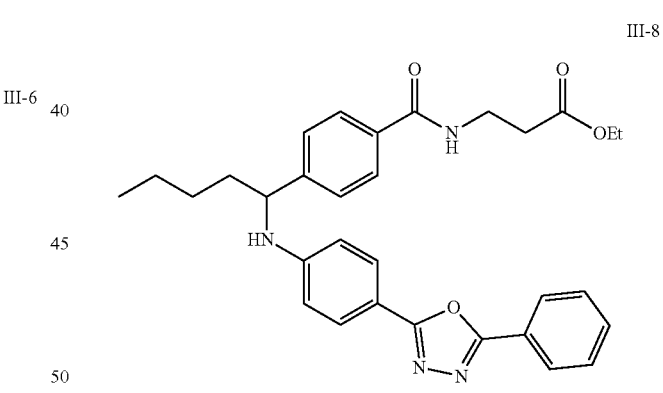

To a Solution of compound III-7 (0.36 g, 0.84 mmol). β-alanine ethyl ester hydrochloride (0.19 g, 1.27 mmol), EDCI (0.24 g, 1.27 mmol), Et₃N (0.26 g, 2.54 mmol) and HOBt (0.19 g, 1.27 mmol) in dry 30 mL THF. The reaction was stirred at room temperature for overnight then concentrated in vacuo. Water was added to the residue and the aqueous layer was extracted with ethyl acetate. It was further concentrated in vacuo to give a residue. Purification of the crude oil residue by column chromatography (EA:Hex=60:40) afforded white solid product III-8 (0.30 g, 68%).

Step IX: Hydrolysis Reaction

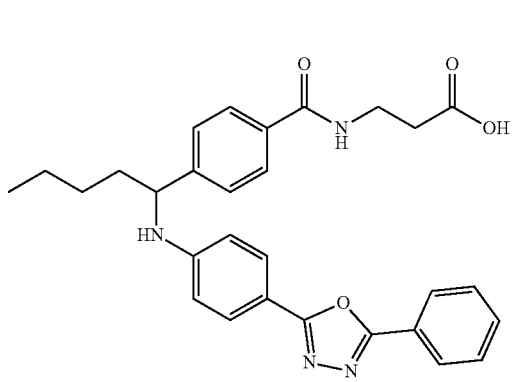

III-9

Compound III-8 (0.20 g, 0.38 mmol) was dissolved in THF (20 mL) followed by addition of 2M LiOH(aq) 20 mL. The reaction mixture stirred at room temperature for 2 h. The reaction was monitored by TLC. With completion of the reaction, the solvent was removed by rotary evaporation and was added $HCl_{(aq)}$ to pH4~5. The mixture cpd. was extracted with EtOAc. The combined organic layer was dried with anhydrous $MgSO_4$ and concentrated in vacuo. Purification of the crude oil residue by column chromatography (EA:Hex=90:10) afforded white solid product III-9 (0.17 g, 89%).

Compound 3-1

3-(4-(1-((4-(5-phenyl-1,3,4-oxadiazol-2-yl)phenyl)amino)pentyl)benzamido)propanoic acid

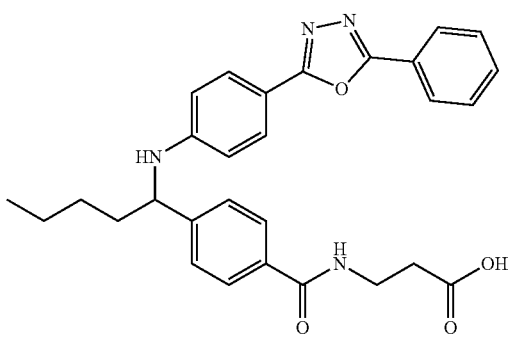 [SMILES: CCCCC(Nc1ccc(-c2nnc(-c3ccccc3)o2)cc1)c1ccc(C(=O)NCCC(=O)O)cc1]

$^1$H NMR (400 MHz, DMSO-$d_6$): δ8.42 (t, J=5.2 Hz, 1H), 8.02-8.07 (m, 2H), 7.76 (d, J=8.0 Hz, 2H), 7.73 (d, J=8.4 Hz, 2H), 7.55-7.63 (m, 3H), 7.45 (d, J=8.4 Hz, 2H), 7.04 (d, J=7.2 Hz, 1H), 6.69 (d, J=8.8 Hz, 2H), 4.46-4.53 (m, 1H), 3.40-3.48 (m, 2H), 2.44-2.49 (m, 2H), 1.65-1.91 (m, 2H), 1.20-1.48 (m, 4H), 0.82-0.90 (m, 3H). MS(M+1): 499.

Compound 3-2

3-(4-(2-methyl-1-((4-(5-phenyl-1,3,4-oxadiazol-2-yl)phenyl)amino)propyl)benzamido)propanoic acid

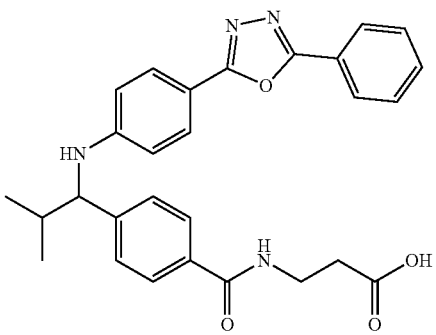 [SMILES: CC(C)C(Nc1ccc(-c2nnc(-c3ccccc3)o2)cc1)c1ccc(C(=O)NCCC(=O)O)cc1]

$^1$H NMR (400 MHz, DMSO-$d_6$): δ8.43 (t, J=5.6 Hz, 1H), 8.00-8.10 (m, 2H), 7.74 (dd, J=15.4, 8.6 Hz, 4H), 7.55-7.63 (m, 3H), 7.44 (d, J=8.3 Hz, 2H), 6.96 (d, J=7.8 Hz, 1H), 6.72 (d, J=8.8 Hz, 2H), 4.27 (t, J=7.6 Hz, 1H), 3.40-3.45 (m, 2H), 1.99-2.10 (m, 1H), 1.04 (d, J=6.8 Hz, 3H), 0.80 (d, J=6.8 Hz, 3H). MS(M+1): 485.

Compound 3-3 ethyl 3-(4-(1-((4-(5-phenyl-1,3,4-oxadiazol-2-yl)phenyl)amino)pentyl)benzamido)propanoate

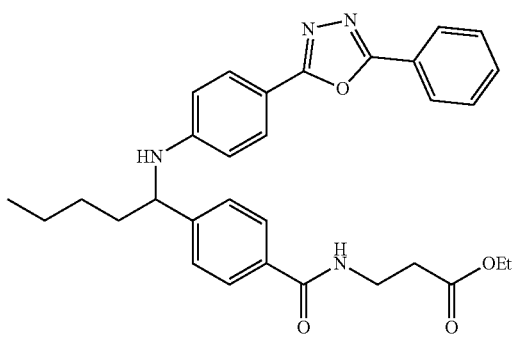 [SMILES: CCCCC(Nc1ccc(-c2nnc(-c3ccccc3)o2)cc1)c1ccc(C(=O)NCCC(=O)OCC)cc1]

$^1$H NMR (400 MHz, DMSO-$d_6$): δ8.37-8.51 (m, 1H), 8.02-8.06 (m, 2H), 7.72-7.76 (m, 4H), 7.56-7.62 (m, 3H), 7.46 (d, J=8.4 Hz, 2H), 6.98-7.12 (m, 1H), 6.69 (d, J=8.8 Hz, 2H), 4.41-4.59 (m, 1H), 4.04 (d, J=6.8 Hz, 2H), 3.46 (m, 2H), 2.54 (t, J=6.8 Hz, 2H), 1.76-1.93 (m, 1H), 1.59-1.76 (m, 1H), 1.20-1.47 (m, 4H), 1.15 (t, J=6.8 Hz, 3H), 0.86 (t, J=6.8 Hz, 3H). MS(M+1): 527.

Compound 3-4 ethyl 3-(4-(2-methyl-1-(4-(5-phenyl-1,3,4-oxadi-azol-2-yl)phenyl)amino)propyl)benzamido)propanoate

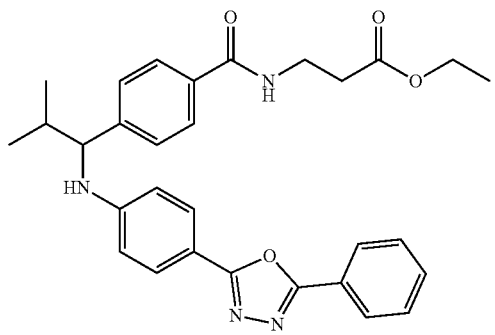 [SMILES: CCOC(=O)CCNC(=O)c1ccc(C(Nc2ccc(-c3nnc(-c4ccccc4)o3)cc2)C(C)C)cc1]

¹H NMR (400 MHz, DMSO-d₆): δ8.36-8.52 (m, 1H), 7.99-8.11 (m, 2H), 7.67-7.83 (m, 4H), 7.53-7.64 (m, 3H), 7.35-7.49 (m, 2H), 6.89-7.02 (m, 1H), 6.64-6.80 (m, 2H), 4.22-4.33 (m, 1H), 3.99-4.13 (m, 2H), 3.43-3.48 (m, 3H), 2.51-2.56 (m, 2H), 1.97-2.10 (m, 1H), 1.15 (s, 3H), 1.01-1.06 (m, 3H), 0.78-0.82 (m, 3H). MS(M+1): 513.

Compound 3-5 ethyl 3-(4-(2-methyl-1-((4-(5-phenyl-1,3,4-oxadi-azol-2-yl)phenyl)amino)butyl)benzamido)propanoate

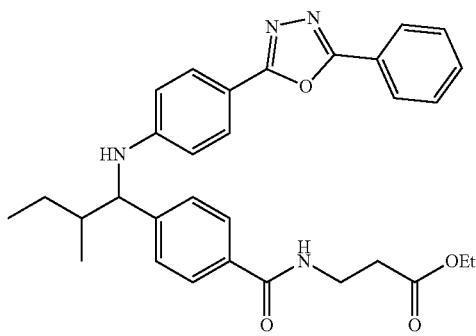 [SMILES: CCOC(=O)CCNC(=O)c1ccc(C(Nc2ccc(-c3nnc(-c4ccccc4)o3)cc2)C(C)CC)cc1]

¹H NMR (400 MHz, DMSO-d₆): δ8.45 (s, 1H), 8.02-8.07 (m, 2H), 7.70-7.77 (m, 4H), 7.56-7.63 (m, 3H), 7.44 (dd, J=8.4, 5.6 Hz, 2H), 6.83-7.04 (m, 1H), 6.73 (dd, J=8.8, 6.0 Hz, 2H), 4.26-4.52 (m, 1H), 4.04 (q, J=7.2 Hz, 2H), 3.46 (m, 2H), 2.54 (t, J=7.2 Hz, 2H), 1.73-1.92 (m, 1H), 1.03-1.46 (m, 5H), 0.65-0.99 (m, 6H). MS(M+1): 527.

Compound 3-6

3-(4-(2-methyl-1-((4-(5-phenyl-1,3,4-oxadiazol-2-yl)phenyl)amino)butyl)benzamido)propanoic acid

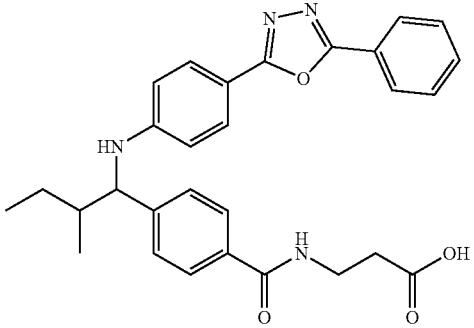 [SMILES: CCC(C)C(Nc1ccc(-c2nnc(-c3ccccc3)o2)cc1)c1ccc(C(=O)NCCC(=O)O)cc1]

¹H NMR (400 MHz, DMSO-d₆): δ12.19 (br. s., 1H), 8.43 (t, J=5.6 Hz, 1H), 8.02-8.07 (m, 2H), 7.70-7.78 (m, 4H), 7.55-7.63 (m, 3H), 7.44 (dd, J=8.4, 5.2 Hz, 2H), 6.84-7.02 (m, 1H), 6.73 (dd, J=8.8, 6.0 Hz, 2H), 4.28-4.47 (m, 1H), 3.37-3.50 (m, 2H), 2.46-2.52 (m, 2H), 1.02-1.93 (m, 3H), 0.66-1.00 (m, 6H). MS(M+1): 499.

Compound 3-7 ethyl 3-(4-(1-((4-(5-(4-fluorophenyl)-1,3,4-oxadi-azol-2-yl)phenyl)amino)-2-methylbutyl)benzamido)propanoate

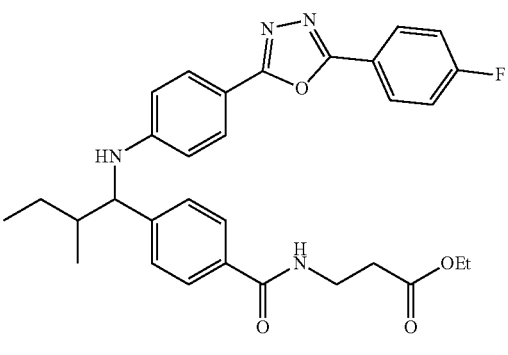

¹H NMR (400 MHz, DMSO-d₆): δ8.45 (t, J=5.6 Hz, 1H), 8.07-8.13 (m, 2H), 7.69-7.77 (m, 4H), 7.41-7.47 (m, 4H), 6.82-7.04 (m, 1H), 6.73 (dd, J=8.4, 6.0 Hz, 2H), 4.26-4.48 (m, 1H), 4.04 (q, J=6.8 Hz, 2H), 3.42-3.49 (m, 2H), 2.54 (t, J=6.8 Hz, 2H), 1.78-1.88 (m, 1H), 1.02-1.45 (m, 5H), 0.66-1.00 (m, 6H). MS(M+1): 545.

Compound 3-8

3-(4-(1-((4-(5-(4-fluorophenyl)-1,3,4-oxadiazol-2-yl)phenyl)amino)-2-methylbutyl)benzamido)propanoic acid

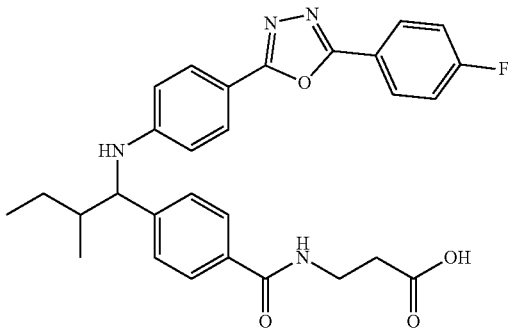 [SMILES: CCC(C)C(Nc1ccc(-c2nnc(-c3ccc(F)cc3)o2)cc1)c1ccc(C(=O)NCCC(=O)O)cc1]

¹H NMR (400 MHz, DMSO-d₆): δ12.19 (br. s., 1H), 8.43 (t, J=5.2 Hz, 1H), 8.10 (dd, J=8.8, 5.6 Hz, 2H), 7.67-7.81 (m, 4H), 7.37-7.50 (m, 4H), 6.84-7.02 (m, 1H), 6.73 (dd, J=8.4, 6.4 Hz, 2H), 4.29-4.44 (m, 1H), 3.37-3.48 (m, 2H), 2.43-2.54 (m, 2H), 1.77-1.88 (m, 1H), 1.21-1.41 (m, 1H), 1.03-1.21 (m, 1H), 0.64-1.00 (m, 6H). MS(M+1): 517.

Compound 3-9 ethyl 3-(4-(1-((4-(5-(4-fluorophenyl)-1,3,4-oxadiazol-2-yl)phenyl)amino)-2-methylpropyl)benzamido)propanoate

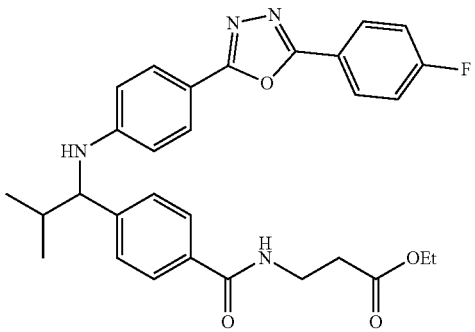 [SMILES: CC(C)C(Nc1ccc(-c2nnc(-c3ccc(F)cc3)o2)cc1)c1ccc(C(=O)NCCC(=O)O)cc1]

¹H NMR (400 MHz, DMSO-d₆): δ8.38-8.50 (m, 1H), 8.10 (dd, J=8.8, 5.4 Hz, 2H), 7.73 (dd, J=12.0, 8.6 Hz, 4H), 7.38-7.50 (m, 4H), 6.90-7.03 (m, 1H), 6.72 (d, J=8.8 Hz, 2H), 4.21-4.34 (m, 1H), 4.04 (d, J=7.3 Hz, 2H), 3.46 (d, J=5.9 Hz, 2H), 2.54 (t, J=6.8 Hz, 2H), 1.95-2.12 (m, 1H), 1.15 (t, J=7.1 Hz, 3H), 1.04 (d, J=6.8 Hz, 3H), 0.80 (d, J=6.8 Hz, 3H). MS(M+1): 531.

Compound 3-10

3-(4-(1-((4-(5-(4-fluorophenyl)-1,3,4-oxadiazol-2-yl)phenyl)amino)-2-methylpropyl)benzamido)propanoic acid

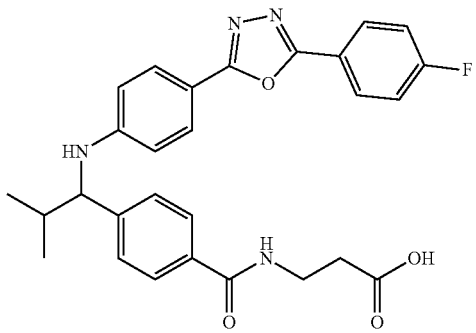

¹H NMR (400 MHz, DMSO-d₆): δ11.78-12.54 (m, 1H), 8.42 (t, J=5.4 Hz, 1H), 8.05-8.16 (m, 2H), 7.74 (dd, J=15.9, 8.6 Hz, 4H), 7.39-7.50 (m, 4H), 6.97 (d, J=7.8 Hz, 1H), 6.72 (d, J=8.8 Hz, 2H), 4.27 (t, J=7.6 Hz, 1H), 3.39-3.47 (m, 2H), 2.43-2.49 (m, 2H), 2.04 (d, J=7.3 Hz, 1H), 1.04 (d, J=6.8 Hz, 3H), 0.80 (d, J=6.8 Hz, 3H). MS(M+1): 503.

Compound 3-11

3-(4-(2-methyl-1-((4-(5-phenyl-1,2,4-oxadiazol-3-yl)phenyl)amino)propyl)benzamido)propanoic acid

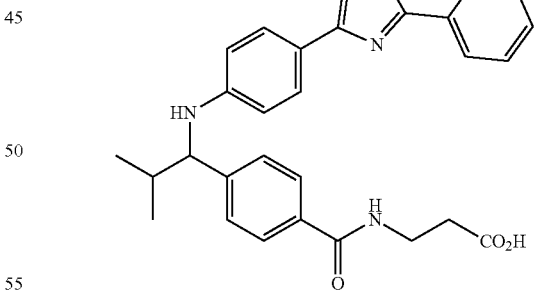

White solid. ¹H NMR. (400 MHz, DMSO-d₆): δ8.43 (d, J=8.6 Hz, 1H), 8.12 (d, J=8.6 Hz, 2H), 7.76-7.61 (m, 7H), 7.44 (d, J=8.6 Hz, 2H), 6.81 (d, J=8.6 Hz, 1H), 6.70 (d, J=8.8 Hz, 2H), 4.24 (t, J=7.6 Hz, 1H), 3.45-3.43 (q, J=6.8 Hz, 2H), 2.47 (t, J=6.8 Hz, 2H), 2.05-2.02 (m, 1H), 1.03 (d, J=6.3 Hz, 3H), 0.80 (d, J=6.3 Hz, 3H). MS(M+1): 485.

Compound 3-12

(S)-ethyl 3-(4-(2-methyl-1-(4-(5-phenyl-1,3,4-oxadiazol-2-yl)phenylamino)propyl)benzamido)propanoate

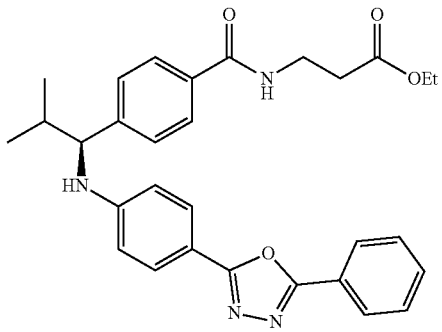 [SMILES: CCOC(=O)CCNC(=O)c1ccc([C@@H](Nc2ccc(-c3nnc(-c4ccccc4)o3)cc2)C(C)C)cc1]

$^1$H NMR (400 MHz, DMSO-d$_6$): δ8.40-8.50 (m, 1H), 7.97-8.12 (m, 2H), 7.74 (dd, J=12.0, 8.8 Hz, 4H), 7.53-7.65 (m, 3H), 7.44 (d, J=8.4 Hz, 2H), 6.71-6.98 (m, 3H), 4.21-4.34 (m, 1H), 4.04 (q, J=7.2 Hz, 2H), 3.46 (d, J=6.0 Hz, 2H), 2.54 (t, J=7.2 Hz, 2H), 1.99-2.11 (m, 1H), 1.15 (t, J=7.2 Hz, 3H), 1.03 (d, J=6.8 Hz, 3H), 0.80 (d, J=6.8 Hz, 3H). MS(M+1): 513.

Compound 3-13

(R)-ethyl 3-(4-(2-methyl-1-(4-(5-phenyl-1,3,4-oxadiazol-2-yl)phenylamino)propyl)benzamido)propanoate

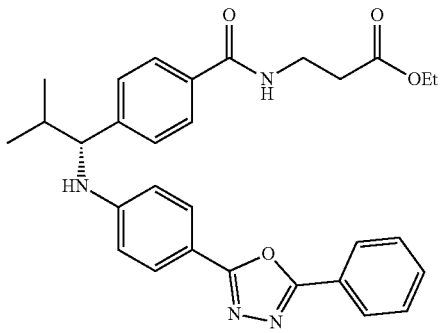 [SMILES: CCOC(=O)CCNC(=O)c1ccc([C@H](Nc2ccc(-c3nnc(-c4ccccc4)o3)cc2)C(C)C)cc1]

$^1$H NMR (400 MHz, DMSO-d$_6$): δ8.45 (s, 1H), 7.99-8.10 (m, 2H), 7.74 (dd, J=12.0, 8.8 Hz, 4H), 7.54-7.64 (m, 3H), 7.44 (d, J=8.4 Hz, 2H), 6.65-7.03 (m, 3H), 4.26 (s, 1H), 4.04 (q, J=7.2 Hz, 2H), 3.46 (d, J=5.6 Hz, 2H), 2.54 (t, J=7.2 Hz, 2H), 1.99-2.12 (m, 1H), 1.15 (t, J=7.2 Hz, 3H), 1.04 (d, J=6.8 Hz, 3H), 0.80 (d, J=6.8 Hz, 3H). MS(M+1): 513.

Compound 3-14

(S)-3-(4-(2-methyl-1-(4-(5-phenyl-1,3,4-oxadiazol-2-yl)phenylamino)propyl)benzamido)propanoic acid

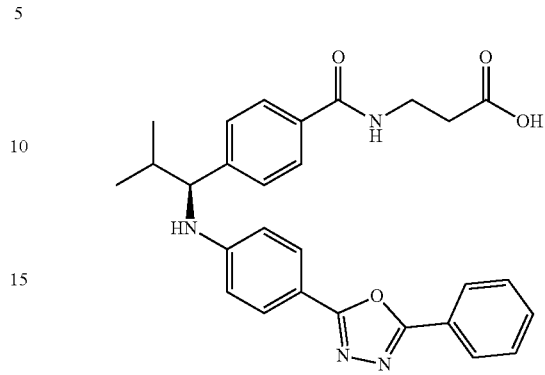

$^1$H NMR (400 MHz, DMSO-d$_6$): δ8.43 (t, J=5.6 Hz, 1H), 7.98-8.11 (m, 2H), 7.74 (dd, J=14.8, 8.8 Hz, 4H), 7.55-7.65 (m, 3H), 7.44 (d, J=8.4 Hz, 2H), 6.65-7.04 (m, 3H), 4.27 (t, J=7.6 Hz, 1H), 3.38-3.51 (m, 2H), 2.43-2.49 (m, 2H), 1.97-2.13 (m, 1H), 1.03 (d, J=6.4 Hz, 3H), 0.80 (d, J=6.8 Hz, 3H). MS(M+1): 485.

Compound 3-15

(R)-3-(4-(2-methyl-1-(4-(5-phenyl-1,3,4-oxadiazol-2-yl)phenylamino)propyl)benzamido)propanoic acid

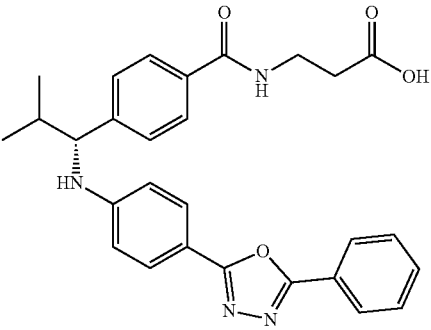 [SMILES: CC(C)[C@@H](Nc1ccc(-c2nnc(-c3ccccc3)o2)cc1)c1ccc(C(=O)NCCC(=O)O)cc1]

$^1$H NMR (400 MHz, DMSO-d$_6$): δ8.43 (t, J=5.6 Hz, 1H), 7.98-8.11 (m, 2H), 7.74 (dd, J=15.6, 8.8 Hz, 4H), 7.53-7.66 (m, 3H), 7.44 (d, J=8.4 Hz, 2H), 6.65-7.02 (m, 3H), 4.27 (t, J=7.6 Hz, 1H), 3.39-3.50 (m, 2H), 2.40-2.49 (m, 2H), 1.98-2.11 (m, 1H), 1.04 (d, J=6.8 Hz, 3H), 0.80 (d, J=6.4 Hz, 3H). MS(M+1): 485.

Example 4: Synthesis of the Compounds Shown in the Following Tables 4 and 5

The following scheme was followed for synthesizing Compounds 4-1 to 4-30 and 5-1 to 5-8

Scheme IV

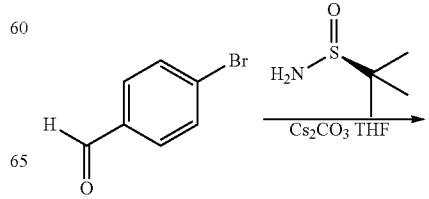

-continued

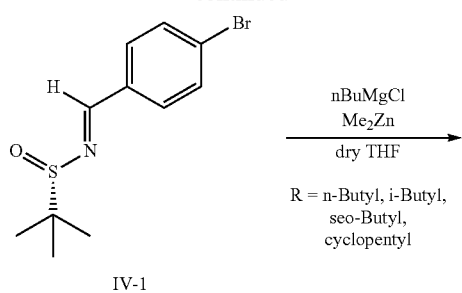

IV-1

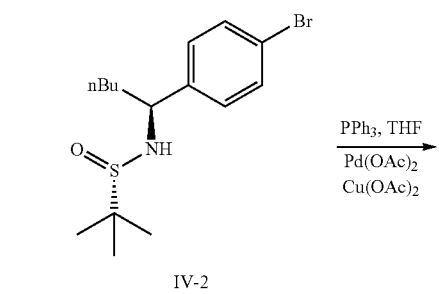

IV-2

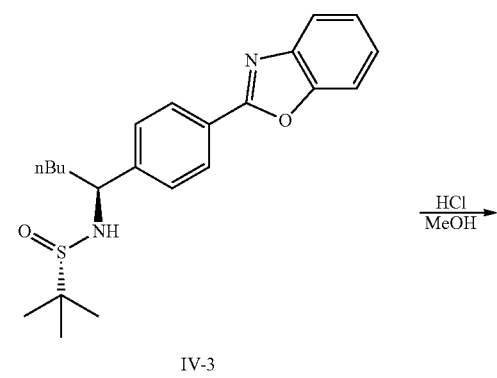

IV-3

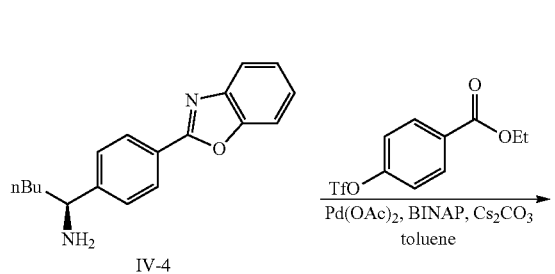

IV-4

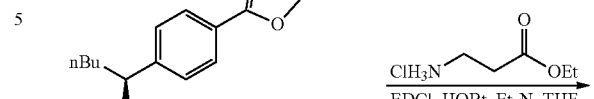

IV-5

-continued

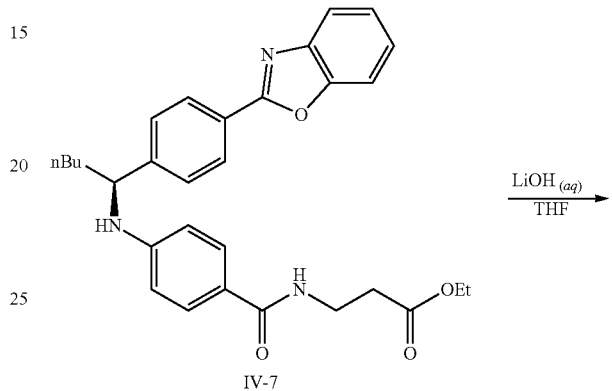

IV-6

IV-7

IV-8

Typical procedure of synthesis aminoamide compound

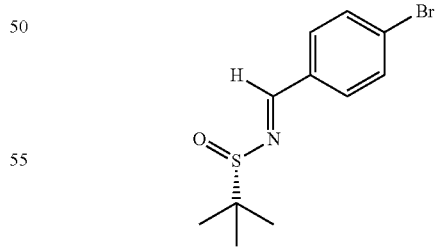

IV-1

To a solution of 4-bromobenzaldehyde (37.0 g, 200.0 mmol), (S)-(+)-tert-butanesulfinamide (29.0 g, 240.0 mmol), and Cs$_2$CO$_3$ (78.1 g, 240 mmol) in 370 mL THF in room temperature overnight. To this reaction solution, concentrated to remove methanol and extracted with EtOAc. The organic layer was washed with water and dried over anhydrous magnesium sulfate. It was filtered, the solvent evaporated under reduced pressure to give (S,E)-N-(4-bromobenzylidene)-2-methylpropane-2-sulfinamide as a white solid. (54.72 g, 95%)

IV-2

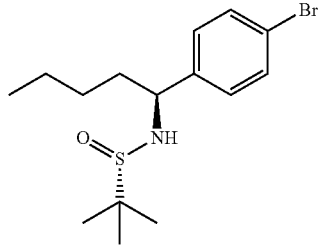

A solution of (S,E)-N-(4-bromobenzylidene)-2-methylpropane-2-sulfinamide (28.8 g, 100 mmol) in tetrahydrofuran (300 mL) was cooled to −78° C. To this solution was added n-butylmagnesium chloride (65 mL, 2M in THF) and dimethyl zinc (12.5 ml, 1.2M in tol) dropwise over 30 minutes. The reaction was stirred at −78° C. for 2 h. The reaction was then quenched by addition of saturated aqueous ammonium chloride. This mixture was extracted with ethyl acetate. The organic layer was dried over with magnesium sulfate, suction and concentrated, Purification by silica gel chromatography with 20% EA in hexane to obtain (S)-N-((S)-1-(4-bromophenyl)pentyl)-2-methylpropane-2-sulfinamide (23.8 g, 69%).

IV-3

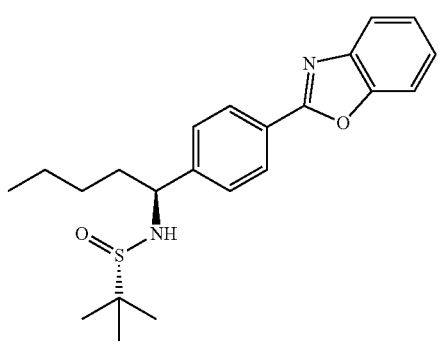

The reaction mixture of benzo[d]oxazole (2.0 g, 16.5 mmol), (S)-N-((S)-1-(4-bromophenyl)pentyl)-2-methylpropane-2-sulfinamide (4.77 g, 13.7 mmol), Pd(OAc)$_2$ (0.31 g, 1.37 mmol), Cu(OAc)$_2$ (0.51 g, 2.75 mmol), and K$_2$CO$_3$ (27.5 mmol) in toluene (50 mL) was refluxed for overnight. Then, the mixture was filtered and the filtrate was evaporated under reduced pressure. The residue was purified by column chromatography with 15% EA in hexane to give (S)-N-((S)-1-(4-(benzo[d]oxazol-2-yl)phenyl)pentyl)-2-methylpropane-2-sulfinamide (3.84 g, 72%).

IV-4

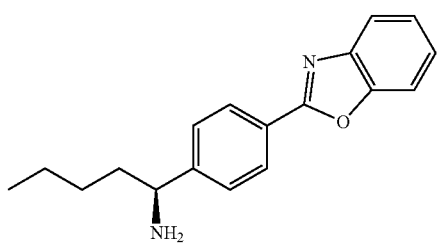

The (S)-N-((S)-1-(4-(benzo[d]oxazol-2-yl)phenyl)pentyl)-2-methylpropane-2-sulfinamide (3.84 g, 10 mmol) was suspended in 2M/HCl in MeOH (30 mL) at room temperature for 1 h. After evaporation, excess HCl was neutralized by dropwised addition of NaHCO$_{3(aq)}$ until pH=10. Then it was extracted with EA and water. The combined organic layer was dried with anhydrous MgSO$_4$ and concentrated to give (S)-1-(4-(benzo[d]oxazol-2-yl)phenyl)pentan-1-amine (2.74 g, 98%)

IV-5

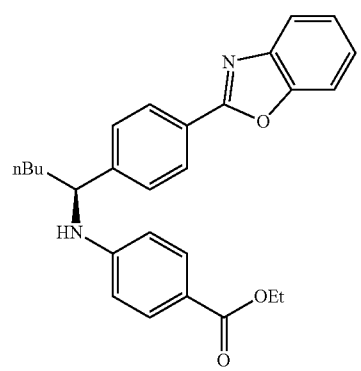

A solution of (S)-1-(4-(benzo[d]oxazol-2-yl)phenyl)pentan-1-amine (2.74 g. 9.8 mmol), ethyl 4-(((trifluoromethyl)sulfonyl)oxy)benzoate (3.5 g, 11.7 mmol), BINAP (3 g, 4.9 mmol) and Cs$_2$CO$_3$ (6.37 g, 19.5 mmol) in 100 ml toluene were purged with nitrogen for 30 min. Pd(OAc)$_2$ (0.55 g, 2.4 mmol) was added to the mixture. The mixture was heated at 90° C. for overnight. Extraction with ethyl acetate and the organic phase was washed with water, dried, and evaporated in vacuo. The residue was purified by column chromatography on silica gel with 15% EA in hexanes to obtain ethyl (S)-4-((1-(4-(benzo[d]oxazol-2-yl)phenyl)pentyl)amino) benzoate (3 g, 72%).

After a general procedure of hydrolysis reaction to afford acid compounds then amidation with beta-alanine ethyl ester to got the ethyl ester compounds and further hydrolysis to acid as SAR analogous compounds.

Compound 4-1 ethyl 3-(4-((1-(4-(benzo[d]oxazol-2-yl)phenyl)-2-methylpropyl)amino)benzamido)propanoate

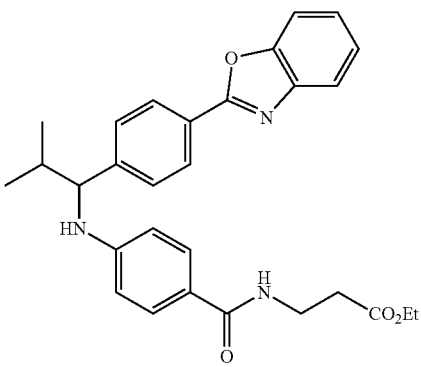 [SMILES: CCOC(=O)CCNC(=O)c1ccc(NC(c2ccc(-c3nc4ccccc4o3)cc2)C(C)C)cc1]

White solid. ¹H NMR (400 MHz, DMSO-d₆): δ8.20 (d, J=8.8 Hz, 2H), 7.77-7.74 (m, 1H), 7.58-7.56 (m, 1H), 7.51 (d, J=8.8 Hz, 2H), 7.44 (d, J=8.8 Hz, 2H), 7.36-7.32 (m, 2H), 6.59 (t, J=6.8 Hz, 1H), 6.49 (d, J=8.8 Hz, 2H), 4.53 (d, J=5.4 Hz, 1H), 4.24 (t, J=5.4 Hz, 1H), 4.12 (q, J=6.8 Hz, 2H), 3.64 (q, J=6.8 Hz, 2H), 2.57 (t, J=6.8 Hz, 2H), 2.17-2.09 (m, 1H), 1.23 (t, J=6.8 Hz, 3H), 1.03 (t, J=6.8 Hz 3H), 0.97 (t, J=6.8 Hz, 3H). MS(M+1): 486.

Compound 4-2 ethyl 3-(4-((1-(4-(benzo[d]oxazol-2-yl)phenyl)pentyl)amino)benzamido)propanoate

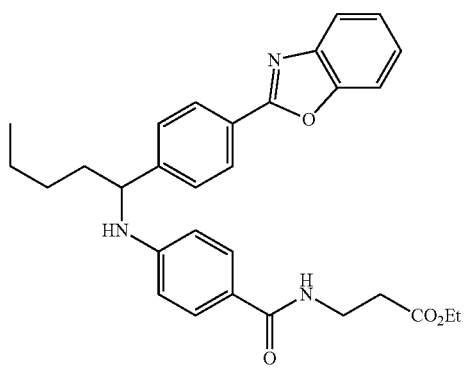 [SMILES: CCCCC(Nc1ccc(C(=O)NCCC(=O)OCC)cc1)c1ccc(-c2nc3ccccc3o2)cc1]

White solid. ¹H NMR (400 MHz, DMSO-d₆): δ8.21 (d, J=8.8 Hz, 2H), 7.77-7.75 (m, 1H), 7.58-7.57 (m, 1H), 7.53 (d, J=8.8 Hz, 2H), 7.47 (d, J=8.8 Hz, 2H), 7.37-7.32 (m, 2H), 6.59 (t, J=6.8 Hz, 1H), 6.49 (d, J=8.8 Hz, 2H), 4.47-4.41 (m, 2H), 4.12 (q, J=6.8 Hz, 2H), 3.64 (q, J=6.8 Hz, 2H), 2.57 (t, J=6.8 Hz, 2H), 1.87-1.82 (m, 2H), 1.43-1.34 (m, 4H), 1.23 (t, J=6.8 Hz, 3H), 0.9 (t, J=6.8 Hz, 3H). MS(M+1): 500.

Compound 4-3

3-(4-((1-(4-(benzo[d]oxazol-2-yl)phenyl)-2-methylpropyl)amino)benzamido)propanoic acid

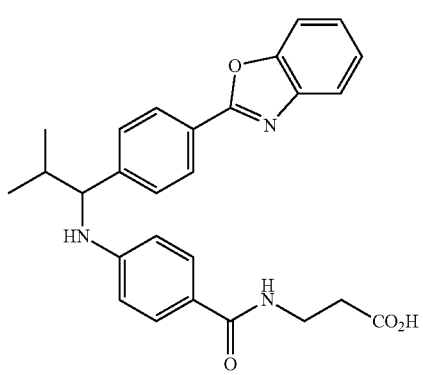 [SMILES: CC(C)C(Nc1ccc(C(=O)NCCC(=O)O)cc1)c1ccc(-c2nc3ccccc3o2)cc1]

White solid. ¹H NMR (400 MHz, DMSO-d₆): δ12 (brs, 1H), 8.13 (d, J=8.8 Hz, 2H), 7.98 (t, J=5.4 Hz, 1H), 7.81-7.74 (m, 2H), 7.58 (d, J=8.8 Hz, 2H), 7.50 (d, J=8.8 Hz, 2H), 7.43-7.37 (m, 2H), 6.69 (d, J=8.8 Hz, 1H), 6.58 (d, J=8.8 Hz, 2H), 4.28 (t J=5.4 Hz, 1H), 3.38-3.33 (m, 2H), 2.42 (t, J=6.8 Hz, 2H), 2.09-2.01 (m, 1H), 1.23 (t, J=6.8 Hz, 3H), 1.04 (t, J=6.8 Hz, 3H), 0.82 (t, J=6.8 Hz, 3H). MS(M+1): 458.

Compound 4-4

3-(4-((1-(4-(benzo[d]oxazol-2-yl)phenyl)pentyl)amino)benzamido)propanoic acid

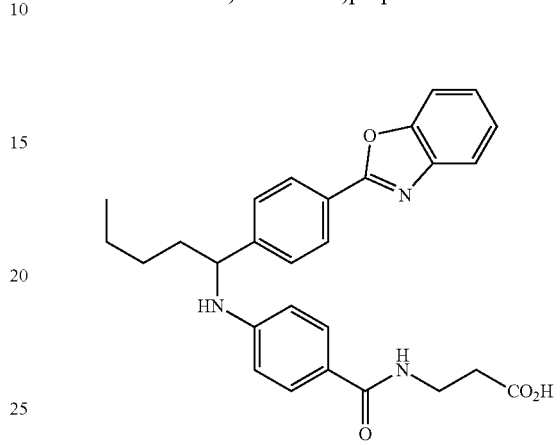

White solid. ¹H NMR (400 MHz, DMSO-d₆): δ7.37 (d, J=8.8 Hz, 2H), 6.92-6.85 (m, 2H), 6.78-6.71 (m, 4H), 6.62-6.56 (m, 2H), 5.77 (d, J=8.8 Hz, 1H), 6.58 (d, J=3-8.8 Hz, 2H), 3.70-3.67 (m, 2H), 2.73 (t, J=6.8 Hz, 2H), 1.76 (t, J=6.8 Hz, 2H), 1.12-0.99 (m, 2H), 0.71-0.54 (m, 4H), 0.12 (t, J=6.8 Hz, 3H). MS(M+1): 503.

Compound 4-5 ethyl (S)-3-(4-((1-(4-(benzo[d]oxazol-2-yl)phenyl)-2-methylpropyl)amino)benzamido)propanoate

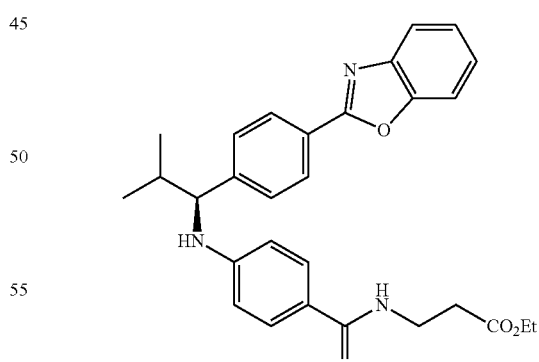

¹H NMR (400 MHz, DMSO-d₆): δ8.13 (d, J=8.4 Hz, 2H), 7.95-8.04 (m, 1H), 7.72-7.83 (m, 2H), 7.58 (d, J=8.4 Hz, 2H), 7.49 (d, J=8.8 Hz, 2H), 7.36-7.44 (m, 2H), 6.52-6.73 (m, 3H), 4.23-4.34 (m, 1H), 4.02 (q, J=6.8 Hz, 2H), 3.38 (d, J=6.0 Hz, 2H), 2.44-2.50 (m, 1H), 1.98-2.12 (m, 1H), 1.13 (t, J=7.2 Hz, 3H), 1.04 (d, J=6.4 Hz, 3H), 0.82 (d, J=6.8 Hz, 3H). MS(M+1): 486.

Compound 4-6 ethyl (R)-3-(4-((1-(4-(benzo[d]oxazol-2-yl)phenyl)-2-methylpropyl)amino)benzamido)propanoate

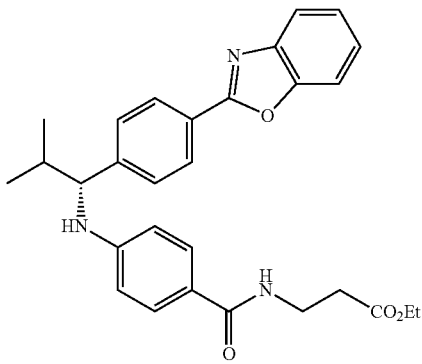 [SMILES: CCOC(=O)CCNC(=O)c1ccc(N[C@@H](c2ccc(-c3nc4ccccc4o3)cc2)C(C)C)cc1]

¹H NMR (400 MHz, DMSO-d₆): δ8.13 (d, J=8.4 Hz, 2H), 7.99 (s, 1H), 7.72-7.82 (m, 2H), 7.58 (d, J=8.4 Hz, 2H), 7.49 (d, J=8.8 Hz, 2H), 7.35-7.44 (m, 2H), 6.53-6.73 (m, 3H), 4.28 (s, 1H), 4.02 (q, J=6.8 Hz, 2H), 3.38 (d, J=6.0 Hz, 2H), 2.44-2.49 (m, 3H), 2.00-2.12 (m, 1H), 1.13 (t, J=7.2 Hz, 3H), 1.04 (d, J=6.4 Hz, 3H), 0.82 (d, J=6.4 Hz, 3H). MS(M+1): 486.

Compound 4-7

(S)-3-(4-((1-(4-(benzo[d]oxazol-2-yl)phenyl)-2-methylpropyl)amino)benzamido)propanoic acid

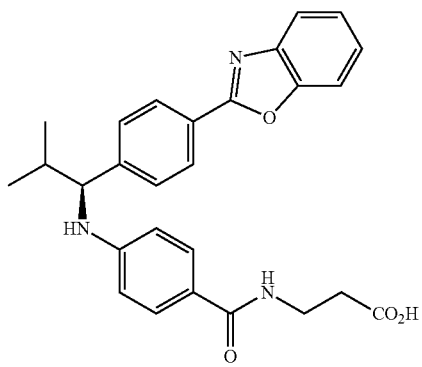 [SMILES: CC(C)[C@H](Nc1ccc(C(=O)NCCC(=O)O)cc1)c1ccc(-c2nc3ccccc3o2)cc1]

¹H NMR (400 MHz, DMSO-d₆): δ8.13 (d, J=8.8 Hz, 2H), 7.97 (t, J=5.6 Hz, 1H), 7.72-7.83 (m, 2H), 7.58 (d, J=8.3 Hz, 2H), 7.50 (d, J=8.8 Hz, 2H), 7.35-7.44 (m, 2H), 6.53-6.73 (m, 3H), 4.28 (t, J=7.6 Hz, 1H), 2.42 (t, J=7.2 Hz, 2H), 2.00-2.12 (m, 1H), 1.04 (d, J=6.8 Hz, 3H), 0.82 (d, J=6.8 Hz, 3H). MS(M+1): 458.

Compound 4-8

(R)-3-(4-((1-(4-(benzo[d]oxazol-2-yl)phenyl)-2-methylpropyl)amino)benzamido)propanoic acid

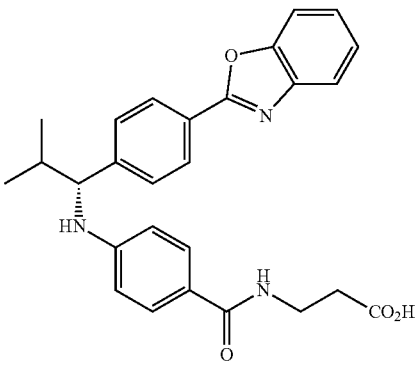 [SMILES: CC(C)[C@@H](Nc1ccc(C(=O)NCCC(=O)O)cc1)c1ccc(-c2nc3ccccc3o2)cc1]

¹H NMR (400 MHz, DMSO-d₆): δ8.13 (d, J=8.4 Hz, 2H), 7.97 (t, J=5.6 Hz, 1H), 7.71-7.84 (m, 2H), 7.59 (d, J=8.4 Hz, 2H), 7.50 (d, J=8.8 Hz, 2H), 7.35-7.45 (m, 2H), 6.52-6.73 (m, 3H), 4.28 (t, J=7.6 Hz, 1H), 3.32-3.44 (m, 2H), 2.42 (t, J=6.8 Hz, 2H), 1.99-2.13 (m, 1H), 1.04 (d, J=6.4 Hz, 3H), 0.82 (d, J=6.8 Hz, 3H). MS(M+1): 458.

Compound 4-9 ethyl (R)-3-(4-((1-(4-(benzo[d]oxazol-2-yl)phenyl)pentyl)amino)benzamido)propanoate

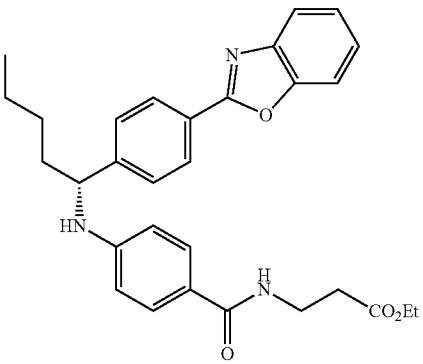 [SMILES: CCCC[C@@H](Nc1ccc(C(=O)NCCC(=O)OCC)cc1)c1ccc(-c2nc3ccccc3o2)cc1]

¹H NMR (400 MHz, DMSO-d₆): δ8.14 (d, J=8.4 Hz, 2H), 7.95-8.03 (m, 1H), 7.77 (s, 2H), 7.60 (d, J=8.4 Hz, 2H), 7.50 (d, J=8.8 Hz, 2H), 7.35-7.45 (m, 2H), 6.55 (d, J=9.2 Hz, 3H), 4.41-4.57 (m, 1H), 4.02 (q, J=6.8 Hz, 2H), 3.39 (d, J=6.0 Hz, 2H), 2.43-2.56 (m, 2H), 1.31 (s, 6H), 1.14 (t, J=7.2 Hz, 3H), 0.78-0.93 (m, 3H).

MS(M+1): 500.

101

Compound 2-10

(R)-3-(4-((1-(4-(benzo[d]oxazol-2-yl)phenyl)amino)benzamido)propanoic acid

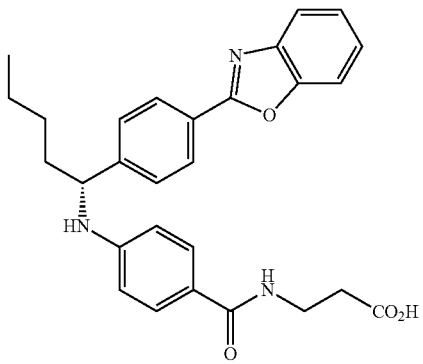 [SMILES: CCCC[C@@H](Nc1ccc(C(=O)NCCC(=O)O)cc1)c1ccc(-c2nc3ccccc3o2)cc1]

¹H NMR (400 MHz, DMSO-d₆): δ 8.14 (d, J=8.4 Hz, 2H), 7.97 (t, J=5.6 Hz, 1H), 7.72-7.82 (m, 2H), 7.60 (d, J=8.4 Hz, 2H), 7.51 (d, J=9.2 Hz, 2H), 7.34-7.45 (m, 2H), 6.50-6.80 (m, 3H), 4.41-4.58 (m, 1H), 3.34-3.45 (m, 2H), 2.43 (t, J=7.2 Hz, 2H), 1.20-4.93 (m, 6H), 0.81-0.91 (m, 3H). MS(M+1): 472.

Compound 4-11 ethyl (R)-3-(4-(((4-(benzo[d]oxazol-2-yl)phenyl)(cyclopentyl)methyl)amino)benzamido)propanoate

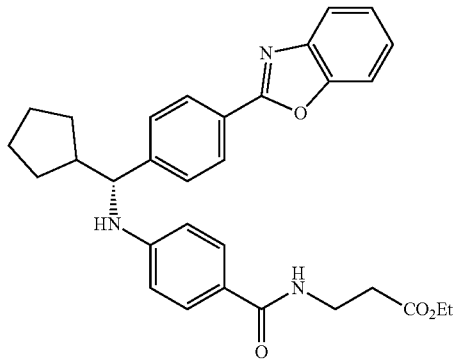 [SMILES: CCOC(=O)CCNC(=O)c1ccc(N[C@@H](c2ccc(-c3nc4ccccc4o3)cc2)C2CCCC2)cc1]

¹H NMR (400 MHz, DMSO-d₆): δ 8.12 (d, J=8.4 Hz, 2H), 7.93-8.02 (m, 1H), 7.71-7.83 (m, 2H), 7.63 (d, J=8.4 Hz, 2H), 7.48 (d, J=8.8 Hz, 2H), 7.35-7.44 (m, 2H), 6.57 (d, J=8.8 Hz, 3H), 4.23-4.37 (m, 1H), 4.02 (q, J=6.8 Hz, 2H), 3.38 (d, J=6.4 Hz, 2H), 2.44-2.49 (m, 2H), 2.13-2.34 (m, 1H), 1.87-2.04 (m, 1H), 1.35-1.72 (m, 5H), 1.18-1.33 (m, 2H), 1.10-1.16 (m, 3H). MS(M+1): 512.

102

Compound 4-12

(R)-3-(4-(((4-(benzo[d]oxazol-2-yl)phenyl)(cyclopentyl)methyl)amino)benzamido)propanoic acid

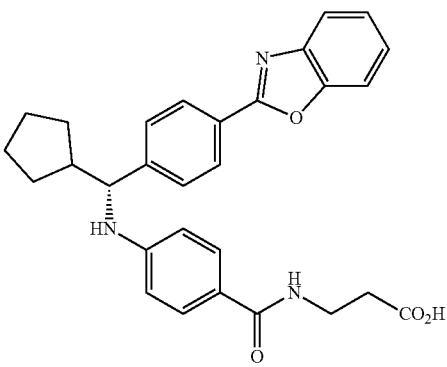 [SMILES: O=C(O)CCNC(=O)c1ccc(N[C@@H](c2ccc(-c3nc4ccccc4o3)cc2)C2CCCC2)cc1]

¹H NMR (400 MHz, DMSO-d₆): δ 8.12 (d, J=8.4 Hz, 2H), 7.95 (t, J=5.6 Hz, 1H), 7.72-7.83 (m, 2H), 7.63 (d, J=8.4 Hz, 2H), 7.49 (d, J=8.8 Hz, 2H), 7.34-7.44 (m, 2H), 6.50-6.83 (m, 3H), 4.29 (t, J=8.4 Hz, 1H), 3.33-3.45 (m, 2H), 2.42 (t, J=7.2 Hz, 2H), 2.23 (m, 1H), 1.87-2.03 (m, 1H), 1.36-1.73 (m, 5H), 1.16-1.35 (m, 2H). MS(M+1): 484.

Compound 4-13 ethyl (R)-3-(4-((1-(4-(benzo[d]oxazol-2-yl)phenyl)-3-methylbutyl)amino)benzamido)propanoate

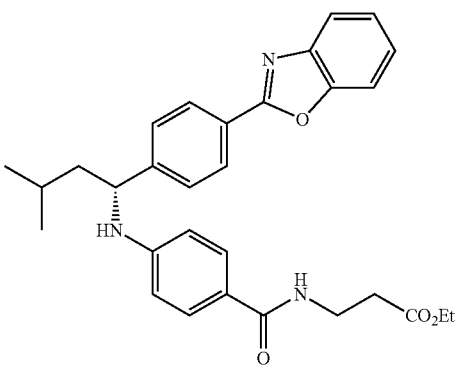 [SMILES: CCOC(=O)CCNC(=O)c1ccc(N[C@H](CC(C)C)c2ccc(-c3nc4ccccc4o3)cc2)cc1]

¹H NMR (400 MHz, DMSO-d₆): δ 8.13 (d, J=8.4 Hz, 2H), 7.95-8.03 (m, 1H), 7.77 (s, 2H), 7.61 (d, J=8.4 Hz, 2H), 7.50 (d, J=8.8 Hz, 2H), 7.35-7.44 (m, 2H), 6.57 (d, J=8.8 Hz, 3H), 4.49-4.64 (m, 1H), 4.02 (q, J=7.2 Hz, 2H), 3.39 (d, J=6.0 Hz, 2H), 2.45-2.49 (m, 2H), 1.39-1.84 (m, 4H), 1.14 (t, J=7.2 Hz, 3H), 0.97 (d, J=6.4 Hz, 3H), 0.91 (d, J=6.4 Hz, 3H). MS(M+1): 500.

Compound 4-14

(R)-3-(4-((1-(4-(benzo[d]oxazol-2-yl)phenyl)-3-methylbutyl)amino)benzamido)propanoic acid

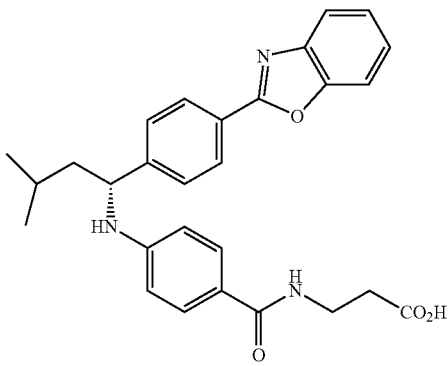 [SMILES: CC(C)C[C@@H](Nc1ccc(C(=O)NCCC(=O)O)cc1)c1ccc(-c2nc3ccccc3o2)cc1]

¹H NMR (400 MHz, DMSO-d₆): δ8.14 (d, J=8.4 Hz, 2H), 7.97 (t, J=5.6 Hz, 1H), 7.72-7.83 (m, 2H), 7.61 (d, J=8.4 Hz, 2H), 7.51 (d, J=8.8 Hz, 2H), 7.34-7.45 (m, 2H), 6.51-6.80 (m, 3H), 4.48-4.65 (m, 1H), 3.33-3.43 (m, 2H), 2.43 (t, J=7.2 Hz, 2H), 1.43-1.86 (m, 4H), 0.97 (d, J=6.4 Hz, 3H), 0.91 (d, J=6.4 Hz, 3H). MS(M+1): 472.

Compound 4-15 ethyl (S)-3-(4-((1-(4-(benzo[d]oxazol-2-yl)phenyl)pentyl)amino)benzamido)propanoate

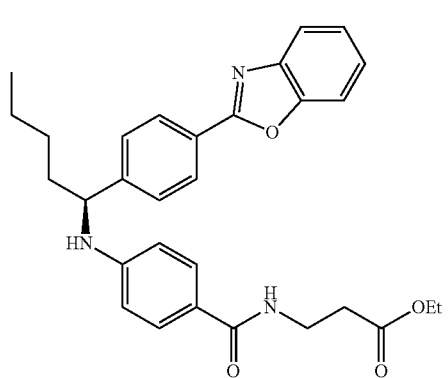 [SMILES: CCCC[C@H](Nc1ccc(C(=O)NCCC(=O)OCC)cc1)c1ccc(-c2nc3ccccc3o2)cc1]

¹H NMR (400 MHz, DMSO-d₆): δ8.14 (d, J=8.3 Hz, 2H), 8.01 (t, J=5.6 Hz, 1H), 7.74-7.80 (m, 2H), 7.60 (d, J=8.3 Hz, 2H), 7.51 (d, J=8.8 Hz, 2H), 7.35-7.45 (m, 2H), 6.77 (d, J=7.8 Hz, 1H), 6.55 (d, J=8.8 Hz, 2H), 4.45-4.56 (m, 1H), 4.03 (q, J=6.8 Hz, 2H), 3.36-3.43 (m, 2H), 2.46-2.50 (m, 2H), 1.77-1.90 (m, 1H), 1.64-1.75 (m, 1H), 1.32 (d, J=6.8 Hz, 4H), 1.14 (t, J=7.1 Hz, 3H), 0.86 (t, J=7.1 Hz, 3H). MS(M+1): 500. HPLC 95%.

Compound 4-16

(S)-3-(4-((1-(4-(benzo[d]oxazol-2-yl)phenyl)pentyl)amino)benzamido)propanoic acid

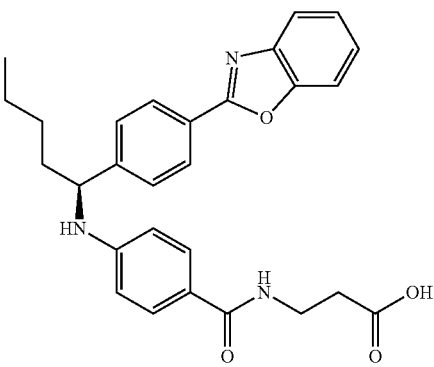 [SMILES: CCCC[C@H](Nc1ccc(C(=O)NCCC(=O)O)cc1)c1ccc(-c2nc3ccccc3o2)cc1]

¹H NMR (400 MHz, DMSO-d₆): δ8.13 (d, J=8.3 Hz, 2H), 7.97-8.04 (m, 1H), 7.68-7.83 (m, 2H), 7.59 (d, J=8.3 Hz, 2H), 7.53 (d, J=8.8 Hz, 2H), 7.34-7.45 (m, 2H), 6.76 (d, J=7.3 Hz, 1H), 6.55 (d, J=8.8 Hz, 2H), 4.44-4.54 (m, 1H), 3.38 (q, J=6.7 Hz, 2H), 2.44 (t, J=7.1 Hz, 2H), 1.77-1.89 (m, 1H), 1.64-1.75 (m, 1H), 1.22-1.46 (m, 4H), 0.84 (t, J=6.8 Hz, 3H). MS(M+1): 472. HPLC 96%.

Compound 4-17 ethyl (S)-3-(4-((1-(4-(benzo[d]oxazol-2-yl)phenyl)-3-methylbutyl)amino)benzamido)propanoate

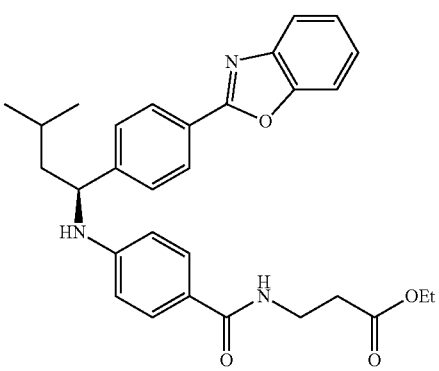 [SMILES: CCOC(=O)CCNC(=O)c1ccc(N[C@@H](CC(C)C)c2ccc(-c3nc4ccccc4o3)cc2)cc1]

¹H NMR. (400 MHz, DMSO-d₆): δ8.13 (d, J=8.3 Hz, 2H), 7.99 (t, J=5.6 Hz, 1H), 7.77 (t, J=8.6 Hz, 2H), 7.61 (d, J=7.8 Hz, 2H), 7.50 (d, J=8.8 Hz, 2H), 7.36-7.44 (m, 2H), 6.74 (d, J=7.8 Hz, 1H), 6.57 (d, J=8.8 Hz, 2H), 4.52-4.64 (m, 1H), 4.02 (q, J=7.3 Hz, 2H), 3.39 (q, J=6.5 Hz, 2H), 2.45-2.49 (m, 2H), 1.65-1.82 (m, 2H), 1.47-1.56 (m, 1H), 1.14 (t, J=7.1 Hz, 3H), 0.96 (d, J=6.4 Hz, 3H), 0.91 (d, J=6.4 Hz, 3H). MS(M+1): 500. HPLC 95%.

Compound 4-18

(S)-3-(4-((1-(4-benzo[d]oxazol-2-yl)phenyl)-3-methylbutyl)amino)benzamido)propanoic acid

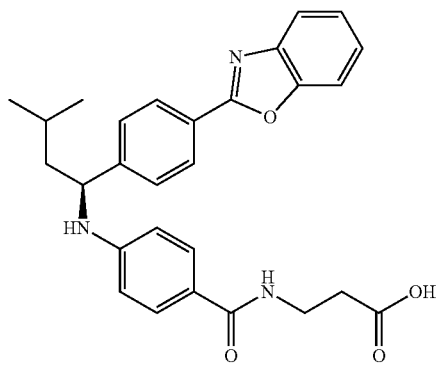 [SMILES: CC(C)C[C@H](Nc1ccc(C(=O)NCCC(=O)O)cc1)c1ccc(-c2nc3ccccc3o2)cc1]

$^1$H NMR (400 MHz, DMSO-d$_6$): δ8.14 (d, J=7.8 Hz, 2H), 7.98 (t, J=5.4 Hz, 1H), 7.71-7.82 (m, 2H), 7.61 (d, J=8.3 Hz, 2H), 7.52 (d, J=8.3 Hz, 2H), 7.34-7.44 (m, 2H), 6.74 (d, J=7.8 Hz, 1H). 6.57 (d, J=8.8 Hz, 2H), 4.51-4.62 (m, 1H), 3.36-3.42 (m, 2H), 2.43 (t, J=7.1 Hz, 2H), 1.65-1.83 (m, 2H), 1.45-1.57 (m, 1H), 0.96 (d, J=5.9 Hz, 3H), 0.91 (d, J=5.9 Hz, 3H). MS(M+1): 472. HPLC 96%.

Compound 4-19

Ethyl 3-(4-(((1S)-1-(4-(benzo[d]oxazol-2-yl)phenyl)-2-methylbutyl)amino)benzamido)propanoate

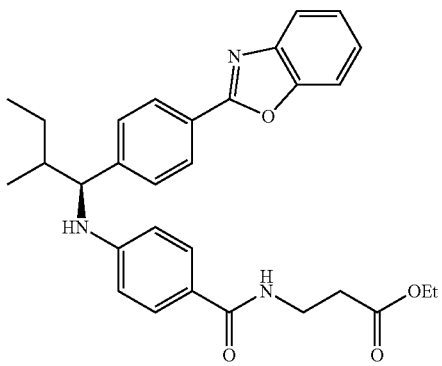 [SMILES: CCOC(=O)CCNC(=O)c1ccc(N[C@H](c2ccc(-c3nc4ccccc4o3)cc2)C(C)CC)cc1]

$^1$H NMR (400 MHz, DMSO-d$_6$): δ8.13 (dd, J=8.6, 1.7 Hz, 2H), 7.97-8.05 (m, 1H), 7.72-7.81 (m, 2H), 7.58 (dd, J=8.3, 5.4 Hz, 2H), 7.50 (dd, J=9.0, 3.2 Hz, 2H), 7.35-7.44 (m, 2H), 6.49-6.73 (m, 3H), 4.26-4.50 (m, 1H), 4.02 (q, J=7.3 Hz, 2H), 3.39 (q, J=6.8 Hz, 2H), 2.42-2.50 (m, 2H), 1.77-1.91 (m, 1H), 1.58-1.71 (m, 1H), 1.22-1.44 (m, 1H), 1.13 (t, J=7.1 Hz, 3H), 0.70-0.99 (m, 6H). MS(M+1): 500. HPLC 94%.

Compound 4-20

3-(4-(((1S)-1-(4-(benzo[d]oxazol-2-yl)phenyl)-2-methylbutyl)amino)benzamido)propanoic acid

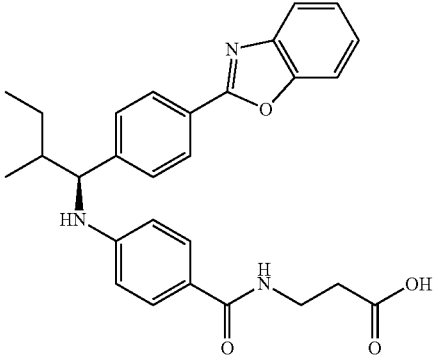 [SMILES: CCC(C)[C@H](Nc1ccc(C(=O)NCCC(=O)O)cc1)c1ccc(-c2nc3ccccc3o2)cc1]

$^1$H NMR (DMSO-d$_6$): δ8.13 (dd, J=8.3, 2.0 Hz, 2H), 7.93-8.01 (m, 1H), 7.73-7.83 (m, 2H), 7.58 (dd, J=8.3, 5.4 Hz, 2H), 7.46-7.52 (m, 2H), 7.31-7.45 (m, 2H), 6.53-6.70 (m, 3H), 4.30-4.47 (m, 1H), 2.42 (t, J=7.1 Hz, 2H), 1.80-1.89 (m, 1H), 1.66 (br. s., 1H), 1.24-1.45 (m, 1H), 0.71-0.99 (m, 6H). MS(M+1): 472. HPLC 94%

Compound 4-21 ethyl 3-(4-(((1R)-1-(4-(benzo[d]oxazol-2-yl)phenyl)-2-methylbutyl)amino)benzamido)propanoate

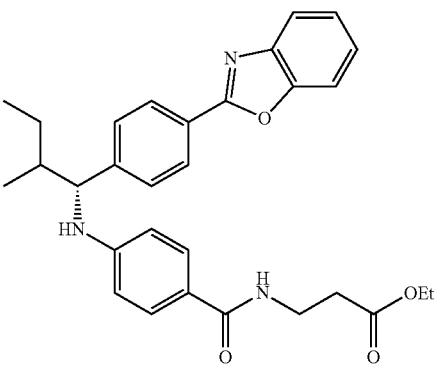 [SMILES: CCOC(=O)CCNC(=O)c1ccc(N[C@@H](c2ccc(-c3nc4ccccc4o3)cc2)C(C)CC)cc1]

$^1$H NMR (400 MHz, DMSO-d$_6$): δ8.13 (dd, J=8.3, 2.0 Hz, 2H), 7.97-8.03 (m, 1H), 7.74-7.80 (m, 2H), 7.58 (dd, J=8.3, 5.4 Hz, 2H), 7.50 (dd, J=8.8, 3.4 Hz, 2H), 7.35-7.44 (m, 2H), 6.54-6.73 (m, 3H), 4.30-4.46 (m, 1H), 4.02 (q, J=7.3 Hz, 2H), 3.39 (q, J=6.8 Hz, 2H), 2.44-2.49 (m, 2H), 1.79-1.90 (m, 1H), 1.59-1.72 (m, 1H), 1.24-1.45 (m, 1H), 1.14 (t, J=7.1 Hz, 3H), 0.73-0.98 (m, 6H). MS(M+1): 500. HPLC 95%.

Compound 4-22

3-(4-(((1R)-1-(4-(benzo[d]oxazol-2-yl)phenyl)-2-methylbutyl)amino)benzamido)propanoic acid

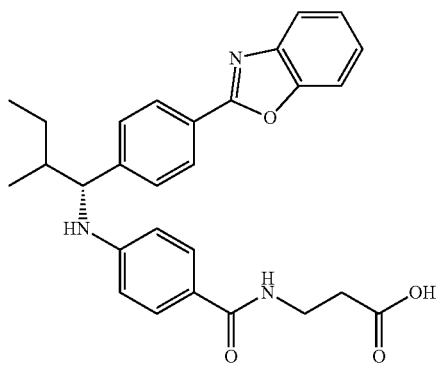 [SMILES: CCC(C)[C@@H](Nc1ccc(C(=O)NCCC(=O)O)cc1)c1ccc(-c2nc3ccccc3o2)cc1]

$^1$H NMR (400 MHz, DMSO-$d_6$): δ 8.13 (dd, J=8.3, 2.0 Hz, 2H), 7.93-8.01 (m, 1H), 7.72-7.82 (m, 2H), 7.58 (dd, J=8.3, 5.4 Hz, 2H), 7.46-7.52 (m, 2H), 7.33-7.46 (m, 2H), 6.50-6.72 (m, 3H), 4.28-4.47 (m, 1H), 2.42 (t, J=7.1 Hz, 2H), 1.79-1.89 (m, 1H), 1.58-1.72 (m, 1H), 1.22-1.46 (m, 1H), 0.71-0.99 (m, 6H). MS(M+1): 472. HPLC 99%.

Compound 4-23 ethyl (S)-3-(4-(((4-(benzo[d]oxazol-2-yl)phenyl)(cyclopentyl)methyl)amino)benzamido)propanoate

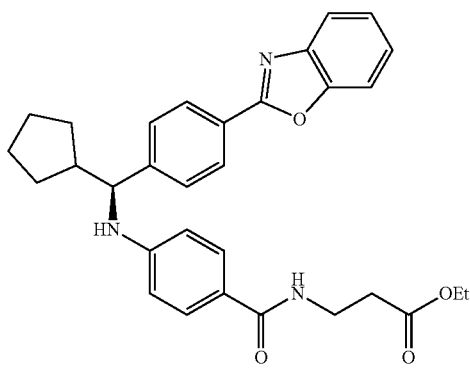 [SMILES: CCOC(=O)CCNC(=O)c1ccc(N[C@H](c2ccc(-c3nc4ccccc4o3)cc2)C2CCCC2)cc1]

$^1$H NMR (400 MHz, DMSO-$d_6$): δ 8.12 (d, J=8.3 Hz, 2H), 7.98 (t, J=5.6 Hz, 1H), 7.73-7.80 (m, 2H), 7.62 (d, J=8.3 Hz, 2H), 7.49 (d, J=8.8 Hz, 2H), 7.36-7.43 (m, 2H), 6.79 (d, J=7.8 Hz, 1H), 6.57 (d, J=8.8 Hz, 2H), 4.28 (t, J=8.6 Hz, 1H), 4.02 (q, J=6.8 Hz, 2H), 3.35-3.42 (m, 2H), 2.45-2.49 (m, 2H), 2.16-2.28 (m, 1H), 1.91-1.99 (m, 1H), 1.37-1.68 (m, 5H), 1.19-1.32 (m, 2H), 1.11-1.16 (t, J=7.3 Hz, 3H). MS(M+1): 512. HPLC 96%.

Compound 4-24

(S)-3-(4-(((4-(benzo[d]oxazol-2-yl)phenyl)(cyclopentyl)methyl)amino)benzamido)propanoic acid

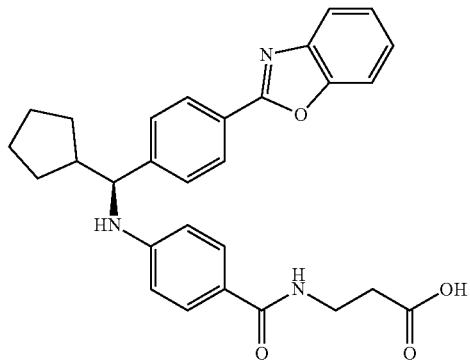 [SMILES: O=C(O)CCNC(=O)c1ccc(N[C@H](c2ccc(-c3nc4ccccc4o3)cc2)C2CCCC2)cc1]

$^1$H NMR (400 MHz, DMSO-$d_6$): δ 8.12 (d, J=8.3 Hz, 2H), 7.97 (t, J=5.4 Hz, 1H), 7.71-7.81 (m, 2H), 7.62 (d, J=8.3 Hz, 2H), 7.50 (d, J=8.8 Hz, 2H), 7.35-7.45 (m, 2H), 6.78 (d, J=8.3 Hz, 1H), 6.57 (d, J=8.8 Hz, 2H), 4.28 (t, J=8.6 Hz, 1H), 3.33-3.40 (m, 2H), 2.42 (t, J=7.3 Hz, 2H), 2.16-2.28 (m, 1H), 1.90-2.00 (m, 1H), 1.36-1.68 (m, 5H), 1.16-1.33 (m, 2H). MS(M+1): 484. HPLC 99%.

Compound 4-25 ethyl (S)-3-(4-((1-(4-(benzo[d]thiazol-2-yl)phenyl)-2-methylpropyl)amino)benzamido)propanoate $^1$H NMR (400 MHz, DMSO-$d_6$): δ 8.12 (d, J=7.8 Hz, 1H), 7.95-8.06 (m, 4H), 7.47-7.56 (m, 5H), 7.41-7.47 (m, 1H), 6.68 (d, J=7.8 Hz, 1H), 6.58 (d, J=8.8 Hz, 2H), 4.25 (t, J=7.6 Hz, 1H), 4.02 (q, J=7.3 Hz, 2H), 3.36-3.43 (m, 2H), 2.45-2.50 (m, 2H), 1.99-2.10 (m, 1H), 1.14 (t, J=7.1 Hz, 3H), 1.04 (d, J=6.8 Hz, 3H), 0.83 (d, J=6.8 Hz, 3H). MS(M+1): 502. HPLC 98%.

Compound 4-26

(S)-3-(4-((1-(4-(benzo[d]thiazol-2-yl)phenyl)-2-methylpropyl)amino)benzamido)propanoic acid

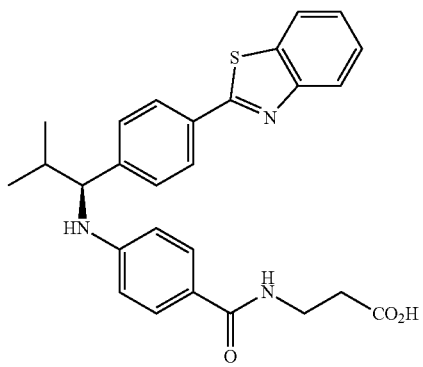 [SMILES: CC(C)[C@H](Nc1ccc(C(=O)NCCC(=O)O)cc1)c1ccc(-c2nc3ccccc3s2)cc1]

¹H NMR (400 MHz, DMSO-d₆): δ12.1 (br. s., 1H), 8.12 (d, J=73 Hz, 1H), 7.93-8.07 (m, 4H), 7.39-7.60 (m, 6H), 6.67 (d, J=7.8 Hz, 1H), 6.58 (d, J=8.3 Hz, 2H), 4.26 (t, J=7.6 Hz, 1H), 3.28-3.37 (m, 2H), 2.42 (t, J=7.1 Hz, 2H), 2.00-2.11 (m, 1H), 1.04 (d, J=6.4 Hz, 3H), 0.83 (d, J=6.4 Hz, 3H). MS(M+1): 474. HPLC 99%.

Compound 4-27 ethyl (S)-3-(6-((1-(4-(benzo[d]thiazol-2-yl)phenyl)-2-methylpropyl)amino)nicotinamido)propanoate

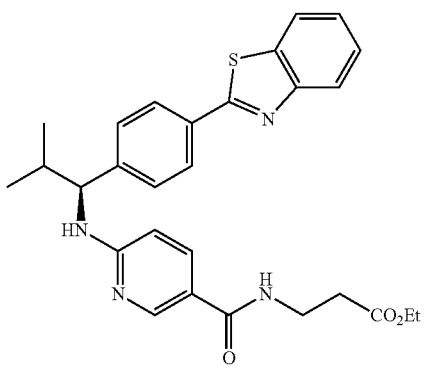 [SMILES: CCOC(=O)CCNC(=O)c1ccc(N[C@H](c2ccc(-c3nc4ccccc4s3)cc2)C(C)C)nc1]

¹H NMR (400 MHz, DMSO-d₆): δ8.39 (d, J=2.4 Hz, 1H), 8.08-8.18 (m, 2H), 7.99-8.06 (m, 3H), 7.74 (dd, J=8.8, 2.4 Hz, 1H), 7.49-7.60 (m, 4H), 7.40-7.47 (m, 1H), 6.59 (d, J=8.8 Hz, 1H), 4.79-4.90 (m, 1H), 4.00-4.05 (m, 2H), 3.37-3.44 (m, 2H), 3.21-3.28 (m, 1H), 2.42 (t, J=6.8 Hz, 1H), 2.10 (d, J=7.3 Hz, 1H), 1.12-1.16 (m, 3H), 1.00 (d, J=6.4 Hz, 3H), 0.82 (d, J=6.8 Hz, 3H). MS(M+1): 503. HPLC 98%.

Compound 4-28

(S)-3-(6-((1-(4-(benzo[d]thiazol-2-yl)phenyl)-2-methylpropyl)amino)nicotinamido)propanoic acid

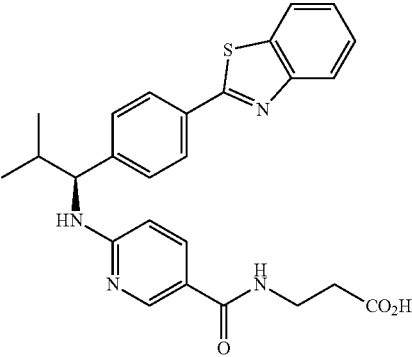

¹H NMR (400 MHz, DMSO-d₆): δ12.09 (br. s., 1H), 8.39 (d, J=2.0 Hz, 1H), 8.09-8.16 (m, 2H), 7.98-8.07 (m, 3H), 7.75 (dd, J=8.8, 2.4 Hz, 1H), 7.50-7.59 (m, 4H), 7.40-7.48 (m, 1H), 6.59 (d, J=8.8 Hz, 1H), 4.85 (br. s., 1H), 3.34-3.42 (m, 2H), 2.44 (t, J=7.1 Hz, 2H), 2.03-2.17 (m, 1H), 1.00 (d, J=6.4 Hz, 3H), 0.82 (d, J=6.8 Hz, 3H). MS(M+1): 475. HPLC 99%.

Compound 4-29 ethyl (S)-3-(6-((1-(4-(benzo[d]oxazol-2-methylpropyl)amino)nicotinamido propanoate

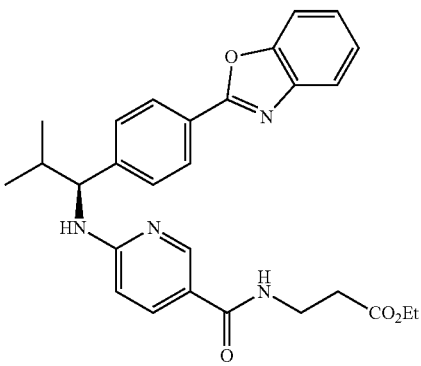 [SMILES: CCOC(=O)CCNC(=O)c1ccc(N[C@H](c2ccc(-c3nc4ccccc4o3)cc2)C(C)C)nc1]

¹H NMR (400 MHz, DMSO-d₆): δ8.39 (s, 1H), 8.07-8.20 (m, 3H), 7.72-7.82 (m, 3H), 7.58 (d, J=8.3 Hz, 3H), 7.33-7.45 (m, 2H), 6.60 (d, J=8.8 Hz, 1H), 3.99-4.07 (m, 2H), 3.41 (q, K=6.7 Hz, 2H), 2.04-2.15 (m, 1H), 1.14 (1, J=7.1 Hz, 3H), 1.00 (d, J=6.4 Hz, 3H), 0.82 (d, J=6.4 Hz, 3H). MS(M+1): 487. HPLC 98%.

Compound 4-30

(S)-3-(6-((1-(4-(benzo[d]oxazol-2-yl)phenyl)-2-methylpropyl)amino)nicotinamido)propanoic acid

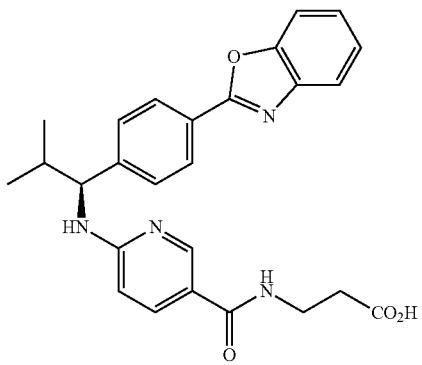 [SMILES: CC(C)[C@H](Nc1ccc(C(=O)NCCC(=O)O)cn1)c1ccc(-c2nc3ccccc3o2)cc1]

$^1$H NMR (400 MHz, DMSO-d$_6$): δ 8.39 (d, J=2.4 Hz, 1H), 8.13 (d, J=8.3 Hz, 3H), 7.69-7.83 (m, 3H), 7.51-7.62 (m, 3H), 7.34-7.44 (m, 2H), 6.59 (d, J=8.8 Hz, 1H), 3.37 (q, J=6.4 Hz, 2H), 2.43 (t, J=7.1 Hz, 2H), 2.05-2.16 (m, 1H), 1.00 (d, J=6.4 Hz, 3H), 0.82 (d, J=6.8 Hz, 3H). MS(M+1): 459. HPLC 97%.

Compound 5-2

(S)-3-(4-((3-methyl-1-(4-(3-phenyl-1,2,4-oxadiazol-5-yl)phenyl)butyl)amino)benzamido)propanoic acid

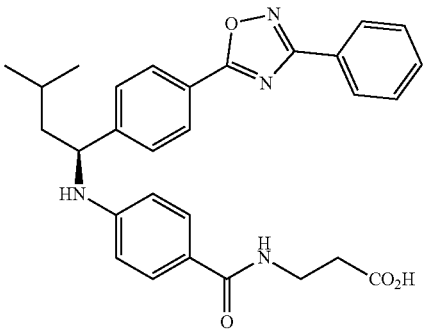

$^1$H NMR (400 MHz, DMSO-d$_6$): δ 8.12 (d, J=7.8 Hz, 2H), 8.08 (dd, J=7.6, 2.2 Hz, 2H), 7.98 (t, J=5.4 Hz, 1H), 7.66 (d, J=8.3 Hz, 2H), 7.56-7.62 (m, 3H), 7.51 (d, J=8.8 Hz, 2H), 6.76 (d, J=7.8 Hz, 1H), 6.56 (d, J=8.8 Hz, 2H), 4.55-4.63 (m, 1H), 3.35-3.40 (m, 2H), 2.43 (t, J=7.1 Hz, 2H), 1.65-1.83 (m, 2H), 1.45-1.57 (m, 1H), 0.97 (d, J=6.4 Hz, 3H), 0.91 (d, J=6.4 Hz, 3H). MS(M+1): 499. HPLC 95%.

Compound 5-1 ethyl (S)-3-(4-((3-methyl-1-(4-(3-phenyl-1,2,4-oxadiazol-5-yl)phenyl)butyl)amino)benzamido)propanoate

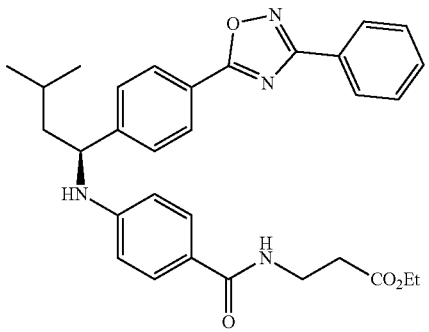 [SMILES: CC(C)C[C@H](Nc1ccc(C(=O)NCCC(=O)O)cc1)c1ccc(-c2nc(-c3ccccc3)no2)cc1]

$^1$H NMR (400 MHz, DMSO-d$_6$): δ 8.04-8.16 (m, 4H), 8.00 (t, J=5.4 Hz, 1H), 7.66 (d, J=7.8 Hz, 2H), 7.55-7.62 (m, 3H), 7.46-7.54 (m, 2H), 6.77 (d, J=7.8 Hz, 1H), 6.57 (d, J=8.8 Hz, 2H), 4.55-4.62 (m, 1H), 4.02 (q, J=7.3 Hz, 2H), 3.36-3.43 (m, 2H), 2.46-2.50 (m, 2H), 1.66-1.82 (m, 2H), 1.46-1.55 (m, 1H), 1.14 (t, J=7.1 Hz, 3H), 0.96 (d, J=6.4 Hz, 3H), 0.91 (d, J=5.9 Hz, 3H). MS(M+1): 527. HPLC 98%.

Compound 5-3 ethyl (S)-3-(4-((2-methyl-1-(4-(3-phenyl-1,2,4-oxadiazol-5-yl)phenyl)propyl)amino)benzamido)propanoate

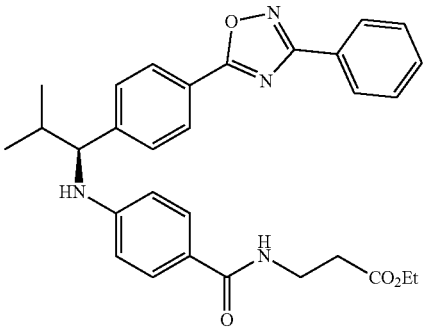 [SMILES: CCOC(=O)CCNC(=O)c1ccc(N[C@H](c2ccc(-c3nc(-c4ccccc4)no3)cc2)C(C)C)cc1]

$^1$H NMR (400 MHz, DMSO-d$_6$): δ 8.12 (d, J=8.3 Hz, 2H), 8.05-8.09 (m, 2H), 8.00 (s, 1H), 7.55-7.65 (m, 5H), 7.50 (d, J=8.8 Hz, 2H), 6.71 (d, J=7.8 Hz, 1H), 6.58 (d, J=8.8 Hz, 2H), 4.30 (s, 1H), 4.02 (q, J=7.2 Hz, 2H), 3.39 (q, J=6.5 Hz, 2H), 2.46-2.50 (m, 2H), 2.05 (d, J=6.8 Hz, 1H), 1.13 (t, J=7.1 Hz, 3H), 1.04 (d, J=6.4 Hz, 3H), 0.82 (d, J=6.8 Hz, 3H). MS(M+1): 513. HPLC 99%.

Compound 5-4

(S)-3-(4-((2-methyl-1-(4-(3-phenyl-1,2,4-oxadiazol-5-yl)phenyl)propyl)amino)benzamido)propanoic acid

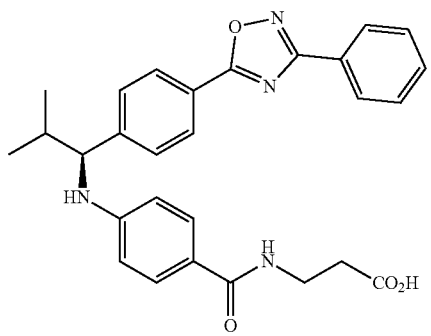 [SMILES: CC(C)[C@H](Nc1ccc(C(=O)NCCC(=O)O)cc1)c1ccc(-c2nc(-c3ccccc3)no2)cc1]

¹H NMR (400 MHz, DMSO-d₆): δ 8.13 (d, J=7.8 Hz, 2H), 8.06-8.10 (m, 2H), 7.98 (t, J=5.4 Hz, 1H), 7.57-7.66 (m, 5H), 7.50 (d, J=8.8 Hz, 2H), 6.70 (d, J=7.8 Hz, 1H), 6.57 (d, J=8.8 Hz, 2H), 4.31 (1, J=7.6 Hz, 1H), 3.35-3.40 (m, 2H), 2.42 (t, J=7.3 Hz, 2H), 2.00-2.11 (m, 1H), 1.04 (d, J=6.4 Hz, 3H), 0.82 (d, J=6.8 Hz, 3H). MS(M+1): 485. HPLC 99%.

Compound 5-6

3-(4-(((1S)-2-methyl-1-(4-(3-phenyl-1,2,4-oxadiazol-5-yl)phenyl)butyl)amino)benzamido)propanoic acid

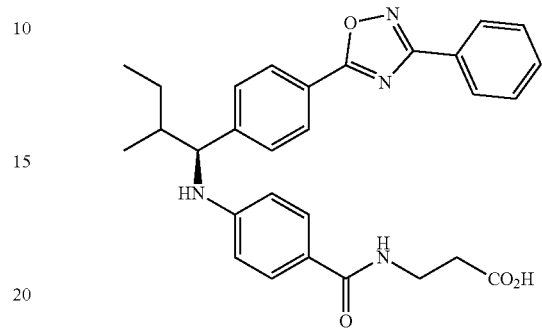

¹H NMR (400 MHz, DMSO-d₆): δ7.96-8.17 (m, 5H), 7.41-7.68 (m, 7H), 6.49-6.74 (m, 3H), 4.29-4.50 (m, 1H), 3.33 (q, J=7.3 Hz, 2H), 2.27-2.35 (m, 2H), 1.60-1.90 (m, 1H), 1.06-1.44 (m, 2H), 0.72-0.98 (m, 6H). MS(M+1): 499. HPLC 97%.

Compound 5-5 ethyl 3-(4-(((1S)-2-methyl-1-(4-(3-phenyl-1,2,4-oxadiazol-5-yl)phenyl)butyl)amino)benzamido)propanoate

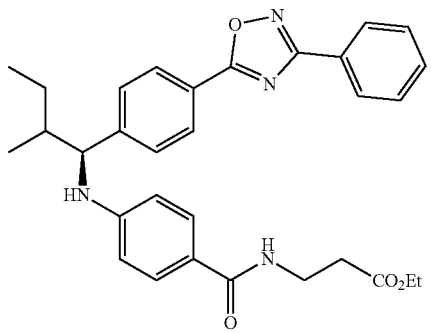 [SMILES: CCC(C)[C@H](Nc1ccc(C(=O)NCCC(=O)O)cc1)c1ccc(-c2nc(-c3ccccc3)no2)cc1]

¹H NMR (400 MHz, DMSO-d₆): δ7.96-8.15 (m, 5H), 7.46-7.68 (m, 7H), 6.71 (d, J=8.3 Hz, 1H), 6.54-6.76 (m, 2H), 4.30-4.50 (m, 1H), 4.02 (q, J=7.3 Hz, 2H), 3.36-3.44 (m, 2H), 2.41-2.50 (m, 2H), 1.77-1.90 (m, 1H), 1.55-1.73 (m, 1H), 1.22-1.48 (m, 1H), 1.09-1.17 (m, 3H), 0.70-0.98 (m, 6H). MS(M+1): 527. HPLC 95%.

Compound 5-7 ethyl (S)-3-(4-((1-(4-(3-phenyl-1,2,4-oxadiazol-5-yl)phenyl)pentyl)amino)benzamido)propanoate

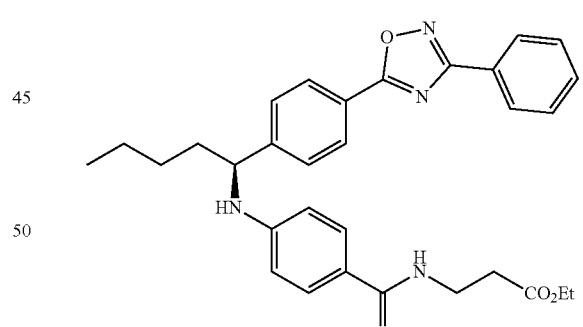

¹H NMR (400 MHz, DMSO-d₆): δ7.97-8.18 (m, 5H), 7.45-7.69 (m, 7H), 6.79 (d, J=7.3 Hz, 1H), 6.55 (d, J=8.3 Hz, 2H), 4.52 (q, J=7.2 Hz, 1H), 4.02 (q, J=7.3 Hz, 2H), 3.38-3.43 (m, 2H), 2.46-2.50 (m, 2H), 1.65-1.90 (m, 2H), 1.23-1.47 (m, 4H), 1.14 (t, J=7.1 Hz, 3H), 0.85 (t, J=6.8 Hz, 3H). MS(M+1): 527. HPLC 96%.

115
Compound 5-8
(S)-3-(4-((1-(4-(3-phenyl-1,2,4-oxadiazol-5-yl)phenyl)pentyl)amino)benzamido)propanoic acid
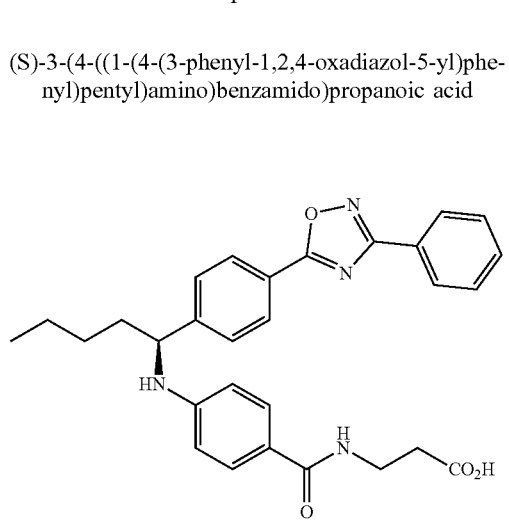
$^1$H NMR (400 MHz, DMSO-d$_6$): δ7.94-8.18 (m, 5H), 7.43-7.69 (m, 7H), 6.77 (d, J=7.3 Hz, 1H), 6.45-6.59 (m, 2H), 4.53 (d, J=6.8 Hz, 1H), 3.29-3.39 (m, 2H), 2.32 (t, J=7.1 Hz, 2H), 1.63-1.90 (m, 2H), 1.20-4.48 (m, 4H), 0.86 (t, J=7.1 Hz, 3H). MS(M+1): 499, HPLC 97%.
Example 5: Synthesis of the Compounds Shown in the Following Tables 6 and 7
The following scheme was followed for synthesizing Compounds 6-1, 6-2, and 7-1 to 7-4.
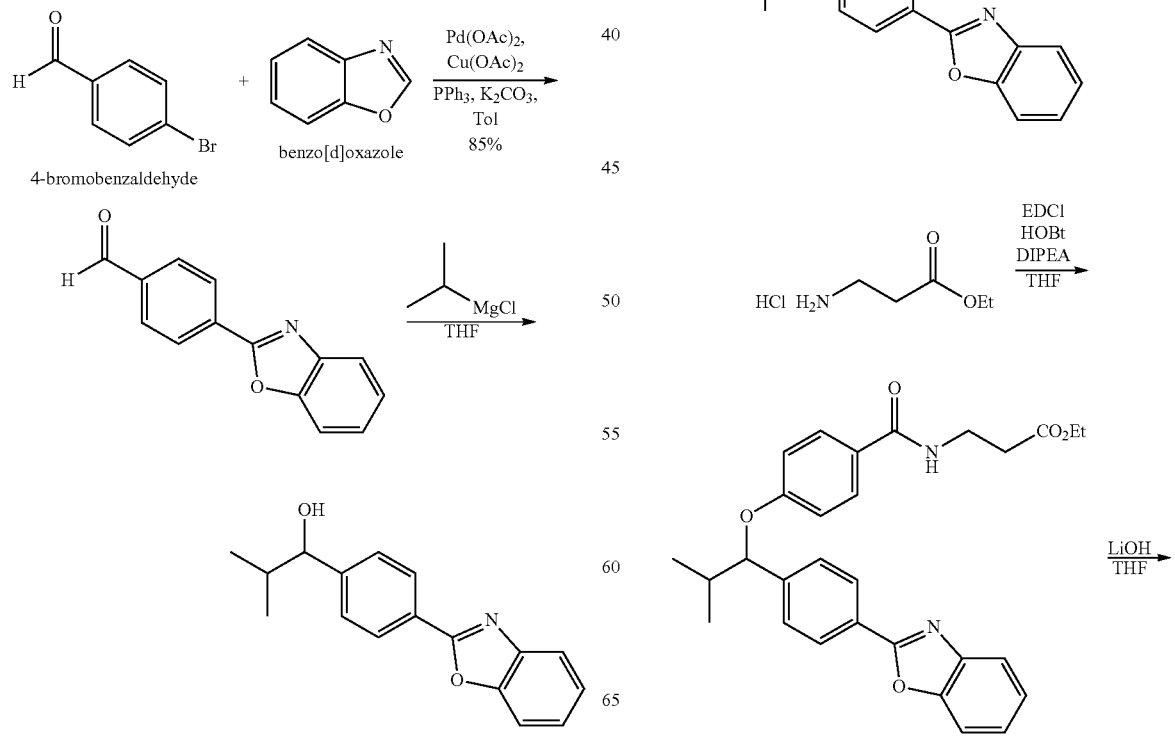

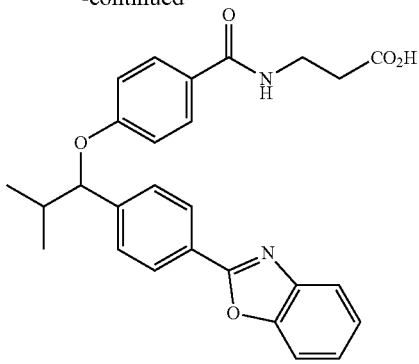

The reaction mixture of benzoazoles (16.5 mmol), 4-bromobenzaldehyde (13.7 mmol), Pd(OAc)$_2$ (1.37 mmol), Cu(OAc)$_2$ (2.75 mmol), and K$_2$CO$_3$ (27.5 mmol) in toluene (50 mL) was refluxed for overnight. Then, the mixture was filtered and the filtrate was evaporated under reduced pressure. The residue was purified by column chromatography to give 4-(benzo[d]oxazol-2-yl)benzaldehyde (2.5 g, 85%).

A solution of 4-(benzo[d]oxazol-2-yl)benzaldehyde (2.50 g, 14 mmol) in tetrahydrofuran (50 mL) was cooled to −78° C. To this solution was added isopropylmagnesium chloride (2M in THF, 10 mL) and dimethyl zinc (4.2 mmol) dropwise over 30 minutes. The reaction was stirred at −78° C. for 2 h. The reaction was then quenched by addition of saturated aqueous ammonium chloride. This mixture was extracted with ethyl acetate. The organic layer was dried over magnesium sulfate, filtered and concentrated. Purification by silica gel chromatography gave 1-(4-(benzo[d]oxazol-2-yl)phenyl)-2-methylpropan-1-ol (2.58 g, 69%).

To a roundbottomed flask was added ethyl 4-hydroxybenzoate (1.66 g, 10 mmol), 1-(4-(benzo[d]oxazol-2-yl)phenyl)-2-methylpropan-1-ol (2.40 g, 9 mmol), trin-butylphosphine (2.02 g, 10 mmol) and THF (10 mL). ADDP (2.52, 10 mmol) was added dropwise to the reaction mixture over the course of 3 min at room temperature. Overall, the reaction mixture was stirred for 3 h. The reaction mixture was dried in vacuum then purified by flash chromatography (silica gel, 15% EtOAc in hexanes) to give ethyl 4-(1-(4-(benzo[d]oxazol-2-yl)phenyl)-2-methyl propoxy)benzoate (2.24 g, 60%).

To a solution of ethyl 4-(1-(4-(benzo[d]oxazol-2-yl)phenyl)-2-methylpropoxy)benzoate (2.10 g, 5 mmol) in dioxane (10 mL) was added 2.5 M aq. LiOH (10 mL). The mixture was warmed to 80° C., stirred for 5 h, and cooled to rt. After the addition of 1 M aq, HCl, the mixture was extracted with ethyl acetate twice. The combined organic layer was dried over MgSO$_4$, filtered, and concentrated then obtained the acid as white crystal (1.78 g, 92%).

4-(1-(4-(benzo[d]oxazol-2-yl)phenyl)-2-methylpropoxy) benzoic acid (1.78 g, 4.6 mmol) was dissolved in THF (50 mL), and HOBt (1.40 g, 9.2 mmol), EDCI (1.76 g, 9.2 mmol), ethyl 3-aminopropanoate hydrochloride (1.41 g, 9.2 mmol) and DIPEA (1.92 g, 9.2 mmol) were added. The reaction mixture was stirred at room temperature for overnight. Extraction with ethyl acetate, brine and dried, filtered, and evaporated in vacuo. The residue was purified by column chromatography on silica gel with 15% EtOAc in hexanes to afford the ethyl 3-(4-(1-(4-(benzo[d]oxazol-2-yl)phenyl)-2-methylpropoxy)benzamido) propanoate (1.43 g, 64%)

Ethyl 3-(4-(1-(4-(benzo[d]oxazol-2-yl)phenyl)-2-methylpropoxy)benzamido) propanoate (1.43 g, 2.94 mmol) was dissolved in THF (20 mL) followed by addition of LiOH 0.24 g in 10 mL H$_2$O. The reaction mixture was stirred at room temperature for overnight. The reaction was monitored by TLC, With completion of the reaction, the solvent was removed by rotary evaporation. After the addition of 2 M aq. HCl, the mixture was extracted with ethyl acetate twice. The combined organic layer was dried, filtered, and evaporated in vacuo to obtained 3-(4-(1-(4-(benzo[d]oxazol-2-yl)phenyl)-2-methylpropoxy)benzamido)propanoic acid (1.21 g, 90%).

Compound 6-1

Ethyl 3-(4-(1-(4-(benzo[d]thiazol-2-yl)phenyl)-2-methylpropoxy)benzamido)propanoate

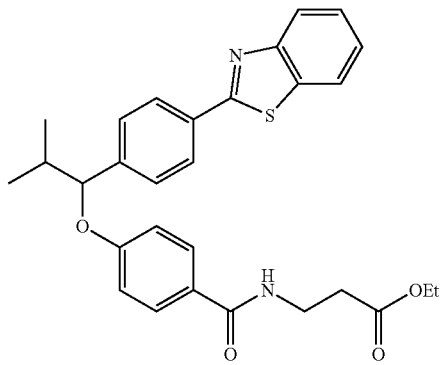 [SMILES: CCOC(=O)CCNC(=O)c1ccc(OC(c2ccc(-c3nc4ccccc4s3)cc2)C(C)C)cc1]

$^1$H NMR (400 MHz, DMSO-d$_6$): δ8.29 (t, J=5.6 Hz, 1H), 8.13 (d, J=7.3 Hz, 1H), 8.02-8.09 (m, 3H), 7.65-7.71 (m, 2H), 7.51-7.57 (m, 3H), 7.42-7.48 (m, 1H), 6.93-6.99 (m, 2H), 5.26 (d, J=6.4 Hz, 1H), 4.03 (q, J=7.2 Hz, 2H), 3.38-3.46 (m, 2H), 2.50-2.54 (m, 2H), 2.16 (dq, J=13.4, 6.6 Hz, 1H), 1.13 (t, J=7.1 Hz, 3H), 1.03 (d, J=6.4 Hz, 3H), 0.89 (d, J=6.8 Hz, 3H). MS(M+1): 503. HPLC 98%.

Compound 6-2

3-(4-(1-(4-(Benzo[d]thiazol-2-yl)phenyl)-2-methylpropoxy)benzamido)propanoic acid

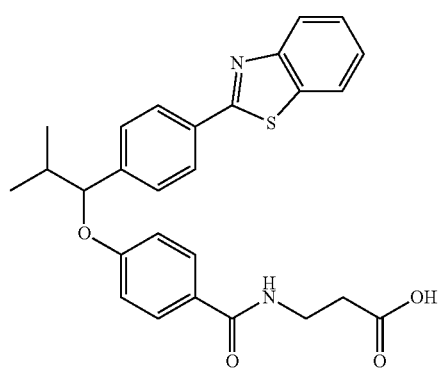 [SMILES: CC(C)C(Oc1ccc(C(=O)NCCC(=O)O)cc1)c1ccc(-c2nc3ccccc3s2)cc1]

$^1$H NMR (400 MHz, DMSO-d$_6$): δ8.27 (t, J=5.6 Hz, 1H), 8.12 (d, J=7.8 Hz, 1H), 8.01-8.08 (m, 3H), 7.70 (d, J=8.8 Hz, 2H), 7.50-7.57 (m, 3H), 7.42-7.47 (m, 1H), 6.93-6.99 (m, 2H), 5.26 (d, J=6.4 Hz, 1H), 3.39-3.43 (m, 2H), 2.45 (t,

J=7.1 Hz, 2H), 2.10-2.20 (m, 1H), 1.03 (d, J=6.8 Hz, 3H), 0.89 (d, J=6.8 Hz, 3H). MS(M+1): 475. HPLC 98%.

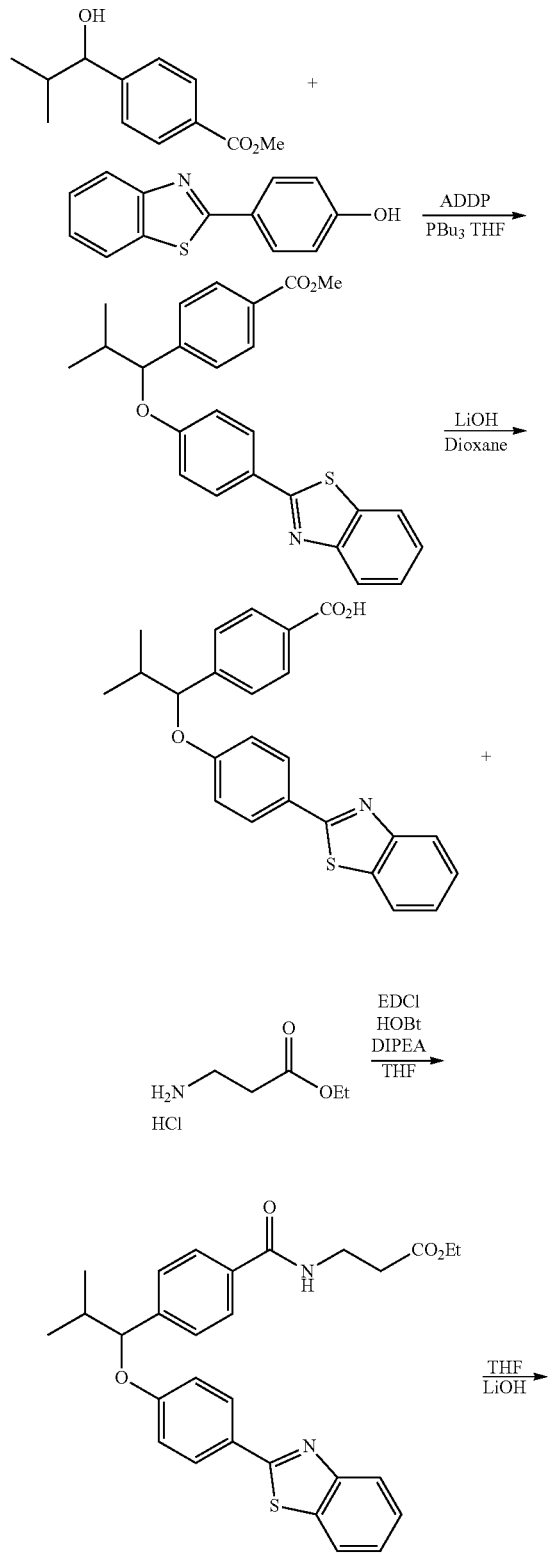

Scheme VI

-continued

To a flask was added 4-(benzo[d]thiazol-2-yl)phenol (2.27 g, 10 mmol), methyl 4-(1-hydroxy-2-methylpropyl)benzoate (2.08 g, 10 mmol), tri-nbutylphosphine (2.02 g, 10 mmol) and THF (10 mL). ADDP (2.52, 10 mmol) was added dropwise to the reaction mixture over the course of 3 min at room temperature. Overall, fee reaction mixture was stirred for 3 h. The reaction mixture was dried in vacuum then purified by flash chromatography with 15% EtOAc in hexanes to give methyl 4-(1-(4-(benzo[d]thiazol-2-yl)phenoxy)-2-methylpropyl)benzoate (2.34 g, 56%).

To a solution of methyl 4-(1-(4-(benzo[d]thiazol-2-yl)phenoxy)-2-methylpropyl)benzoate (2.34 g, 5.6 mmol) in dioxane (10 mL) was added 2.5 M aq, LiOH (10 mL). The mixture was warmed to 80° C. stirred for 5 h, and cooled to rt. After the addition of 1 M aq. HCl, the mixture was extracted with ethyl acetate twice. The combined organic layer was dried over MgSO$_4$, filtered, and concentrated then obtained the acid as white crystal (2.03 g, 90%).

4-(1-(4-(benzo[d]thiazol-2-yl)phenoxy)-2-methylpropyl)benzoic acid (2.03 g, 5.04 mmol) was dissolved in THF (50 mL), and HOBt (1.40 g, 9.2 mmol), EDCI (1.76 g, 9.2 mmol), ethyl 3-aminopropanoate hydrochloride (1.41 g, 9.2 mmol) and DIPEA (1.92 g, 9.2 mmol) were added. The reaction mixture was stirred at room temperature for overnight. Extraction with ethyl acetate, brine and dried, filtered, and evaporated in vacuo. The residue was purified by column chromatography on silica gel with 15% EtOAc in hexanes to afford the ethyl 3-(4-(1-(4-(benzo[d]thiazol-2-yl)phenoxy)-2-methylpropyl)benzamido)propanoate (1.72 g, 68%).

Ethyl ester (1.72 g, 3.42 mmol) was dissolved in THF (20 mL) followed by addition of LiOH 0.24 g in 10 mL H$_2$O. The reaction mixture was stirred at room temperature for overnight. The reaction was monitored by TLC. With completion of the reaction, the solvent was removed by rotary evaporation. After the addition of 2 M aq. HCl, the mixture was extracted with ethyl acetate twice. The combined organic layer was dried, filtered, and evaporated in vacuo to obtained 3-(4-(1-(4-(benzo[d]thiazol-2-yl)phenoxy)-2-methylpropyl)benzamido)propanoic acid (1.40 g, 87%).

Compound 7-1

Ethyl 3-(4-(1-(4-(benzo[d]oxazol-2-yl)phenoxy)-2-methylpropyl)benzamido)propanoate

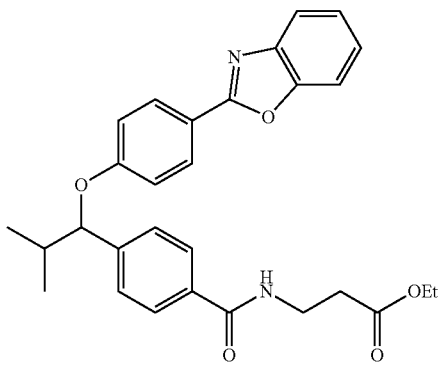 [SMILES: CCOC(=O)CCNC(=O)c1ccc(C(Oc2ccc(-c3nc4ccccc4o3)cc2)C(C)C)cc1]

$^1$H NMR (400 MHz, DMSO-d$_6$): δ8.49 (s, 1H), 7.98-8.08 (m, 2H), 7.79 (d, J=8.3 Hz, 2H), 7.68-7.75 (m, 2H), 7.47 (d, J=8.3 Hz, 2H), 7.33-7.39 (m, 2H), 7.06-7.11 (m, 2H), 5.27 (d, J=6.4 Hz, 1H), 4.04 (q, J=7.2 Hz, 2H), 3.46 (d, J=5.9 Hz, 2H), 2.54 (t, J=6.8 Hz, 2H), 2.10-2.20 (m, 1H), 1.15 (t, J=7.1 Hz, 3H), 1.02 (d, J=6.8 Hz, 3H), 0.87 (d, J=6.8 Hz, 3H). MS(M+1): 487. HPLC 96%.

Compound 7-2

3-(4-(1-(4-(Benzo[d]oxazol-2-yl)phenoxy)-2-methylpropyl)benzamido)propanoic acid

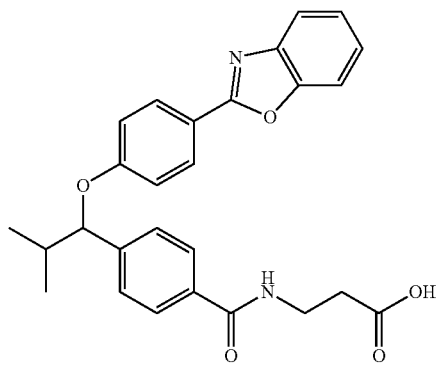 [SMILES: CC(C)C(Oc1ccc(-c2nc3ccccc3o2)cc1)c1ccc(C(=O)NCCC(=O)O)cc1]

$^1$H NMR (400 MHz, DMSO-d$_6$): δ8.48 (t, J=5.4 Hz, 1H), 7.98-8.08 (m, 2H), 7.80 (d, J=7.8 Hz, 2H), 7.67-7.75 (m, 2H), 7.47 (d, J=8.3 Hz, 2H), 7.30-7.41 (m, 2H), 7.04-7.13 (m, 2H), 5.27 (d, J=6.4 Hz, 1H), 3.41-3.48 (m, 2H), 2.45-2.49 (m, 2H), 2.07-2.22 (m, 1H), 1.02 (d, J=6.8 Hz, 3H), 0.87 (d, J=6.8 Hz, 3H). MS(M+1): 459. HPLC 94%.

Compound 7-3

Ethyl 3-(4-(1-(4-(benzo[d]thiazol-2-yl)phenoxy)-2-methylpropyl)benzamido)propanoate

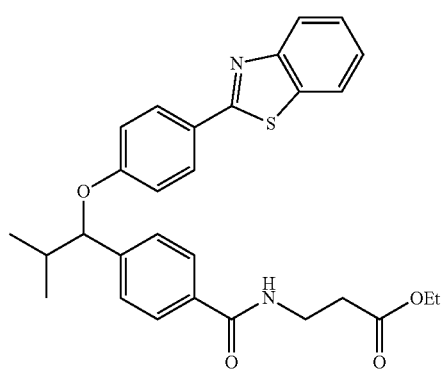 [SMILES: CCOC(=O)CCNC(=O)c1ccc(C(Oc2ccc(-c3nc4ccccc4s3)cc2)C(C)C)cc1]

$^1$H NMR (400 MHz, DMSO-d$_6$): δ8.49 (t, J=5.4 Hz, 1H), 8.07 (d, J=7.8 Hz, 1H), 7.97 (d, J=8.3 Hz, 1H), 7.92 (d, J=8.8 Hz, 2H), 7.79 (d, J=8.3 Hz, 2H), 7.35-7.56 (m, 4H), 7.04 (d, J=8.8 Hz, 2H), 5.24 (d, J=6.4 Hz, 1H), 4.04 (q, J=7.3 Hz, 2H), 3.41-3.52 (m, 2H), 2.54 (t, J=7.1 Hz, 2H), 2.14 (d, J=6.8 Hz, 1H), 1.15 (t, J=7.1 Hz, 3H), 1.02 (d, J=6.8 Hz, 3H), 0.87 (d, J=6.8 Hz, 3H). MS(M+1); 503. HPLC 99%.

Compound 7-4

3-(4-(1-(4-(Benzo[d]thiazol-2-yl)phenoxy)-2-methylpropyl)benzamido)propanoic acid

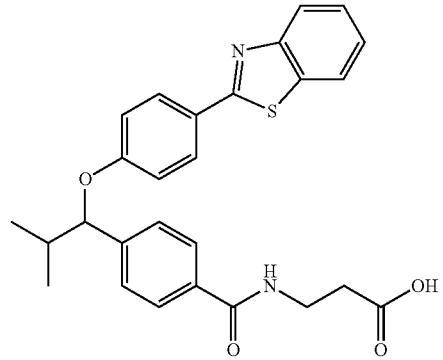 [SMILES: CC(C)C(Oc1ccc(-c2nc3ccccc3s2)cc1)c1ccc(C(=O)NCCC(=O)O)cc1]

$^1$H NMR (400 MHz, DMSO-d$_6$): δ12.19 (br. s., 1H), 8.49 (t, J=5.4 Hz, 1H), 8.06 (d, J=7.3 Hz, 1H), 7.98 (d, J=7.8 Hz, 1H), 7.89-7.95 (m, 2H), 7.82 (d, J=8.3 Hz, 2H), 7.44-7.52 (m, 3H), 7.37-7.43 (m, 1H), 7.02-7.07 (m, 2H), 5.23 (d, J=6.4 Hz, 1H), 3.41-3.50 (m, 2H), 2.48-2.54 (m, 2H), 2.09-2.19 (m, 1H), 1.02 (d, J=6.4 Hz, 3H), 0.84-0.89 (m, 3H). MS(M+1): 475. HPLC 97%.

In EXAMPLES 1-5, the detail synthesized procedures of some compounds are not repeated again if the synthesized procedures thereof are similar to those of the forgoing compounds.

Example 6: Evaluation of Compounds of Formula (I) in In Vitro Assays

The compounds prepared in EXAMPLES 1-5 were tested in two in vitro assays described below. The results are shown in Tables 1-7 shown below.

Glucagon eAMP Inhibition Assay

Downstream secondary messenger eAMP induced by glucagon was detected by Cisbio cAMP Dynamic 2 kit. Testing compounds were each prepared as a dimethyl sulfoxide (DMSO) solution at the concentration of 10 mM. To evaluate the potency of compounds in inhibiting the cAMP production, glucagon receptor (GCGR) overexpressed CHO-K1 cells or human primary hepatocytes were treated with compounds with a serial dilution. The cells were re-suspended in Hank's Balanced Salt solution (HBSS) contained 0.1% (w/v) bovine serum albumin and 800 nM 3-isobutyl-1-methylxanthine (IBMX) and seeded into low volume, 384 wells white plate. The diluted compounds were then added into the plate for 30 minutes pre-incubation where the final DMSO concentration was 1%. The cells were stimulated with glucagon at the concentration equaled to EC50 (an indicium of the concentration of a drag that gives half-maximal response) for 30 minutes at room temperature. After incubation, lysis buffer contain cAMP antibody and fluorescence acceptor were added into each well for additional 60 minutes incubation. Results were recorded by Molecular Devices SpectraMax Paradigm with the HTRF Detection Cartridges and the $IC_{50}$ value of each compound in inhibiting the cAMP production was calculated with non-linear regression based on the amount of cAMP production.

$I^{125}$-Glucagon Binding Assay

The binding affinity of each compound was evaluated by a competition assay with $I^{125}$-glucagon. GCGR membrane fractions were obtained from GCGR overexpressed CHO-K1 cells as a stock of 1 mg/ml concentration. To evaluate the $IC_{50}$ of compounds binding to GCGR, GCGR membrane fractions were treated with compounds with a serial dilution. The membrane fractions were diluted to 7.5 microgram per well in 70 microliter assay buffer contained 50 mM Tris pH 7.4 and 0.5% (w/v) bovine serum albumin and added into 96 wells plate. The membrane fractions were then mixed with 10 microliter diluted compounds. After 5 minutes pre-incubation, 20 microliter $I^{125}$ labeled glucagon (Perkin Elmer) was added into each well at the final concentration of 0.0625 nM. The assay mixtures were incubated at 25° C. for 30 minutes and then transferred onto the Millipore Multiscreen GF/B Plate coated with 0.5% (w/v) Polyethyleneimine. The filter plate was washed with wash buffer contained 50 mM Tris pH 7.4 for 2 times, 300 microliter each time. The residual isotope was detected by Hidex CHAMELEON V micro-beta counter and the $IC_{50}$ value of each compound binding to GCGR was calculated with non-linear regression.

Shown in Tables 1-7 below are the structures and in vitro activities of 172 exemplary compounds of formula (I). All 172 compounds were found to bind to glucagon receptor and inhibit the level of glucagon downstream cAMP to various degrees as indicated by their $IC_{50}$ values ($IC_{50}$ being the concentration of an inhibitor where the response or binding is reduced by half) included in the following tables.

TABLE 1

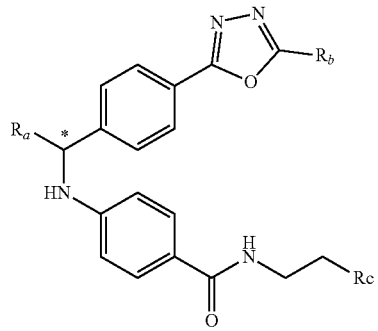

Rc =
D: $CO_2H$
E: $CO_2Et$
F: $CO_2Me$
G: $SO_3H$

| Compound | $R_a$ | $R_b$ | $R_c$ | Chirality | $IC_{50}^{binding}$ (nM)$^a$ | $IC_{50}^{cAMP}$ (nM) |
|---|---|---|---|---|---|---|
| 1-1 | isopropyl | Ph | D | SR | 27 | 4690 |
| 1-2 | isopropyl | Ph | F | SR | 1216 | 113 |
| 1-3 | isopropyl | Ph | E | SR | 1871(43%) | 55 |
| 1-4 | isopropyl | $CF_3$ | D | SR | 433 | >30000 |
| 1-5 | isobutyl | Ph | D | SR | 175 | 4134 |
| 1-6 | n-propyl | Ph | E | SR | 2614 | 31 |
| 1-7 | n-propyl | Ph | D | SR | 211 | 3330 |
| 1-8 | n-propyl | $CF_3$ | D | SR | 651 | >30000 |
| 1-9 | isobutyl | $CF_3$ | D | SR | 956 | 17108 |
| 1-10 | sec-Butyl | Ph | E | SR | 1867(34%) | 25 |
| 1-11 | sec-Butyl | Ph | D | SR | 72 | 2538 |
| 1-12 | isobutyl | $^tBu$ | D | SR | 455 | 6709 |
| 1-13 | n-butyl | Ph | G | SR | 314 | >30000 |
| 1-14 | n-butyl | $CF_3$ | D | SR | 379 | 3454 |
| 1-15 | n-butyl | pyridin-2-yl | E | SR | 578 | 306 |

TABLE 1-continued

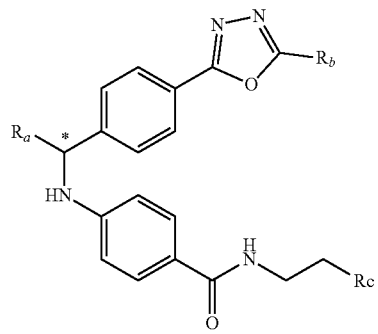

Rc =
D: CO$_2$H
E: CO$_2$Et
F: CO$_2$Me
G: SO$_3$H

| Compound | R$_a$ | R$_b$ | R$_c$ | Chirality | IC$_{50}^{binding}$ (nM)$^a$ | IC$_{50}^{cAMP}$ (nM) |
|---|---|---|---|---|---|---|
| 1-16 | n-butyl | pyridin-2-yl | D | SR | 203 | 15690 |
| 1-17 | isopropyl | 4-fluorophenyl | E | SR | 3511(53%) | 322 |
| 1-18 | isopropyl | 4-fluorophenyl | D | SR | 122 | 4351 |
| 1-19 | n-butyl | $^t$Bu | E | SR | 4408 | 203 |
| 1-20 | n-butyl | $^t$Bu | D | SR | 562 | 15240 |
| 1-21 | sec-Butyl | $^t$Bu | E | SR | 3311 | 126 |
| 1-22 | sec-Butyl | $^t$Bu | D | SR | 246 | 10321 |
| 1-23 | isopropyl | $^t$Bu | E | SR | 18674 | 180 |
| 1-24 | isopropyl | $^t$Bu | D | SR | 314 | >30000 |
| 1-25 | isopropyl | 4-methoxyphenyl | E | SR | >30000 | 284 |
| 1-26 | isopropyl | 4-methoxyphenyl | D | SR | 198 | 4384 |
| 1-27 | isobutyl | 4-fluorophenyl | E | SR | >30000 | 118 |
| 1-28 | isobutyl | 4-fluorophenyl | D | SR | 563 | 4761 |
| 1-29 | sec-Butyl | 4-fluorophenyl | E | SR | 4717 | 114 |
| 1-30 | sec-Butyl | 4-fluorophenyl | D | SR | 347 | 3411 |
| 1-31 | sec-Butyl | CF$_3$ | E | SR | >30000 | 88 |
| 1-32 | sec-Butyl | CF$_3$ | D | SR | 885 | 3478 |
| 1-33 | n-butyl | CF$_3$ | E | SR | >30000 | 142.3 |
| 1-34 | sec-Butyl | CF$_3$ | E | S | 16103 | 42 |
| 1-35 | sec-Butyl | CF$_3$ | E | R | >30000 | 384 |
| 1-36 | sec-Butyl | CF$_3$ | D | S | 359 | 2042 |
| 1-37 | sec-Butyl | CF$_3$ | D | R | 1644 | 3264 |
| 1-38 | n-butyl | pyridin-2-yl | F | SR | 1579 | 80 |
| 1-39 | isopropyl | Ph | E | S | 2853 | 40.33 |
| 1-40 | isopropyl | Ph | E | R | >30000 | 162 |
| 1-41 | isopropyl | Ph | D | S | 107 | 2714 |
| 1-42 | isopropyl | Ph | D | R | 2921 | 2930 |
| 1-43 | n-butyl | Pyridin-2-yl | E | S | 1479 | 46.37 |
| 1-44 | n-butyl | Pyridin-2-yl | E | R | >30000 | 829.9 |
| 1-45 | n-butyl | Pyridin-2-yl | D | S | 339 | 2537 |
| 1-46 | n-butyl | Pyridin-2-yl | D | R | 702 | >30000 |
| 1-47 | sec-Butyl | Ph | E | S | 226(28%) | 36.96 |
| 1-48 | sec-Butyl | Ph | E | R | >30000 | 164.1 |
| 1-49 | sec-Butyl | Ph | D | S | 92 | 2047 |
| 1-50 | sec-Butyl | Ph | D | R | 82 | 2732 |
| 1-51 | n-butyl | CF$_3$ | E | S | 6174 | 33.9 |
| 1-52 | n-butyl | CF$_3$ | E | R | >30000 | 438.7 |
| 1-53 | n-butyl | CF$_3$ | D | S | 351 | 1874 |
| 1-54 | n-butyl | CF$_3$ | D | R | 3073 | 3671 |
| 1-55 | isopropyl | CF$_3$ | E | S | >30000 | 1357 |
| 1-56 | isopropyl | CF$_3$ | E | R | >30000 | 164 |
| 1-57 | isopropyl | CF$_3$ | D | S | 2498 | >30000 |
| 1-58 | isopropyl | CF$_3$ | D | R | 875 | >30000 |
| 1-59 | isobutyl | Ph | E | S | >30000 | 26 |
| 1-60 | isobutyl | Ph | E | R | >30000 | 114 |
| 1-61 | isobutyl | Ph | D | S | 201 | 3246 |
| 1-62 | isobutyl | Ph | D | R | 876 | 2049 |
| 1-63 | isopropyl | Ph | F | S | 1528 | 28 |
| 1-64 | isopropyl | Ph | G | S | 101 | >30000 |

* indicium of chirality
$^a$the number in pathenthesis represents the percentage of inhibition when a compound was administered at the concentration of 30 μM.

TABLE 2

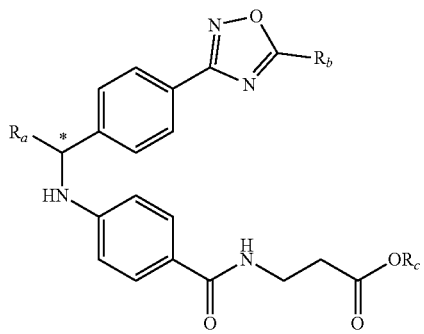

| Compound | $R_a$ | $R_b$ | $R_c$ | Chirality | $IC_{50}^{binding}$ (nM) | $IC_{50}^{cAMP}$ (nM) |
|---|---|---|---|---|---|---|
| 2-1 | isopropyl | tBu | Et | SR | 2905 | 240 |
| 2-2 | isopropyl | tBu | H | SR | 171 | 878 |
| 2-3 | n-butyl | tBu | Et | SR | >30000 | 225 |
| 2-4 | n-butyl | tBu | H | SR | 164 | 329 |
| 2-5 | isobutyl | tBu | Et | SR | 6245(63%) | 395 |
| 2-6 | isobutyl | tBu | H | SR | 226 | 8631 |
| 2-7 | n-butyl | Ph | Et | SR | 1206(27%) | 49 |
| 2-8 | n-butyl | Ph | H | SR | 70 | 934 |
| 2-9 | isobutyl | Ph | Et | SR | 1492(31%) | 105 |
| 2-10 | isobutyl | Ph | H | SR | 124 | 959 |
| 2-11 | isopropyl | Thiophene | Et | SR | 3063(38%) | 180 |
| 2-12 | isopropyl | Thiophene | H | SR | 354 | 503.55 |
| 2-13 | n-butyl | Thiophene | H | SR | 126 | 312.1 |
| 2-14 | isobutyl | Thiophene | H | SR | 274 | 1386 |
| 2-15 | cyclopentyl | Ph | H | SR | 106 | 450.3 |
| 2-16 | cyclohexyl | Ph | Et | SR | 178 | 438.1 |
| 2-17 | cyclohexyl | Ph | H | SR | 54 | 511 |
| 2-18 | sec-Butyl | Ph | Et | S | 830 | 46.7 |
| 2-19 | sec-Butyl | Ph | H | S | 49 | 473.4 |
| 2-20 | sec-Butyl | Ph | Et | R | 217 | 338.3 |
| 2-21 | sec-Butyl | Ph | H | R | 85 | 569.4 |
| 2-22 | isopropyl | Ph | Et | R | 673 | 245.1 |
| 2-23 | isopropyl | Ph | H | R | 537 | 1002 |
| 2-24 | isopropyl | 4-F—Ph | Et | SR | 2682(35%) | 247.9 |
| 2-25 | isopropyl | 4-F—Ph | H | SR | 58 | 1187 |
| 2-26 | isopropyl | Ph | H | SR | 40 | 570 |
| 2-27 | isopropyl | Ph | Et | S | 634 | 61 |
| 2-28 | isopropyl | Ph | H | S | 29 | 295 |
| 2-29 | sec-Butyl | $CF_3$ | Et | S | 1816(18%) | 172 |
| 2-30 | sec-Butyl | $CF_3$ | H | S | 166 | 550 |
| 2-31 | isopropyl | Ph | Me | SR | 204 | 97 |
| 2-32 | n-butyl | Ph | Me | SR | 616 | 147 |
| 2-33 | n-butyl | Ph | Et | S | 1038 | 283.4 |
| 2-34 | n-butyl | Ph | Et | S | >30000 | 39.37 |
| 2-35 | n-butyl | Ph | H | R | 40 | 851.8 |
| 2-36 | n-butyl | Ph | H | R | 199 | 338.4 |
| 2-37 | n-butyl | pyridin-2-yl | Et | S | 1098 | 89.7 |
| 2-38 | n-butyl | pyridin-2-yl | Et | S | 226 | 686 |
| 2-39 | n-butyl | pyridin-2-yl | H | R | >30000 | 671.7 |
| 2-40 | n-butyl | pyridin-2-yl | H | R | 1025 | 138.4 |
| 2-41 | isobutyl | Ph | Et | S | 389 | 71.15 |
| 2-42 | isobutyl | Ph | Et | R | 42 | 247.9 |
| 2-43 | isobutyl | Ph | H | S | >30000 | 391.3 |
| 2-44 | isobutyl | Ph | H | R | 199 | 334.2 |
| 2-45 | n-butyl | $CF_3$ | Et | S | >30000 | 118.2 |
| 2-46 | n-butyl | $CF_3$ | Et | R | >30000 | 2882 |
| 2-47 | n-butyl | $CF_3$ | H | S | 254 | 427.6 |
| 2-48 | n-butyl | $CF_3$ | H | R | 1181 | 1571 |
| 2-49 | isopropyl | Ph | Me | S | 285 | 55.8 |

TABLE 3

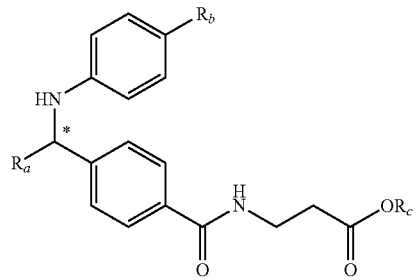

| Compound | $R_a$ | $R_b$ | $R_c$ | Chirality | IC$_{50}^{binding}$ (nM) | IC$_{50}^{cAMP}$ (nM) |
|---|---|---|---|---|---|---|
| 3-1 | n-butyl | 5-phenyl-1,3,4-oxadiazole | H | SR | 25 | 1743 |
| 3-2 | isopropyl | 5-phenyl-1,3,4-oxadiazole | H | SR | 17 | 2902 |
| 3-3 | n-butyl | 5-phenyl-1,3,4-oxadiazole | Et | SR | 1323 | 932.6 |
| 3-4 | isopropyl | 5-phenyl-1,3,4-oxadiazole | Et | SR | 2788 | 1231 |
| 3-5 | sec-Butyl | 5-phenyl-1,3,4-oxadiazole | Et | SR | 963 | 311 |
| 3-6 | sec-Butyl | 5-phenyl-1,3,4-oxadiazole | H | SR | 58 | 650 |
| 3-7 | sec-Butyl | 5-(4-fluorophenyl)-1,3,4-oxadiazol-2-yl | Et | SR | 246 | 159 |
| 3-8 | sec-Butyl | 5-(4-fluorophenyl)-1,3,4-oxadiazol-2-yl | H | SR | 74 | 1027 |
| 3-9 | isopropyl | 5-(4-fluorophenyl)-1,3,4-oxadiazol-2-yl | Et | SR | >30000 | 442 |
| 3-10 | isopropyl | 5-(4-fluorophenyl)-1,3,4-oxadiazol-2-yl | H | SR | 143 | 4504 |
| 3-11 | isopropyl | 5-phenyl-1,2,4-oxadiazole | H | SR | 318 | 717 |
| 3-12 | isopropyl | 5-phenyl-1,3,4-oxadiazole | Et | S | >30000 | 277 |
| 3-13 | isopropyl | 5-phenyl-1,3,4-oxadiazole | Et | R | >30000 | 206.7 |
| 3-14 | isopropyl | 5-phenyl-1,3,4-oxadiazole | H | S | 956.9 | 1776 |
| 3-15 | isopropyl | 5-phenyl-1,3,4-oxadiazole | H | R | 21 | 631.8 |

TABLE 4

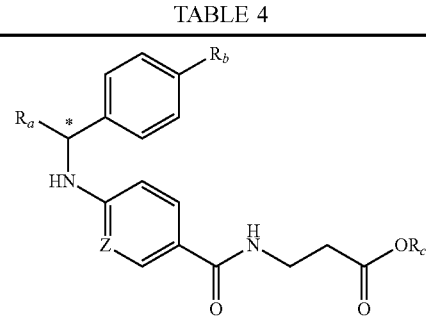

| Compound | $R_a$ | $R_b$ | Z | $R_c$ | Chirality | IC$_{50}^{binding}$ (nM) | IC$_{50}^{cAMP}$ (nM) |
|---|---|---|---|---|---|---|---|
| 4-1 | isopropyl | benzo[d]oxazole | C | Et | SR | 968 | 95.7 |
| 4-2 | n-butyl | benzo[d]oxazole | C | Et | SR | 799 | 118.7 |
| 4-3 | isopropyl | benzo[d]oxazole | C | H | SR | 34 | 2219 |
| 4-4 | n-butyl | benzo[d]oxazole | C | H | SR | 101 | 1084 |
| 4-5 | isopropyl | benzo[d]oxazole | C | Et | S | 714 | 26.5 |
| 4-6 | isopropyl | benzo[d]oxazole | C | Et | R | >3000 | 124 |
| 4-7 | isopropyl | benzo[d]oxazole | C | H | S | 20 | 650.7 |
| 4-8 | isopropyl | benzo[d]oxazole | C | H | R | 372 | 1078 |
| 4-9 | n-butyl | benzo[d]oxazole | C | Et | R | 601.5 | 185.7 |
| 4-10 | n-butyl | benzo[d]oxazole | C | H | R | 149.6 | 1500 |
| 4-11 | cyclopentyl | benzo[d]oxazole | C | Et | R | 755.5 | 236.9 |
| 4-12 | cyclopentyl | benzo[d]oxazole | C | H | R | 23.85 | 753.5 |
| 4-13 | isobutyl | benzo[d]oxazole | C | Et | R | 31559 | 360.6 |
| 4-14 | isobutyl | benzo[d]oxazole | C | H | R | 111.8 | 917.2 |
| 4-15 | n-butyl | benzo[d]oxazole | C | Et | S | 350 | 43 |
| 4-16 | n-butyl | benzo[d]oxazole | C | H | S | 36 | 785 |
| 4-17 | isobutyl | benzo[d]oxazole | C | Et | S | 745 | 96 |
| 4-18 | isobutyl | benzo[d]oxazole | C | H | S | 83 | 1751 |
| 4-19 | sec-butyl | benzo[d]oxazole | C | Et | S | 446 | 52 |
| 4-20 | sec-butyl | benzo[d]oxazole | C | H | S | 17 | 984 |
| 4-21 | sec-butyl | benzo[d]oxazole | C | Et | R | 923 | 242 |
| 4-22 | sec-butyl | benzo[d]oxazole | C | H | R | 60 | 899 |

TABLE 4-continued

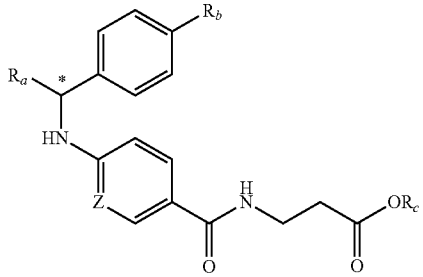

| Compound | $R_a$ | $R_b$ | Z | $R_c$ | Chirality | $IC_{50}^{binding}$ (nM) | $IC_{50}^{cAMP}$ (nM) |
|---|---|---|---|---|---|---|---|
| 4-23 | cyclopentyl | benzo[d]oxazole | C | Et | S | 308 | 65 |
| 4-24 | cyclopentyl | benzo[d]oxazole | C | H | S | 95 | 862 |
| 4-25 | isopropyl | benzo[d]thiazole | C | Et | S | 188.1 | 30.3 |
| 4-26 | isopropyl | benzo[d]thiazole | C | H | S | 42.3 | 1019 |
| 4-27 | isopropyl | benzo[d]thiazole | N | Et | S | 126.6 | 42.3 |
| 4-28 | isopropyl | benzo[d]thiazole | N | H | S | 47.7 | 2688 |
| 4-29 | isopropyl | benzo[d]oxazole | N | Et | S | 284.8 | 53.4 |
| 4-30 | isopropyl | benzo[d]oxazole | N | H | S | 41.8 | 2377 |

TABLE 5

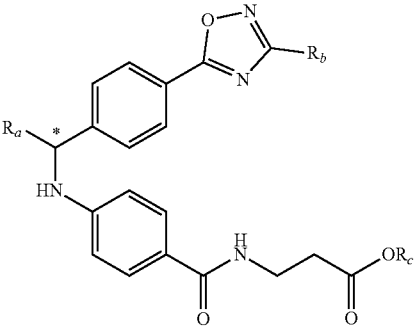

| Compound | $R_a$ | $R_b$ | $R_c$ | Chirality | $IC_{50}^{binding}$ (nM) | $IC_{50}^{cAMP}$ (nM) |
|---|---|---|---|---|---|---|
| 5-1 | isopropyl | Ph | Et | S | 637 | 52 |
| 5-2 | isopropyl | Ph | H | S | 20 | 211 |
| 5-3 | isopropyl | Ph | Et | S | 1744 | 71.4 |
| 5-4 | isopropyl | Ph | H | S | 34.1 | 292 |
| 5-5 | sec-Butyl | Ph | Et | S | 876 | 46 |
| 5-6 | sec-Butyl | Ph | H | S | 13.07 | 239 |
| 5-7 | n-butyl | Ph | Et | S | 1023 (32%) | 59 |
| 5-8 | n-butyl | Ph | H | S | 14.04 | 202 |

TABLE 6

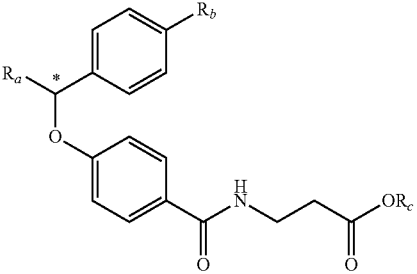

| Compound | $R_a$ | $R_b$ | $R_c$ | Chirality | $IC_{50}^{binding}$ (nM) | $IC_{50}^{cAMP}$ (nM) |
|---|---|---|---|---|---|---|
| 6-1 | isopropyl | benzo[d]thiazole | Et | SR | >30000 | 85.6 |
| 6-2 | isopropyl | benzo[d]thiazole | H | SR | 1109 | 132.6 |

TABLE 7

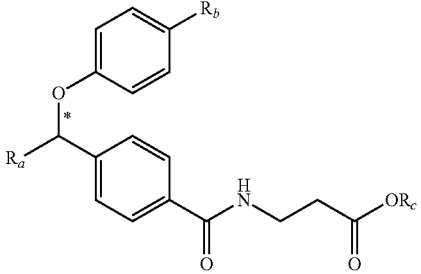

| Compound | $R_a$ | $R_b$ | $R_c$ | Chirality | $IC_{50}^{binding}$ (nM) | $IC_{50}^{cAMP}$ (nM) |
|---|---|---|---|---|---|---|
| 7-1 | isopropyl | benzo[d]oxazole | Et | SR | >30000 | 487 |
| 7-2 | isopropyl | benzo[d]oxazole | H | SR | 176.5 | 292 |
| 7-3 | isopropyl | benzo[d]thiazole | Et | SR | 2109 | 292 |
| 7-4 | isopropyl | benzo[d]thiazole | H | SR | 207.5 | 209 |

Example 7: Comparison of the Potency of Compounds of Formula (I) with a Structurally Close Known Compound Four tested compounds were selected to compare their in vitro potency with a structurally close known compound. The structure of the known compound is shown in Table 8 below.

A functional assay with secondary messenger cAMP detection by the HTRF method shows downstream signaling to GCGR upon treatment with tested compounds. The HTRF cAMP assay was performed by following the manufacturer guidance. Primary human hepatocytes, pre-incubated with tested compounds at various concentrations, were stimulated with recombinant glucagon and the $IC_{50}$ values were determined by the non-linear regression based on the amount of cAMP production.

Results obtained from this study are demonstrated in the table below.

TABLE 8

Comparison in vitro potency of compounds of formula (I) with a known compound.

| Compound | $IC_{50}^{cAMP}$ human hepatocytes |
|---|---|
| 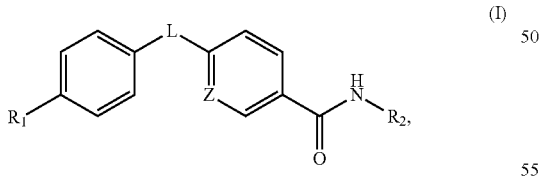 | 135 |
| Compound 1-49 | 19 |
| Compound 2-19 | 15 |
| Compound 4-28 | 62 |
| Compound 4-30 | 53 |

These results show that four compounds of formula (I) exhibited much higher potency in inhibiting cAMP production in human hepatocytes, as compared to a structurally close compound known in the field.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Further, from the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A compound of formula (I):

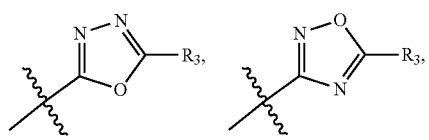

or a pharmaceutically acceptable salt thereof, wherein
$R_1$ is

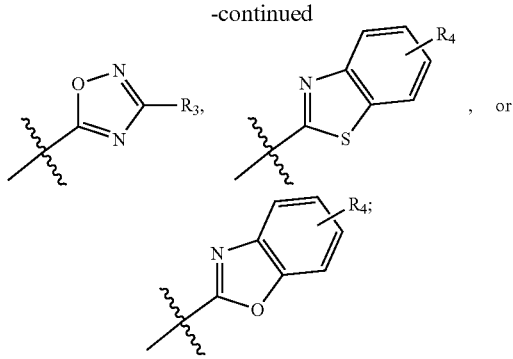

$R_2$ is —$CH_2CH_2CO_2R_5$ or —$CH_2CH_2SO_3H$;

L is —X—CH($R_6$)— or —CH($R_6$)—X—, X being NH or O; and

Z is C or N, in which $R_3$ is $C_{1-6}$ alkyl, aryl, or heteroaryl, the $C_{1-6}$ alkyl being optionally substituted with one to three halo moieties and each of the aryl and heteroaryl being optionally substituted with one to three moieties selected from the group consisting of $C_{1-6}$ alkyl, $C_{3-10}$ cycloalkyl, aryl, halogen substituted $C_{1-6}$ alkyl, $C_{1-6}$ alkoxy, and halo; $R_4$ represents one to three moieties selected from the group consisting of H, halo, hydroxyl, cyano, amino, $C_{1-6}$ alkyl, $C_{1-6}$ alkoxy, halogen substituted $C_{1-6}$ alkyl, and $C_{3-10}$ cycloalkyl; $R_5$ is H, $C_{1-6}$ alkyl, $C_{3-10}$ cycloalkyl or halogen substituted $C_{1-6}$ alkyl; and $R_6$ is $C_{1-6}$ alkyl, $C_{3-10}$ cycloalkyl, or $C_{1-10}$ heterocycloalkyl, the $C_{1-6}$ alkyl being optionally substituted with one to three moieties selected from the group consisting of halo, hydroxyl, $C_{1-6}$ alkoxy, and aryl, and each of the $C_{3-10}$ cycloalkyl and $C_{1-10}$ heterocycloalkyl being optionally substituted with one to two moieties selected from the group consisting of $C_{1-6}$ alkyl, $C_{1-6}$ alkoxy, and halo.

2. The compound or salt of claim 1, wherein $R_1$ is

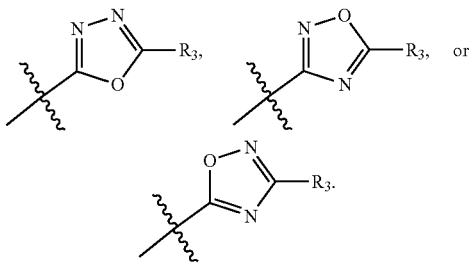

3. The compound or salt of claim 2, wherein L is —CH($R_6$)—X—, X being NH or O.

4. The compound or salt of claim 3, wherein $R_1$ is

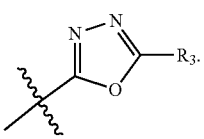

5. The compound or salt of claim 3, wherein $R_1$ is

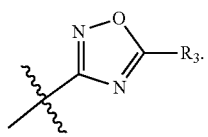

6. The compound or salt of claim 3, wherein $R_1$ is

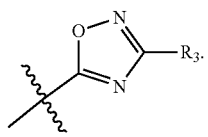

7. The compound or salt of claim 2, wherein L is —X—CH($R_6$)—, X being NH or O.

8. The compound or salt of claim 2, wherein $R_3$ is $C_{1-6}$ alkyl, optionally substituted phenyl or pyridinyl.

9. The compound or salt of claim 2, wherein L is —CH($R_6$)—X—, and $R_6$ being $C_{1-6}$ alkyl.

10. The compound or salt of claim 1, wherein $R_1$ is

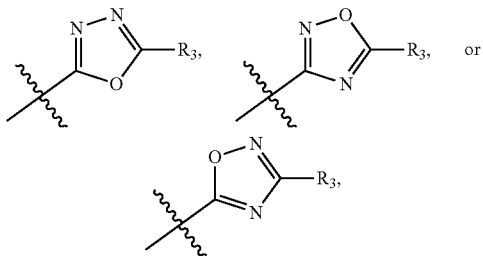

$R_3$ being $C_{1-6}$ alkyl, optionally substituted phenyl or pyridinyl; L is —X—CH($R_6$)— or —CH($R_6$)—X—, $R_6$ being $C_{1-6}$ alkyl; and Z is C.

11. The compound or salt of claim 1, wherein $R_1$ is

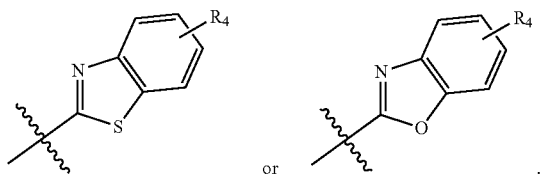

12. The compound or salt of claim 11, wherein L is —CH($R_6$)—X—.

13. The compound or salt of claim 12, wherein X is NH and Z is N.

14. The compound or salt of claim 12, wherein $R_6$ is $C_{1-6}$ alkyl.

15. The compound or salt of claim 11, wherein L is —X—CH($R_6$)— and Z is C.

16. The compound or salt of claim 15, wherein $R_6$ is $C_{1-6}$ alkyl.

17. The compound or salt of claim 11, wherein $R_4$ is H.

18. The compound or salt of claim 1, wherein $R_1$ is

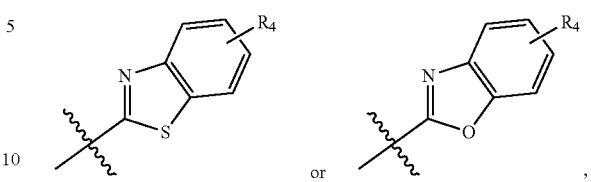

$R_4$ being H; and L is —X—CH($R_6$)— or —CH($R_6$)—X—, $R_6$ being $C_{1-6}$ alkyl.

19. The compound or salt of claim 1, wherein $R_3$ is $C_{1-6}$ alkyl, aryl, or 6-membered heteroaryl, the $C_{1-6}$ alkyl being optionally substituted with one to three halo moieties and each of the aryl and 6-membered heteroaryl being optionally substituted with one to three moieties selected from the group consisting of methyl, trifluoromethyl, ethyl, propyl, isopropyl, butyl, tert-butyl, F and Cl.

20. The compound or salt of claim 1, wherein $R_6$ is $C_{1-6}$ alkyl or $C_{3-10}$ cycloalkyl, the $C_{1-6}$ alkyl being optionally substituted with one to three moieties selected from the group consisting of fluoro, hydroxyl, methoxy, and phenyl.

21. The compound or salt of claim 1, which is any one selected from the group consisting of:
- 3-(4-((2-methyl-1-(4-(5-phenyl-1,3,4-oxadiazol-2-yl)phenyl)propyl)amino)benzamido) propanoic acid;
- methyl 3-(4-((2-methyl-1-(4-(5-phenyl-1,3,4-oxadiazol-2-yl)phenyl)propyl)amino)benzamido)propanoate;
- ethyl 3-(4-((2-methyl-1-(4-(5-phenyl-1,3,4-oxadiazol-2-yl)phenyl)propyl)amino)benzamido)propanoate;
- 3-(4-((2-methyl-1-(4-(5-(trifluoromethyl)-1,3,4-oxadiazol-2-yl)phenyl)propyl)amino)benzamido)propanoic acid;
- 3-(4-((3-methyl-1-(4-(5-phenyl-1,3,4-oxadiazol-2-yl)phenyl)butyl)amino)benzamido) propanoic acid;
- ethyl 3-(4-((1-(4-(5-phenyl-1,3,4-oxadiazol-2-yl)phenyl)butyl)amino)benzamido) propanoate;
- 3-(4-((1-(4-(5-Phenyl-1,3,4-oxadiazol-2-yl)phenyl)butyl)amino)benzamido)propanoic acid;
- 3-(4-((1-(4-(5-(Trifluoromethyl)-1,3,4-oxadiazol-2-yl)phenyl)butyl)amino)benzamido)propanoic acid;
- 3-(4-((3-methyl-1-(4-(5-(trifluoromethyl)-1,3,4-oxadiazol-2-yl)phenyl)butyl)amino)benzamido)propanoic acid;
- ethyl 3-(4-((2-methyl-1-(4-(5-phenyl-1,3,4-oxadiazol-2-yl)phenyl)butyl)amino)benzamido)propanoate;
- 3-(4-((2-methyl-1-(4-(5-phenyl-1,3,4-oxadiazol-2-yl)phenyl)butyl)amino)benzamido) propanoic acid;
- 3-(4-((1-(4-(5-(tert-butyl)-1,3,4-oxadiazol-2-yl)phenyl)-3-methylbutyl)amino)benzamido)propanoic acid;
- 2-(4-((1-(4-(5-phenyl-1,3,4-oxadiazol-2-yl)phenyl)pentyl)amino)benzamido)ethane-1-sulfonic acid;
- 3-(4-((1-(4-(5-(trifluoromethyl)-1,3,4-oxadiazol-2-yl)phenyl)pentyl)amino)benzamido) propanoic acid;
- ethyl 3-(4-((1-(4-(5-(pyridin-2-yl)-1,3,4-oxadiazol-2-yl)phenyl)pentyl)amino)benzamido)propanoate;
- 3-(4-((1-(4-(5-(Pyridin-2-yl)-1,3,4-oxadiazol-2-yl)phenyl)pentyl)amino)benzamido) propanoic acid;
- ethyl 3-(4-((1-(4-(5-(4-fluorophenyl)-1,3,4-oxadiazol-2-yl)phenyl)-2-methylpropyl)amino)benzamido)propanoate;
- 3-(4-((1-(4-(5-(4-Fluorophenyl)-1,3,4-oxadiazol-2-yl)phenyl)-2-methyl propyl)amino)benzamido)propanoic acid;

ethyl 3-(4-((1-(4-(5-(tert-butyl)-1,3,4-oxadiazol-2-yl)phenyl)pentyl)amino)benzamido) propanoate;
3-(4-((1-(4-(5-(tert-butyl)-1,3,4-oxadiazol-2-yl)phenyl)pentyl)amino)benzamido) propanoic acid;
ethyl 3-(4-((1-(4-(5-(tert-butyl)-1,3,4-oxadiazol-2-yl)phenyl)-2-methylbutyl)amino)benzamido)propanoate;
3-(4-((1-(4-(5-(tert-butyl)-1,3,4-oxadiazol-2-yl)phenyl)-2-methylbutyl)amino)benzami do)propanoic acid;
ethyl 3-(4-((1-(4-(5-(tert-butyl)-1,3,4-oxadiazol-2-yl)phenyl)-2-methyl propyl)amino)benzamido)propanoate;
3-(4-((1-(4-(5-(tert-butyl)-1,3,4-oxadiazol-2-yl)phenyl)-2-methyl propyl)amino)benzamido)propanoic acid;
ethyl 3-(4-((1-(4-(5-(4-methoxyphenyl)-1,3,4-oxadiazol-2-yl)phenyl)-2-methyl propyl)amino)benzamido)propanoate;
3-(4-((1-(4-(5-(4-methoxyphenyl)-1,3,4-oxadiazol-2-yl)phenyl)-2-methyl propyl)amino)benzamido)propanoic acid;
ethyl 3-(4-((1-(4-(5-(4-fluorophenyl)-1,3,4-oxadiazol-2-yl)phenyl)-3-methylbutyl)amino)benzamido)propanoate;
3-(4-((1-(4-(5-(4-fluorophenyl)-1,3,4-oxadiazol-2-yl)phenyl)-3-methylbutyl)amino)benzamido)propanoic acid;
ethyl 3-(4-((1-(4-(5-(4-fluorophenyl)-1,3,4-oxadiazol-2-yl)phenyl)-2-methylbutyl)amino)benzamido)propanoate;
3-(4-((1-(4-(5-(4-fluorophenyl)-1,3,4-oxadiazol-2-yl)phenyl)-2-methylbutyl)amino)benzamido)propanoic acid;
ethyl 3-(4-((2-methyl-1-(4-(5-(trifluoromethyl)-1,3,4-oxadiazol-2-yl)phenyl)butyl)amino)benzamido)propanoate;
3-(4-((2-methyl-1-(4-(5-(trifluoromethyl)-1,3,4-oxadiazol-2-yl)phenyl)butyl)amino)benzamido)propanoic acid;
ethyl 3-(4-((1-(4-(5-(trifluoromethyl)-1,3,4-oxadiazol-2-yl)phenyl)pentyl)amino)benzamido)propanoate;
ethyl 3-(4-(((1S)-2-methyl-1-(4-(5-(trifluoromethyl)-1,3,4-oxadiazol-2-yl)phenyl)butyl)amino)benzamido)propanoate;
ethyl 3-(4-(((1R)-2-methyl-1-(4-(5-(trifluoromethyl)-1,3,4-oxadiazol-2-yl)phenyl)butyl)amino)benzamido)propanoate;
3-(4-(((1S)-2-methyl-1-(4-(5-(trifluoromethyl)-1,3,4-oxadiazol-2-yl)phenyl)butyl)amino)benzamido)propanoic acid;
3-(4-(((1R)-2-methyl-1-(4-(5-(trifluoromethyl)-1,3,4-oxadiazol-2-yl)phenyl)butyl)amino)benzamido)propanoic acid;
methyl 3-(4-((1-(4-(5-(pyridin-2-yl)-1,3,4-oxadiazol-2-yl)phenyl)pentyl)amino)benzamido)propanoate;
(S)-ethyl 3-(4-(2-methyl-1-(4-(5-phenyl-1,3,4-oxadiazol-2-yl)phenyl)propylamino)benzamido)propanoate;
(R)-ethyl 3-(4-(2-methyl-1-(4-(5-phenyl-1,3,4-oxadiazol-2-yl)phenyl)propylamino)benzamido)propanoate;
(S)-3-(4-(2-methyl-1-(4-(5-phenyl-1,3,4-oxadiazol-2-yl)phenyl)propylamino)benzamido)propanoic acid;
(R)-3-(4-(2-methyl-1-(4-(5-phenyl-1,3,4-oxadiazol-2-yl)phenyl)propylamino)benzamido)propanoic acid;
ethyl (S)-3-(4-((1-(4-(5-(pyridin-2-yl)-1,3,4-oxadiazol-2-yl)phenyl)pentyl)amino)benzamido)propanoate;
ethyl (R)-3-(4-((1-(4-(5-(pyridin-2-yl)-1,3,4-oxadiazol-2-yl)phenyl)pentyl)amino)benzamido)propanoate;
(S)-3-(4-((1-(4-(5-(pyridin-2-yl)-1,3,4-oxadiazol-2yl)phenyl)pentyl)amino)benzamido)propanoic acid;
(R)-3-(4-((1-(4-(5-(pyridin-2-yl)-1,3,4-oxadiazol-2-yl)phenyl)pentyl)amino)benzamido)propanoic acid;
ethyl 3-(4-(((1S)-2-methyl-1-(4-(5-phenyl-1,3,4-oxadiazol-2-yl)phenyl)butyl)amino)benzamido)propanoate;
ethyl 3-(4-(((1R)-2-methyl-1-(4-(5-phenyl-1,3,4-oxadiazol-2-yl)phenyl)butyl)amino)benzamido)propanoate;
3-(4-(((1S)-2-methyl-1-(4-(5-phenyl-1,3,4-oxadiazol-2-yl)phenyl)butyl)amino)benzamido)propanoic acid;
3-(4-(((1R)-2-methyl-1-(4-(5-phenyl-1,3,4-oxadiazol-2-yl)phenyl)butyl)amino)benzamido)propanoic acid;
ethyl (S)-3-(4-((1-(4-(5-(trifluoromethyl)-1,3,4-oxadiazol-2-yl)phenyl)pentyl)amino)benzamido)propanoate;
ethyl (R)-3-(4-((1-(4-(5-(trifluoromethyl)-1,3,4-oxadiazol-2-yl)phenyl)pentyl)amino)benzamido)propanoate;
(S)-3-(4-((1-(4-(5-(trifluoromethyl)-1,3,4-oxadiazol-2-yl)phenyl)pentyl)amino)benzamido)propanoic acid;
(R)-3-(4-((1-(4-(5-(trifluoromethyl)-1,3,4-oxadiazol-2-yl)phenyl)pentyl)amino)benzamido)propanoic acid;
ethyl (S)-3-(4-((2-methyl-1-(4-(5-(trifluoromethyl)-1,3,4-oxadiazol-2-yl)phenyl)propyl)amino)benzamido)propanoate;
ethyl (R)-3-(4-((2-methyl-1-(4-(5-(trifluoromethyl)-1,3,4-oxadiazol-2-yl)phenyl)propyl)amino)benzamido) propanoate;
(S)-3-(4-((2-methyl-1-(4-(5-(trifluoromethyl)-1,3,4-oxadiazol-2-yl)phenyl)propyl)amino)benzamido)propanoic acid;
(R)-3-(4-((2-methyl-1-(4-(5-(trifluoromethyl)-1,3,4-oxadiazol-2-yl)phenyl)propyl)amino)benzamido)propanoic acid;
ethyl (S)-3-(4-((3-methyl-1-(4-(5-phenyl-1,3,4-oxadiazol-2-yl)phenyl)butyl)amino)benzamido)propanoate;
ethyl (R)-3-(4-((3-methyl-1-(4-(5-phenyl-1,3,4-oxadiazol-2-yl)phenyl)butyl)amino)benzamido)propanoate;
(S)-3-(4-((3-methyl-1-(4-(5-phenyl-1,3,4-oxadiazol-2-yl)phenyl)butyl)amino)benzamido)propanoic acid;
(R)-3-(4-((3-methyl-1-(4-(5-phenyl-1,3,4-oxadiazol-2-yl)phenyl)butyl)amino)benzamido)propanoic acid;
methyl (S)-3-(4-((2-methyl-1-(4-(5-phenyl-1,3,4-oxadiazol-2-yl)phenyl)propyl)amino)benzamido)propanoate;
(S)-2-(4-((2-methyl-1-(4-(5-phenyl-1,3,4-oxadiazol-2-yl)phenyl)propyl)amino)benzamido)ethane-1-sulfonic acid;
ethyl 3-(4-((1-(4-(5-(tert-butyl)-1,2,4-oxadiazol-3-yl)phenyl)-2-methyl propyl)amino)benzamido)propanoate;
3-(4-((1-(4-(5-(tert-butyl)-1,2,4-oxadiazol-3-yl)phenyl)-2-methyl propyl)amino)benzamido)propanoic acid;
ethyl 3-(4-((1-(4-(5-(tert-butyl)-1,2,4-oxadiazol-3-yl)phenyl)pentyl)amino)benzamido)propanoate;
3-(4-((1-(4-(5-(tert-butyl)-1,2,4-oxadiazol-3-yl)phenyl)pentyl)amino)benzamido)propanoic acid;
ethyl 3-(4-((1-(4-(5-(tert-butyl)-1,2,4-oxadiazol-3-yl)phenyl)-3-methylbutyl)amino)benzamido)propanoate;
3-(4-((1-(4-(5-(tert-butyl)-1,2,4-oxadiazol-3-yl)phenyl)-3-methylbutyl)amino)benzamido)propanoic acid;
ethyl 3-(4-((1-(4-(5-phenyl-1,2,4-oxadiazol-3-yl)phenyl)pentyl)amino)benzamido) propanoate;
3-(4-((1-(4-(5-phenyl-1,2,4-oxadiazol-3-yl)phenyl)pentyl)amino)benzamido)propanoic acid;
ethyl 3-(4-((3-methyl-1-(4-(5-phenyl-1,2,4-oxadiazol-3-yl)phenyl)butyl)amino)benzamido)propanoate;
3-(4-((3-methyl-1-(4-(5-phenyl-1,2,4-oxadiazol-3-yl)phenyl)butyl)amino)benzamido) propanoic acid;

ethyl 3-(4-((2-methyl-1-(4-(5-(thiophen-2-yl)-1,2,4-oxadiazol-3-yl)phenyl)propyl)amino)benzamido)propanoate;

3-(4-((2-methyl-1-(4-(5-(thiophen-2-yl)-1,2,4-oxadiazol-3-yl)phenyl)propyl)amino)benzamido)propanoic acid;

3-(4-((1-(4-(5-(thiophen-2-yl)-1,2,4-oxadiazol-3-yl)phenyl)pentyl)amino)benzamido)propanoic acid;

3-(4-((3-methyl-1-(4-(5-(thiophen-2-yl)-1,2,4-oxadiazol-3-yl)phenyl)butyl)amino)benzamido)propanoic acid;

3-(4-((cyclopentyl(4-(5-phenyl-1,2,4-oxadiazol-3-yl)phenyl)methyl)amino)benzamido)propanoic acid;

ethyl 3-(4-((cyclohexyl(4-(5-phenyl-1,2,4-oxadiazol-3-yl)phenyl)methyl)amino)benzamido)propanoate;

3-(4-((cyclohexyl(4-(5-phenyl-1,2,4-oxadiazol-3-yl)phenyl)methyl)amino)benzamido) propanoic acid;

ethyl 3-(4-(((1S)-2-methyl-1-(4-(5-phenyl-1,2,4-oxadiazol-3-yl)phenyl)butyl)amino)benzamido)propanoate;

3-(4-(((1S)-2-methyl-1-(4-(5-phenyl-1,2,4-oxadiazol-3-yl)phenyl)butyl)amino)benzamido)propanoic acid;

ethyl 3-(4-(((1R)-2-methyl-1-(4-(5-phenyl-1,2,4-oxadiazol-3-yl)phenyl)butyl)amino)benzamido)propanoate;

3-(4-(((1R)-2-methyl-1-(4-(5-phenyl-1,2,4-oxadiazol-3-yl)phenyl)butyl)amino)benzamido)propanoic acid;

ethyl (R)-3-(4-((2-methyl-1-(4-(5-phenyl-1,2,4-oxadiazol-3-yl)phenyl)propyl)amino)benzamido)propanoate;

(R)-3-(4-((2-methyl-1-(4-(5-phenyl-1,2,4-oxadiazol-3-yl)phenyl)propyl)amino)benzamido)propanoic acid;

ethyl 3-(4-((1-(4-(5-(4-fluorophenyl)-1,2,4-oxadiazol-3-yl)phenyl)-2-methylpropyl)amino)benzamido)propanoate;

3-(4-((1-(4-(5-(4-fluorophenyl)-1,2,4-oxadiazol-3-yl)phenyl)-2-methylpropyl)amino)benzamido)propanoic acid;

3-(4-((2-methyl-1-(4-(5-phenyl-1,2,4-oxadiazol-3-yl)phenyl)propyl)amino)benzamido) propanoic acid;

ethyl (S)-3-(4-((2-methyl-1-(4-(5-phenyl-1,2,4-oxadiazol-3-yl)phenyl)propyl)amino)benzamido)propanoate;

(S)-3-(4-((2-methyl-1-(4-(5-phenyl-1,2,4-oxadiazol-3-yl)phenyl)propyl)amino)benzamido)propanoic acid;

ethyl 3-(4-(((1S)-2-methyl-1-(4-(5-(trifluoromethyl)-1,2,4-oxadiazol-3-yl)phenyl)butyl)amino)benzamido)propanoate;

3-(4-(((1S)-2-methyl-1-(4-(5-(trifluoromethyl)-1,2,4-oxadiazol-3-yl)phenyl)butyl)amino)benzamido)propanoic acid;

methyl 3-(4-((2-methyl-1-(4-(5-phenyl-1,2,4-oxadiazol-3-yl)phenyl)propyl)amino)benzamido)propanoate;

methyl 3-(4-((1-(4-(5-phenyl-1,2,4-oxadiazol-3-yl)phenyl)pentyl)amino)benzamido) propanoate;

ethyl (S)-3-(4-((1-(4-(5-phenyl-1,2,4-oxadiazol-3-yl)phenyl)pentyl)amino)benzamido) propanoate;

(S)-3-(4-((1-(4-(5-phenyl-1,2,4-oxadiazol-3-yl)phenyl)pentyl)amino)benzamido)propanoic acid;

ethyl (R)-3-(4-((1-(4-(5-phenyl-1,2,4-oxadiazol-3-yl)phenyl)pentyl)amino)benzamido) propanoate;

(R)-3-(4-((1-(4-(5-phenyl-1,2,4-oxadiazol-3-yl)phenyl)pentyl)amino)benzamido) propanoic acid;

ethyl (S)-3-(4-((1-(4-(5-(pyridin-2-yl)-1,2,4-oxadiazol-3-yl)phenyl)pentyl)amino)benzamido)propanoate;

(S)-3-(4-((1-(4-(5-(pyridin-2-yl)-1,2,4-oxadiazol-3-yl)phenyl)pentyl)amino)benzamido)propanoic acid;

ethyl (R)-3-(4-((1-(4-(5-(pyridin-2-yl)-1,2,4-oxadiazol-3-yl)phenyl)pentyl)amino)benzamido)propanoate;

(R)-3-(4-((1-(4-(5-(pyridin-2-yl)-1,2,4-oxadiazol-3-yl)phenyl)pentyl)amino)benzamido)propanoic acid;

ethyl (S)-3-(4-((3-methyl-1-(4-(5-phenyl-1,2,4-oxadiazol-3-yl)phenyl)butyl)amino)benzamido)propanoate;

ethyl (R)-3-(4-((3-methyl-1-(4-(5-phenyl-1,2,4-oxadiazol-3-yl)phenyl)butyl)amino)benzamido)propanoate;

(S)-3-(4-((3-methyl-1-(4-(5-phenyl-1,2,4-oxadiazol-3-yl)phenyl)butyl)amino)benzamido)propanoic acid;

(R)-3-(4-((3-methyl-1-(4-(5-phenyl-1,2,4-oxadiazol-3-yl)phenyl)butyl)amino)benzamido)propanoic acid;

ethyl (S)-3-(4-((1-(4-(5-(trifluoromethyl)-1,2,4-oxadiazol-3-yl)phenyl)pentyl)amino)benzamido)propanoate;

ethyl (R)-3-(4-((1-(4-(5-(trifluoromethyl)-1,2,4-oxadiazol-3-yl)phenyl)pentyl)amino)benzamido)propanoate;

(S)-3-(4-((1-(4-(5-(trifluoromethyl)-1,2,4-oxadiazol-3-yl)phenyl)pentyl)amino)benzamido)propanoic acid;

(R)-3-(4-((1-(4-(5-(trifluoromethyl)-1,2,4-oxadiazol-3-yl)phenyl)pentyl)amino)benzamido)propanoic acid;

methyl (S)-3-(4-((2-methyl-1-(4-(5-phenyl-1,2,4-oxadiazol-3-yl)phenyl)propyl)amino)benzamido)propanoate;

3-(4-(1-((4-(5-phenyl-1,3,4-oxadiazol-2-yl)phenyl)amino)pentyl)benzamido)propanoic acid;

3-(4-(2-methyl-1-((4-(5-phenyl-1,3,4-oxadiazol-2-yl)phenyl)amino)propyl)benzamido) propanoic acid;

ethyl 3-(4-(1-((4-(5-phenyl-1,3,4-oxadiazol-2-yl)phenyl)amino)pentyl)benzamido) propanoate;

ethyl 3-(4-(2-methyl-1-((4-(5-phenyl-1,3,4-oxadiazol-2-yl)phenyl)amino)propyl)benzamido)propanoate;

ethyl 3-(4-(2-methyl-1-((4-(5-phenyl-1,3,4-oxadiazol-2-yl)phenyl)amino)butyl)benzamido)propanoate;

3-(4-(2-methyl-1-((4-(5-phenyl-1,3,4-oxadiazol-2-yl)phenyl)amino)butyl)benzamido) propanoic acid;

ethyl 3-(4-(1-((4-(5-(4-fluorophenyl)-1,3,4-oxadiazol-2-yl)phenyl)amino)-2-methylbutyl)benzamido)propanoate;

3-(4-(1-((4-(5-(4-fluorophenyl)-1,3,4-oxadiazol-2-yl)phenyl)amino)-2-methylbutyl)benzamido)propanoic acid;

ethyl 3-(4-(1-((4-(5-(4-fluorophenyl)-1,3,4-oxadiazol-2-yl)phenyl)amino)-2-methylpropyl)benzamido)propanoate;

3-(4-(1-((4-(5-(4-fluorophenyl)-1,3,4-oxadiazol-2-yl)phenyl)amino)-2-methylpropyl)benzamido)propanoic acid;

3-(4-(2-methyl-1-((4-(5-phenyl-1,2,4-oxadiazol-3-yl)phenyl)amino)propyl)benzamido) propanoic acid;

(S)-ethyl 3-(4-(2-methyl-1-(4-(5-phenyl-1,3,4-oxadiazol-2-yl)phenylamino)propyl)benzamido)propanoate;

(R)-ethyl 3-(4-(2-methyl-1-(4-(5-phenyl-1,3,4-oxadiazol-2-yl)phenylamino)propyl)benzamido)propanoate;

(S)-3-(4-(2-methyl-1-(4-(5-phenyl-1,3,4-oxadiazol-2-yl)phenylamino)propyl)benzamido)propanoic acid;

(R)-3-(4-(2-methyl-1-(4-(5-phenyl-1,3,4-oxadiazol-2-yl)phenylamino)propyl)benzamido)propanoic acid;

ethyl 3-(4-((1-(4-(benzo[d]oxazol-2-yl)phenyl)-2-methylpropyl)amino)benzamido) propanoate;

ethyl 3-(4-((1-(4-(benzo[d]oxazol-2-yl)phenyl)pentyl)amino)benzamido)propanoate;

3-(4-((1-(4-(benzo[d]oxazol-2-yl)phenyl)-2-methylpropyl)amino)benzamido) propanoic acid;

3-(4-((1-(4-(benzo[d]oxazol-2-yl)phenyl)pentyl)amino)benzamido)propanoic acid;

ethyl (S)-3-(4-((1-(4-(benzo[d]oxazol-2-yl)phenyl)-2-methylpropyl)amino)benzamido) propanoate;

ethyl (R)-3-(4-((1-(4-(benzo[d]oxazol-2-yl)phenyl)-2-methylpropyl)amino)benzamido)propanoate;

(S)-3-(4-((1-(4-(benzo[d]oxazol-2-yl)phenyl)-2-methylpropyl)amino)benzamido)propanoic acid;
(R)-3-(4-((1-(4-(benzo[d]oxazol-2-yl)phenyl)-2-methylpropyl)amino)benzamido)propanoic acid;
ethyl (R)-3-(4-((1-(4-(benzo[d]oxazol-2-yl)phenyl)pentyl)amino)benzamido) propanoate;
(R)-3-(4-((1-(4-(benzo[d]oxazol-2-yl)phenyl)pentyl)amino)benzamido)propanoic acid;
ethyl (R)-3-(4-(((4-(benzo[d]oxazol-2-yl)phenyl)(cyclopentyl)methyl)amino)benzamido)propanoate;
(R)-3-(4-(((4-(benzo[d]oxazol-2-yl)phenyl)(cyclopentyl)methyl)amino)benzamido)propanoic acid;
ethyl (R)-3-(4-((1-(4-(benzo[d]oxazol-2-yl)phenyl)-3-methylbutyl)amino)benzamido) propanoate;
(R)-3-(4-((1-(4-(benzo[d]oxazol-2-yl)phenyl)-3-methylbutyl)amino)benzamido) propanoic acid;
ethyl (S)-3-(4-((1-(4-(benzo[d]oxazol-2-yl)phenyl)pentyl)amino)benzamido) propanoate;
(S)-3-(4-((1-(4-(benzo[d]oxazol-2-yl)phenyl)pentyl)amino)benzamido)propanoic acid;
ethyl (S)-3-(4-((1-(4-(benzo[d]oxazol-2-yl)phenyl)-3-methylbutyl)amino)benzamido) propanoate;
(S)-3-(4-((1-(4-(benzo[d]oxazol-2-yl)phenyl)-3-methylbutyl)amino)benzamido)propanoic acid;
ethyl 3-(4-(((1S)-1-(4-(benzo[d]oxazol-2-yl)phenyl)-2-methylbutyl)amino)benzamido)propanoate;
3-(4-(((1S)-1-(4-(benzo[d]oxazol-2-yl)phenyl)-2-methylbutyl)amino)benzamido)propanoic acid;
ethyl 3-(4-(((1R)-1-(4-(benzo[d]oxazol-2-yl)phenyl)-2-methylbutyl)amino)benzamido)propanoate;
3-(4-(((1R)-1-(4-(benzo[d]oxazol-2-yl)phenyl)-2-methylbutyl)amino)benzamido)propanoic acid;
ethyl (S)-3-(4-(((4-(benzo[d]oxazol-2-yl)phenyl)(cyclopentyl)methyl)amino)benzamido)propanoate;
(S)-3-(4-(((4-(benzo[d]oxazol-2-yl)phenyl)(cyclopentyl)methyl)amino)benzamido)propanoic acid;
ethyl (S)-3-(4-((1-(4-(benzo[d]thiazol-2-yl)phenyl)-2-methylpropyl)amino)benzamido) propanoate;
(S)-3-(4-((1-(4-(benzo[d]thiazol-2-yl)phenyl)-2-methylpropyl)amino)benzamido)propanoic acid;
ethyl (S)-3-(6-((1-(4-(benzo[d]thiazol-2-yl)phenyl)-2-methylpropyl)amino)nicotinamido) propanoate;
(S)-3-(6-((1-(4-(benzo[d]thiazol-2-yl)phenyl)-2-methylpropyl)amino)nicotinamido)propanoic acid;
ethyl (S)-3-(6-((1-(4-(benzo[d]oxazol-2-yl)phenyl)-2-methylpropyl)amino)nicotinamido) propanoate;
(S)-3-(6-((1-(4-(benzo[d]oxazol-2-yl)phenyl)-2-methylpropyl)amino)nicotinamido)propanoic acid;
ethyl (S)-3-(4-((3-methyl-1-(4-(3-phenyl-1,2,4-oxadiazol-5-yl)phenyl)butyl)amino)benzamido)propanoate;
(S)-3-(4-((3-methyl-1-(4-(3-phenyl-1,2,4-oxadiazol-5-yl)phenyl)butyl)amino)benzamido)propanoic acid;
ethyl (S)-3-(4-((2-methyl-1-(4-(3-phenyl-1,2,4-oxadiazol-5-yl)phenyl)propyl)amino)benzamido)propanoate;
(S)-3-(4-((2-methyl-1-(4-(3-phenyl-1,2,4-oxadiazol-5-yl)phenyl)propyl)amino)benzamido)propanoic acid;
ethyl 3-(4-(((1S)-2-methyl-1-(4-(3-phenyl-1,2,4-oxadiazol-5-yl)phenyl)butyl)amino)benzamido)propanoate;
3-(4-(((1S)-2-methyl-1-(4-(3-phenyl-1,2,4-oxadiazol-5-yl)phenyl)butyl)amino)benzamido)propanoic acid;
ethyl (S)-3-(4-((1-(4-(3-phenyl-1,2,4-oxadiazol-5-yl)phenyl)pentyl)amino)benzamido) propanoate;
(S)-3-(4-((1-(4-(3-phenyl-1,2,4-oxadiazol-5-yl)phenyl)pentyl)amino)benzamido) propanoic acid;
ethyl 3-(4-(1-(4-(benzo[d]thiazol-2-yl)phenyl)-2-methylpropoxy)benzamido)propanoate;
3-(4-(1-(4-(Benzo[d]thiazol-2-yl)phenyl)-2-methylpropoxy)benzamido)propanoic acid;
ethyl 3-(4-(1-(4-(benzo[d]oxazol-2-yl)phenoxy)-2-methylpropyl)benzamido)propanoate;
3-(4-(1-(4-(Benzo[d]oxazol-2-yl)phenoxy)-2-methylpropyl)benzamido)propanoic acid;
ethyl 3-(4-(1-(4-(benzo[d]thiazol-2-yl)phenoxy)-2-methylpropyl)benzamido)propanoate; and
3-(4-(1-(4-(Benzo[d]thiazol-2-yl)phenoxy)-2-methylpropyl)benzamido)propanoic acid.

22. The compound or salt of claim 21, which is any one selected from the group consisting of:
methyl 3-(4-((2-methyl-1-(4-(5-phenyl-1,3,4-oxadiazol-2-yl)phenyl)propyl)amino)benzamido)propanoate;
methyl 3-(4-((1-(4-(5-(pyridin-2-yl)-1,3,4-oxadiazol-2-yl)phenyl)pentyl)amino)benzamido)propanoate;
(S)-ethyl 3-(4-(2-methyl-1-(4-(5-phenyl-1,3,4-oxadiazol-2-yl)phenyl)propylamino)benzamido)propanoate;
(S)-3-(4-(2-methyl-1-(4-(5-phenyl-1,3,4-oxadiazol-2-yl)phenyl)propylamino)benzamido)propanoic acid;
ethyl (S)-3-(4-((1-(4-(5-(pyridin-2-yl)-1,3,4-oxadiazol-2-yl)phenyl)pentyl)amino)benzamido)propanoate;
(S)-3-(4-((1-(4-(5-(pyridin-2-yl)-1,3,4-oxadiazol-2-yl)phenyl)pentyl)amino)benzamido) propanoic acid;
ethyl 3-(4-(((1S)-2-methyl-1-(4-(5-phenyl-1,3,4-oxadiazol-2-yl)phenyl)butyl)amino)benzamido)propanoate;
3-(4-(((1S)-2-methyl-1-(4-(5-phenyl-1,3,4-oxadiazol-2-yl)phenyl)butyl)amino)benzamido)propanoic acid;
ethyl 3-(4-(((1S)-2-methyl-1-(4-(5-phenyl-1,2,4-oxadiazol-3-yl)phenyl)butyl)amino)benzamido)propanoate;
3-(4-(((1S)-2-methyl-1-(4-(5-phenyl-1,2,4-oxadiazol-3-yl)phenyl)butyl)amino)benzamido)propanoic acid;
ethyl (S)-3-(4-((2-methyl-1-(4-(5-phenyl-1,2,4-oxadiazol-3-yl)phenyl)propyl)amino)benzamido)propanoate;
(S)-3-(4-((2-methyl-1-(4-(5-phenyl-1,2,4-oxadiazol-3-yl)phenyl)propyl)amino)benzamido)propanoic acid;
ethyl (S)-3-(6-((1-(4-(benzo[d]thiazol-2-yl)phenyl)-2-methylpropyl)amino)nicotinamido) propanoate;
(S)-3-(6-((1-(4-(benzo[d]thiazol-2-yl)phenyl)-2-methylpropyl)amino)nicotinamido)propanoic acid;
ethyl (S)-3-(6-((1-(4-(benzo[d]oxazol-2-yl)phenyl)-2-methylpropyl)amino)nicotinamido) propanoate; and
(S)-3-(6-((1-(4-(benzo[d]oxazol-2-yl)phenyl)-2-methylpropyl)amino)nicotinamido)propanoic acid.

23. A pharmaceutical composition comprising a compound or salt of claim 1 and a pharmaceutically acceptable carrier.

24. A method for reducing the glycemic level in a subject, the method comprising administering to the subject in need thereof an effective amount of a compound or salt of claim 1.

25. A method of treating alleviating disorders associated with glucagon, the method comprising administering to a subject in need thereof an effective amount of a compound or salt of claim 1.

* * * * *